US011236188B2

(12) United States Patent
Otomo et al.

(10) Patent No.: US 11,236,188 B2
(45) Date of Patent: Feb. 1, 2022

(54) ELECTRO-OPTIC POLYMER

(71) Applicant: NATIONAL INSTITUTE OF INFORMATION AND COMMUNICATIONS TECHNOLOGY, Tokyo (JP)

(72) Inventors: Akira Otomo, Tokyo (JP); Isao Aoki, Tokyo (JP); Toshiki Yamada, Tokyo (JP)

(73) Assignee: NATIONAL INSTITUTE OF INFORMATION AND COMMUNICATIONS TECHNOLOGY, Tokyo (JP)

( * ) Notice: Subject to any disclaimer, the term of this patent is extended or adjusted under 35 U.S.C. 154(b) by 190 days.

(21) Appl. No.: 16/314,086

(22) PCT Filed: Jun. 28, 2017

(86) PCT No.: PCT/JP2017/023716

§ 371 (c)(1),
(2) Date: Dec. 28, 2018

(87) PCT Pub. No.: WO2018/003842

PCT Pub. Date: Jan. 4, 2018

(65) Prior Publication Data

US 2019/0225728 A1 Jul. 25, 2019

(30) Foreign Application Priority Data

Jun. 29, 2016 (JP) ............................ JP2016-129453

(51) Int. Cl.

| | |
|---|---|
| ***C08F 265/04*** | (2006.01) |
| ***C07D 409/06*** | (2006.01) |
| ***C07D 495/04*** | (2006.01) |
| ***C08F 220/36*** | (2006.01) |
| ***C08F 265/00*** | (2006.01) |
| ***C08F 20/10*** | (2006.01) |
| ***G02F 1/361*** | (2006.01) |
| ***G02F 1/061*** | (2006.01) |
| ***G02F 1/00*** | (2006.01) |

(52) U.S. Cl.

CPC .......... *C08F 265/04* (2013.01); *C07D 409/06* (2013.01); *C07D 495/04* (2013.01); *C08F 20/10* (2013.01); *C08F 220/36* (2013.01); *C08F 265/00* (2013.01); *G02F 1/0018* (2013.01); *G02F 1/061* (2013.01); *G02F 1/361* (2013.01)

(58) Field of Classification Search

CPC ..... C08F 265/04; C07D 495/04; G02F 1/061; G02F 1/0018

See application file for complete search history.

(56) References Cited

U.S. PATENT DOCUMENTS

| | | | |
|---|---|---|---|
| 6,067,186 | A | 5/2000 | Dalton et al. |
| 2008/0312355 | A1 | 12/2008 | Jung et al. |
| 2012/0172599 | A1 | 7/2012 | Otomo et al. |
| 2015/0048284 | A1 | 2/2015 | Otomo et al. |
| 2016/0200845 | A1 | 7/2016 | Carlson et al. |
| 2016/0318889 | A1 | 11/2016 | Otomo et al. |
| 2017/0088654 | A1 | 3/2017 | Otomo et al. |
| 2018/0224577 | A1 | 8/2018 | Otomo et al. |

FOREIGN PATENT DOCUMENTS

| | | |
|---|---|---|
| JP | 5-34743 | 2/1993 |
| JP | 2006-307200 | 11/2006 |
| JP | 2008-528755 | 7/2008 |
| JP | 2013-076015 | 4/2013 |
| JP | 2014-44272 | 3/2014 |
| JP | 2015-178544 | 10/2015 |
| WO | 2011/024774 | 3/2011 |
| WO | 2015/026370 | 2/2015 |

OTHER PUBLICATIONS

Piao et al. Thin Solid Films 518, 481-484 (Year: 2009).*

Partial supplementary European Search Report dated Jan. 31, 2020 in corresponding European Patent Application No. 17820196.8.

International Search Report dated Oct. 3, 2017 in International Application No. PCT/JP2017/023716.

"Introduction to Nonlinear Optical Effects in Molecules & Polymers", Paras N. Prasad and David J. Williams, John Wiley & Sons, Inc. (1991).

"Hisenkei Kougaku no Tameno Yuuki Zairyo", edited by the Chemical Society of Japan, Kikan Kagaku Sosetsu No. 15 (1992), with partial translation.

"Organic Nonlinear Optical Materials", Ch. Bosshard, et al., Gordon and Breach Publishers (1995).

"Recent Advance on Photonic Organic Materials for Information and Telecommunication Applications", supervised by Toshikuni Kaino, CMC Publishing Co., Ltd., 2007, with partial translation.

X. Q. Piao, X. M. Zhang, Y. Mori, M. Koishi, A. Nakaya, S. Inoue, I. Aoki, A. Otomo, S. Yokoyama, "Nonlinear Optical Side-Chain Polymers Post-Functionalized with High-beta Chromophores Exhibiting Large Electro-Optic Property" Journal of Polymer Science: Part A: Polymer Chemistry, vol. 49, pp. 47-54 (2011).

* cited by examiner

*Primary Examiner* — Mark S Kaucher

(74) *Attorney, Agent, or Firm* — Wenderoth, Lind & Ponack, L.L.P.

(57) ABSTRACT

An object of the present invention is to provide a novel electro-optic polymer. Another object of the present invention is to provide a novel electro-optic polymer with a low alicyclic methacrylate monomer content. The polymer according to the present invention is a polymer comprising (a) a base polymer having a reactive group (A), (b) an electro-optic molecule having a plurality of reactive groups (B), and a bond (C) formed by reaction of the reactive group (A) with the plurality of reactive groups (B), the bond (C) being at least one type of bond selected from the group consisting of a (thio)ester bond, a (thio)urethane bond, a (thio)urea bond and a (thio)amide bond.

15 Claims, No Drawings

ELECTRO-OPTIC POLYMER

TECHNICAL FIELD

The present invention relates to a polymer useful as an electro-optic polymer.

BACKGROUND ART

The electro-optic effect is a phenomenon in which the refractive index of a material changes when an electric field is applied to the material.

Materials exhibiting the electro-optic effect (which may simply be called "electro-optic materials") are used in optical control elements (optical elements), such as optical modulators, optical switches, optical interconnect modules, optoelectronic circuits, wavelength converters, electric field sensors, THz wave generators and detectors, optical phased arrays, etc. For such applications, inorganic ferroelectric materials (in particular, lithium niobate) have often been used as electro-optic materials.

In recent years, ultra-high-speed miniaturized optical elements are desired. Inorganic ferroelectric materials, however, cannot satisfy the performance requirements for such optical elements.

Polymers exhibiting the electro-optic effect (which may simply be called "electro-optic polymers") can be produced by allowing an organic compound exhibiting the electro-optic effect (which may simply be called "an electro-optic molecule", "an EO molecule", etc.) to bind to or disperse in a base polymer (Non-patent Literature 1 to 4). Electro-optic polymers have attracted interest as materials for next-generation optical communication due to their advantages of exhibiting larger electro-optic effect than inorganic ferroelectric materials, achieving high-speed operation, and being able to produce hybrid miniaturized or integrated elements with silicon photonics.

Electro-optic polymers require the orientation of the EO molecules to exhibit the electro-optic effect. The EO molecule orientation can be achieved by poling process, in which an electric field is applied to an electro-optic polymer at a temperature near the glass transition temperature (Tg) of the electro-optic polymer, then the temperature is reduced to room temperature while the electric field is being applied, and finally the electric field is released. However, under finite temperature, the orientation of the molecules is gradually relaxed by thermal energy, and the electro-optic effect decreases as time lapses. The orientation of the molecules is more rapidly relaxed when the temperature is closer to the Tg. Accordingly, electro-optic polymers are desired to have a high Tg to exhibit large electro-optic effect for a long period of time.

Non-patent Literature 5 discloses a production process of an electro-optic polymer, which process involves copolymerizing methyl methacrylate (MMA) with 2-isocyanatoethyl methacrylate (MOI) to produce a base polymer, and reacting the isocyanato groups on the side chains of the base polymer with the hydroxy groups of EO molecules.

The Tg of the electro-optic polymer produced by this method can be increased by increasing the EO molecule content. However, even when the EO molecule content is increased in the method in an attempt to increase the Tg of the electro-optic polymer, the Tg is able to be increased only up to about 135° C.

Patent Literature 1 discloses a base polymer produced by copolymerizing MOI with a cycloalkyl methacrylate (CAMA), such as dicyclopentanyl methacrylate (DCPMA) and adamantyl methacrylate (AdMA). The literature proposes that, by adjusting the CAMA content in the base polymer, the Tg of the base polymer can be adjusted, and also the Tg of an electro-optic polymer produced by binding EO molecules to the base polymer can be adjusted.

In accordance with this method, the Tg of the base polymer can be increased by increasing the CAMA content.

Patent Literature 1 also discloses in Examples that an electro-optic polymer with a Tg of about 160° C. can be produced by binding monool EO molecules to the base polymer with a high CAMA content.

However, when the CAMA content in the base polymer is increased in the method of Patent Literature 1, several problems may arise, including fragility of a film made from the electro-optic polymer, poor film-forming properties, crack generation, etc.

Also when the CAMA content is increased to increase the Tg, the ratio of MOI that binds to EO molecules decreases, and the concentration of EO molecules decreases, resulting in failure to achieve both a high Tg and high EO effect.

CITATION LIST

Patent Literature

Patent Literature 1: JP 2015-178544 A

Non-Patent Literature

Non-patent Literature 1: "Introduction to Nonlinear Optical Effects in Molecules & Polymers", Paras N. Prasad and David J. Williams, John Wiley & Sons, Inc. (1991).

Non-patent Literature 2: "Hisenkei Kougaku no Tameno Yuuki Zairyo", edited by the Chemical Society of Japan, KIKAN KAGAKU SOSETSU No. 15 (1992).

Non-patent Literature 3: "Organic Nonlinear Optical Materials", Ch. Bosshard, et. al., Gordon and Breach Publishers (1995).

Non-patent Literature 4: "Recent Advance on Photonic Organic Materials for Information and Telecommunication Applications", supervised by Toshikuni Kaino, CMC Publishing CO., LTD., 2007.

Non-patent Literature 5: X. Q. Piao, X. M. Zhang, Y. Mori, M. Koishi, A. Nakaya, S. Inoue, I. Aoki, A. Otomo, S. Yokoyama, "Nonlinear Optical Side-Chain Polymers Post-Functionalized with High-beta Chromophores Exhibiting Large Electro-Optic Property" Journal of Polymer Science: Part A: Polymer Chemistry, vol. 49, pp. 47-54 (2011).

SUMMARY OF INVENTION

Technical Problem

An object of the present invention is to provide a novel electro-optic polymer.

Another object of the present invention is to provide a novel electro-optic polymer with a low alicyclic methacrylate monomer content.

A further object of the present invention is to provide an electro-optic polymer with favorable film-forming properties.

A still further object of the present invention is to provide an electro-optic polymer with a high Tg.

Solution to Problem

The inventors conducted extensive research to solve the above problems, and as a result found that a polymer comprising (a) a base polymer having a reactive group (A), (b) an electro-optic molecule having a plurality of reactive groups (B), and a bond (C) formed by reaction of the reactive group (A) with the plurality of reactive groups (B) is useful as an electro-optic polymer.

The inventors also found that the above polymer in which the bond (C) is at least one type of bond selected from the group consisting of a (thio)urethane bond, a (thio)urea bond and a (thio)amide bond (e.g., a polymer in which a methacrylate-based base polymer having an iso(thio)cyanato group is bound to an electro-optic molecule having two or more groups reactive to the iso(thio)cyanato group) is especially useful as an electro-optic polymer.

The inventors also found that, when the methacrylate-based base polymer contains alicyclic methacrylate monomers, a high Tg of the polymer can be achieved even at a low alicyclic methacrylate monomer content.

The inventors further found that such a polymer has favorable film-forming properties.

In general, when electro-optic polymers are heated at a high temperature, the EO molecules contained in the polymers dimerize. The inventors found that the EO molecules in the polymer of the present invention as described above dimerize at a higher temperature than in conventional EO polymers, and are thus less likely to dimerize upon heating.

That is, the present invention includes a polymer comprising (a) a base polymer having a reactive group (A), (b) an electro-optic molecule having a plurality of reactive groups (B), and a bond (C) formed by reaction of the reactive group (A) with the plurality of reactive groups (B), the bond (C) being at least one type of bond selected from the group consisting of a (thio)ester bond, a (thio)urethane bond, a (thio)urea bond and a (thio)amide bond.

In the polymer of the present invention, the reactive group (A) or the reactive groups (B) may be at least one type of group selected from the group consisting of an iso (thio) cyanato group, a hydroxy group, a thiol group, an amino group, a carboxyl group and an acid anhydride group.

In the polymer of the present invention, the reactive group (A) or the reactive groups (B) may comprise an iso (thio) cyanato group.

In the polymer of the present invention, the (a) base polymer may be a methacrylate-based base polymer having an iso(thio)cyanato group.

The methacrylate-based base polymer may comprise a structural unit derived from (a1) an iso(thio)cyanato group-containing (meth)acrylate.

The methacrylate-based base polymer may comprise a structural unit derived from (a2) an iso(thio)cyanato group-free methacrylate containing an alicyclic methacrylate.

The methacrylate-based base polymer may comprise the structural unit derived from (a2) an iso(thio)cyanato group-free methacrylate and the structural unit derived from (a1) an iso(thio)cyanato group-containing (meth)acrylate at a molar ratio of 0.1:1 to 19:1.

The methacrylate-based base polymer may comprise a structural unit derived from an alicyclic methacrylate and the structural unit derived from (a1) an iso(thio)cyanato group-containing (meth)acrylate at a molar ratio of 0.01:1 to 19:1.

In the polymer of the present invention, the (b) electro-optic molecule may be a compound having a structure represented by D (a donor structure)-B (a bridge structure)-A (an acceptor structure).

In the polymer of the present invention, the reactive group (A) may be an iso(thio)cyanato group, and the reactive groups (B) may be at least one type of group selected from the group consisting of a hydroxy group, a thiol group, an amino group, a carboxyl group and an acid anhydride group.

In the polymer of the present invention, the (b) electro-optic molecule may comprise a compound represented by the following formula (1):

[Chem. 1]

(1)

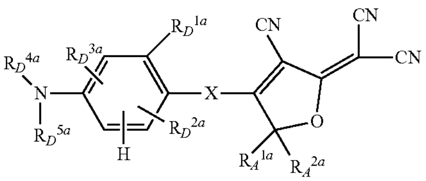

wherein $R_D^{1a}$, $R_D^{2a}$ and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, $-R^1-OH$ (wherein $R^1$ is a hydrocarbon group), $-OR^2-OH$ (wherein $R^2$ is a hydrocarbon group), $-OC(=O)R^3$ (wherein $R^3$ is a hydrocarbon group), an amino group, $-R^4-NH_2$ (wherein $R^4$ is a hydrocarbon group), a thiol group, $-R^5-SH$ (wherein $R^5$ is a hydrocarbon group), $-NCO$ or $-R^6-NCO$ (wherein $R^6$ is a hydrocarbon group);

$R_D^{4a}$ and $R_D^{5a}$ independently represent a hydrogen atom, an alkyl group, a haloalkyl group, an acyloxyalkyl group, a silyloxyalkyl group, $-R^1-OH$ (wherein $R^1$ is a hydrocarbon group), $-R^4-NH_2$ (wherein $R^4$ is a hydrocarbon group), an aryl group, $-R^5-SH$ (wherein $R^5$ is a hydrocarbon group) or $-R^6-NCO$ (wherein $R^6$ is a hydrocarbon group);

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, a haloalkyl group, an aryl group, a hydroxy group, $-R^1-OH$ (wherein $R^1$ is a hydrocarbon group), $-OR^2-OH$ (wherein $R^2$ is a hydrocarbon group), an amino group, $-R^4-NH_2$ (wherein $R^4$ is a hydrocarbon group), a thiol group, $-R^5-SH$ (wherein $R^5$ is a hydrocarbon group), $-NCO$ or $-R^6-NCO$ (wherein $R^6$ is a hydrocarbon group), with the proviso that the compound has two or more groups selected from the group consisting of hydroxy, $-R^1-OH$, $-OR^2-OH$, amino, $-R^4-NH_2$, thiol, $-R^5-SH$, $-NCO$ and $-R^6-NCO$ groups contained in the formula (1).

The above formula (1) may satisfy any one of the following (A), (B) and (C):

(A) $R_D^{1a}$ is a hydroxyalkoxy group, and at least one of $R_D^{4a}$, $R_D^{5a}$, $R_A^{1a}$ and $R_A^{2a}$ is a hydroxyalkyl group, a hydroxyaryl group or a hydroxyaralkyl group;

(B) $R_D^{4a}$ and $R_D^{5}$a are each a hydroxyalkyl group, a hydroxyaryl group or a hydroxyaralkyl group; and (C) at least one of $R_A^{1a}$ and $R_A^{2a}$ is a hydroxyalkyl group, a hydroxyaryl group or a hydroxyaralkyl group, and at least one of $R_D^{4a}$ and $R_D^{5a}$ is a hydroxyalkyl group, a hydroxyaryl group or a hydroxyaralkyl group.

In the polymer of the present invention, the (a) base polymer and the (b) electro-optic molecule may be contained at a weight ratio of 30:70 to 90:10.

The present invention also includes a process for producing a polymer having a bond (C), the process comprising reacting (a) a base polymer having a reactive group (A) with (b) an electro-optic molecule having a plurality of reactive groups (B), wherein the bond (C) is at least one type of bond selected from the group consisting of a (thio)ester bond, a (thio) urethane bond, a (thio) urea bond and a (thio)amide bond.

In the process for producing a polymer according to the present invention, the (a) base polymer may be a methacrylate-based base polymer having an iso(thio)cyanato group, and the reactive groups (B) may be groups reactive to the iso(thio)cyanato group.

The present invention also includes a compound represented by the following formula (1):

[Chem. 2]

(1)

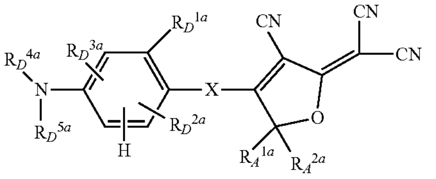

wherein $R_D^{1a}$, $R_D^{2a}$ and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group);

$R_D^{4a}$ and $R_D^{5a}$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group) or —$R^6$—NCO (wherein $R^6$ is a hydrocarbon group);

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, a haloalkyl group, an aryl group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), with the proviso that the compound has two or more groups selected from the group consisting of hydroxy, —$R^1$—OH, —$OR^2$—OH, amino, —$R^4$—$NH_2$, thiol, —$R^5$—SH, —NCO and —$R^6$—NCO groups contained in the formula (1).

The above formula (1) may satisfy any one of the following (A), (B) and (C):

(A) $R_D^{1a}$ is a hydroxyalkoxy group, and at least one of $R_D^{4a}$, $R_D^{5a}$, $R_A^{1a}$ and $R_A^{2a}$ is a hydroxyalkyl group, a hydroxyaryl group or a hydroxyaralkyl group;

(B) $R_D^{4a}$ and $R_D^{5}$a are each a hydroxyalkyl group, a hydroxyaryl group or a hydroxyaralkyl group; and (C) at least one of $R_A^{1a}$ and $R_A^{2a}$ is a hydroxyalkyl group, a hydroxyaryl group or a hydroxyaralkyl group, and at least one of $R_D^{4a}$ and $R_D^{5a}$ is a hydroxyalkyl group, a hydroxyaryl group or a hydroxyaralkyl group.

The present invention also includes an optical element comprising the polymer according to the present invention.

Advantageous Effects of Invention

The present invention provides a novel electro-optic polymer.

The present invention provides a novel electro-optic polymer with a low alicyclic methacrylate monomer content.

The electro-optic polymer of the present invention has favorable film-forming properties and is less susceptible to crack generation upon film formation. Specifically, when an alicyclic methacrylate monomer is blended in the base polymer, a small amount of the alicyclic methacrylate monomer will suffice, and thus the electro-optic polymer exhibits favorable film-forming properties.

The present invention provides an electro-optic polymer with a high Tg. Specifically, even when the base polymer has a low alicyclic methacrylate monomer content, the electro-optic polymer has a high Tg. Also, even when the electro-optic polymer contains the same amount of EO molecules as in the electro-optic polymer of Patent Literature 1, the electro-optic polymer of the present invention has a higher Tg than that of Patent Literature 1.

The present invention also provides an electro-optic polymer in which the EO molecules are less likely to dimerize upon heating.

The electro-optic polymer of the present invention maintains stable electro-optic effect for a long period of time.

DESCRIPTION OF EMBODIMENTS

The present invention will be described in detail below.

The polymer of the present invention (hereinafter may simply be called "the polymer (I)") is a polymer comprising (a) a base polymer having a reactive group (A), (b) an electro-optic molecule having a plurality of reactive groups (B), and a bond (C) formed by reaction of the reactive group (A) with the plurality of reactive groups (B). For example, when the (b) electro-optic molecule has two reactive groups (B), each of the reactive groups (B) forms the bond (C) with the reactive group (A).

The reactive groups (B) may be any groups capable of reacting with the reactive group (A) to form bonds.

The reactive group (A) and the reactive groups (B) are not particularly limited as long as they together can form a bond.

The reactive group (A) and the reactive groups (B) may be, for example, a hydroxy group, a thiol group, an amino group, a carboxyl group, an acid anhydride group, an iso (thio) cyanato group, etc. The term iso(thio)cyanato group is intended to include both an isocyanato group and an isothiocyanato group. The reactive group (A) and the reactive groups (B) may be one or more types of the above listed groups.

Preferably, either the reactive group (A) or the reactive groups (B) contain an iso (thio) cyanato group. More preferably, the reactive group (A) contains an iso(thio)cyanato group. When one reactive group contains an iso (thio) cyanato group, the reactive counterpart is a group reactive to the iso (thio) cyanato group, such as a hydroxy group, a thiol group, an amino group, a carboxyl group, an acid anhydride group, etc.

The bond (C) or the type of bond (C) contained in the polymer (I) may be selected depending on the type of reactive groups (A) and (B), and examples of the bond (C) include an ester bond, a thioester bond, a urethane bond, a urea bond, a thiourethane bond, a thiourea bond, an amide bond, a thioamide bond, etc. In particular when either the reactive group (A) or (B) is an iso(thio)cyanato group, the bond (C) may be a urethane bond, a urea bond, a thiourethane bond, a thiourea bond, an amide bond, a thioamide bond, etc.

(a) Base Polymer

The (a) base polymer may be, for example, a methacrylate-based base polymer etc.

The methacrylate-based base polymer preferably contains at least a structural unit derived from (a1) an iso(thio)cyanato group-containing (meth)acrylate (hereinafter may simply be called "the (a1) iso(thio)cyanato group-containing (meth)acrylate unit"; hereinafter the same applies to similar phrases).

Examples of the (a1) iso(thio)cyanato group-containing (meth)acrylate include iso(thio)cyanato alkyl esters of (meth)acrylic acid {e.g., iso(thio)cyanato $C_{1-10}$ alkyl esters of (meth)acrylic acid (e.g., 2-iso(thio)cyanatoethyl (meth)acrylate) etc.)} etc.

Preferably, the (a1) iso(thio)cyanato group-containing (meth)acrylate contains at least a methacrylate.

The methacrylate-based base polymer may contain one or more types of the (a1) iso(thio)cyanato group-containing (meth)acrylate units.

The methacrylate-based base polymer may contain a structural unit derived from (a2) an iso(thio)cyanato group-free methacrylate.

Examples of the (a2) iso(thio)cyanato group-free methacrylate include aliphatic methacrylates [e.g., methacrylic acid alkyl esters (e.g., $C_{1-18}$ alkyl methacrylates, such as methyl methacrylate, ethyl methacrylate, propyl methacrylate, butyl methacrylate, pentyl methacrylate, hexyl methacrylate, heptyl methacrylate, octyl methacrylate, decyl methacrylate, dodecyl methacrylate, pentadecyl methacrylate, hexadecyl methacrylate, heptadecyl methacrylate, octadecyl methacrylate, etc., preferably $C_{1-12}$ alkyl methacrylates) etc.], alicyclic methacrylates [e.g., methacrylic acid cycloalkyl esters (e.g., $C_{3-20}$ cycloalkyl methacrylates, such as cyclopropyl methacrylate, cyclobutyl methacrylate, cyclopentyl methacrylate, cyclohexyl methacrylate, cycloheptyl methacrylate, etc., preferably $C_{3-12}$ cycloalkyl methacrylates), bridged cyclic methacrylates (e.g., dicyclopentanyl methacrylate, adamantyl methacrylate, isobornyl methacrylate), etc.], etc.

The methacrylate-based base polymer may contain one or more types of the (a2) iso(thio)cyanato group-free methacrylate units.

Of the above (a2) iso(thio)cyanato group-free methacrylates, preferably at least an aliphatic methacrylate and/or an alicyclic methacrylate is contained in the methacrylate-based base polymer, and more preferably at least an alicyclic methacrylate is contained in the methacrylate-based base polymer.

Preferred (a2) iso(thio)cyanato group-free methacrylates are methacrylic acid alkyl esters, methacrylic acid cycloalkyl esters, and bridged cyclic methacrylates. More preferred are $C_{1-12}$ alkyl methacrylates, $C_{3-12}$ cycloalkyl methacrylates, dicyclopentanyl methacrylate, adamantyl methacrylate, and isobornyl methacrylate.

The methacrylate-based base polymer may contain one or more types of additional units, i.e., one or more types of structural units derived from a monomer other than the (a1) iso(thio)cyanato group-containing (meth)acrylate or the (a2) iso(thio)cyanato group-free methacrylate.

Examples of the additional unit include units derived from other monomers, such as acrylic acid esters, methacrylic acid, acrylic acid, vinyl compounds, etc.

The amount of the (a1) iso(thio)cyanato group-containing (meth)acrylate unit contained in the methacrylate-based base polymer is, for example, 5 to 90% by weight, preferably 10 to 70% by weight, more preferably 20 to 70% by weight.

The amount of the (a1) iso(thio)cyanato group-containing (meth)acrylate unit contained in the methacrylate-based base polymer is, for example, 5 to 90 mol %, preferably 10 to 80 mol %, more preferably 20 to 80 mol %.

When the amount is in the above range, the polymer (I) has improved film-forming properties, a high Tg and other advantages. For this reason, the above range is preferred.

The amount of the (a2) iso(thio)cyanato group-free (meth)acrylate unit contained in the methacrylate-based base polymer is, for example, 10 to 95% by weight, preferably 20 to 90% by weight, more preferably 30 to 80% by weight.

The amount of the (a2) iso(thio)cyanato group-free (meth)acrylate unit contained in the methacrylate-based base polymer is, for example, 10 to 95 mol %, preferably 15 to 90 mol %, more preferably 20 to 80 mol %.

When the amount is in the above range, the polymer (I) has improved film-forming properties, a high Tg and other advantages. For this reason, the above range is preferred.

The amount of the alicyclic methacrylate unit is, for example, 0 to 100% by weight, preferably 10 to 100% by weight, more preferably 20 to 100% by weight, in the (a2) iso(thio)cyanato group-free methacrylate unit.

The amount of the alicyclic methacrylate unit is, for example, 0 to 100 mol %, preferably 20 to 100 mol %, more preferably 30 to 100 mol %.

The molar ratio of the (a2) iso(thio)cyanato group-free methacrylate unit relative to the (a1) iso(thio)cyanato group-containing (meth)acrylate unit in the methacrylate-based base polymer is, for example, 0.1:1 to 20:1 (e.g., 0.1:1 to 19:1), preferably 0.15:1 to 10:1 (e.g., 0.17:1 to 9:1), more preferably 0.2:1 to 5:1 (e.g., 0.25:1 to 4:1).

When the molar ratio is in the above range, the polymer (I) has improved film-forming properties, a high Tg and other advantages. For this reason, the above range is preferred.

In cases where the methacrylate-based base polymer contains the alicyclic methacrylate unit, even when the amount of the alicyclic methacrylate unit is not so high, a high Tg of the polymer (I) can be achieved.

The molar ratio of the alicyclic methacrylate unit relative to the (a1) iso(thio)cyanato group-containing (meth)acrylate unit in the methacrylate-based base polymer is, for example, 0.01:1 to 20:1 (e.g., 0.01:1 to 19:1), preferably 0.05:1 to 10:1 (e.g., 0.08:1 to 9:1), more preferably 0.1:1 to 5:1 (e.g., 0.2:1 to 4:1).

The amount of the additional unit contained in the methacrylate-based base polymer is, for example, 0 to 30% by weight, preferably 0 to 20% by weight, more preferably 0 to 10% by weight.

The amount of the additional unit contained in the base polymer is, for example, 0 to 30 mol %, preferably 0 to 20 mol %, more preferably 0 to 10 mol %.

The production process of the methacrylate-based base polymer is not particularly limited as long as it involves polymerization of methacrylic monomers, and may be performed in accordance with a known conventional production process. The (a) base polymer can be produced by, for example, copolymerizing the (a1) iso(thio)cyanato group-containing (meth)acrylate with the (a2) iso(thio)cyanato group-free methacrylate.

The Tg of the (a) base polymer is, for example, 90° C. or more (e.g., 90 to 260° C.), preferably 95 to 240° C., more preferably 95 to 220° C.

The weight average molecular weight (Mw) of the (a) base polymer is not particularly limited, and is, for example, 10,000 to 500,000, preferably 10,000 to 200,000.

The number average molecular weight (Mn) of the (a) base polymer is also not particularly limited, and is, for example, 5,000 to 300,000, preferably 5,000 to 200,000. The Mw and Mn of the (a) base polymer can be usually determined by GPC. The analytical standard for GPC may be, for example, polystyrene etc.

(b) Electro-Optic Molecule (EO Molecule)

The (b) EO molecule has a plurality of reactive groups (B) The number of the reactive groups (B) contained in the (b) EO molecule is, for example, 2 to 8, preferably 2 to 6, more preferably 2 to 4.

One type of (b) EO molecule may be used alone, or two or more types of (b) EO molecules may be used in combination.

The reactive groups (B) may be contained in any manner in the (b) EO molecule without particular limitation. In particular, the reactive groups may originally be present in the EO molecule, or may be introduced into the EO molecule used as a base molecule. When the reactive groups (B) are later introduced into the EO molecule used as a base molecule, the reactive groups (B) may be introduced using, for example, organic chemical techniques. One type of EO molecule may be used alone as a base molecule, or two or more types of EO molecules may be used in combination as base molecules.

The (b) EO molecule is, for example, a compound having a structure represented by D (a donor structure)-B (a bridge structure)-A (an acceptor structure) (a compound in which D is bound to A via B) and having a plurality of reactive groups (B).

Such a compound having a structure represented by D-B-A may have a plurality of reactive groups (B) on at least one or more of D, B and A. For example, the compound may have two or more reactive groups (B) on D, may have two or more reactive groups (B) on B, and/or may have two or more reactive groups (B) on A. Such a compound includes novel compounds, and therefore the present invention includes such novel compounds.

The donor structure D of the (b) EO molecule is, for example, a structure represented by the following formula (D-1):

[Chem. 3]

(D-1)

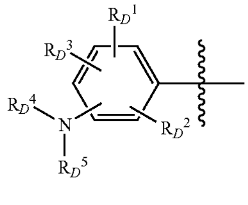

wherein $R_D^1$, $R_D^2$ and $R_D^3$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), and $R_D^1$, $R_D^2$ and $R_D^3$ each may have a substituent that is the same as or different from each other, wherein, when $R_D^2$ and $R_D^3$ are attached to adjacent carbon atoms of the aryl of the donor structure D, (1) $R_D^2$ and $R_D^3$ may form, together with the two adjacent carbon atoms, a ring optionally having a substituent, and $R_D^1$ represents a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O) $R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), and $R_D^1$ may have a substituent, or (2) $R_D^2$ and $R_D^3$ may form, together with the two adjacent carbon atoms, a heterocyclic ring containing an oxygen atom as a hetero atom and optionally having a substituent; and $R_D^4$ and $R_D^5$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group) or —$R^6$—NCO (wherein $R^6$ is a hydrocarbon group), and $R_D^4$ and $R_D^5$ each may have a substituent that is the same as or different from each other, or $R_D^4$ and $R_D^5$ form, together with the nitrogen atom to which they are attached, a heterocyclic ring containing the nitrogen atom as a hetero atom and optionally having a substituent, or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent.

In the structure represented by the above formula (D-1), the substitutable position other than those substituted with $R_D^1$, $R_D^2$ and $R_D^3$ in the benzene ring is occupied by a hydrogen atom. The same applies to the formulas (D-1-1) and (D-1-2) below.

The structure represented by the above formula (D-1) may be a structure represented by, for example, the following formula (D-1-1) or (D-1-2).

[Chem. 4]

(D-1-1)

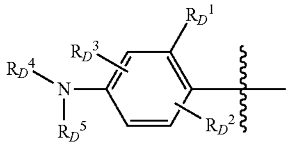

wherein $R_D^1$, $R_D^2$ and $R_D^3$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), and $R_D^1$, $R_D^2$ and $R_D^3$ each may have a substituent that is the same as or different from each other, wherein, when $R_D^2$ and $R_D^3$ are attached to adjacent carbon atoms of the aryl of the donor structure D, $R_D^2$ and $R_D^3$ may form, together with the two adjacent carbon atoms, a ring optionally having a substituent; and $R_D^4$ and $R_D^5$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group) or —$R^6$—NCO (wherein $R^6$ is a hydrocarbon group), and $R_D^4$ and $R_D^5$ each may have a substituent that is the same as or different from each other, or $R_D^4$ and $R_D^5$ form, together with the nitrogen atom to which they are attached, a heterocyclic ring containing the nitrogen atom as a hetero atom and optionally having a substituent, or (a) $R_D^2$ and —$NR_D^4R_D^5$ and (b) $R_D^3$ and —$NR_D^4R_D^5$ independently form, together with the carbon atoms to which they are attached, a heterocyclic ring containing the nitrogen atom as a hetero atom and optionally having a substituent.

[Chem. 5]

(D-1-2)

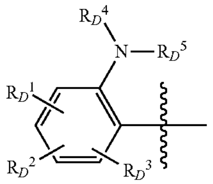

wherein $R_D^1$, $R_D^2$ and $R_D^3$ independently represent a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), and $R_D^1$, $R_D^2$ and $R_D^3$ each may have a substituent that is the same as or different from each other, wherein, when $R_D^2$ and $R_D^3$ are attached to adjacent carbon atoms of the aryl of the donor structure D, (1) $R_D^2$ and $R_D^3$ may form, together with the two adjacent carbon atoms, a ring optionally having a substituent, and $R_D^1$ represents a hydrogen atom, an alkyl group, an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O) $R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), and $R_D^1$ may have a substituent, or (2) $R_D^2$ and $R_D^3$ may form, together with the two adjacent carbon atoms, a heterocyclic ring containing an oxygen atom as a hetero atom and optionally having a substituent; and $R_D^4$ and $R_D^5$ independently represent a hydrogen atom, an alkyl group, a haloalkyl group, an acyloxyalkyl group, a silyloxyalkyl group, —$R^1$—OH (wherein $R^1$ is a hydrocarbon group), —$R^4$—$NH_2$ (wherein $R^4$ is a hydrocarbon group), an aryl group, —$R^5$—SH (wherein $R^5$ is a hydrocarbon group) or —$R^6$—NCO (wherein $R^6$ is a hydrocarbon group), and $R_D^4$ and $R_D^5$ each may have a substituent that is the same as or different from each other, $R_D^4$ and $R_D^5$ form, together with the nitrogen atom to which they are attached, a saturated heterocyclic ring optionally having a substituent, or $R_D^4$ and $R_D^5$ form, together with the nitrogen atom to which they are attached, with the aryl carbon atom to which said nitrogen atom is attached, and with the aryl carbon atom adjacent to said carbon atom, a heterocyclic ring containing the nitrogen atom as a hetero atom and optionally having a substituent.

Examples of the alkyl group represented by $R_D^1$, $R_D^2$ and $R_D^3$ include linear or branched $C_{1-20}$ alkyl groups etc. Preferred are $C_{1-6}$ alkyl groups etc., and more preferred are a methyl group, an ethyl group, a propyl group, an isopropyl group, a butyl group, etc.

Examples of the alkoxy group represented by $R_D^1$, $R_D^2$ and $R_D^3$ include linear or branched $C_{1-20}$ alkoxy groups etc. Preferred are, for example, $C_{1-6}$ alkoxy groups, etc. More preferred are, for example, a methoxy group, an ethoxy group, a propoxy group, an isopropoxy group, a butoxy group, an isobutoxy group, a sec-butoxy group, and a tert-butoxy group.

Examples of the aryloxy group represented by $R_D^1$, $R_D^2$ and $R_D^3$ include $C_{5-10}$ monocyclic aryloxy groups, $C_{8-12}$ bicyclic aryloxy groups, etc. Preferred are, for example, a phenoxy group, a naphthyloxy group, etc., and more preferred are, for example, a phenoxy group etc.

Examples of the aralkyloxy group represented by $R_D^1$, $R_D^2$ and $R_D^3$ include alkyloxy groups substituted with at least one aryl group, etc.

Examples of the aryl group include monocyclic aromatic hydrocarbon groups (hereinafter called monocyclic aryl groups), polycyclic aromatic hydrocarbon groups (hereinafter called polycyclic aryl groups), etc.

The "monocyclic aryl groups" include, for example, preferably a $C_{5-10}$ monocyclic aryl group, more preferably a $C_{5-7}$ monocyclic aryl group, further preferably a $C_{5-6}$ monocyclic aryl group, most preferably a $C_6$ monocyclic aryl group (i.e., a phenyl group). For example, a $C_{5-10}$ cyclic ring means that the number of carbon atoms forming the cyclic ring is 5 to 10, and hereinafter the same applies to other cyclic ring groups.

The "polycyclic aryl groups" include, for example, two-ring fused aryl groups, three-ring fused aryl groups, etc. The two-ring fused aryl groups include, for example, preferably a $C_{8-12}$ two-ring fused aryl group etc., more preferably a $C_{9-10}$ two-ring fused aryl group etc., most preferably a $C_{10}$ two-ring fused aryl group (i.e., a naphthyl group) etc.

The above "alkyloxy groups" include, for example, linear or branched $C_{1-20}$ alkyloxy groups etc. Examples of the alkyloxy groups include a methoxy group, an ethoxy group, a n-propoxy group, an isopropoxy group, a n-butoxy group, an isobutoxy group, a sec-butoxy group, a tert-butoxy group, a pentyloxy group, an isopentyloxy group, a hexyloxy group, an isohexyloxy group, a heptyloxygroup, anoctyloxy-group, anonyloxygroup, adecyloxy group, an undecyloxy group, a dodecyloxy group, a tridecyloxy group, a tetradecyloxy group, a pentadecyloxy group, a hexadecyloxy group, a heptadecyloxy group, an octadecyloxy group, a nonadecyloxy group, an icosyloxy group, etc. The above alkyloxy groups are preferably $C_{1-6}$ alkyloxy groups etc. More preferred are, for example, a methoxy group, an ethoxy group, a n-propoxy group, an isopropoxy group, a n-butoxy group, an isobutoxy group, a sec-butoxy group, a tert-butoxy group, a pentyloxy group, an isopentyloxy group, a hexyloxy group, an isohexyloxy group, etc.

Examples of the above aralkyloxy group include a benzyloxy group, a 1-phenylethyloxy group, a phenethyloxy group, a 1-naphthylmethyloxy group, a 2-naphthylmethyloxy group, a 1-naphthylethyloxy group, a 2-naphthylethyloxy group, etc.

Examples of the silyloxy group represented by $R_D^1$, $R_D^2$ and $R_D^3$ include a tert-butyldiphenylsiloxy group, a tert-butyldimethylsiloxy group, etc.

Examples of the alkenyloxy group represented by $R_D^1$, $R_D^2$ and $R_D^3$ include linear or branched $C_{2-20}$ alkenyloxy groups etc. Preferred are, for example, $C_{2-6}$ alkenyloxy groups, etc. More preferred are, for example, an ethenyloxy group, a 1-propenyloxy group, a 2-propenyloxy group, a 1-methylethenyloxy group, a 1-butenyloxy group, a 2-butenyloxy group, a 3-butenyloxy group, a 1-methyl-1-propenyloxy group, a 1-methyl-2-propenyloxy group, a 2-methyl-1-propenyloxy group, a 2-methyl-2-propenyloxy group, etc.

Examples of the alkynyloxy group represented by $R_D^1$, $R_D^2$ and $R_D^3$ include linear or branched $C_{2-20}$ alkynyloxy groups etc. Preferred are, for example, $C_{36}$ alkynyloxy groups, etc. More preferred are, for example, a 2-propynyloxy group, a 1-methyl-2-propynyloxy group, a 1,1-dimethyl-2-propynyloxy group, a 2-butynyloxy group, a 3-butynyloxy group, a 1-pentynyloxy group, a 2-pentynyloxy group, a 3-pentynyloxy group, a 4-pentynyloxy group, etc.

Examples of the hydrocarbon group represented by $R^1$, $R^2$, $R^4$, $R^5$ and $R^6$ in —$R^1$—OH, —$OR^2$—OH, —$R^4$—$NH_2$, —$R^5$—SH and —$R^6$—NCO include aliphatic groups {e.g., alkylene groups [e.g., $C_{1-10}$ alkylene groups (e.g., a methylene group, an ethylene group, a propylene group, a butylene group, etc.), preferably $C_{1-4}$ alkylene groups etc.]}, aromatic groups [e.g., $C_{6-20}$ aromatic groups (e.g., a phenylene group, a benzylene group, etc.) etc.] etc. Of these, preferred are $C_{1-10}$ alkylene groups and $C_{6-20}$ aromatic groups.

Specific examples of —$R^1$—OH include hydroxyalkyl groups (e.g., hydroxy $C_{1-10}$ alkyl groups, such as a hydroxymethyl group, a hydroxyethyl group, a hydroxypropyl group, a hydroxybutyl group, etc.), hydroxyaryl groups (e.g., hydroxy $C_{6-10}$ aryl groups, such as a hydroxyphenyl group etc.), hydroxyaralkyl groups (e.g., hydroxy $C_{6-10}$ aryl $C_{1-4}$ alkyl groups, such as a hydroxybenzyl group etc.), etc.

Specific examples of —$OR^2$—OH include hydroxyalkoxy groups (e.g., hydroxy $C_{1-10}$ alkoxy groups, such as a hydroxymethoxy group, a hydroxyethoxy group, a hydroxypropoxy group, a hydroxybutoxy group, etc.), hydroxyaryloxy groups (e.g., hydroxy $C_{6-10}$ aryloxy groups, such as a hydroxyphenoxy group etc.), hydroxyaralkyloxy groups (e.g., hydroxy $C_{6-10}$ aryl $C_{1-4}$ alkyloxy groups, such as a hydroxybenzyloxy group etc.), etc.

Specific examples of —$R^4$—$NH_2$ include aminoalkyl groups (e.g., amino $C_{1-10}$ alkyl groups, such as an aminomethyl group, an aminoethyl group, an aminopropyl group, an aminobutyl group, etc.) etc.

Specific examples of —$R^5$—SH include mercaptoalkyl groups (e.g., mercapto $C_{1-10}$ alkyl groups, such as a mercaptomethyl group, a mercaptoethyl group, a mercaptopropyl group, a mercaptobutyl group, etc.) etc.

Specific examples of —$R^6$—NCO include isocyanatoalkyl groups (e.g., isocyanato $C_{1-10}$ alkyl groups, such as an isocyanatomethyl group, an isocyanatoethyl group, an isocyanatopropyl group, an isocyanatobutyl group, etc.) etc.

Examples of the hydrocarbon group represented by $R^3$ in —OC(═O) $R^3$ include aliphatic groups [e.g., $C_{1-10}$ alkyl groups (e.g., a methyl group, an ethyl group, a propyl group, a butyl group, etc.), $C_{2-10}$ alkenyl groups (e.g., an ethenyl group, a propenyl group, a butenyl group, etc.), preferably $C_{1-6}$ alkyl groups, $C_{2-6}$ alkenyl groups, etc.], alicyclic groups [e.g., $C_{3-12}$ cycloalkyl groups (e.g., a cyclopropyl group, a cyclobutyl group, a cyclopentyl group, a cyclohexyl group, etc.), preferably $C_{3-7}$ cycloalkyl groups etc.], aromatic groups {e.g., $C_{6-20}$ aromatic groups [e.g., $C_{6-20}$ aryl groups (e.g., a phenyl group, a tolyl group, a xylyl group, a naphthyl group, etc.), $C_{7-20}$ aralkyl groups (e.g., a benzyl group etc.), etc.]}, etc. Of these, preferred are aliphatic groups and more preferred are $C_{2-10}$ alkenyl groups.

Any one of $R_D^1$, $R_D^2$ and $R_D^3$ is preferably an alkoxy group, an aryloxy group, an aralkyloxy group, a silyloxy group, an alkenyloxy group, an alkynyloxy group, a hydroxy group, —$R^1$—OH (wherein $R^1$ is a hydrocarbon group), —$OR^2$—OH (wherein $R^2$ is a hydrocarbon group), —OC(═O)$R^3$ (wherein $R^3$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group)

Examples of the alkyl group represented by $R_D^4$ and $R_D^5$ include linear or branched $C_{1-20}$ alkyl groups etc. Examples of the alkyl groups include a methyl group, an ethyl group, a n-propyl group, an isopropyl group, a n-butyl group, an isobutyl group, a sec-butyl group, a tert-butyl group, a pentyl group, an isopentyl group, a hexyl group, an isohexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, etc. Preferred examples of the alkyl group include $C_{1-6}$ alkyl groups. More preferred are, for example, a methyl group, an ethyl group, a n-propyl group, an isopropyl group, a n-butyl group, an isobutyl group, a sec-butyl group, a tert-butyl group, a pentyl group, an isopentyl group, a hexyl group, an isohexyl group, etc. Preferred are, for example, $C_{1-6}$ alkyl groups etc., and more preferred are, for example, a methyl group, an ethyl group, a propyl group, an isopropyl group, a butyl group, an isobutyl group, a sec-butyl group, a tert-butyl group, etc.

Examples of the haloalkyl group represented by $R_D^4$ and $R_D^5$ include linear or branched $C_{1-20}$ alkyl groups substituted with the same or different one or more halogen atoms (e.g., fluorine atoms, chlorine atoms, bromine atoms, iodine atoms, etc.). Preferred examples of the haloalkyl group include halo $C_{1-6}$ alkyl groups. More preferred are, for example, a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, a 2-bromoethyl group, a 1-bromopropyl group, a 2-bromopropyl group, a 3-bromopropyl group, an iodomethyl group, etc.

Examples of the acyloxyalkyl group represented by $R_D^4$ and $R_D^5$ include linear or branched $C_{1-20}$ alkyl groups substituted with the same or different one or more acyloxy groups.

Examples of the silyloxyalkyl group represented by $R_D^4$ and $R_D^5$ include linear or branched $C_{1-20}$ alkyl groups substituted with one or more silyloxy groups.

Examples of the aryl group represented by $R_D^4$ and $R_D^5$ include monocyclic aryl groups, polycyclic aryl groups, etc.

The "monocyclic aryl groups" include, for example, preferably a $C_{5-10}$ monocyclic aryl group, more preferably a $C_{5-7}$ monocyclic aryl group, further preferably a $C_{5-6}$ monocyclic aryl group, most preferably a $C_6$ monocyclic aryl group (i.e., a phenyl group). For example, a $C_{5-10}$ cyclic ring means that the number of carbon atoms forming the cyclic ring is 5 to 10, and hereinafter the same applies to other cyclic ring groups.

The "polycyclic aryl groups" include, for example, two-ring fused aryl groups, three-ring fused aryl groups, etc. The two-ring fused aryl groups include, for example, preferably a $C_{8-12}$ two-ring fused aryl group etc., more preferably a $C_{9-10}$ two-ring fused aryl group etc., most preferably a $C_{10}$ two-ring fused aryl group (i.e., a naphthyl group) etc.

Examples of the hydrocarbon group in $—R^1—OH$, $—R^4—NH_2$, $—R^5—SH$ and $—R^6—NCO$ represented by $R_D^4$ and $R_D^5$ include the hydrocarbon groups as exemplified above (e.g., an alkylene group, an aromatic group or an arylene group).

Specific examples of $—R^1—OH$, $—R^4—NH_2$, $—R^5—SH$ and $—R^6—NCO$ represented by $R_D^4$ and $R_D^5$ include those as exemplified above [e.g., hydroxyalkyl groups (e.g., hydroxy $C_{1-10}$ alkyl groups, such as a hydroxymethyl group, a hydroxyethyl group, a hydroxypropyl group, a hydroxybutyl group, etc.), hydroxyaryl groups (e.g., hydroxy $C_{6-10}$ aryl groups, such as a hydroxyphenyl group etc.), hydroxyaralkyl groups (e.g., hydroxy $C_{6-10}$ aryl $C_{1-4}$ alkyl groups, such as a hydroxybenzyl group etc.), etc.].

Examples of the bridge structure B of the EO molecule as a base molecule include molecules having a conjugated system (e.g., structures represented by the following formulas (B-I), (B-II), (B-III) and (B-IV), etc.), as well as (B-V), which represents a direct binding (indicated by solid lines), etc.

[Chem. 6]

(B-I)

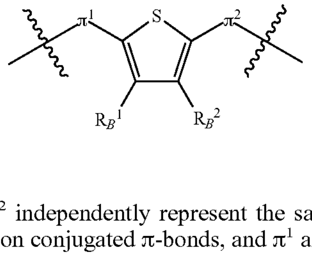

wherein $\pi^1$ and $\pi^2$ independently represent the same or different carbon-carbon conjugated π-bonds, and $\pi^1$ and $\pi^2$ each may have a substituent that is the same as or different from each other; and $R_B^1$ and $R_B^2$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, $—R^1—OH$ (wherein $R^1$ is a hydrocarbon group), $—OR^2—OH$ (wherein $R^2$ is a hydrocarbon group), an amino group, $—R^4—NH_2$ (wherein $R^4$ is a hydrocarbon group), a thiol group, $—R^5—SH$ (wherein $R^5$ is a hydrocarbon group), $—NCO$ or $—R^6—NCO$ (wherein $R^6$ is a hydrocarbon group), $R_B^1$ and $R_B^2$ each may have a substituent that is the same as or different from each other, and $R_B^1$ and $R_B^2$ may form a ring together with the two carbon atoms to which they are attached.

[Chem. 7]

(B-II)

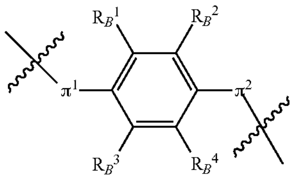

wherein $\pi^1$ and $\pi^2$ independently represent the same or different carbon-carbon conjugated π-bonds, and $\pi^1$ and $\pi^2$ each may have a substituent that is the same as or different from each other; and $R_B^1$, $R_B^2$, $R_B^3$ and $R_B^4$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, $—R^1—OH$ (wherein $R^1$ is a hydrocarbon group), $—OR^2—OH$ (wherein $R^2$ is a hydrocarbon group), an amino group, $—R^4—NH_2$ (wherein $R^4$ is a hydrocarbon group), a thiol group, $—R^5—SH$ (wherein $R^5$ is a hydrocarbon group), $—NCO$ or $—R^6—NCO$ (wherein $R^6$ is a hydrocarbon group), $R_B^1$, $R_B^2$, $R_B^3$ and $R_B^4$ each may have a substituent that is the same as or different from each other, $R_B^1$ and $R_B^2$ may form a ring together with the two carbon atoms to which they are attached, and $R_B^3$ and $R_B^4$ may form a ring together with the two carbon atoms to which they are attached.

[Chem. 8]

(B-III)

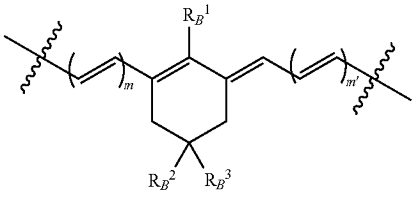

wherein m and m' independently represent an integer of 0 to 3; and $R_B^1$, $R_B^2$ and $R_B^3$ independently represent a hydrogen atom, an alkyl group, an alkoxy group, an aryl group, an alkenyl group, a cycloalkyl group, a cycloalkenyl group, a haloalkyl group, an aralkyl group, an aryloxy group, an aralkyloxy group, a hydroxy group, $—R^1—OH$ (wherein $R^1$ is a hydrocarbon group), $—OR^2—OH$ (wherein $R^2$ is a hydrocarbon group), an amino group, $—R^4—NH_2$ (wherein $R^4$ is a hydrocarbon group), a thiol group, $—R^5—SH$ (wherein $R^5$ is a hydrocarbon group), $—NCO$ or $—R^6—NCO$ (wherein $R^6$ is a hydrocarbon group), $R_B^1$, $R_B^2$ and $R_B^3$ each may have a substituent that is the same as or different from each other, and $R_B^2$ and $R_B^3$ may form a ring.

[Chem. 9]

(B-IV)

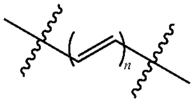

wherein n represents an integer of 1 to 5.

Examples of the carbon-carbon conjugated π-bonds represented by $\pi^1$ and $\pi^2$ include a structure represented by the above formula (B-IV), etc.

Examples of the alkyl group represented by $R_B^1$, $R_B^2$, $R_B^3$ and $R_B^4$ include the above alkyl groups etc. represented by $R_D^4$ and $R_D^5$ as exemplified above. The alkyl group represented by $R_B$, $R_B^2$, $R_B^3$ and $R_B^4$ is preferably, for example, a methyl group, an ethyl group, a propyl group, an isopropyl group, a n-butyl group, an isobutyl group, a sec-butyl group, a tert-butyl group, a pentyl group, an isopentyl group, a hexyl group, an isohexyl group, a heptyl group, etc.

Examples of the alkoxy group represented by $R_B^1$, $R_B^2$, $R_B^3$ and $R_B^4$ include the above alkoxy groups etc. represented by $R_D^1$, $R_D^2$ and $R_D^3$ as exemplified above. Examples of the alkoxy group represented by $R_B^1$, $R_B^2$, $R_B^3$ and $R_B^4$ include a methoxy group, an ethoxy group, a propoxy group, an isopropoxy group, a butoxy group, an isobutoxy group, a sec-butoxy group, a tert-butoxy group, etc. Preferred are a methoxy group etc.

Examples of the aryl group represented by $R_B^1$, $R_B^2$, $R_B^3$ and $R_B^4$ include the above aryl groups etc. represented by $R_D^4$ and $R_D^5$ as exemplified above. Examples of the aryl group represented by $R_B^1$, $R_B^2$, $R_B^3$ and $R_B^4$ include a phenyl group, a naphthyl group, etc. Preferred are a phenyl group etc.

Examples of the alkenyl group represented by $R_B^1$, $R_B^2$, $R_B^3$ and $R_B^4$ include linear or branched $C_{2-20}$ alkenyl groups etc. Examples of the alkenyl group include an ethenyl group, a propenyl group, a butenyl group, a pentenyl group, a hexenyl group, etc.

Examples of the cycloalkyl group represented by $R_B^1$, $R_B^2$, $R_B^3$ and $R_B^4$ include $C_{3-15}$ monocyclic or polycyclic saturated aliphatic ring groups etc. Examples of the cycloalkyl group include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, etc. More preferred are a cyclohexyl group etc.

Examples of the cycloalkenyl group represented by $R_B^1$, $R_B^2$, $R_B^3$ and $R_B^4$ include $C_{3-15}$ monocyclic or polycyclic unsaturated aliphatic ring groups etc. Examples of the cycloalkenyl group include a cyclopropenyl group, a cyclopentenyl group, a cyclohexenyl group, a cycloheptynyl group, a cyclooctenyl group, a cyclopentadienyl group, a cyclohexadienyl group, a cycloheptadienyl group, a cyclooctadienyl group, etc.

Examples of the haloalkyl group represented by $R_B^1$, $R_B^2$, $R_B^3$ and $R_B^4$ include the above haloalkyl groups etc. represented by $R_D^4$ and $R_D^5$ as exemplified above. Examples of the haloalkyl group represented by $R_B^1$, $R_B^2$, $R_B^3$ and $R_B^4$ include a fluoromethyl group, a difluoromethyl group, a trifluoromethyl group, a 2-fluoroethyl group, a 1,2-difluoroethyl group, a chloromethyl group, a 2-chloroethyl group, a 1,2-dichloroethyl group, a bromomethyl group, an iodomethyl group, etc. Preferred are, for example, a trifluoromethyl group etc.

Examples of the aralkyl group represented by $R_B^1$, $R_B^2$, $R_B^3$ and $R_B^4$ include alkyl groups substituted with at least one aryl group, etc. Examples of the aryl group include the above aryl groups etc. represented by $R_D^4$ and $R_D^5$ as exemplified above. Examples of the "alkyl group" include the above alkyl groups etc. represented by $R_D^4$ and $R_D^5$ as exemplified above.

Examples of the aralkyl group include a benzyl group, a 1-phenylethyl group, a phenethyl group, a 1-naphthylmethyl group, a 2-naphthylmethyl group, a 1-naphthylethyl group, a 2-naphthylethyl group, etc. Preferred are a benzyl group etc.

Examples of the aryloxy group represented by $R_B^1$, $R_B^2$, $R_B^3$ and $R_B^4$ include the above aryloxy groups etc. represented by $R_D^1$, $R_D^2$ and $R_D^3$ as exemplified above. Examples of the aryloxy group represented by $R_B^1$, $R_B^2$, $R_B^3$ and $R_B^4$ include a phenoxy group, a naphthyloxy group, etc. Preferred are a phenoxy group etc.

Examples of the aralkyloxy group represented by $R_B^1$, $R_B^2$, $R_B^3$ and $R_B^4$ include the above aralkyloxy groups etc. represented by $R_D^1$, $R_D^2$ and $R_D^3$ as exemplified above. Examples of the aralkyloxy group represented by $R_B^1$, $R_B^2$, $R_B^3$ and $R_B^4$ include a benzyloxy group, a phenethyloxy group, a 1-naphthylmethoxy group, a 2-naphthylmethoxy group, etc. Preferred are a benzyloxy group etc.

Examples of the hydrocarbon group represented by $R^1$, $R^2$, $R^4$, $R^5$ and $R^6$ in the formulas (B-I), (B-II), (B-III) and (B-IV) include the above hydrocarbon groups etc. represented by $R^1$, $R^2$, $R^4$, $R^5$ and $R^6$ in the above formulas (D-1), (D-1-1) and (D-1-2), as exemplified above.

The ring that may be formed by $R_B^1$ and $R_B^2$, or $R_B^3$ and $R_B^4$, or $R_B^2$ and $R_B^3$ in the formulas (B-I), (B-II) and (B-III) is not particularly limited, and may be, for example, a structure represented by the following formula:

[Chem. 10]

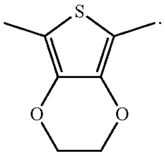

The acceptor structure A of the EO molecule as a base molecule is, for example, a structure represented by a formula selected from the group consisting of:

[Chem. 11]

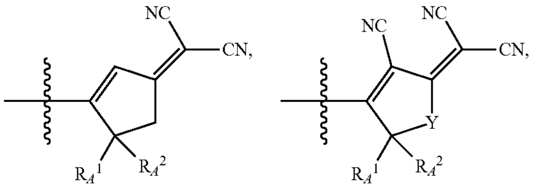

-continued

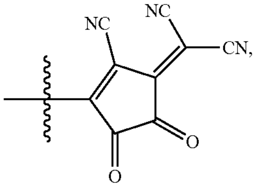

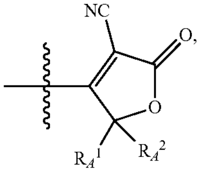

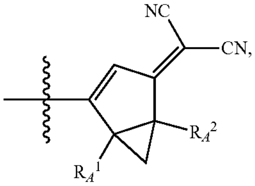

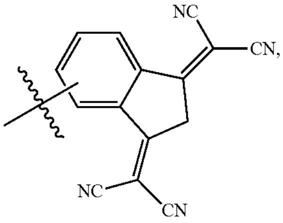

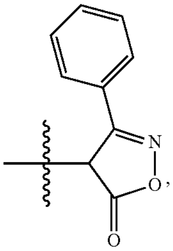

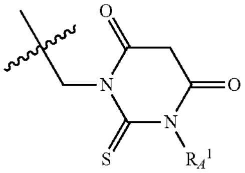

,

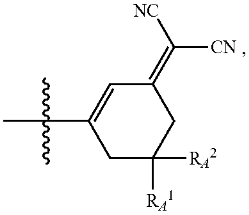

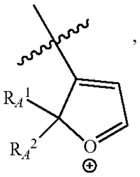

,

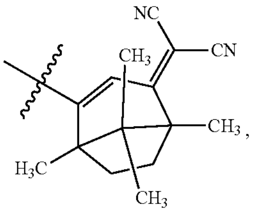

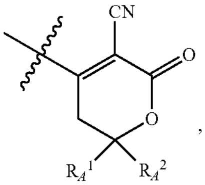

,

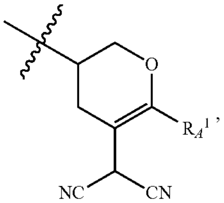

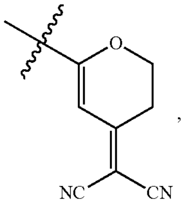

,

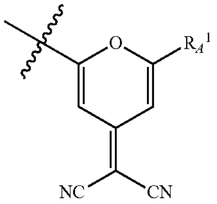

,

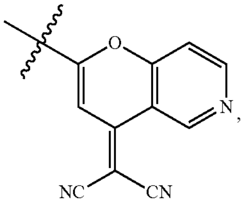

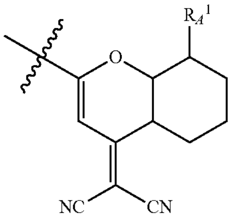

,

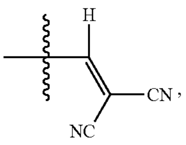

-continued

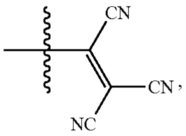

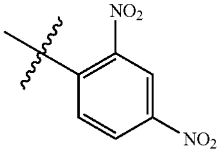

,

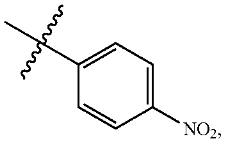

[Chem. 12]

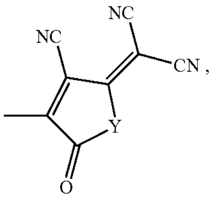

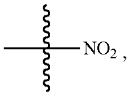

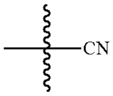

and

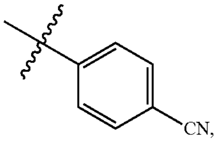

wherein

Y represents —$CR_A{}^1R_A{}^2$—, —O—, —S—, —SO—, —$SiR_A{}^1R_A{}^2$—, —$NR_A{}^1$— or —C(=$CH_2$)—; and $R_A{}^1$ and $R_A{}^2$ independently represent a hydrogen atom, an alkyl group, an alkenyl group, a cycloalkyl group, a cycloalkenyl group, an alkoxy group, a haloalkyl group, an aryl group, an aralkyl group, a hydroxy group, —$R^1$—OH (wherein $R^1$ is a hydrocarbon group), —$OR^2$—OH (wherein $R^2$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), $R_A{}^1$ and $R_A{}^2$ each may have a substituent that is the same as or different from each other, or $R_A{}^1$ and $R_A{}^2$ may form, together with the carbon atom to which they are attached, a structure that may have a substituent and is represented by the following formula:

[Chem. 13]

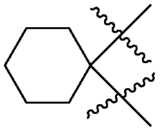

or

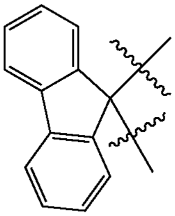

.

Examples of the alkyl group represented by $R_A{}^1$ and $R_A{}^2$ include the above alkyl groups etc. represented by $R_D{}^4$ and $R_D{}^5$ as exemplified above.

Examples of the alkenyl group represented by $R_A{}^1$ and $R_A{}^2$ include the above alkenyl groups etc. represented by $R_B{}^1$, $R_B{}^2$, $R_B{}^3$ and $R_B{}^4$ as exemplified above.

Examples of the cycloalkyl group represented by $R_A{}^1$ and $R_A{}^2$ include the above cycloalkyl groups etc. represented by $R_B$, $R_B{}^2$, $R_B{}^3$ and $R_B{}^4$ as exemplified above.

Examples of the cycloalkenyl group represented by $R_A^1$ and $R_A^2$ include the above cycloalkenyl groups etc. represented by $R_B^1$, $R_B^2$, $R_B^3$ and $R_B^4$ as exemplified above.

Examples of the alkoxy group represented by $R_A^1$ and $R_A^2$ include the above alkoxy groups etc. represented by $R_D^1$, $R_D^2$ and $R_D^3$ as exemplified above.

Examples of the haloalkyl group represented by $R_A^1$ and $R_A^2$ include the above haloalkyl groups etc. represented by $R_D^4$ and $R_D^5$ as exemplified above.

Examples of the aryl group represented by $R_A^1$ and $R_A^2$ include the above aryl groups etc. represented by $R_D^4$ and $R_D^5$ as exemplified above.

Examples of the hydrocarbon group represented by $R^1$, $R^2$, $R^4$, $R^5$ and $R^6$ in $R_A^1$ and $R_A^2$ include the above hydrocarbon groups etc. represented by $R^1$, $R^2$, $R^4$, $R^5$ and $R^6$ in the above formulas (D-1), (D-1-1) and (D-1-2), as exemplified above.

Examples of the "substituent" that $R_D^1$, $R_D^2$, $R_D^3$, $R_D^4$, $R_D^5$, $R_B^1$, $R_B^2$, $R_B^3$, $R_B^4$, $R_A^1$ and $R_A^2$ may have include an alkyl group, a haloalkyl group, an aryl group, an alkenyl group, an alkynyl group, an alkoxy group, a hydroxy group, an oxiranyl group, a mercapto group, an amino group, a carbamoyl group, a sulfamoyl group, a carboxy group, an alkoxycarbonyl group, a sulfo group, a sulfino group, a phosphono group, a nitro group, a cyano group, an amidino group, an imino group, a dihydroborono group, a halogen atom (fluorine, chlorine, bromine and iodine atoms, etc.), a sulfinyl group, a sulfonyl group, an acyl group, an oxo group, a thioxo group, etc. $R_D^1$, $R_D^2$, $R_D^3$, $R_D^4$, $R_D^5$, $R_B^1$, $R_B^2$, $R_B^3$, $R_B^4$, $R_A^1$ and $R_A^2$ each may have a single substituent, or may have two or more substituents that are the same or different.

Examples of $—NR_A^1—$ include a structure represented by the following formula:

[Chem. 14]

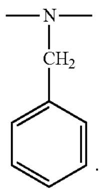

The compound having a structure represented by D (a donor structure)-B (a bridge structure)-A (an acceptor structure) includes any and all combinations of the D, B and A as exemplified above.

The compound having a structure represented by D-B-A also includes compounds containing a combination of the D, B and A as shown in (i) to (iii) in Table 1 below.

TABLE 1

| | D | B | A |
|---|---|---|---|
| (i) | (D-1) | (B-I), (B-II), (B-III), (B-IV) or (B-V) | Any of above exemplified A |
| (ii) | (D-1-1) | (B-I), (B-II), (B-III), (B-IV) or (B-V) | Any of above exemplified A |
| (iii) | (D-1-2) | (B-I), (B-II), (B-III), (B-IV) or (B-V) | Any of above exemplified A |

A preferred (b) EO molecule is, for example, a compound represented by the following formula (1):

[Chem. 15]

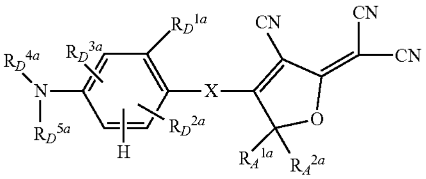

(1)

wherein $R_D^{1a}$, $R_D^{2a}$ and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, $—R^1—OH$ (wherein $R^1$ is a hydrocarbon group), $—OR^2—OH$ (wherein $R^2$ is a hydrocarbon group), $—OC(═O)R^3$ (wherein $R^3$ is a hydrocarbon group), an amino group, $—R^4—NH_2$ (wherein $R^4$ is a hydrocarbon group), a thiol group, $—R^5—SH$ (wherein $R^5$ is a hydrocarbon group), —NCO or $—R^6—NCO$ (wherein $R^6$ is a hydrocarbon group);

$R_D^{4a}$ and $R_D^{5a}$ independently represent a hydrogen atom, an alkyl group, a haloalkyl group, an acyloxyalkyl group, a silyloxyalkyl group, $—R^1—OH$ (wherein $R^1$ is a hydrocarbon group), $—R^4—NH_2$ (wherein $R^4$ is a hydrocarbon group), an aryl group, $—R^5—SH$ (wherein $R^5$ is a hydrocarbon group) or $—R^6—NCO$ (wherein $R^6$ is a hydrocarbon group);

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, a haloalkyl group, an aryl group, a hydroxy group, $—R^1—OH$ (wherein $R^1$ is a hydrocarbon group), $—OR^2—OH$ (wherein $R^2$ is a hydrocarbon group), an amino group, $—R^4—NH_2$ (wherein $R^4$ is a hydrocarbon group), a thiol group, $—R^5—SH$ (wherein $R^5$ is a hydrocarbon group), —NCO or $—R^6—NCO$ (wherein $R^6$ is a hydrocarbon group).

Examples of the groups or atoms represented by $R_D^{1a}$, $R_D^{2a}$, $R_D^{3a}$, $R_D^{4a}$, $R_D^{5a}$, $R_A^{1a}$ and $R_A^{2a}$ in the formula (1) include the groups or atoms represented by $R_D^1$, $R_D^2$, $R_D^3$, $R_D^4$, $R_D^5$, $R_A^1$ and $R_A^2$, respectively, as exemplified above.

Examples of the hydrocarbon group represented by $R^1$, $R^2$, $R^3$, $R^4$, $R^5$ and $R^6$ in the formula (1) include the above hydrocarbon groups etc. represented by $R^1$, $R^2$, $R^3$, $R^4$, $R^5$ and $R^6$ in the above formulas (D-1), (D-1-1) and (D-1-2), as exemplified above.

Examples of X in the formula (1) include molecules having a conjugated system (e.g., structures represented by the above formulas (B-I), (B-II), (B-III) and (B-IV), etc.), as well as (B-V), which represents a direct binding (indicated by solid lines), etc. Preferred is a structure represented by the formula (B-I).

The positions of the reactive groups (B) in the (b) EO molecule are not particularly limited.

For example, the reactive groups (B) may be present in any one of D, B and A in a compound having a structure represented by D (a donor structure)-B (a bridge structure)-A (an acceptor structure). Preferably two or more reactive groups (B) are present in D.

The positions of the reactive groups (B) in the compound represented by the above formula (1) are not particularly limited. For example, the reactive groups (B) may be present in at least two or more of $R_D^{1a}$, $R_D^{2a}$, $R_D^{3a}$, $R_D^{4a}$, $R_D^{5a}$, $R_A^{1a}$ and $R_A^{2a}$ in the compound represented by the above formula (1). Preferably, the reactive groups (B) are present in at least two or more of $R_D{}^{1a}$, $R_D{}^{2a}$, $R_D{}^{3a}$, $R_D{}^{4a}$ and $R_D{}^{5a}$. Preferably, the reactive groups (B) are present in at least one of $R_A{}^{1a}$ and $R_A{}^{2a}$.

The compound represented by the above formula (1) may have two or more reactive groups (B) that are selected from the group consisting of a hydroxy group, —$R^1$—OH, —$OR^2$—OH, an amino group, —$R^4$—$NH_2$, a thiol group, —$R^5$—SH, —NCO and —$R^6$—NCO.

When $R_D{}^{1a}$ is a hydroxy group, —$R^1$—OH, —$OR^2$—OH, an amino group, —$R^4$—$NH_2$, a thiol group or —$R^5$—SH, $R_D{}^{4a}$ and/or $R_D{}^5$a may be —$R^1$—OH, —$R^4$—$NH_2$ or —$R^5$—SH.

When $R_A{}^{1a}$ and/or $R_A{}^{2a}$ is a hydroxy group, —$R^1$—OH, —$OR^2$—OH, an amino group, —$R^4$—$NH_2$, a thiol group or —$R^5$—SH, $R_D{}^{4a}$ and/or $R_D{}^{5a}$ may be —$R^1$—OH, —$R^4$—$NH_2$ or —$R^5$—SH.

When $R_D{}^{4a}$ and/or $R_D{}^{5a}$ is —$R^1$—OH, —$R^4$—$NH_2$ or —$R^5$—SH, X may have a hydroxy group, —$R^1$—OH, —$OR^2$—OH, an amino group, —$R^4$—$NH_2$, a thiol group or —$R^5$—SH.

Specific embodiments showing the positions of the reactive groups (B) in the (b) EO molecule include the following embodiments (1), (2) and (3).

(1) An embodiment where $R_D{}^{1a}$ is the reactive group (B) [e.g., a hydroxyalkoxy group (a hydroxy $C_{1-10}$ alkyl group, such as a hydroxyethoxy group, a hydroxybutoxy group, etc.) etc.], and at least one of $R_D{}^{4a}$, $R_D{}^{5a}$, $R_A{}^{1a}$ and $R_A{}^{2a}$ is the reactive group (B) [e.g., a hydroxyalkyl group (e.g., a hydroxy $C_{1-10}$ alkyl group, such as a hydroxymethyl group, a hydroxyethyl group, a hydroxypropyl group, a hydroxybutyl group, etc.), a hydroxyaryl group (e.g., a hydroxy $C_{6-10}$ aryl group, such as a hydroxyphenyl group etc.), a hydroxyaralkyl group (e.g., a hydroxy $C_{6-10}$ aryl $C_{1-4}$ alkyl group, such as a hydroxybenzyl group etc.), etc.].

(2) An embodiment where $R_D{}^{4a}$ and $R_D{}^5$a are the reactive groups (B) [e.g., a hydroxyalkyl group (e.g., a hydroxy $C_{1-10}$ alkyl group, such as a hydroxymethyl group, a hydroxyethyl group, a hydroxypropyl group, a hydroxybutyl group, etc.), a hydroxyaryl group (e.g., a hydroxy $C_{6-10}$ aryl group, such as a hydroxyphenyl group etc.), a hydroxyaralkyl group (e.g., a hydroxy $C_{6-10}$ aryl $C_{1-4}$ alkyl group, such as a hydroxybenzyl group etc.), etc.].

(3) An embodiment where at least one of $R_A{}^{1a}$ and $R_A{}^{2a}$ is the reactive group (B) [e.g., a hydroxyalkyl group (e.g., a hydroxy $C_{1-10}$ alkyl group, such as a hydroxymethyl group, a hydroxyethyl group, a hydroxypropyl group, a hydroxybutyl group, etc.), a hydroxyaryl group (e.g., a hydroxy $C_{6-10}$ aryl group, such as a hydroxyphenyl group etc.), a hydroxyaralkyl group (e.g., a hydroxy $C_{6-10}$ aryl $C_{1-4}$ alkyl group, such as a hydroxybenzyl group etc.), etc.], and at least one of $R_D{}^{4a}$ and $R_D{}^5$a is the reactive group (B) [e.g., a hydroxyalkyl group (e.g., a hydroxy$C_{1-10}$ alkyl group, such as a hydroxymethyl group, a hydroxyethyl group, a hydroxypropyl group, a hydroxybutyl group, etc.), a hydroxyaryl group (e.g., a hydroxy $C_{6-10}$ aryl group, such as a hydroxyphenyl group etc.), a hydroxyaralkyl group (e.g., a hydroxy $C_{6-10}$ aryl $C_{1-4}$ alkyl group, such as a hydroxybenzyl group etc.), etc.].

When $R_D{}^{1a}$, $R_D{}^{2a}$, $R_D{}^{3a}$, $R_D{}^{4a}$, $R_D{}^{5a}$, $R_A{}^{1a}$ or $R_A{}^{2a}$ is not the reactive group (B) (i.e., when any one of these is a non-reactive group), the groups or atoms represented by $R_D{}^{1a}$, $R_D{}^{2a}$, $R_D{}^{3a}$, $R_D{}^{4a}$, $R_D{}^{5a}$, $R_A{}^{1a}$ and $R_A{}^{2a}$ are as described above and are not particularly limited.

When any one of $R_D{}^{1a}$, $R_D{}^{2a}$, $R_D{}^{3a}$, $R_D{}^{4a}$, $R_D{}^{5a}$, $R_A{}^{1a}$ and $R_A{}^{2a}$ is a non-reactive group, specific groups represented by these are as follows.

$R_D{}^{1a}$: a hydrogen atom, an alkoxy group (e.g., a $C_{1-10}$ alkoxy group, such as a methoxy group, an ethoxy group, a butoxy group, etc.), an aryloxy group (e.g., a $C_{6-10}$ aryloxy group, such as a phenoxy group etc.), an aralkyloxy group (e.g., a $C_{6-10}$ aryl $C_{1-10}$ alkyloxy group, such as a benzyloxy group, a phenethyloxy group, etc.), etc.

$R_D{}^{2a}$ and $R_D{}^{3a}$: a hydrogen atom etc.

$R_D{}^{4a}$ and $R_D{}^{5a}$: an alkyl group (e.g., a $C_{1-10}$ alkyl group, such as a methyl group, an ethyl group, a butyl group, etc.), an aryl group (e.g., a $C_{6-10}$ aryl group, such as a phenyl group etc.), an aralkyl group (e.g., a $C_{6-10}$ aryl $C_{1-10}$ alkyloxy group, such as a benzyl group, a phenethyl group, etc.), etc.

$R_A{}^{1a}$ and $R_A{}^{2a}$: an alkyl group (e.g., a $C_{1-10}$ alkyl group, such as a methyl group, an ethyl group, a butyl group, etc.), an aryl group (e.g., a $C_{6-10}$ aryl group, such as a phenyl group, etc.), a cycloalkyl aryl group (e.g., a $C_{3-10}$ cycloalkyl $C_{6-10}$ aryl group, such as a cyclohexylphenyl group etc.), an arylaryl group (e.g., a $C_{6-10}$ aryl $C_{6-10}$ aryl group, such as a biphenylyl group etc.), an aralkyl group (e.g., a $C_{6-10}$ aryl $C_{1-10}$ alkyloxy group, such as a benzyl group, a phenethyl group, etc.), a halogenated hydrocarbon group [e.g., a haloalkyl group (e.g., a halo $C_{1-10}$ alkyl group, such as a trifluoromethyl group etc.), a haloaryl group (e.g., a halo $C_{6-10}$ aryl group, such as a pentafluorophenyl group etc.), etc.], etc.

Another preferred EO molecule (b) is, for example, a compound represented by the following formula (2):

[Chem. 16]

(2)

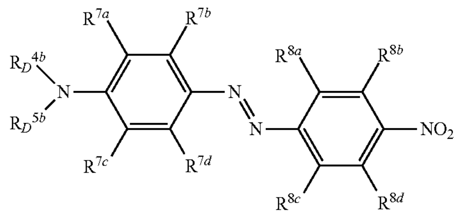

wherein $R_D{}^{4b}$, $R_D{}^{5b}$, $R^{7a}$, $R^{7b}$, $R^{7c}$, $R^{7d}$, $R^{8a}$, $R^{8b}$, $R^{8c}$ and $R^{8d}$ independently represent a hydrogen atom, a hydrocarbon group, a hydroxy group, —$R^1$—OH (wherein $R^1$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group), with the exception of the case where $R_D{}^{4b}$ and $R_D{}^{5b}$ each are a hydroxy group, a thiol group, an amino group, or —NCO, wherein at least two of $R_D{}^4$b, $R_D{}^{5b}$, $R^{7a}$, $R^{7b}$, $R^{7c}$, $R^{7d}$, $R^{8a}$, $R^{8b}$, $R^{8c}$ and $R^{8d}$ are a hydroxy group, —$R^1$—OH (wherein $R^1$ is a hydrocarbon group), an amino group, —$R^4$—$NH_2$ (wherein $R^4$ is a hydrocarbon group), a thiol group, —$R^5$—SH (wherein $R^5$ is a hydrocarbon group), —NCO or —$R^6$—NCO (wherein $R^6$ is a hydrocarbon group)

Examples of the hydrocarbon group represented by $R_D{}^{4b}$, $R_D{}^{5b}$, $R^{7a}$, $R^{7b}$, $R^{7c}$, $R^{7d}$, $R^{8a}$, $R^{8b}$, $R^{8c}$ and $R^{8d}$ include aliphatic groups [e.g., $C_{1-10}$ alkyl groups (e.g., a methyl group, an ethyl group, a propyl group, a butyl group, etc.), $C_{2-10}$ alkenyl groups (e.g., an ethenyl group, a propenyl group, a butenyl group, etc.), preferably $C_{1-6}$ alkyl groups, $C_{2-6}$ alkenyl groups, etc.], alicyclic groups [e.g., $C_{3-12}$ cycloalkyl groups (e.g., a cyclopropyl group, a cyclobutyl group, a cyclopentyl group, a cyclohexyl group, etc.), preferably $C_{3-7}$ cycloalkyl groups etc.], aromatic groups {e.g., $C_{6-20}$ aromatic groups [e.g., $C_{6-20}$ aryl groups (e.g., a phenyl group, a tolyl group, a xylyl group, a naphthyl group, etc.), $C_{7-20}$ aralkyl groups (e.g., a benzyl group etc.), etc.]}, etc. Of these, preferred are aliphatic groups, and more preferred are $C_{1-10}$ alkyl groups.

Examples of the hydrocarbon group represented by $R^1$, $R^4$, $R^5$ and $R^6$ in the formula (2) include the above hydrocarbon groups etc. represented by $R^1$, $R^4$, $R^5$ and $R^6$ in the above formulas (D-1), (D-1-1) and (D-1-2), as exemplified above.

The (b) EO molecule preferably contains at least the compound represented by the above formula (1).

When a combination of the compound represented by the above formula (1) and the compound represented by the above formula (2) is used as the (b) EO molecule, the weight ratio of the compound represented by the formula (1) relative to the compound represented by the formula (2) is, for example, 3:1 to 1:1, preferably 2:1 to 1:1.

The molar ratio of the compound represented by the formula (1) relative to the compound represented by the formula (2) is, for example, 3:1 to 1:1, preferably 2:1 to 1:1.

By using a combination of the compound represented by the above formula (1) and the compound represented by the formula (2) as the (b) EO molecule, the refractive index and the electro-optic coefficient of the polymer (I) can be increased without reducing the resistivity, as compared with the case where the percentage of the (b) EO molecule in the polymer (I) is increased by adding the compound represented by the formula (1) alone.

The polymer (I) may contain one or more types of additional EO molecules that are not included in the (b) EO molecule.

The additional EO molecule is, for example, a compound having a structure represented by D (a donor structure)-B (a bridge structure)-A (an acceptor structure) with one or more reactive groups (B) or without any reactive group (B). The additional EO molecule is, for example, a compound represented by the above formula (1) or (2) having zero or one reactive group (B).

The (b) EO molecule can be produced by a conventional method. The (b) EO molecule can be produced by various methods, for example, the methods described in, for example, Ann., 580, 44 (1953); *Angew. Chem.*, 92, 671 (1980); *Chem. Ber.*, 95, 581 (1962); *Macromolecules*, 2001, 34, 253; *Chem. Mater.*, 2007, 19, 1154; *Org. Synth.*, VI, 901 (1980); *Chem. Mater.*, 2002, 14, 2393; *J. Mater. Sci.*, 39, 2335 (2004); "*Preparative Organic Chemistry*", John Wiley (1975), p. 217; *J. Org. Chem.*, 42, 353 (1977); *J. Org. Chem.*, 33, 3382 (1968); *Synthesis*, 1981, 165; WO 2011/024774, etc., appropriately modified methods thereof, a combination thereof, etc.

Introduction of the reactive groups (B) may be performed during the production process of the (b) EO molecule. For example, the reactive groups (B) can be introduced into $R_D^4$ and $R_D^5$ of the above formula (D-1) to give the (b) EO molecule.

When the polymer (I) contains the additional EO molecule, the molar ratio of the (b) EO molecule relative to the additional EO molecule is, for example, 0.1:1 to 1:0.1, preferably 1:1 to 1:0.1.

Polymer (I)

The production process of the polymer (I) may be any process as long as it involves reaction of the (a) base polymer having a reactive group (A) with the (b) electro-optic molecule having a plurality of reactive groups (B).

The reaction of the (a) base polymer with the (b) electro-optic molecule may be achieved by, for example, allowing the (a) base polymer to react with the (b) electro-optic molecule in the presence of a solvent.

The reaction may be performed under heating (e.g., at an internal temperature of 50 to 100° C.) etc.

The reaction may be performed in the presence of a catalyst.

The weight ratio of the (a) base polymer relative to the (b) electro-optic molecule in the polymer (I) is, for example, 30:70 to 95:5 (e.g., 30:70 to 90:10), preferably 40:60 to 90:10, more preferably 50:50 to 80:20.

The (b) electro-optic molecule may be bound to the (a) base polymer in any suitable manner in the polymer (I). For example, one (b) electro-optic molecule may be bound to one (a) base polymer or bound to different (a) base polymers, or both binding forms may exist in the polymer (I).

The polymer (I) may contain a compound having a functional group (e.g., a hydroxyl group, a thiol group, an amino group, etc.), such as polyols {e.g., diols [e.g., aliphatic diols (e.g., $C_{2-10}$ alkylene glycols, such as ethylene glycol etc.), aromatic diols (e.g., dihydroxyarenes, such as resorcinol, bisphenol A, etc.) etc.], triols [e.g., aliphatic triols (glycerol, trimethylolpropane, etc.) etc.], tetraols [e.g., aliphatic tetraols (e.g., pentaerythritol etc.)] etc.}, polythiols {e.g., dithiols [e.g., aliphatic dithiols (ethanedithiol etc.) etc.], tetrathiols [e.g., pentaerythritoltetrakis(3-mercaptobutyrate) etc.] etc.}, polyamines {e.g., diamines [e.g., aliphatic diamines (e.g., $C_{2-10}$ alkane diamines, such as ethylenediamine, butane-1,4-diamine, etc.) etc.] etc.}, etc. The functional group (an OH group or a hydroxyl group, a thiol group, an amino group, etc.) of such a functional group-containing compound (e.g., diols) may react with the iso(thio)cyanato group of the (a) base polymer to form a bond between the functional group-containing compound and the (a) base polymer. All of the functional groups (an OH group or a hydroxyl group, a thiol group, an amino group, etc.) may be bound to the (a) base polymer, or alternatively, part of the functional groups remains unreacted.

Optical Elements

The polymer of the present invention can be used as an electro-optic polymer, and may be used in an optical element.

The production process of the optical element is not particularly limited, and the optical element can be produced by a known method.

The applications of the optical element are not particularly limited. The optical element can be used in optical modulators, electric field sensors, optical switches, optical memories, wavelength converters, generators and detectors for terahertz electromagnetic waves, optical scanners, etc.

EXAMPLES

The present invention will be illustrated in detail by the following Examples and Comparative Examples, but the present invention is not limited thereto.

Measurement of Tg

The Tgs of the polymers obtained in Synthesis Examples, Examples and Comparative Examples were determined with a differential scanning calorimeter (Rigaku Thermo plus DSC8230, manufactured by Rigaku Corporation) in the following conditions: sample: 10 mg, reference: empty aluminum (Al) pan, atmosphere: nitrogen, heating rate: 10° C./minute.

Measurement of Mw and Mn

To determine the molecular weights of the polymers obtained in Synthesis Examples, the polymers were converted to their more stable molecules, such as their methyl carbamate derivatives, and the molecular weights of such molecules were measured by GPC using Alliance e2695 (manufactured by Nihon Waters K.K.) (column: Shodex GPC KF-804L (8 mm ID x 300 mm L), developing solvent: THF, column temperature: 40° C.).

Film-Forming Method of Electro-Optic Polymers

The polymer obtained in each Example was dissolved in cyclohexanone to prepare a 1 to 20 wt % solution. The solution was applied on a cleaned substrate (silicon, glass, quarts glass) using a spin coater 1H-DX2 manufactured by MIKASA, CO., LTD. at 500 to 6000 rpm. The coated substrate was vacuum dried using a vacuum drying oven DRV220DC manufactured by Advantec Toyo Kaisha, Ltd., at the glass transition temperature (Tg) for 1 hour. The concentration of each polymer solution and the rotational speed of the spin coater were selected as appropriate to provide the desired film thickness of about 0.7 μm.

Measurement of $^1$H-NMR and $^{13}$C-NMR

Nuclear magnetic resonance spectra ($^1$H-NMR and $^{13}$C-NMR) were recorded on JNM-ECA 60011 manufactured by JEOL Ltd. The solvent used was $CDCl_3$, THF-$d_8$ or DMSO-$d_6$. Chemical shifts (δ) were expressed in ppm relative to tetramethylsilane as an internal standard. The symbols used have the following meanings.

s: singlet, d: doublet, dd: double doublet, t: triplet, m: multiplet, b: broad, J: J-coupling constant Preparation Method of Sample for Measurement of Electro-Optic Coefficient ($r_{33}$)

An electro-optic polymer film was formed on a glass substrate with a 9-nm-thick indium tin oxide (ITO) film (0008: manufactured by GEOMATIC CO., Ltd.) according the above film-forming method. On top of the polymer film, a 100-nm-thick indium zinc oxide (IZO) film was deposited by a magnetron sputtering technique to prepare a sample for the measurement of electro-optic coefficient ($r_{33}$). The sample was heated to around the glass transition temperature (Tg). Voltage was applied to the sample such that the strength of the electric field between the ITO and IZO films would be 120 V/μm. The sample was kept for 5 minutes while the voltage was being applied, and then cooled to room temperature. After that, the voltage was set to 0 V.

Measurement Method of Electro-Optic Coefficient ($r_{33}$)

The measurement of the electro-optic coefficient ($r_{33}$) was performed as described in the reference ("Transmission ellipsometric method without an aperture for simple and reliable evaluation of electro-optic properties", Toshiki Yamada and Akira Otomo, Optics Express, vol. 21, pages 29240-48 (2013)). The laser used as a light source was DFB laser 81663A manufactured by Agilent Technologies (wavelengths: 1308 nm and 1550 nm)

Synthesis Example 1: Copolymer ($A_1$)

[Chem. 17]

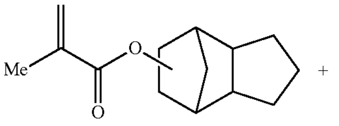

DCPMA

-continued

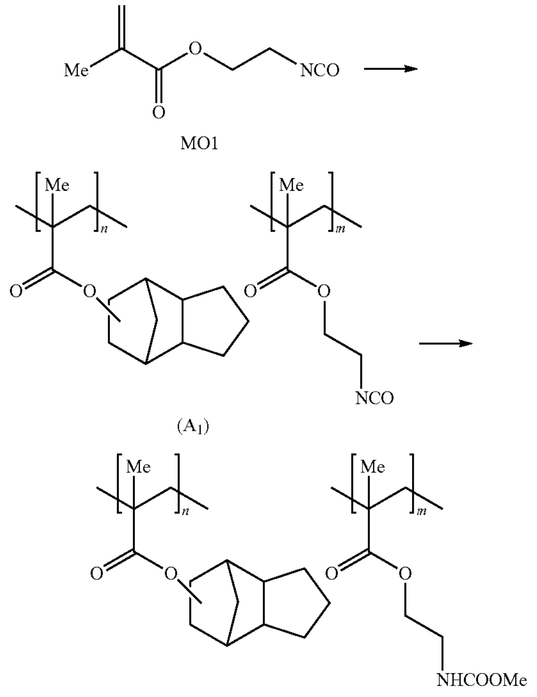

MO1

($A_1$)

8.51 g (38.63 mol) of dicyclopentanylmethacrylate (DCPMA), 4.9 g (31.58 mmol) of 2-isocyanatoethyl methacrylate (MOI), and 338 mg (2.24 mmol) of azoisobutyronitrile (AIBN) were dissolved in 22 mL of toluene. After purging with argon, the solution was stirred in an oil bath at 70° C. in a light-shielding condition for 2 hours. The reaction mixture was cooled and then poured into 660 mL of diisopropyl ether (IPE), and the precipitate was collected by filtration. The precipitate was washed with IPE and dried in vacuo with heating at 70° C. to give 12.71 g of a copolymer ($A_1$).

1.0 g of the copolymer ($A_1$) was dissolved in 35 mL of THF. To this, 3.0 mL of methanol and 40 μL of dibutyltin dilaurate (DBTDL) were added, and the mixture was stirred in an oil bath at 60° C. for 2 hours. The reaction mixture was cooled and then poured into 400 mL of IPE, and the mixture was stirred. The precipitated powder was collected by filtration, washed with IPE, and dried in vacuo with heating at 70° C. to give 0.89 g of a methyl carbamate derivative of the copolymer ($A_1$) as a colorless powder. The methyl carbamate derivative had a Tg of 108° C., a Mw of 53,305 and a Mn of 24,581.

Synthesis Example 2: Copolymer ($A_2$)

[Chem. 18]

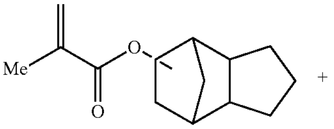

DCPMA

-continued

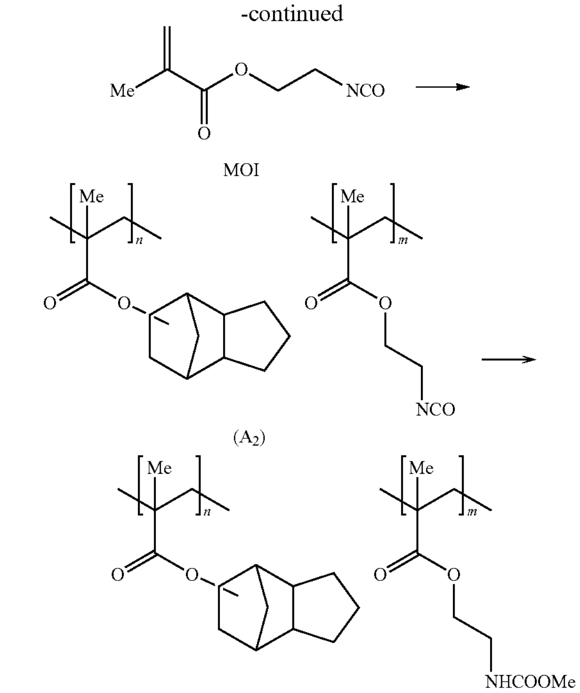

5.30 g (23.01 mmol) of DCPMA, 2.20 g (14.18 mmol) of MOI, and 184 mg (1.12 mmol) of AIBN were dissolved in 12.5 mL of toluene, and the same reaction as in Synthesis Example 1 was carried out to give 7.1 g of a copolymer ($A_2$). The methyl carbamate derivative of the copolymer ($A_2$) had a Tg of 119° C., a Mw of 64,033 and a Mn of 32,548.

Synthesis Example 3: Copolymer ($B_1$)

[Chem. 19]

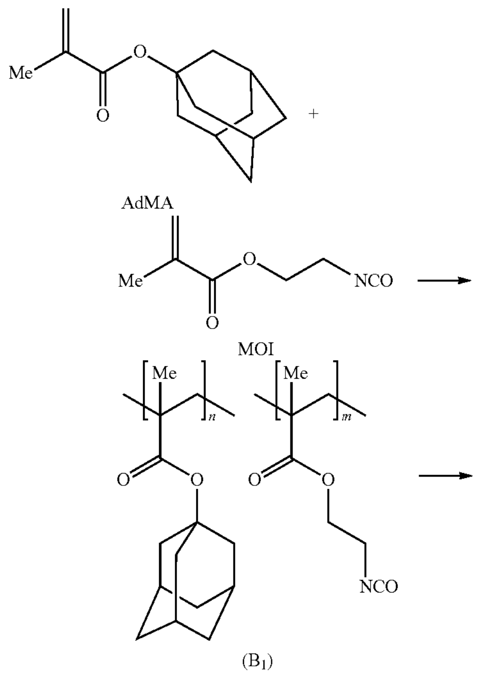

-continued

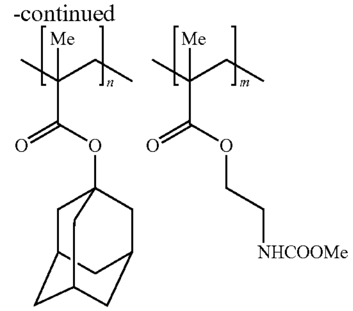

6.53 g (29.64 mmol) of adamantyl methacrylate (AdMA), 3.76 g (24.23 mmol) of 2-isocyanatoethyl methacrylate (MOI), and 265 mg (1.61 mmol) of azoisobutyronitrile (AIBN) were dissolved in 15.6 mL of toluene. After purging with argon, the solution was stirred in an oil bath at 70° C. in a light-shielding condition for 2 hours. The reaction mixture was cooled and then poured into 470 mL of diisopropyl ether (IPE), and the precipitate was collected by filtration. The precipitate was washed with IPE and dried in vacuo with heating at 70° C. to give 10.22 g of a copolymer ($B_1$).

1.0 g of the copolymer ($B_1$) was dissolved in 35 mL of THF. To this, 3.0 mL of methanol and 40 μL of dibutyltin dilaurate (DBTDL) were added, and the mixture was stirred in an oil bath at 60° C. for 2 hours. The reaction mixture was cooled and then poured into 400 mL of IPE, and the mixture was stirred. The precipitated powder was collected by filtration, washed with IPE, and dried in vacuo with heating at 70° C. to give 0.87 g of a methyl carbamate derivative of the copolymer ($B_1$) as a colorless powder. The methyl carbamate derivative had a Tg of 135° C., a Mw of 72,257 and a Mn of 27,212.

Synthesis Example 4: Copolymer ($B_2$)

[Chem. 20]

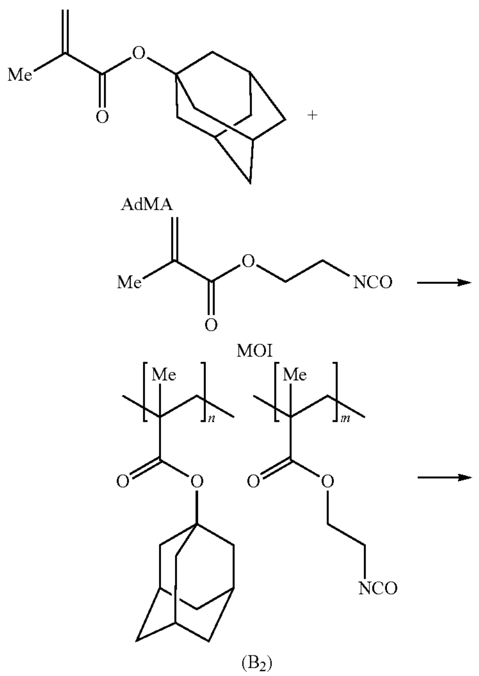

-continued

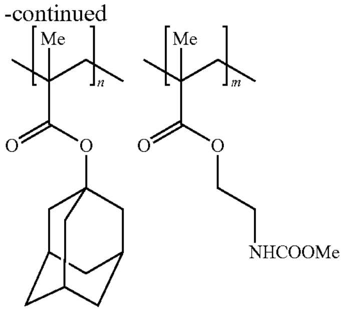

10.60 g (48.11 mmol) of AdMA, 4.40 g (28.36 mmol) of MOI, and 377 mg (2.80 mmol) of AIBN were dissolved in 25 mL of toluene, and the same reaction as in Synthesis Example 3 was carried out to give 14.88 g of a copolymer ($B_2$). The methyl carbamate derivative of the copolymer ($B_2$) had a Tg of 148° C., a Mw of 91,541 and a Mn of 31,639.

Synthesis Example 5: Copolymer ($C_1$)

[Chem. 21]

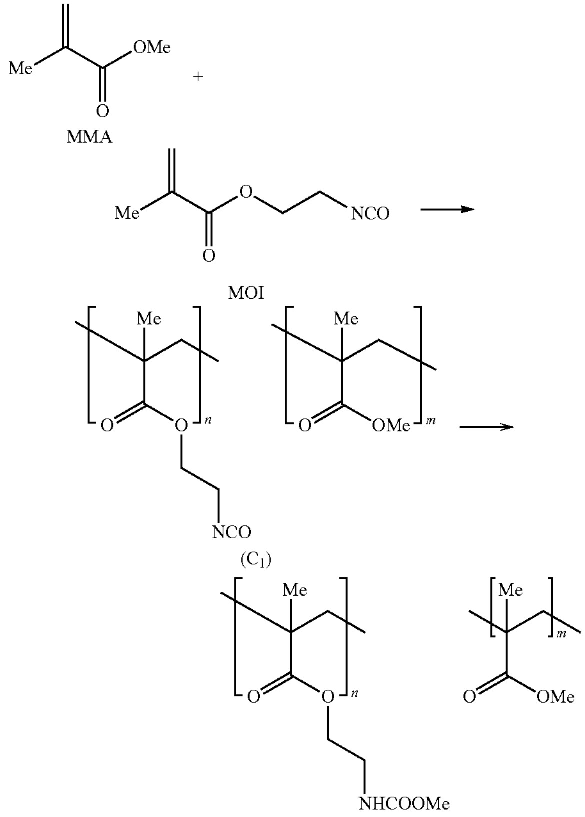

3.0 g (29.97 mmol) of methyl methacrylate (MMA), 9.1 g (58.65 mmol) of 2-isocyanatoethyl methacrylate (MOI), and 437 mg (2.66 mmol) of azoisobutyronitrile (AIBN) were dissolved in 20.0 mL of toluene. After purging with argon, the solution was stirred in an oil bath at 60° C. in a light-shielding condition for 2 hours. The reaction mixture was cooled and then poured into 400 mL of diisopropyl ether (IPE), and the precipitate was collected by filtration. The precipitate was washed with IPE and dried in vacuo with heating at 70° C. to give 8.48 g of a copolymer ($C_1$).

1.0 g of the copolymer ($C_1$) was dissolved in 35 mL of THF. To this, 3.0 mL of methanol and 40 μL of dibutyltin dilaurate (DBTDL) were added, and the mixture was stirred in an oil bath at 60° C. for 2 hours. The reaction mixture was cooled and then poured into 400 mL of IPE, and the mixture was stirred. The precipitated powder was collected by filtration, washed with IPE, and dried in vacuo with heating at 70° C. to give 1.09 g of a methyl carbamate derivative of the copolymer ($C_1$) as a colorless powder. The methyl carbamate derivative had a Mw of 148,005 and a Mn of 45,798.

Synthesis Example 6: Copolymer ($C_2$) PGP

[Chem. 22]

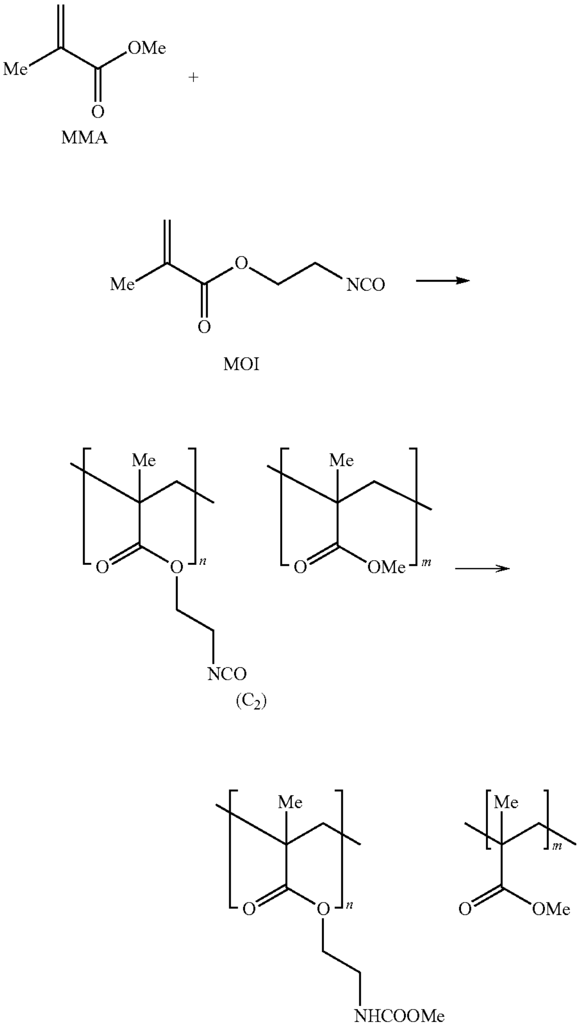

7.24 g (72.32 mmol) of MMA, 3.0 g (19.34 mmol) of MOI, and 451 mg (2.75 mmol) of AIBN were dissolved in 17 mL of toluene, and the same reaction as in Synthesis Example 5 was carried out to give 7.47 g of a copolymer ($C_2$). The methyl carbamate derivative of the copolymer ($C_2$) had a Tg of 96° C., a Mw of 54,926 and a Mn of 31,810.

Synthesis Example 7: Copolymer ($C_3$)

[Chem. 23]

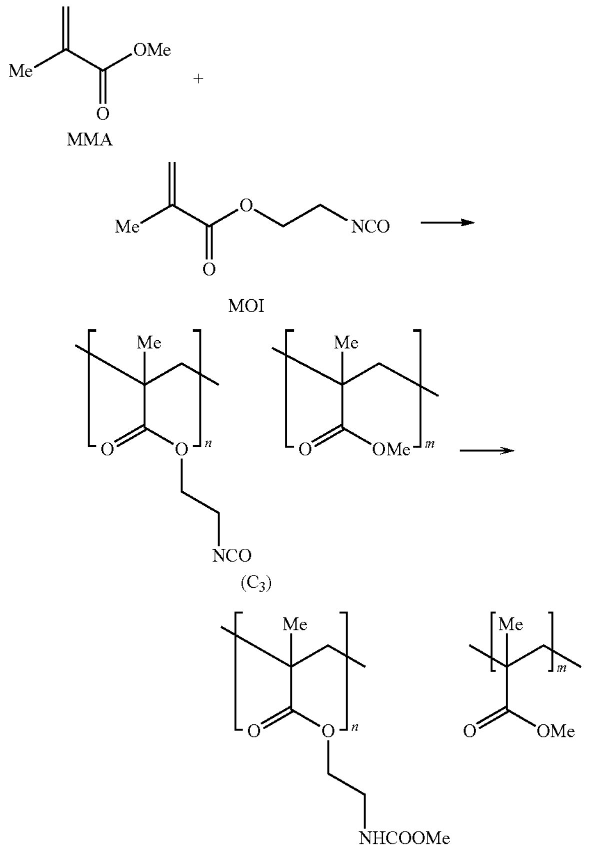

MMA

MOI ($C_3$)

5.10 g (50.94 mmol) of MMA, 6.9 g (44.47 mmol) of MOI, and 470 mg (2.86 mmol) of AIBN were dissolved in 20 mL of toluene, and the same reaction as in Synthesis Example 5 was carried out to give 8.80 g of a copolymer ($C_3$). The methyl carbamate derivative of the copolymer ($C_3$) had a Mw of 77,446 and a Mn of 37,879.

Synthesis Example 8: Copolymer ($A_3$)

[Chem. 24]

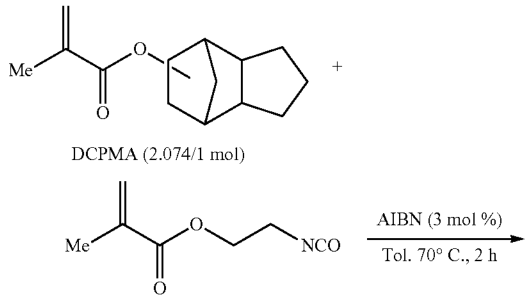

DCPMA (2.074/1 mol)

MOI

-continued

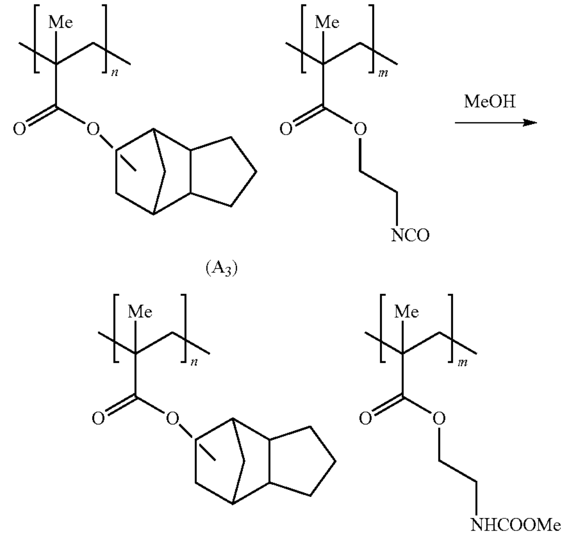

($A_3$)

(DCPMA/MOI:2.074/1 mol)

5.89 g (26.74 mmol) of DCPMA, 2.0 g (12.89 mmol) of MOI, and 195 mg (1.19 mmol) of AIBN were dissolved in 13 mL of toluene, and the same reaction as in Synthesis Example 1 was carried out to give 7.0 g of a copolymer ($A_3$). The methyl carbamate derivative of the copolymer ($A_3$) had a Tg of 124° C., a Mw of 96,001 and a Mn of 32,493.

Synthesis Example 9: Production Method of EO Molecule (EO-1)

[Chem. 25]

(EO-1)

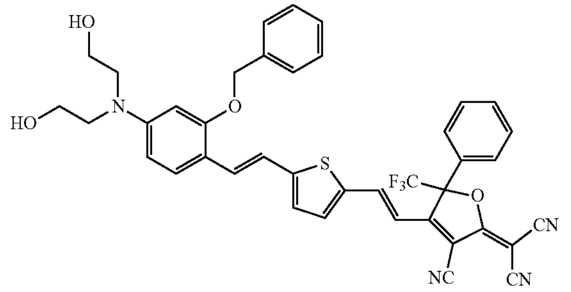

(1) Bis[2-(tert-butyldiphenylsilyl)oxy]ethylamine (Compound 2)

[Chem. 26]

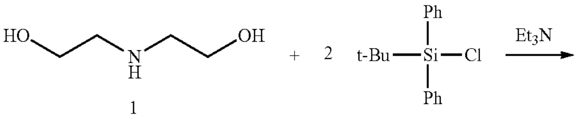

1

-continued

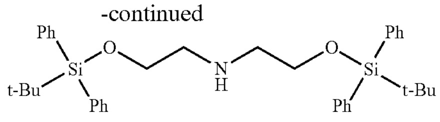

2

18.35 g (0.175 mol) of diethanolamine (1) and 71.0 g (0.702 mol) of triethylamine were dissolved in 500 mL of acetonitrile. To this, 96.0 g (0.349 mol) of tert-butylchlorodiphenylsilane was added dropwise with stirring at room temperature, and the mixture was stirred for 5 hours. The precipitated crystals were filtered off, and the filtrate was concentrated to dryness. The white solid residue was subjected to extraction with 750 mL of hexane. The hexane was evaporated off to give 81.27 g of the desired compound 2 as a colorless oil (which spontaneously solidified at room temperature). 24.86 g of the hexane-insoluble fraction was suspended in 200 mL of water. To this, 200 mL of a saturated aqueous sodium hydrogen carbonate solution and 300 mL of hexane were added, and the mixture was stirred (the crystals dissolved). The hexane layer was separated, dehydrated over anhydrous magnesium sulfate, and concentrated to give 20.62 g of the desired compound 2. 101.89 g in total (crude yield: 101.9%)

The NMR measurement results of compound 2 are shown below.

$^{1}$H-NMR (600 MHz, $CDCl_3$) δ ppm: 1.05 (18H, s), 2.78 (4H, t, J=5.5 Hz), 3.78 (4H, t, J=5.5 Hz), 7.36-7.43 (12H, m), 7.64-7.69 (8H, m)

$^{13}$C-NMR (150 MHz, $CDCl_3$) δ ppm: 19.19, 26.87, 51.71, 63.54, 127.67, 129.61, 133.65, 135.59

(2) 3-(Benzyloxy)-N,N-bis[2-[(tert-butyldiphenylsilyl)oxy]ethyl]aniline (compound 4)

[Chem. 27]

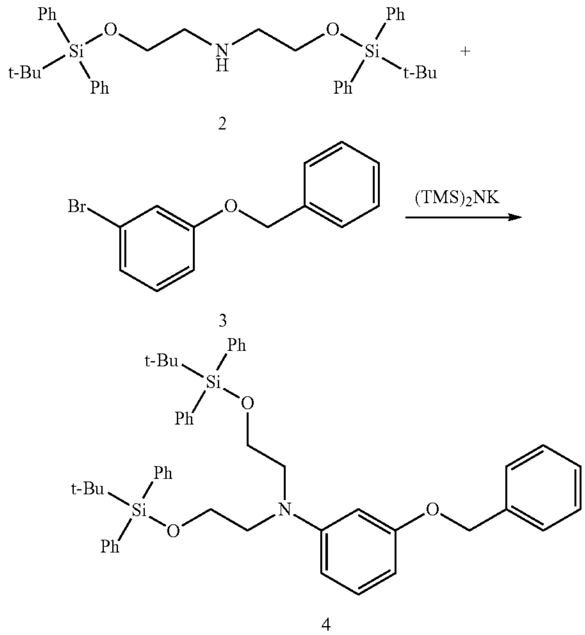

75.5 g (0.13 mol) of bis[2-(tert-butyldiphenylsilyl)oxy]ethylamine (2) and 34.0 g (0.13 mol) of 1-benzyloxy-3-bromobenzene (3) were dissolved in 500 mL of anhydrous toluene. To this, 30.9 g (0.155 mol) of potassium bis(trimethylsilyl)amide was added with stirring at room temperature. The mixture was stirred in an oil bath at 110° C. for 2 hours, cooled, and washed twice with a saturated aqueous sodium chloride solution. The organic layer was dehydrated over anhydrous sodium sulfate and concentrated to give 102.43 g of the desired compound 4 as an oil (crude yield: 103.7%).

The NMR measurement results of compound 4 are shown below.

$^{1}$H-NMR (600 MHz, $CDCl_3$) δ ppm: 1.03 (18H, s), 3.45 (4H, t, J=6.2 Hz), 3.72 (4H, t, J=6.2 Hz), 4.93 (2H, s), 5.93 (1H, dd, J=2.1 Hz, 8.3 Hz), 6.15 (1H, t, J=2.1 Hz), 6.22 (1H, dd, J=2.1 Hz, 8.3 Hz), 7.16-7.18 (1H, m), 6.91 (1H, t, J=8.3 Hz), 7.26-7.40 (16H, m), 7.61-7.63 (8H, m)

$^{13}$C-NMR (150 MHz, $CDCl_3$) δ ppm: 19.08, 26.81, 53.05, 60.92, 69.80, 98.91, 101.22, 104.84, 127.56, 127.68, 127.78, 128.47, 129.64, 129.82, 133.46, 135.55, 137.39, 149.07, 160.02

(3) 2,2'-[[3-(Benzyloxy)phenyl]azanediyl]diethanol (compound 5)

[Chem. 28]

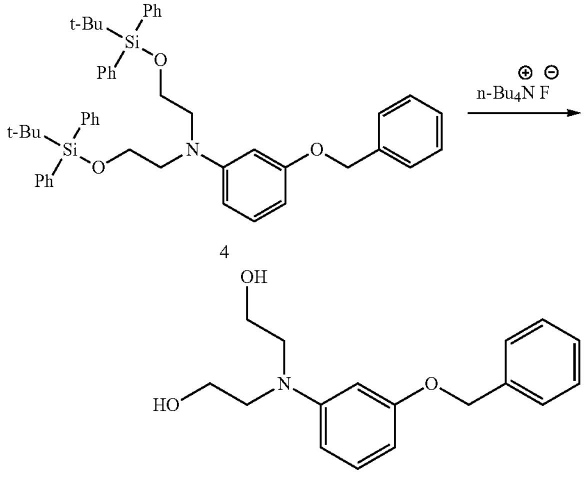

102.43 g (0.134 mol) of the crude 3-(benzyloxy)-N,N-bis[2-[(tert-butyldiphenylsilyl)oxy]ethyl]aniline (4) was dissolved in 250 mL of tetrahydrofuran. To this, 372 mL of tetrabutylammonium fluoride (1 mol solution in tetrahydrofuran) was added dropwise with stirring at room temperature. After 30-minute stirring, the reaction mixture was poured into 1000 mL of water, and ethyl acetate extraction was performed. The ethyl acetate layer was washed with a saturated aqueous sodium chloride solution, dehydrated over anhydrous sodium sulfate, and concentrated. To the residue, 500 mL of hexane was added, and the mixture was stirred. The hexane layer was then decanted. The remaining layer was concentrated, and the residue was purified by silica gel column chromatography (chloroform/methanol=10/1) to give 27.03 g of the desired compound 5 as a light-yellow oil (yield: 72.8%).

The NMR measurement results of compound 5 are shown below.

$^1$H-NMR (600 MHz, $CDCl_3$) δ ppm: 3.53 (4H, t, J=4.8 Hz), 3.80 (4H, t, J=4.8 Hz), 5.03 (2H, s), 6.29 (1H, s), 6.31 (1H, d, J=8.3 Hz), 6.37 (1H, dd, J=2.1 Hz, 8.2 Hz), 7.13 (1H, t, J=8.3 Hz), 7.30-7.40 (5H, m)

$^{13}$C-NMR (150 MHz, $CDCl_3$) δ ppm: 55.48, 60.87, 69.98, 100.24, 102.35, 105.89, 127.54, 127.95, 128.60, 129.99, 137.19, 149.17, 160.00

(4) [[3-(Benzyloxy)phenyl]azanediyl]bis(ethane-2,1-diyl)diacetate (compound 6)

[Chem. 29]

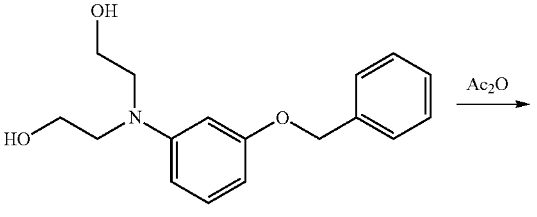

5

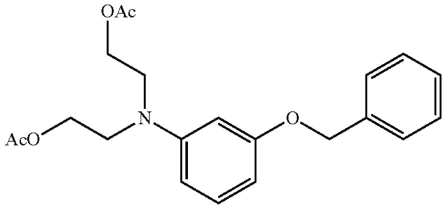

6

40 mL of acetic anhydride was added to 27.03 g (0.094 mol) of 2,2'-[[3-(benzyloxy)phenyl]azanediyl]diethanol (5), and the mixture was stirred in an oil bath at 100° C. for 1 hour and 45 minutes. After cooling, 300 mL of ether and 400 mL of water were added, and the mixture was stirred for 30 minutes. The organic layer was separated, and the aqueous layer was further subjected to extraction with 200 mL of ether. The organic layers were combined and washed with a saturated aqueous sodium hydrogen carbonate solution and subsequently with a saturated aqueous sodium chloride solution. The washed organic layer was dehydrated over anhydrous magnesium sulfate and concentrated. The residual liquid was purified by silica gel column chromatography (ethyl acetate/hexane=1/1) to give 31.75 g of the desired compound 6 as a light-yellow oil (yield: 90.9%)

The NMR measurement results of compound 6 are shown below.

$^1$H-NMR (600 MHz, $CDCl_3$) δ ppm: 2.05 (6H, s), 3.60 (4H, t, J=6.2 Hz), 4.21 (4H, t, J=6.2 Hz), 5.05 (2H, s), 6.36-6.38 (3H, m), 7.14 (1H, t, J=7.5 Hz), 7.31-7.45 (5H, m)

$^{13}$C-NMR (150 MHz, $CDCl_3$) δ ppm: 20.90, 49.84, 61.41, 69.93, 99.60, 102.65, 105.24, 127.57, 127.92, 128.58, 130.20, 137.22, 148.51, 160.20, 170.96

(5) [[3-(Benzyloxy)-4-formylphenyl]azanediyl]bis(ethane-2,1-diyl)diacetate (compound 7)

[Chem. 30]

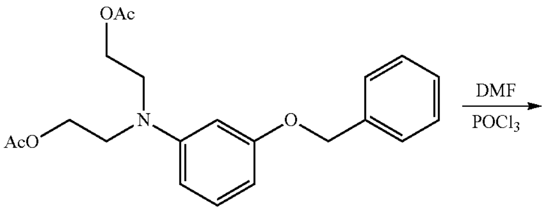

6

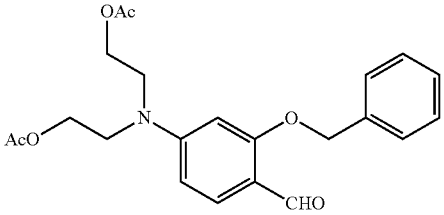

7

1.32 g (8.61 mmol) of phosphorus oxychloride was added dropwise to 8 mL of N,N-dimethylformamide with stirring under ice-cooling. After 20 minutes, the ice bath was removed, and the reaction mixture was heated to 12° C. and stirred at the same temperature for 5 minutes. The reaction mixture was ice-cooled again, and a solution of 3.08 g (8.29 mmol) of [[3-(benzyloxy)phenyl]azanediyl]bis(ethane-2,1-diyl)diacetate (6) in 4 mL of N,N-dimethylformamide was added dropwise. After 30-minute stirring, the reaction mixture was gradually heated to 70° C. and stirred at the same temperature for 2 hours. To the reaction mixture under cooling in an ice bath, 18 mL of a 20% aqueous sodium acetate solution was added dropwise, and the mixture was stirred for 40 minutes. Chloroform extraction was performed twice, and the extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residue was crystallized from ethanol, and the crystals were collected by filtration. As a result, 2.80 g of the desired compound 7 was obtained as colorless crystals with a melting point of 86 to 87° C. The filtrate was concentrated, and the residue was purified by silica gel column chromatography (ethyl acetate/hexane=3/2) to further give 0.27 g of the desired compound 7. 3.07 g in total (yield: 92.7%)

(6) 2-(Benzyloxy)-4-[bis(2-hydroxyethyl)amino] benzaldehyde (compound 8)

[Chem. 31]

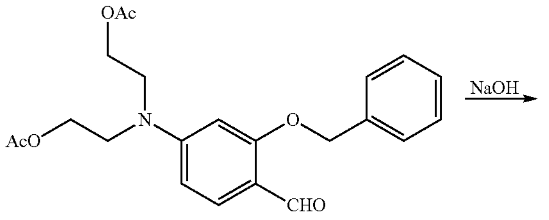

7

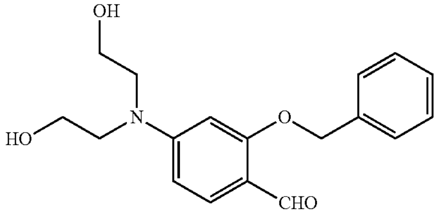

8

28.29 g (70.82 mmol) of [[3-(benzyloxy)-4-formylphenyl]azanediyl]bis(ethane-2,1-diyl)diacetate (7) was dissolved in 150 mL of ethanol. To this, 100 mL of a 7.4% aqueous sodium hydroxide solution was added dropwise, and the mixture was stirred at room temperature for 30 minutes. The reaction mixture was poured into 600 mL of a saturated aqueous sodium chloride solution, and chloroform extraction was performed. The extract was washed with a saturated aqueous sodium chloride solution, dehydrated over anhydrous sodium sulfate, and concentrated. The residual powder was recrystallized from ethyl acetate to give 21.79 g of the desired compound 8 as white crystals with a melting point of 108 to 109° C. (yield: 97.5%).

The NMR measurement results of compound 8 are shown below.

$^1$H-NMR (600 MHz, $CDCl_3$) δ ppm: 3.03 (2H, s), 3.62 (4H, t, J=4.8 Hz), 3.83 (4H, t, J=4.8 Hz), 5.16 (2H, s), 6.11 (1H, d, J=2.1 Hz), 6.30 (1H, dd, J=2.1 Hz, 9.0 Hz), 7.33-7.43 (5H, m), 7.68 (1H, d, J=9.0 Hz), 10.22 (1H, s)

$^{13}$C-NMR (150 MHz, $CDCl_3$) δ ppm: 55.12, 60.44, 70.26, 95.87, 105.38, 115.43, 126.95, 128.17, 128.78, 130.27, 136.54, 154.24, 162.90, 187.48

(7) 2-(Benzyloxy)-4-[bis[2-[(tert-butyldiphenylsilyl) oxy]ethyl]amino]benzaldehyde (compound 9)

[Chem. 32]

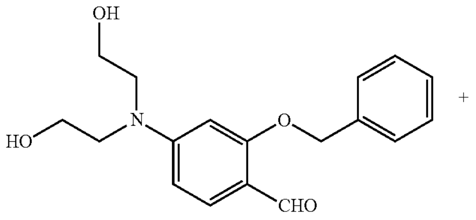

8

-continued

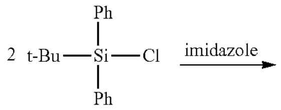

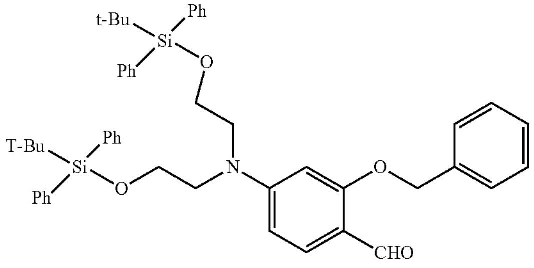

9

21.78 g (69.06 mmol) of 2-(benzyloxy)-4-[bis(2-hydroxyethyl)amino]benzaldehyde (8) and 21.6 g (317.28 mmol) of imidazole were dissolved in 100 mL of N,N-dimethylformamide. To this, 39.0 g (141.9 mmol) of tert-butylchlorodiphenylsilane was added dropwise with stirring at room temperature. After 40-minute stirring, the reaction mixture was added to 400 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (ethyl acetate/hexane=2/5) to give 51.3 g of the desired compound 9 as a light-yellow oil (yield: 93.8%).

The NMR measurement results of compound 9 are shown below. $^1$H-NMR (600 MHz, $CDCl_3$) δ ppm: 1.03 (18H, s), 3.60 (4H, t, J=6.2 Hz), 3.70 (4H, t, J=6.2 Hz), 4.94 (2H, s), 5.91-5.93 (2H, m), 7.20-7.42 (17H, m), 7.55 (1H, d, J=8.9 Hz), 7.57-7.59 (8H, m), 10.21 (1H, s) 13C-NMR (150 MHz, $CDCl_3$) δ ppm: 19.05, 26.78, 53.13, 60.69, 70.04, 94.57, 104.75, 114.85, 127.02, 127.77, 128.01, 128.60, 129.84, 130.27, 133.04, 135.50, 136.45, 154.13, 162.97, 187.25

(8) 3-(Benzyloxy)-N,N-[bis[2-[(tert-butyldiphenylsilyl)oxy]ethyl]-4-[2-(thiophen-2-yl)vinyl]aniline (compound 11-(Z/E))

[Chem. 33]

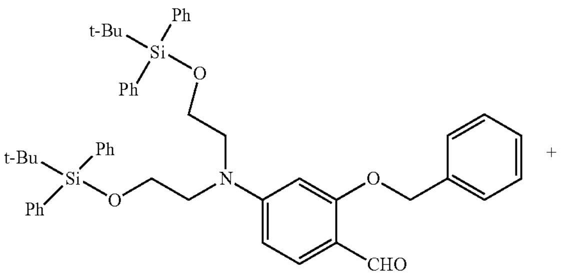

9

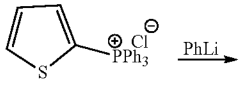

10

-continued

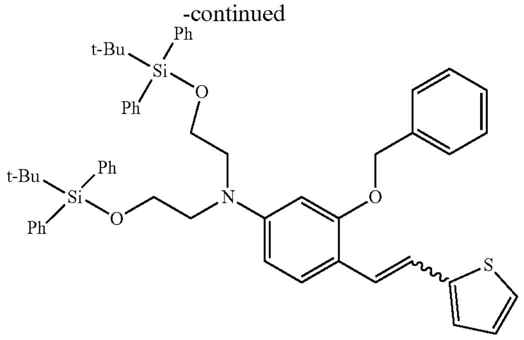

11-(Z/E)

27.6 mL (57.9 mmol) of phenyllithium (2.1 mol solution in dibutyl ether) was added to 250 mL of tetrahydrofuran under an argon atmosphere. To this, 20.8 g (52.7 mmol) of 2-thenyl triphenyl phosphonium chloride (10) was added with stirring under ice-cooling. After 10-minute stirring, 80 mL of a solution of 28.68 g (52.7 mmol) of 2-(benzyloxy)-4-[bis[2-[(tert-butyldiphenylsilyl)oxy]ethyl]amino]benzaldehyde (9) in tetrahydrofuran was added dropwise. After 2-hour stirring under ice-cooling, the reaction mixture was poured into 550 mL of water, and ethyl acetate extraction was performed. The extract was washed with a saturated aqueous sodium chloride solution, dehydrated over anhydrous sodium sulfate, and concentrated. To the residue, 240 mL of an ethyl acetate/hexane (1/5) mixture was added, and the mixture was stirred and then ice-cooled. The precipitate was filtered off, and the filtrate was concentrated. The residual liquid was purified by silica gel column chromatography (ethyl acetate/hexane=1/5) to give 30.18 g of the desired compound 11-(Z/E) as an orange oil (yield: 91.7%).

(9) 5-[(E)-2-(Benzyloxy)-4-[bis[2-[(tert-butyldiphenylsilyl)oxy]ethyl]amino]styryl]thiophene-2-carbaldehyde (compound 12-(E))

[Chem. 34]

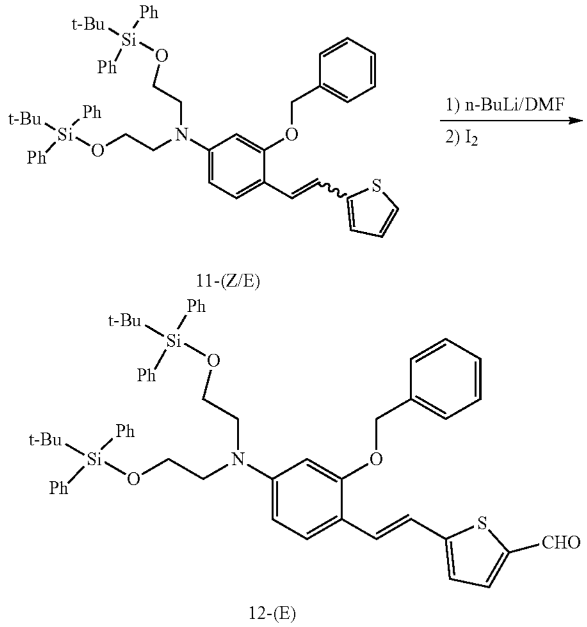

11-(Z/E)

12-(E)

47.8 g (54.8 mmol) of 3-(benzyloxy)-N,N-[bis[2-[(tert-butyldiphenylsilyl)oxy]ethyl]-4-[2-(thiophen-2-yl)vinyl] aniline (11-(Z/E)) was dissolved in 320 mL of tetrahydrofuran under an argon atmosphere. To this, 44.6 mL (71.4 mmol) of n-butyllithium (1.6 mol solution in hexane) was added dropwise with cooling in a dry ice/acetone bath. After 20-minute stirring, 4.47 g (61.2 mmol) of N,N-dimethylformamide was added dropwise. After 40-minute stirring, the bath was removed, the reaction mixture was heated, and 20 mL of water was added dropwise. After 35-minute stirring, the reaction mixture was poured into 600 mL of water, and ethyl acetate extraction was performed. The extract was washed with a saturated aqueous sodium chloride solution, dehydrated over anhydrous sodium sulfate, and concentrated. 49.63 g of the residual dark red oil was dissolved in 800 mL of ether. To this, 1.5 g of iodine flakes were added. After 30-minute stirring at room temperature, the reaction mixture was washed twice with 200 mL of a 5% aqueous sodium hydrogen sulfite solution. The reaction mixture was further washed with a saturated aqueous sodium chloride solution, dehydrated over anhydrous magnesium sulfate, and concentrated. The residue was purified by silica gel column chromatography (ethyl acetate/hexane=1/3) to give 40.59 g of the desired compound 12-(E) as a red oil (yield: 82.3%).

The NMR measurement results of compound 12-(E) are shown below.

$^1$H-NMR (600 MHz, $CDCl_3$) δ ppm: 1.04 (18H, s), 3.48 (4H, t, J=6.2 Hz), 3.70 (4H, t, J=6.2 Hz), 4.93 (2H, s), 5.97 (1H, dd, J=2.1 Hz, 8.9 Hz), 6.03 (1H, d, J=2.1 Hz), 6.98 (1H, d, J=4.1 Hz), 7.09 (1H, d, J=15.8 Hz), 7.19 (1H, d, J=8.9 Hz), 7.21-7.24 (1H, m), 7.27-7.34 (12H, m), 7.39-7.42 (5H, m), 7.59-7.61 (9H, m), 9.79 (1H, s)

$^{13}$C-NMR (150 MHz, $CDCl_3$) δ ppm: 19.07, 26.80, 53.17, 60.88, 70.38, 96.34, 104.87, 113.21, 116.53, 124.51, 127.19, 127.73, 127.93, 128.58, 128.98, 129.21, 129.75, 133.25, 135.53, 136.88, 137.75, 139.72, 149.61, 155.63, 158.11, 182.32

(10) (E)-5-[2-(Benzyloxy)-4-[bis[2-(hydroxyethyl)amino]styryl]thiophene-2-carbaldehyde (compound 13-(E))

[Chem. 35]

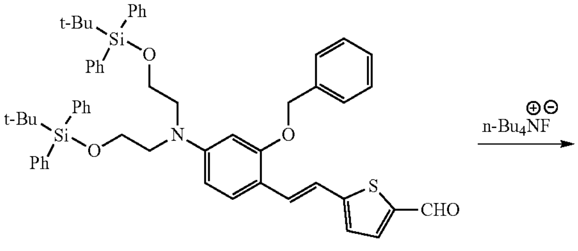

12-(E)

-continued

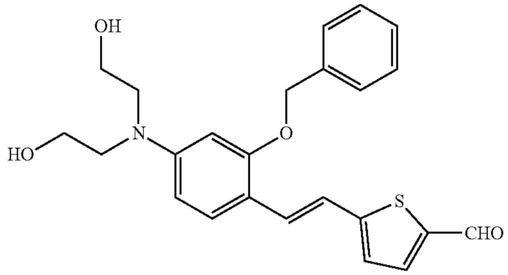

13-(E)

38.0 g (42.2 mmol) of 5-[(E)-2-(benzyloxy)-4-[bis[2-[(tert-butyldiphenylsilyl)oxy]ethyl]amino]styryl]thiophene-2-carbaldehyde (12-(E)) was dissolved in 150 mL of tetrahydrofuran. To this, 125 mL of tetrabutylammonium fluoride (1 mol solution in tetrahydrofuran) was added dropwise with stirring at room temperature. After 30-minute stirring, the reaction mixture was poured into 500 mL of water, and extraction with 250 mL of ethyl acetate was performed. The extract was washed with a saturated aqueous sodium chloride solution, dehydrated over anhydrous sodium sulfate, and concentrated. The residue was purified by silica gel column chromatography (chloroform/methanol=10/1) to give 17.08 g of the desired compound 13-(E) as a red oil (yield: 95.6%).

The NMR measurement results of compound 13-(E) are shown below.

$^1$H-NMR (600 MHz, $CDCl_3$) δ ppm: 3.10 (2H, s), 3.57 (4H, t, J=4.8 Hz), 3.79 (4H, t, J=4.8 Hz), 5.15 (2H, s), 6.19 (1H, d, J=2.1 Hz), 6.30 (1H, dd, J=2.1 Hz, 8.9 Hz), 7.00 (1H, d, J=4.1 Hz), 7.14 (1H, d, J=16.5 Hz), 7.33-7.35 (1H, m), 7.37 (1H, d, J=8.9 Hz), 7.39-7.46 (5H, m), 7.61 (1H, d, J=4.1 Hz), 9.78 (1H, s)

$^{13}$C-NMR (150 MHz, $CDCl_3$) δ ppm: 55.18, 60.68, 70.57, 97.73, 105.66, 114.39, 117.41, 124.89, 127.08, 128.06, 128.73, 128.76, 128.81, 137.01, 137.74, 140.00, 149.56, 155.20, 157.96, 182.45

(11) 2-[4-[(E)-2-[5-[(E)-2-Benzyloxy-4-[bis(2-(hydroxyethyl)amino]styryl]thiophen-2-yl]vinyl)-3-cyano-5-phenyl-5-(trifluoro methyl)furan-2(5H)-ylidene]malononitrile (EO-1)

[Chem. 36]

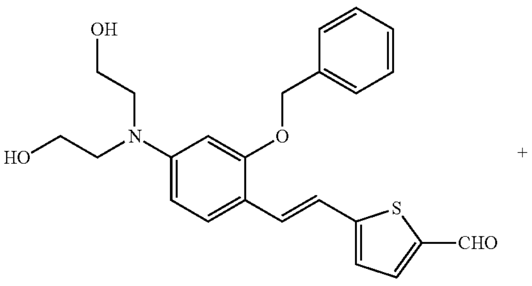

13-(E)

-continued

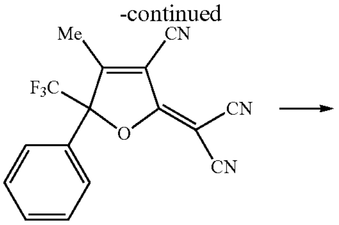

14

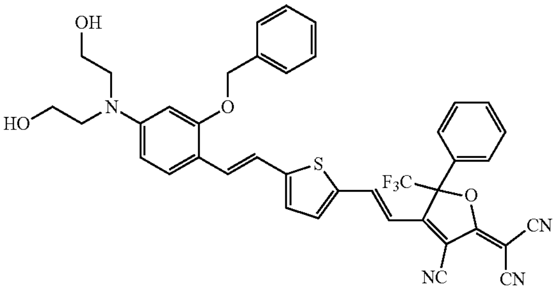

EO-1

To 18 mL of ethanol and 2 mL of tetrahydrofuran, 2.0 g (4.72 mmol) of (E)-5-[2-(benzyloxy)-4-[bis[2-(hydroxyethyl)amino] styryl]thiophene-2-carbaldehyde (13-(E)) and 1.64 g (5.20 mmol) of 2-(3-cyano-4-methyl-5-phenyl-5-trifluoromethyl-2(5H)-furanylidene)propanedinitrile (14) were dissolved. The solution was heated to 50° C. and stirred at the same temperature for 2 hours. The reaction mixture was ice-cooled, and the precipitated crystals were collected by filtration and washed with ethanol. The crystals were purified by silica gel column chromatography (chloroform/methanol=10/1) and then washed with ethanol. As a result, 2.93 g of the desired compound EO-1 was obtained as dark red-brown crystals with a melting point of 153 to 156° C. (yield: 86.2%).

The NMR measurement results of EO-1 are shown below.

$^1$H-NMR (600 MHz, $CDCl_3$) δ ppm: 2.88 (2H, s), 3.60 (4H, t, J=4.8 Hz), 3.80 (4H, t, J=4.8 Hz), 5.20 (2H, s), 6.19 (1H, d, J=2.1 Hz), 6.33 (1H, dd, J=2.1 Hz, 9.0 Hz), 6.55 (1H, d, J=15.1 Hz), 6.94 (1H, d, J=4.1 Hz), 7.17 (1H, d, J=15.8 Hz), 7.26 (1H, d, J=4.1 Hz), 7.34-7.57 (12H, m), 7.77 (1H, d, J=15.1 Hz)

$^{13}$C-NMR (150 MHz, $CDCl_3$) δ ppm: 55.08, 57.95, 60.57, 70.58, 97.47, 106.04, 110.70, 111.03, 111.15, 111.46, 114.15, 117.07, 125.50, 126.82, 127.07, 127.63, 128.20, 128.79, 129.63, 129.77, 131.53, 131.80, 136.82, 138.01, 139.86, 141.69, 150.64, 158.44, 158.72, 161.84, 175.39

Synthesis Example 10: Production method of EO molecule (EO-2)

[Chem. 37]

(EO-2)

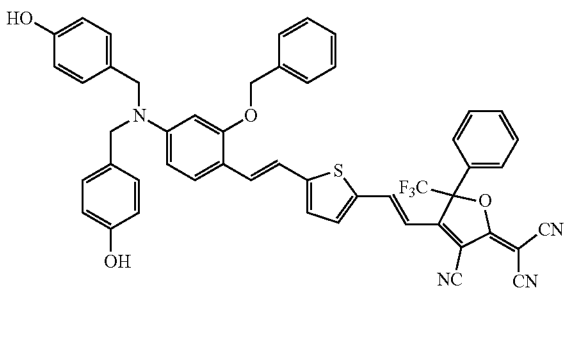

(1) Di-4,4'-[azanediylbis(methylene)]diphenol (compound 3a)

[Chem. 38]

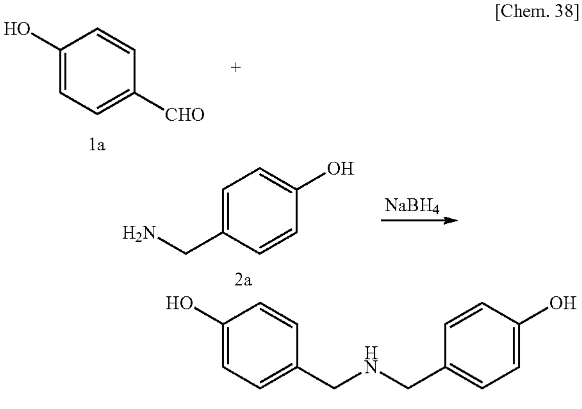

1a

2a

3a 12.12 g (0.099 mmol) of p-hydroxybenzaldehyde (1a) and 10.27 g (0.083 mmol) of 4-(aminomethyl)phenol (2a) were dissolved in 200 mL of methanol. The solution was stirred in an oil bath at 60° C. for 4 hours. The reaction mixture was ice-cooled, and 4.7 g (0.124 mol) of sodium borohydride was added over 1 hour and 20 minutes. After 2-hour stirring at a temperature of 7 to 10° C., the reaction mixture was concentrated. To the residual syrup, 100 mL of chloroform and 100 mL of water were added, and the mixture was stirred overnight. The resulting crystals were separated by filtration, washed with water, and dried. As a result, 16.3 g of the desired compound 3a was obtained as an off-white powder with a melting point of 123 to 124° C. (yield: 85.3%).

The NMR measurement results of compound 3a are shown below.

$^1$H-NMR (600 MHz, DMSO-$d_6$) δ ppm: 3.51 (4H, s), 6.68 (4H, d, J=8.2 Hz), 7.10 (4H, d, J=8.2 Hz), 9.19 (2H, s)

$^{13}$C-NMR (150 MHz, DMSO-$d_6$) δ ppm: 51.54, 114.70, 128.92, 130.93, 155.82

(2) Bis[4-[(tert-butyldiphenylsilyl)oxy]benzyl]amine (compound 4a)

[Chem. 39]

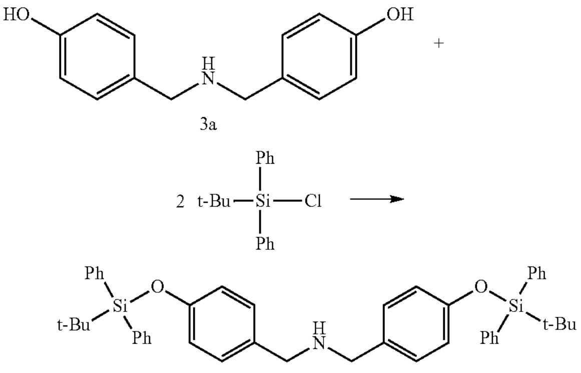

3a

4a 6.5 g (28.35 mmol) of di-4,4'-[azanediylbis(methylene)]diphenol (3a) and 8.1 g (118.98 mmol) of imidazole were dissolved in 70 mL of N,N-dimethylformamide. To this, 16.3 g (59.3 mmol) of tert-butylchlorodiphenylsilane was added dropwise with stirring at room temperature. After 35-minute stirring, 200 mL of water and 300 mL of ethyl acetate were added, and extraction was performed. The organic layer was washed with a saturated aqueous sodium chloride solution, dehydrated over anhydrous sodium sulfate, and concentrated. The residue was purified by silica gel column chromatography (chloroform/methanol=15/1) to give 14.73 g of the desired compound 4a as a yellow oil (yield: 73.5%).

The NMR measurement results of compound 4a are shown below.

$^1$H-NMR (600 MHz, $CDCl_3$) δ ppm: 1.08 (18H, s), 3.58 (4H, s), 6.68 (4H, d, J=8.3 Hz), 6.98 (4H, d, J=8.3 Hz), 7.33-7.43 (12H, m), 7.69-7.71 (8H, m)

(3) 3-(Benzyloxy)-N,N-bis[4-[(tert-butyldiphenylsilyl)oxy]benzyl]aniline (compound 6a)

[Chem. 40]

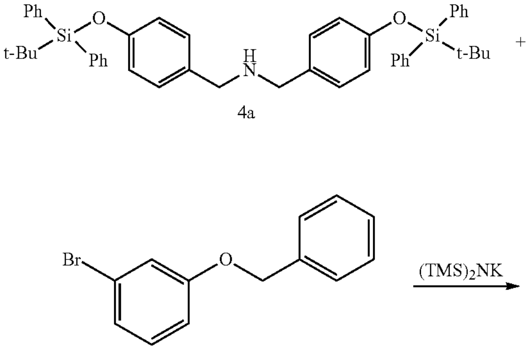

4a

5a

-continued

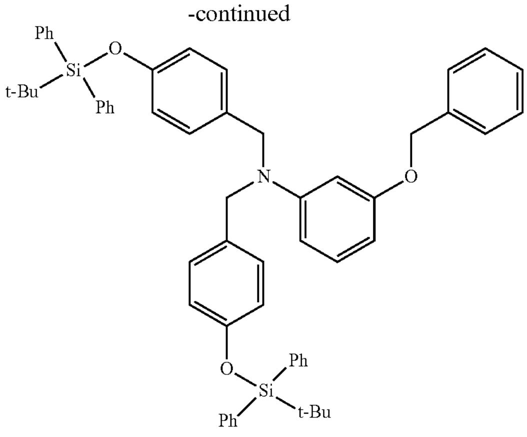

6a

-continued

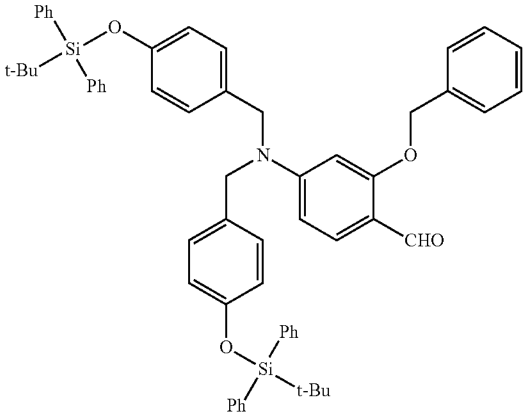

7a 8.10 g (11.47 mmol) of bis[4-[(tert-butyldiphenylsilyl)oxy]benzyl]amine (4a) and 3.02 g (11.48 mmol) of 1-benzyloxy-3-bromobenzene (5a) were dissolved in 80 mL of toluene. To this, 2.9 g (14.54 mmol) of potassium bis(trimethylsilyl)amide was added with stirring at room temperature. The mixture was stirred in an oil bath at 110° C. for 2.5 hours and then cooled. To this, 250 mL of water was added, and the mixture was stirred. The resulting layers were separated, and the aqueous layer was subjected to extraction with 75 mL of toluene. The organic layers were combined, washed with a saturated aqueous sodium chloride solution, dried over anhydrous sodium sulfate, and concentrated. The residual oil was purified by silica gel column chromatography (ethyl acetate/hexane=1/6) to give 5.38 g of the desired compound 6a as a light-brown oil (yield: 52.8%)

The NMR measurement results of compound 6a are shown below.

$^1$H-NMR (600 MHz, $CDCl_3$) δ ppm: 1.08 (18H, s), 4.36 (4H, s), 5.04 (2H, s), 6.26-6.30 (3H, m), 6.66 (4H, d, J=8.3 Hz), 6.86 (4H, d, J=8.3 Hz), 7.01 (1H, t, J=7.9 Hz), 7.26-7.29 (1H, m), 7.32-7.35 (12H, m), 7.38-7.43 (4H, m), 7.68-7.70 (8H, m)

$^{13}$C-NMR (150 MHz, $CDCl_3$) δ ppm: 19.45, 26.52, 53.33, 69.82, 99.74, 102.42, 105.81, 119.69, 127.56, 127.59, 127.72, 127.79, 128.48, 129.71, 129.83, 130.71, 132.97, 135.51, 137.30, 150.73, 154.42, 159.92

(4) 2-(Benzyloxy)-4-[bis[4-[(tert-butyldiphenylsilyl)oxy]benzyl]amino]benzaldehyde (compound 7a)

[Chem. 41]

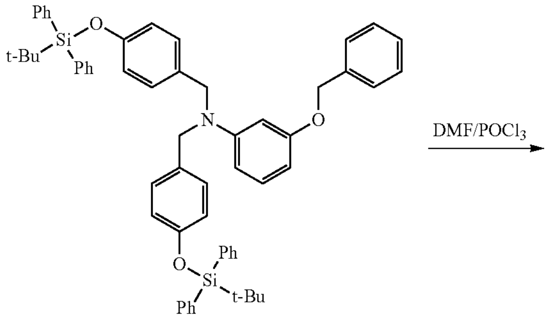

6a 1.0 g (6.52 mmol) of phosphorus oxychloride was added dropwise to 20 mL of N,N-dimethylformamide with stirring under ice-cooling. After 10 minutes, the reaction mixture was heated to 11° C., stirred at the same temperature for 5 minutes, and ice-cooled again. To this, a solution of 5.38 g (6.06 mmol) of 3-(benzyloxy)-N,N-bis[4-[(tert-butyldiphenylsilyl)oxy]benzyl]aniline (6a) in 20 mL of N,N-dimethylformamide was added dropwise. After 20-minute stirring, the reaction mixture was gradually heated to 50° C. and stirred at the same temperature for 1 hour and 20 minutes. The reaction mixture was ice-cooled, and 14 mL of a 20% aqueous sodium acetate solution was added dropwise. Further, 50 mL of water and 70 mL of ethyl acetate were added, and the mixture was stirred for 50 minutes. The reaction mixture was allowed to stand, and the resulting layers were separated. The aqueous layer was further subjected to ethyl acetate extraction. The combined organic layers were washed successively with a saturated aqueous sodium hydrogen carbonate solution and a saturated aqueous sodium chloride solution. The washed organic layer was dehydrated over anhydrous sodium sulfate and then concentrated. The residue was purified by silica gel column chromatography (ethyl acetate/hexane=1/3) to give 4.69 g of the desired compound 7a as a light-yellow oil (yield: 84.5%).

The NMR measurement results of compound 7a are shown below.

$^1$H-NMR (600 MHz, $CDCl_3$) δ ppm: 1.08 (18H, s), 4.42 (4H, s), 4.86 (2H, s), 6.05 (1H, d, J=2.1 Hz), 6.30 (1H, dd, J=2.1 Hz, 8.9 Hz), 6.69 (4H, d, J=8.2 Hz), 6.83 (4H, d, J=8.2 Hz), 7.21-7.41 (17H, m), 7.63 (1H, d, J=8.9 Hz), 7.68-7.70 (8H, m), 10.21 (1H, s)

$^{13}$C-NMR (150 MHz, $CDCl_3$) δ ppm: 19.42, 26.48, 53.63, 70.03, 95.66, 105.41, 115.45, 120.00, 127.08, 127.39, 127.76, 127.98, 128.57, 129.12, 129.93, 130.17, 132.78, 135.49, 136.39, 154.87, 155.25, 162.91, 187.27

(5) (Z/E)-3-(Benzyloxy)-N,N-[bis[4-[(tert-butyldiphenylsilyl)ox y]benzyl]-4-[2-(thiophen-2-yl)vinyl] aniline (compound 9-(Z/E) a)

[Chem. 42]

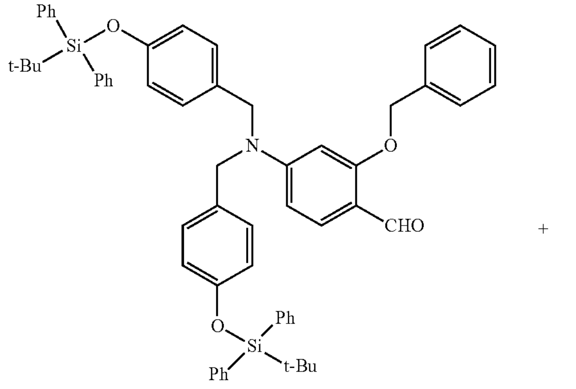

7a

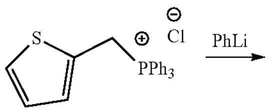

8a

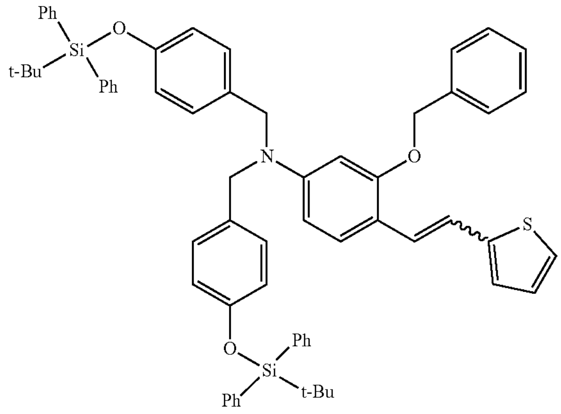

9-(Z/E)a 4.5 mL (9.45 mmol) of phenyllithium (2.1 mol solution in dibutyl ether) was added to 50 mL of tetrahydrofuran under an argon atmosphere. To this, 3.03 g (7.67 mmol) of 2-thenyl triphenyl phosphonium chloride (8a) was added under ice-cooling over 10 minutes. After 5-minute stirring, 20 mL of a solution of 6.82 g (7.44 mmol) of 2-(benzyloxy)-4-[bis[4-[(tert-butyldiphenylsilyl)oxy]benzyl]amino]benzaldehyde (7a) in tetrahydrofuran was added dropwise. After 1-hour stirring under ice-cooling, the reaction mixture was poured into 150 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (ethyl acetate/hexane=1/4) to give 6.07 g of the desired compound 9-(Z/E)a as a yellow caramel (yield: 81.9%).

(6 ) (E)-5-[2-(Benzyloxy)-4-[bis[4-[(tert-butyldiphenylsilyl)oxy]benzyl]amino]styryl]thiophene-2-carbaldehyde (compound 10-(E)a)

[Chem. 43]

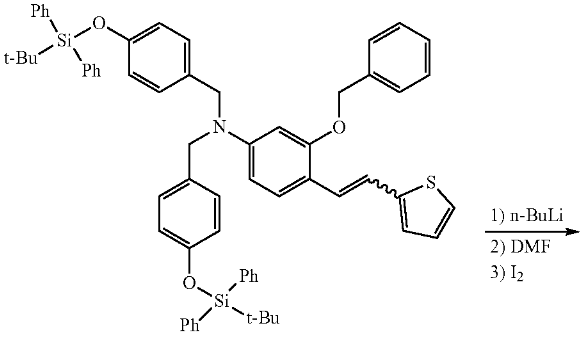

9-(Z/E)a

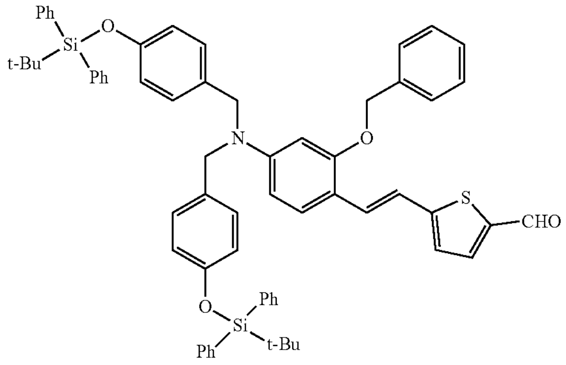

10-(E)a 6.07 g (6.09 mmol) of (Z/E)-3-(benzyloxy)-N,N-[bis[4-[(tert-butyldiphenylsilyl)ox y]benzyl]-4-[2-(thiophen-2-yl) vinyl]aniline (9-(Z/E)a) was dissolved in 60 mL of tetrahydrofuran under an argon atmosphere. To this, 4.6 mL (7.36 mmol) of n-butyllithium (1.6 mol solution in hexane) was added dropwise with cooling in a dry ice/acetone bath. After 35-minute stirring, 0.61 mL (7.91 mmol) of N,N-dimethylformamide was added dropwise. After 2.5-hour stirring, the bath was removed, the reaction mixture was heated, and 5 mL of water was added dropwise. After 30-minute stirring, the reaction mixture was poured into 150 mL of water, and ethyl acetate extraction was performed. The extract was washed with a saturated aqueous sodium chloride solution, dehydrated over anhydrous sodium sulfate, and concentrated. 6.47 g of the residual dark red oil was dissolved in 250 mL of ether. To this, 0.19 g of iodine flakes were added, and the mixture was stirred at room temperature for 30 minutes. The reaction mixture was washed with a 5% aqueous sodium hydrogen sulfite solution and subsequently with a saturated aqueous sodium chloride solution, dehydrated over anhydrous magnesium sulfate, and concentrated. The residue was purified by silica gel column chromatography (ethyl acetate/hexane=1/3) to give 5.5 g of the desired compound 10-(E)a as a red oil (yield: 88.1%).

The NMR measurement results of compound 10-(E)a are shown below.

$^1$H-NMR (600 MHz, $CDCl_3$) δ ppm: 1.08 (18H, s), 4.39 (4H, s), 4.85 (2H, s), 6.13 (1H, d, J=2.1 Hz), 6.29 (1H, dd, J=2.1 Hz, 8.9 Hz), 6.68 (4H, d, J=8.2 Hz), 6.85 (4H, d, J=8.2 Hz), 6.96 (1H, d, J=4.1 Hz), 7.08 (1H, d, J=16.5 Hz), 7.24-7.42 (19H, m), 7.59 (1H, d, J=4.1 Hz), 7.69-7.70 (8H, m), 9.78 (1H, s)

$^{13}$C-NMR (150 MHz, $CDCl_3$) δ ppm: 19.44, 26.49, 53.68, 70.27, 97.43, 105.65, 113.89, 116.89, 119.85, 124.64, 127.18, 127.48, 127.61, 127.74, 127.87, 128.55, 128.69, 129.01, 129.89, 130.07, 132.86, 135.49, 136.85, 137.68, 139.83, 150.93, 154.65, 155.46, 157.93, 182.32

(7 ) (E)-5-[2-(Benzyloxy)-4-[bis(4-hydroxybenzyl) amino]styryl]thiophene-2-carbaldehyde (compound 11-(E)a)

[Chem. 44]

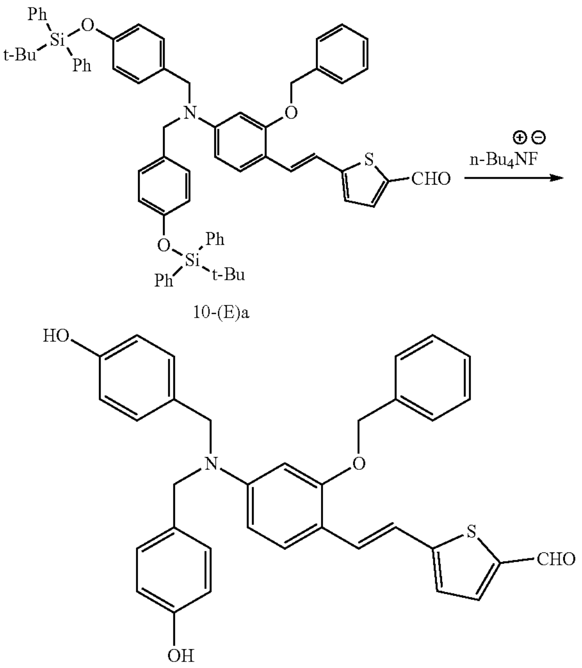

10-(E)a 11-(E)a 5.5 g (5.37 mmol) of (E)-5-[2-(benzyloxy)-4-[bis[4-[(tert-butyldiphenylsilyl)oxy]benzyl]amino]styryl]thiophene-2-carbaldehyde (10-(E)a) was dissolved in 30 mL of tetrahydrofuran. To this, 7.2 mL of tetrabutylammonium fluoride (1 mol solution in tetrahydrofuran) was added dropwise with stirring at room temperature. After 45-minute stirring, the reaction mixture was poured into 120 mL of water, and ethyl acetate extraction was performed. The extract was washed with a saturated aqueous sodium chloride solution, dehydrated over anhydrous sodium sulfate, and concentrated. To the residue, about 30 mL of a chloroform/methanol (30/1) mixture were added, and the precipitated crystals were collected and washed. As a result, 1.82 g of the desired compound 11-(E) a was obtained as crystals with a melting point of 151 to 152° C. The filtrate and the wash solution were combined and concentrated. The residual liquid was purified by silica gel column chromatography (chloroform/methanol=30/1) and then crystallized from chloroform to give 0.78 g of the desired compound. 2.6 g in total (yield: 88.4%)

The NMR measurement results of compound 11-(E)a are shown below.

$^1$H-NMR (600 MHz, DMSO-$d_6$) δ ppm: 4.56 (4H, s), 5.05 (2H, s), 6.36 (1H, dd, J=2.1 Hz, 9.0 Hz), 6.44 (1H, d, J=2.1 Hz), 6.71 (4H, d, J=8.2 Hz), 7.03 (4H, d, J=8.2 Hz), 7.14 (1H, d, J=4.1 Hz), 7.22 (1H, d, J=15.8 Hz), 7.33 (1H, d, J=15.8 Hz), 7.33-7.39 (6H, m), 7.88 (1H, d, J=4.1 Hz), 9.31 (2H, s), 9.79 (1H, s) 13C-NMR (150 MHz, DMSO-$d_6$) δ ppm: 53.17, 69.42, 97.26, 105.83, 112.52, 115.16, 116.17, 125.38, 127.41, 127.76, 127.88, 128.14, 128.30, 128.38, 128.44, 136.84, 139.12, 139.25, 150.35, 153.94, 156.16, 157.21, 183.07

(8) 2-[4-[(E)-2-[5-[(E)-2-(Benzyloxy)-4-[bis(4-hydroxybenzyl)amino]styryl]thiophen-2-yl]vinyl]-3-cyano-5-phenyl-5-(trifluoromethyl)furan-2(5H)-ylidene]malononitrile (EO-2)

[Chem. 45]

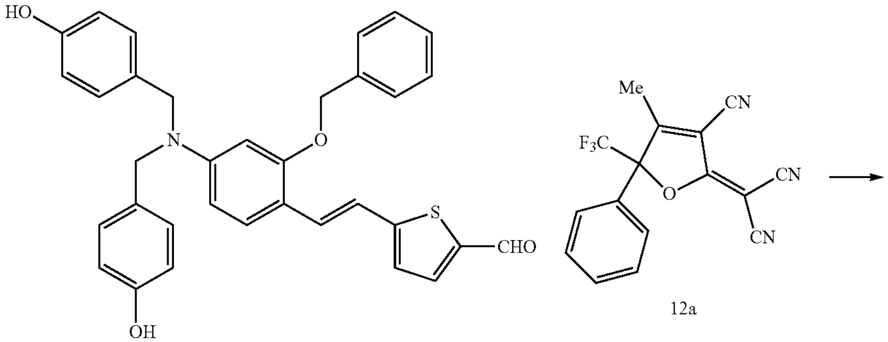

11-(E)a

12a

-continued

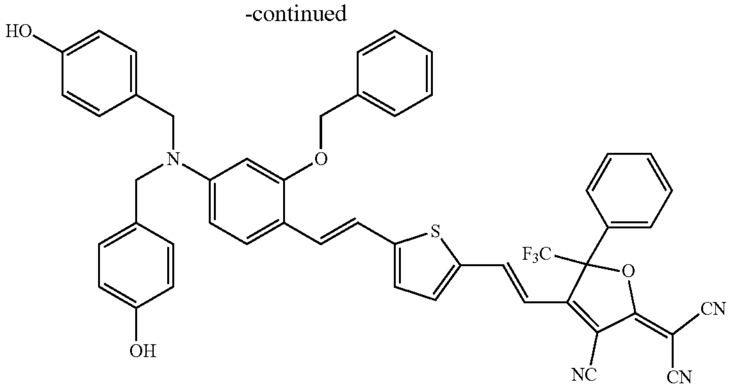

(EO-2)

1.88 g (3.43 mmol) of (E)-5-[2-(benzyloxy)-4-[bis(4-hydroxybenzyl)amino]styryl]thiophene-2-carbaldehyde (11-(E)a) and 1.25 g (3.96 mmol) of 2-(3-cyano-4-methyl-5-phenyl-5-trifluoromethyl-2(5H)-furanylidene)propanedinitrile (12a) were suspended in 25 mL of ethanol and 5 mL of tetrahydrofuran. The suspension was stirred with heating at 50° C. for 2 hours. The reaction mixture was concentrated to dryness. The resulting solid was purified by silica gel column chromatography (chloroform/methanol=20/1). The purified product was crystallized from about 40 mL of an ethyl acetate/hexane (3/2) mixture. The crystals were collected, washed, and dried. As a result, 2.3 g of the desired compound EO-2 was obtained as dark red-brown crystals with a melting point of 190 to 192° C. (yield: 79.3%).

The NMR measurement results of EO-2 are shown below.

$^1$H-NMR (600 MHz, DMSO-$d_6$) δ ppm: 4.59 (4H, s), 5.09 (2H, s), 6.41 (1H, dd, J=2.1 Hz, 8.9 Hz), 6.45 (1H, d, J=2.1 Hz), 6.53 (1H, d, J=15.1 Hz), 6.71 (4H, d, J=8.2 Hz), 7.02 (4H, d, J=8.2 Hz), 7.15 (1H, d, J=4.2 Hz), 7.31 (1H, d, J=15.8 Hz), 7.33-7.38 (5H, m), 7.43 (1H, d, J=8.9 Hz), 7.47 (1H, d, J=15.8 Hz), 7.60-7.73 (7H, m), 9.33 (1H, s)

$^{13}$C-NMR (150 MHz, DMSO-$d_6$) δ ppm: 53.14, 55.96, 69.48, 97.03, 106.40, 110.66, 110.92, 111.16, 111.80, 113.02, 115.20, 116.34, 121.80, 126.88, 127.35, 127.79, 127.90, 127.96, 128.38, 128.46, 129.06, 129.60, 129.78, 131.54, 131.72, 136.69, 137.22, 140.99, 141.53, 151.48, 156.25, 158.20, 158.49, 160.50, 175.74

Synthesis Example 11: Production Method of EO-Molecule (EO-3)

(1) 2,3-Dihydrothieno[3,4-b][1,4]dioxin-5-carbaldehyde (compound 2b)

[Chem. 46]

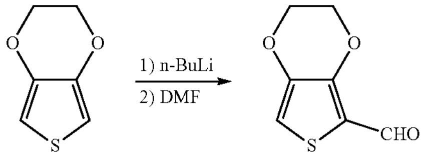

1b 2b 25.08 g (0.1764 mol) of 3,4-ethylene dioxythiophene (1b) was dissolved in 300 mL of tetrahydrofuran. To this, 120 mL (0.192 mol) of n-butyllithium (1.6 mol solution in hexane) was added dropwise with cooling in a dry ice/acetone bath at −70° C. After 35-minute stirring at the same temperature, 14.1 g (0.193 mol) of N,N-dimethylformamide was added dropwise. After further 45-minute stirring, the reaction mixture was heated, and 50 mL of water was added dropwise. After 15-minute stirring, the reaction mixture was poured into 150 mL of water, and ethyl acetate extraction was performed. The extract was washed with a saturated aqueous sodium chloride solution, dehydrated over anhydrous sodium sulfate, and concentrated. The precipitated crystals were recrystallized from 150 mL of ethyl acetate to give 23.8 g of the desired compound 2b as yellow crystals (yield: 79.3%).

[Chem. 47]

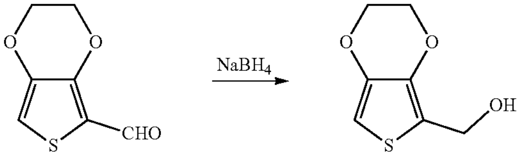

2b 3b (2) (2,3-Dihydrothieno[3,4-b][1,4]dioxin-5-yl) methanol (compound 3b)

4.64 g (27.26 mmol) of 2,3-dihydrothieno[3,4-b][1,4]dioxin-5-carbaldehyde (2b) was dissolved in 30 mL of ethanol. To this, 0.68 g (17.98 mmol) of sodium borohydride was added with cooling in a water bath over 20 minutes. After 30-minute stirring, 100 mL of water was added to the reaction mixture, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=3/2) to give 4.57 g of the desired compound 3b as colorless crystals with a melting point of 67 to 68° C. (yield: 97.3%)

The NMR measurement results of compound 3b are shown below.

$^1$H-NMR (600 MHz, $CDCl_3$) δ ppm: 1.87-1.89 (1H, m), 4.18-4.22 (4H, m), 4.66 (2H, d, J=5.5 Hz), 6.29 (1H, s)

$^{13}C$-NMR (150 MHz, $CDCl_3$) δ ppm: 56.19, 64.58, 64.71, 98.45, 116.03, 138.94, 141.45

(3) Diethyl [(2,3-dihydrothieno[3,4-b][1,4]dioxin-5-yl)methyl]phosphonate (compound 4b)

[Chem. 48]

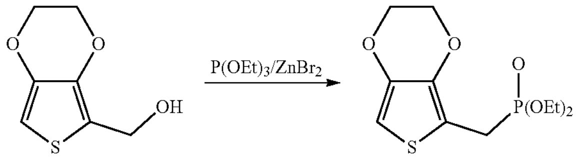

3b 4b 46.25 g (0.278 mol) of trimethyl phosphite and 11.86 g (0.069 mol) of (2,3-dihydrothieno[3,4-b][1,4]dioxin-5-yl) methanol (3b) were dissolved in 100 mL of dichloromethane. To this, 17.0 g (0.076 mol) of zinc bromide (99.9%) was added with stirring at room temperature. The mixture was stirred in an oil bath at 40° C. for 45 minutes and then cooled. The reaction mixture was poured into 250 mL of iced water and 15 mL of concentrated hydrochloric acid, and the mixture was stirred for 5 minutes. The organic layer was separated, washed with a saturated aqueous sodium chloride solution, and dried over anhydrous sodium sulfate. After Celite filtration, the filtrate was concentrated in vacuo, and the residual liquid was purified by silica gel column chromatography (chloroform/ethyl acetate=2/3) to give 9.71 g of the desired compound 4b (yield: 48.7%).

The NMR measurement results of compound 4b are shown below.

$^{1}H$-NMR (600 MHz, $CDCl_3$) δ ppm: 1.30 (6H, t, J=6.9 Hz), 3.21 (2H, d, J=20.6 Hz), 4.08-4.13 (4H, m), 4.17-4.21 (4H, m), 6.21 (1H, d, J=2.7 Hz)

$^{13}C$-NMR (150 MHz, $CDCl_3$) δ ppm: 16.40 (d, J=5.8 Hz), 23.98 (d, J=146.0 Hz), 62.31 (d, J=5.8 Hz), 64.64 (d, J=7.3 Hz), 97.68 (d, J=5.8 Hz), 106.16 (d, J=11.6 Hz), 139.35 (d, J=10.1 Hz), 141.15 (d)

(4 ) (E)-3-(Benzyloxy)-N,N-bis[2-[(tert-butyldiphenylsilyl)oxy]ethyl]-4-[2-(2,3-dihydrothieno[3,4-b][1,4]dioxin-5-yl)vinyl]aniline (compound 6-(E)b)

[Chem. 49]

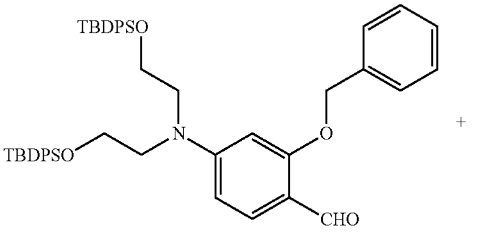

5b

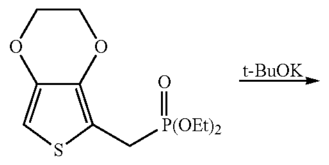

4b

-continued

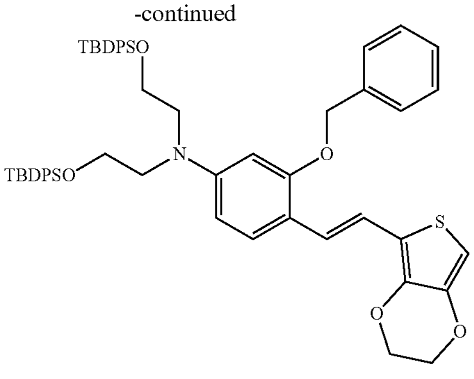

6-(E)b 4.63 g (5.84 mmol) of 2-(benzyloxy)-4-[bis[2-[(tert-butyldiphenylsilyl)oxy]ethyl]amino]benzaldehyde (5b) and 1.9 g (6.50 mmol) of diethyl[(2,3-dihydrothieno[3,4-b][1,4]dioxin-5-yl)methyl]phosphonate (4b) were dissolved in 40 mL of tetrahydrofuran under an argon atmosphere. To this, a solution of 0.78 g (6.95 mmol) of potassium tert-butoxide in 30 mL of tetrahydrofuran was added dropwise with cooling in a dry ice/acetone bath. After 1-hour stirring, the bath was removed, and the reaction mixture was gradually heated. This was poured into 200 mL of water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/2) to give 4.47 g of the desired compound 6-(E)b as an orange-red oil (yield: 82.2%).

The NMR measurement results of compound 6-(E)b are shown below.

$^{1}H$-NMR (600 MHz, $CDCl_3$) δ ppm: 1.03 (18H, s), 3.47 (4H, t, J=6.2 Hz), 3.70 (4H, t, J=6.2H), 4.20-4.21 (2H, m), 4.24-4.25 (2H, m), 4.92 (2H, s), 5.96 (1H, d, J=8.9 Hz), 6.03 (1H, s), 6.11 (1H, s), 7.00 (1H, d, J=16.5 Hz), 7.15 (1H, d, J=16.5 Hz), 7.18-7.41 (18H, m), 7.60-7.61 (8H, m) 13C-NMR (150 MHz, $CDCl_3$) δ ppm: 19.07, 26.81, 53.23, 60.95, 64.71, 64.76, 70.44, 95.82, 96.97, 104.85, 114.19, 114.91, 119.00, 121.93, 127.09, 127.45, 127.56, 127.70, 128.39, 129.71, 133.35, 135.53, 137.42, 137.70, 141.93, 148.21, 157.13

(5 ) (E)-7-[2-(Benzyloxy)-4-[bis[2-[(tert-butyldiphenylsilyl)oxy]ethyl]amino]styryl]-2,3-dihydrothieno[3,4-b][1,4]dioxin-5-carbaldehyde (compound 7-(E)b)

[Chem. 50]

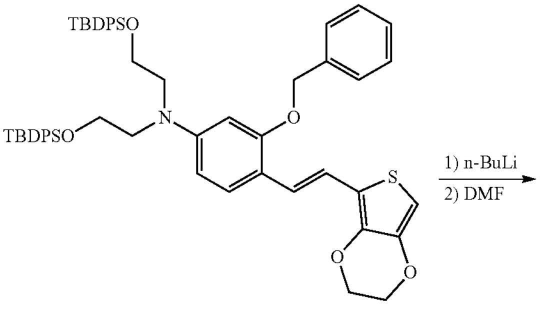

6-(E)b

-continued

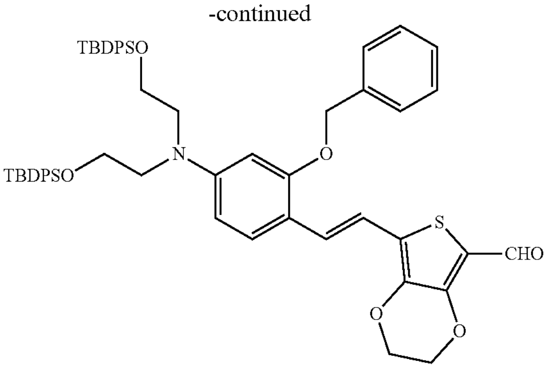

7-(E)b 6.64 g (7.14 mmol) of (E)-3-(benzyloxy)-N,N-bis[2-[(tert-butyldiphenylsilyl)oxy]ethyl]-4-[2-(2,3-dihydrothieno[3,4-b][1,4]dioxin-5-yl)vinyl]aniline (6-(E)b) was dissolved in 70 mL of tetrahydrofuran under an argon atmosphere. To this, 5.6 mL (8.96 mmol) of n-butyllithium (1.6 mol solution in hexane) was added dropwise with cooling in a dry ice/acetone bath. After 45-minute stirring, 0.64 g (8.77 mmol) of N,N-dimethylformamide was added dropwise. After 1-hour stirring, the bath was removed, the reaction mixture was heated, and 50 mL of water was added dropwise. After 25-minute stirring, ethyl acetate extraction was performed, and the extract was washed with a saturated aqueous sodium chloride solution. The washed extract was dehydrated over anhydrous sodium sulfate and concentrated. The residual oil was crystallized from an ethyl acetate/hexane mixture, and the crystals were collected by filtration. As a result, 6.27 g of the desired compound 7-(E)b was obtained as orange crystals with a melting point of 130 to 132° C. (yield: 91.7%).

The NMR measurement results of compound 7-(E)b are shown below.

$^1$H-NMR (600 MHz, $CDCl_3$) δ ppm: 1.03 (18H, s), 3.49 (4H, t, J=6.2 Hz), 3.71 (4H, t, J=6.2 Hz), 4.29-4.30 (2H, m), 4.35-4.36 (2H, m), 4.92 (2H, s), 5.98 (1H, d, J=9.0 Hz), 6.04 (1H, b), 7.03 (1H, d, J=16.5 Hz), 7.19-7.41 (19H, m), 7.59-7.60 (8H, m), 9.83 (1H, s)

$^{13}$C-NMR (150 MHz, $CDCl_3$) δ ppm: 19.07, 26.80, 53.19, 60.90, 64.42, 65.42, 70.31, 96.37, 104.91, 112.95, 113.69, 113.92, 127.14, 127.71, 127.76, 127.94, 128.49, 128.66, 129.75, 131.55, 133.25, 135.52, 136.97, 137.12, 148.62, 149.42, 157.99, 178.94

(6 ) (E)-7-[2-(Benzyloxy)-4-[bis(2-hydroxyethyl) amino] styryl]-2,3-dihydrothieno[3,4-b][1,4]dioxin-5-carbaldehyde (compound 8-(E)b)

[Chem. 51]

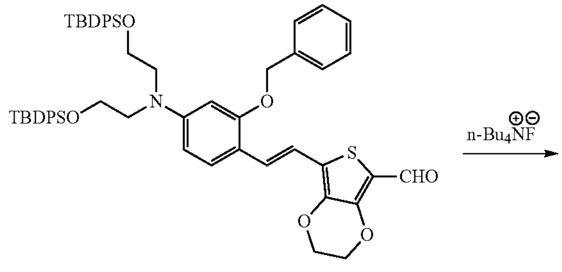

7-(E)b

-continued

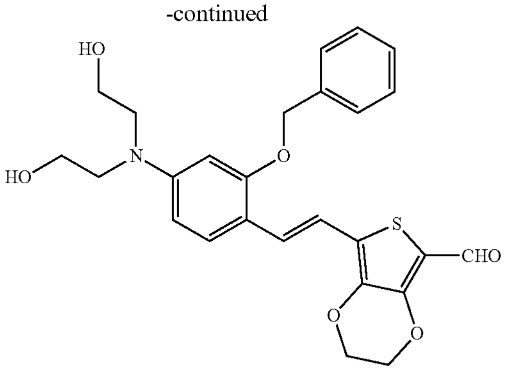

8-(E)b 7.32 g (7.64 mmol) of (E)-7-[2-(benzyloxy)-4-[bis[2-[(tert-butyldiphenylsilyl) oxy]ethyl]amino]styryl]-2,3-dihydrothieno[3,4-b][1,4]dioxin-5-carbaldehyde (7-(E)b) was dissolved in 30 mL of tetrahydrofuran. To this, 25 mL of tetrabutylammonium fluoride (1 mol solution in tetrahydrofuran) was added dropwise with stirring at room temperature. After 1-hour stirring, the reaction mixture was poured into 150 mL of water, and ethyl acetate extraction was performed. The extract was washed with a saturated aqueous sodium chloride solution, dehydrated over anhydrous sodium sulfate, and concentrated. The residue was purified by silica gel column chromatography (chloroform/methanol=10/1) to give 2.89 g of the desired compound 8-(E)b as a red oil (yield: 78.7%).

The NMR measurement results of compound 8-(E)b are shown below.

$^1$H-NMR (600 MHz, $CDCl_3$) δ ppm: 2.94 (2H, s), 3.57 (4H, t, J=4.8 Hz), 3.80 (4H, t, J=4.8 Hz), 4.28-4.30 (2H, m), 4.35-4.37 (2H, m), 5.14 (2H, s), 6.19 (1H, s), 6.30 (1H, d, J=8.2 Hz), 7.08 (1H, d, J=15.8 Hz), 7.32-7.47 (7H, m), 9.82 (1H, s)

$^{13}$C-NMR (150 MHz, $CDCl_3$) δ ppm: 55.15, 60.70, 64.45, 65.42, 70.51, 97.74, 105.69, 113.83, 114.19, 114.85, 127.04, 127.42, 127.93, 128.50, 128.68, 131.07, 137.08, 137.41, 149.41, 157.83, 179.08

(7) 2-[4-[(E)-2-[7-[(E)-2-(Benzyloxy)-4-[bis(2-hydroxyethyl)amino]styryl]-2,3-dihydrothieno[3,4-b][1,4]dioxin-5-yl]vinyl]-3-cyano-5-phenyl-5-(trifluoromethyl) furan-2(5H)-ylidene]malononitrile (EO-3)

[Chem. 52]

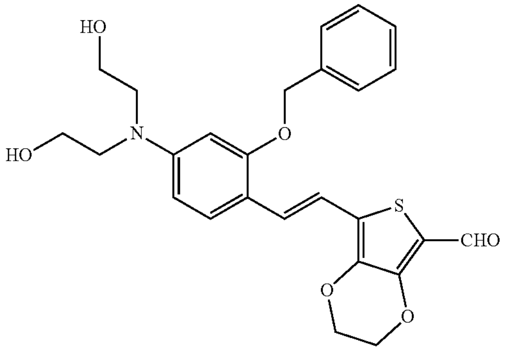

+

8-(E)b

-continued

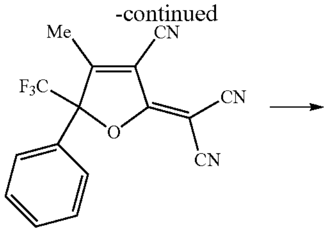

9b

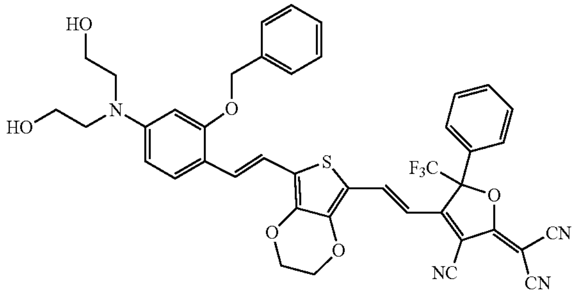

(EO-3)

1.3 g (2.70 mmol) of (E)-7-[2-(benzyloxy)-4-[bis(2-hydroxyethyl)amino]styryl]-2,3-dihydrothieno[3,4-b][1,4]dioxin-5-carbaldehyde (8-(E)b) and 0.94 g (2.98 mmol) of 2-(3-cyano-4-methyl-5-phenyl-5-trifluoromethyl-2(5H)-furanylidene)propanedinitrile (9b) were dissolved in 40 mL of ethanol. The solution was heated to 50° C. and stirred at the same temperature for 1.5 hours. The reaction mixture was ice-cooled, and the precipitated crystals were collected by filtration and washed with ethanol. The crystals were purified by silica gel column chromatography (chloroform/methanol=10/1) and then washed with ethanol. As a result, 1.6 g of the desired compound EO-3 was obtained as dark red-brown crystals with a melting point of 160 to 163° C. (yield: 76.3%).

The NMR measurement results of EO-3 are shown below.

$^1$H-NMR (600 MHz, $CDCl_3$) δ ppm: 2.88 (2H, s), 3.61 (4H, t, J=4.8 Hz), 3.81 (4H, t, J=4.8 Hz), 4.27 (2H, s), 4.36 (2H, s), 5.18 (2H, s), 6.19 (1H, s), 6.30 (1H, b), 6.33 (1H, d, J=8.3 Hz), 7.16 (1H, d, J=15.8 Hz), 7.33-7.53 (12H, m), 7.95 (1H, b)

$^{13}$C-NMR (150 MHz, $CDCl_3$) δ ppm: 55.09, 60.49, 64.42, 65.98, 70.51, 97.32, 106.22, 111.57, 112.05, 113.25, 126.75, 127.08, 128.08, 128.71, 129.53, 129.81, 130.45, 131.15, 136.78, 137.76, 150.95, 158.97, 176.00

Synthesis Example 12: Production method of EO-molecule (EO-4) 2-[4-[(E)-2-[7-[(E)-2-(Benzyloxy)-4-[bis(2-hydroxyethyl)amino]styryl]-2,3-dihydrothieno[3,4-b][1,4]dioxin-5-yl]vinyl]-3-cyano-5,5-dimethylfuran-2(5H)-ylidene]malononitrile (EO-4)

[Chem. 53]

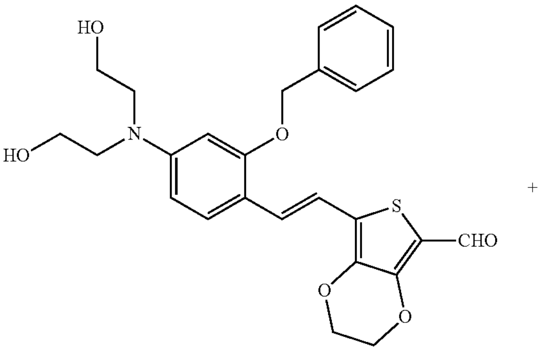

8-(E)b

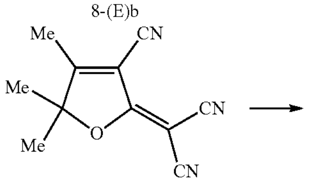

10b

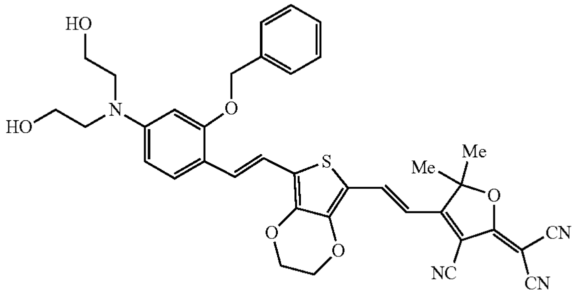

(EO-4)

1.4 g (2.91 mmol) of (E)-7-[2-(benzyloxy)-4-[bis(2-hydroxyethyl)amino] styryl]-2,3-dihydrothieno[3,4-b][1,4]dioxin-5-carbaldehyde (8-(E)b) and 0.69 g (3.46 mmol) 2-(3-cyano-4,5,5-trimethyl-2(5H)-furanylidene)propanedinitrile (10b) were dissolved in 40 mL of ethanol. To this, 225 mg of ammonium acetate was added, and the mixture was heated to 50° C. and stirred at the same temperature overnight. The reaction mixture was ice-cooled, and the precipitated crystals were collected by filtration and washed with ethanol. As a result, 1.5 g of the desired compound EO-4 was obtained as dark red-brown crystals with a melting point of 258 to 259° C. (yield: 77.8%).

The NMR measurement results of EO-4 are shown below.

$^1$H-NMR (600 MHz, $CDCl_3$) δ ppm: 1.72 (6H, s), 2.64 (2H, s), 3.60 (4H, t, J=4.8 Hz), 3.81 (4H, t, J=4.8 Hz), 4.31 (2H, s), 4.41 (2H, s), 5.20 (2H, s), 6.20 (1H, s), 6.33 (1H, d, J=8.3 Hz), 6.48 (1H, b), 7.15 (1H, d, J=15.8 Hz), 7.34-7.48 (7H, m), 7.70 (1H, b)

Synthesis Example 13: Production method of EO molecule (EO-5)

[Chem. 54]

(EO-5)

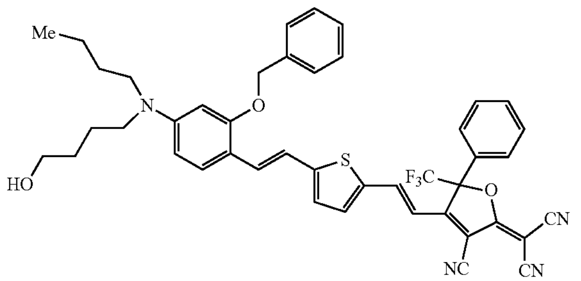

(1) N-Butyl-4-[(tert-butyldiphenylsilyl)oxy]-1-butylamine (compound 2c)

[Chem. 55]

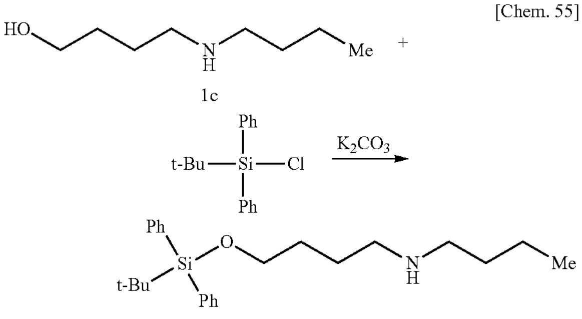

1c

2c 26.4 g (0.182 mol) of 4-(butylamino)-1-butanol (1c) was dissolved in 350 mL of acetonitrile, and 50.0 g (0.362 mol) of anhydrous potassium carbonate was added. To this, 50.45 g (0.184 mol) of tert-butylchlorodiphenylsilane was added dropwise with stirring at room temperature. After overnight stirring at the same temperature, the reaction mixture was filtered, and the filtrate was concentrated. The residual liquid was purified by vacuum distillation to give 59.41 g of the desired compound 2c as a colorless oil with a boiling point of 178 to 190° C./1 mmHg (yield: 85.2%)

(2) 3-Benzyloxy-N-butyl-N-[4-[(tert-butyldiphenylsilyl)oxy]buty 1]aniline (compound 4c)

[Chem. 56]

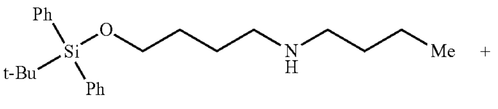

2c

-continued

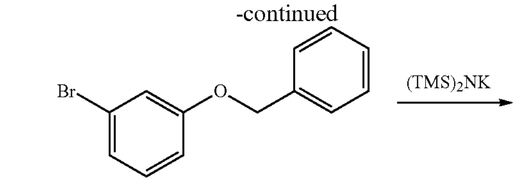

3c

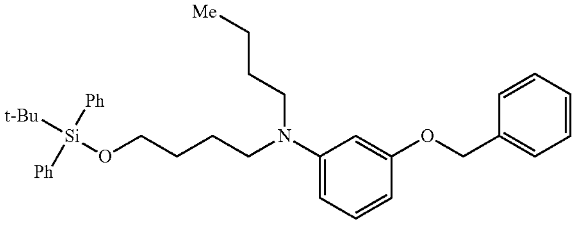

4c 29.42 g (0.0767 mol) of N-butyl-4-[(tert-butyldiphenylsilyl)oxy]-1-butylamine (2c) and 19.16 g (0.0728 mol) of 1-benzyloxy-3-bromobenzene (3c) were dissolved in 300 mL of toluene. To this, 17.43 g (0.0874 mol) of potassium bis(trimethylsilyl)amide was added with stirring at room temperature. The mixture was stirred in an oil bath at 110° C. for 5 hours and then cooled. This was added to 200 mL of water, and the mixture was stirred. The resulting layers were separated, and the aqueous layer was subjected to extraction with 150 mL of toluene. The organic layers were combined and washed with a saturated aqueous sodium chloride solution. The washed organic layer was dehydrated over anhydrous sodium sulfate and concentrated to give 44.69 g of the desired compound 4c as an oil (crude yield: 102.8%).

(3) 4-[[(3-Benzyloxy)phenyl] (butyl)amino]-1-butanol (compound 5c)

[Chem. 57]

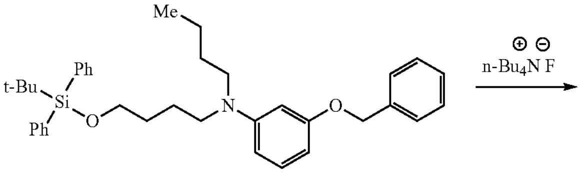

4c

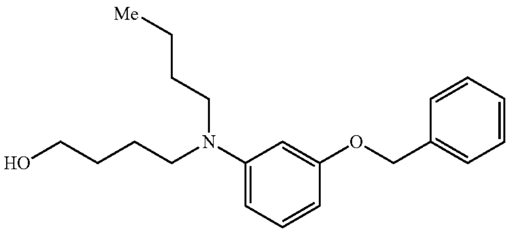

5c 17.98 g (31.77 mmol) of 3-benzyloxy-N-butyl-N-[4-[(tert-butyldiphenylsilyl)oxy]buty 1] (4c) was dissolved in 70 mL of tetrahydrofuran. To this, 48 mL of tetrabutylammonium fluoride (1 mol solution in tetrahydrofuran) was added dropwise with stirring at room temperature. After 2-hour stirring, the reaction mixture was poured into 250 mL of water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=3/2) to give 9.93 g of the desired compound 5c as a light-yellow oil (yield: 95.5%).

$^1$H-NMR (600 MHz, $CDCl_3$) δ ppm: 0.93 (3H, t, J=7.7 Hz), 1.28-1.35 (2H, m), 1.41 (1H, s), 1.51-1.65 (6H, m), 3.22 (2H, t, J=7.7 Hz), 3.26 (2H, t, J=6.6 Hz), 3.66 (2H, s), 5.05 (2H, s), 6.27 (1H, d, J=2.2 Hz), 6.30 (2H, dd, J=2.2 Hz, 8.3 Hz), 7.12 (1H, t, J=8.3 Hz), 7.30-7.45 (5H, m)

(4) 4-[[3-(Benzyloxy)phenyl] (butyl)amino]butyl acetate (compound 6c)

[Chem. 58]

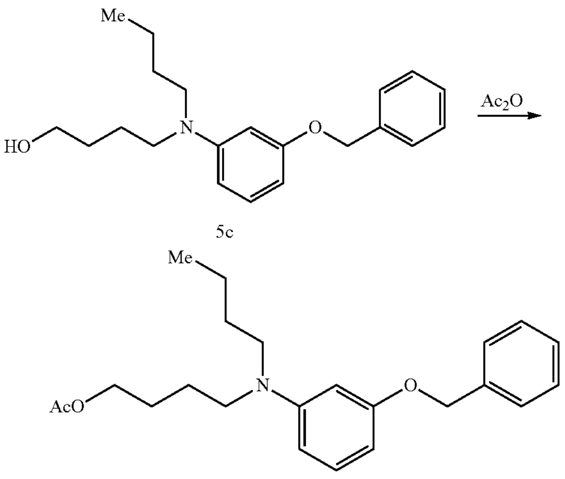

5c

6c 9.93 g (30.3 mmol) of 4-[[(3-benzyloxy)phenyl] (butyl) amino]-1-butanol (5c) was dissolved in 14 mL of acetic anhydride. The solution was heated to 80° C. and stirred at the same temperature for 1.5 hours. The reaction mixture was cooled and then poured into 100 mL of water and 75 mL of ether, and the mixture was stirred for 45 minutes. The resulting layers were separated, and the aqueous layer was subjected to extraction with 75 mL of ether. The organic layers were combined and washed successively with a saturated aqueous sodium chloride solution and a saturated aqueous sodium bicarbonate solution. The washed organic layer was dehydrated over anhydrous magnesium sulfate and concentrated. The residual liquid was purified by silica gel column chromatography (ethyl acetate/hexane=1/2) to give 10.56 g of the desired compound 6c as a pale yellow oil (yield: 94.3%).

The NMR measurement results of compound 6c are shown below.

$^1$H-NMR (600 MHz, $CDCl_3$) δ ppm: 0.93 (3H, t, J=7.1 Hz), 1.29-1.35 (2H, m), 1.51-1.56 (2H, m), 1.62-1.63 (4H, m), 2.04 (3H, s), 3.22 (2H, t, J=7.7 Hz), 3.25 (2H, t, J=7.1 Hz), 4.07 (2H, t, J=6.0 Hz), 5.04 (2H, s), 6.25-6.30 (3H, m), 7.10 (1H, dt, J=1.1 Hz, 8.2 Hz), 7.30-7.32 (1H, m), 7.36-7.39 (2H, m), 7.43-7.44 (2H, m)

$^{13}$C-NMR (150 MHz, $CDCl_3$) δ ppm: 14.01, 20.3, 21.0, 23.8, 26.2, 29.4, 50.6, 50.9, 64.3, 69.9, 99.4, 101.1, 105.3, 127.5, 127.8, 128.6, 129.9, 137.5, 149.4, 160.2, 171.2

(5) 4-[[3-(Benzyloxy)-4-formylphenyl] (butyl)amino]butyl acetate (compound 7c)

[Chem. 59]

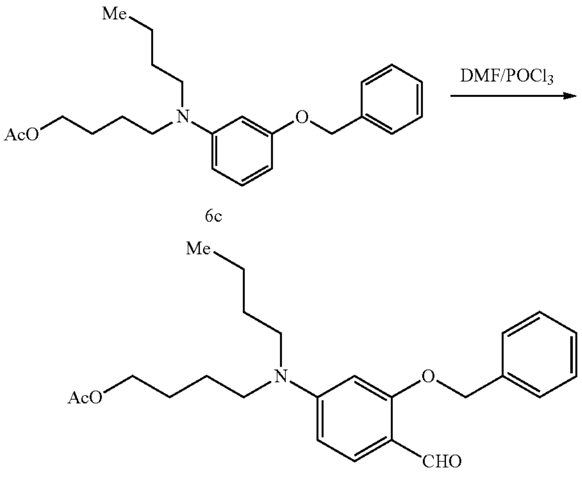

6c

7c 12.0 g (0.078 mol) of phosphorus oxychloride was added dropwise over 10 minutes to 70 mL of N,N-dimethylformamide with stirring under ice-cooling (at a temperature of 3 to 5° C.). After 10 minutes, the ice bath was removed, and the reaction mixture was heated to 12° C. and stirred at the same temperature for 5 minutes. The reaction mixture was ice-cooled again, and a solution of 28.49 g (0.077 mol) of 4-[[3-(benzyloxy)phenyl] (butyl)amino]butyl acetate (6c) in 25 mL of N,N-dimethylformamide was added dropwise. After 30 minutes, the ice bath was removed, and the reaction mixture was gradually heated to 70° C. and stirred at the same temperature for 2 hours. To the reaction mixture under cooling in an ice bath, 125 mL of a 20% aqueous sodium acetate solution was added dropwise, and the mixture was stirred for 35 minutes. Ethyl acetate extraction was performed, and the extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residual liquid was purified by silica gel column chromatography (ethyl acetate/hexane=2/3) to give 27.48 g of the desired compound 7c as a yellow oil (yield: 89.7%).

(6) 2-Benzyloxy-4-[butyl(4-hydroxybutyl)amino]benzaldehyde (compound 8c)

[Chem. 60]

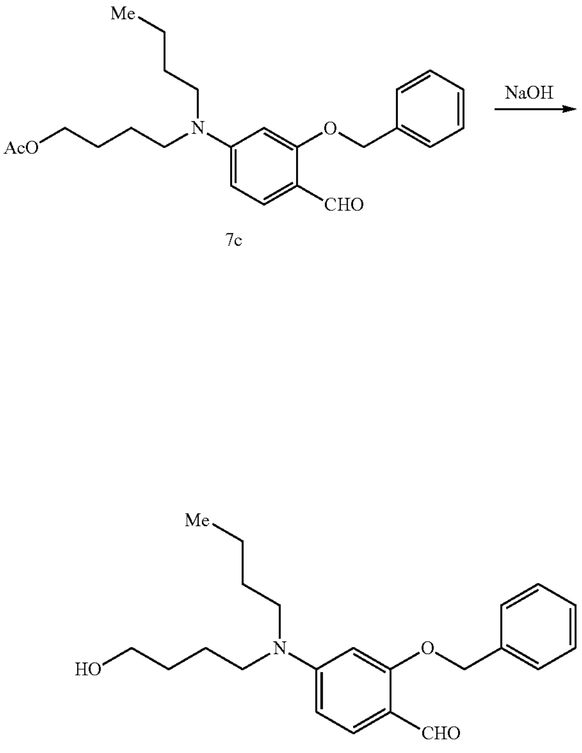

7c

8c 2.14 g (5.38 mmol) of 4-[[3-(benzyloxy)-4-formylphenyl](butyl)amino]butyl acetate (7c) was dissolved in 10 mL of ethanol. To this, 8 mL of a 10% aqueous sodium hydroxide solution was added, and the mixture was stirred at room temperature for 30 minutes. The reaction mixture was poured into 100 mL of water, and chloroform extraction was performed. The extract was washed with a saturated aqueous sodium chloride solution, dehydrated over anhydrous sodium sulfate, and concentrated. The residual liquid was purified by silica gel column chromatography (chloroform/methanol=10/1) to give 1.63 g of the desired compound 8c as a yellow liquid (yield: 85.2%).

The NMR measurement results of compound 8c are shown below.

$^1$H-NMR (600 MHz, $CDCl_3$) δ ppm: 0.94 (3H, t, J=7.7 Hz), 1.29-1.35 (2H, m), 1.50-1.66 (6H, m), 3.27 (2H, t, J=7.7 Hz), 3.32 (2H, t, J=7.7 Hz), 3.66 (2H, t, J=6.0 Hz), 5.18 (2H, s), 6.03 (1H, d, J=2.2 Hz), 6.26 (1H, dd, J=2.2 Hz, 8.8 Hz), 7.31-7.43 (5H, m), 7.72 (1H, d, J=8.8 Hz), 10.24 (1H, s)

$^{13}$C-NMR (150 MHz, $CDCl_3$) δ ppm: 14.0, 20.3, 23.8, 29.5, 30.0, 51.0, 51.1, 62.5, 70.2, 94.6, 104.8, 114.6, 127.0, 128.1, 128.8, 130.4, 136.9, 154.16, 163.3, 187.2

(7) 2-Benzyloxy-4-[butyl[4-[(tert-butyldiphenylsilyl)oxy]butyl]amino]benzaldehyde (compound 9c)

[Chem. 61]

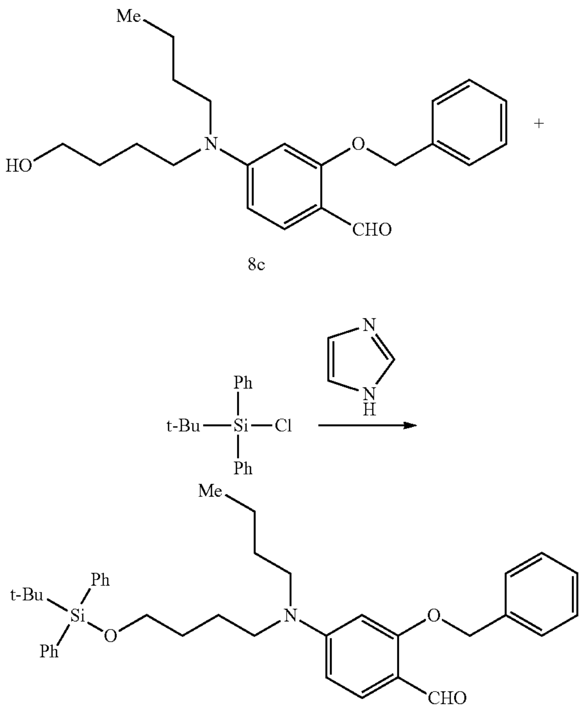

8c

9c 1.63 g (4.59 mmol) of 2-benzyloxy-4-[butyl(4-hydroxybutyl)amino]benzaldehyde (8c) and 1.2 g (17.63 mmol) of imidazole were dissolved in 20 mL of N,N-dimethylformamide. To this, 1.27 g (4.62 mmol) of tert-butylchlorodiphenylsilane was added dropwise with stirring at room temperature. After 2-hour stirring, the reaction mixture was added to 100 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (ethyl acetate/hexane=1/3) to give 2.08 g of the desired compound 9c as a colorless oil (yield: 76.5%).

The NMR measurement results of compound 9c are shown below.

$^1$H-NMR (600 MHz, $CDCl_3$) δ ppm: 0.94 (3H, t, J=7.7 Hz), 1.29-1.35 (2H, m), 1.49-1.54 (2H, m), 1.58-1.64 (4H, m), 2.05 (3H, s), 3.26 (2H, t, J=7.7 Hz), 3.31 (2H, t, J=7.7 Hz), 4.07 (2H, t, J=6.0 Hz), 5.18 (2H, s), 6.01 (1H, d, J=2.2 Hz), 6.25 (1H, dd, J=2.2 Hz, 8.8 Hz), 7.33 (1H, t, J=7.1 Hz), 7.38-7.44 (4H, m), 7.73 (1H, d, J=8.8 Hz), 10.25 (1H, s) 13C-NMR (150 MHz, $CDCl_3$) δ ppm: 13.7, 20.0, 20.7, 23.6, 25.9, 29.1, 50.4, 50.7, 63.7, 69.9, 94.3, 104.5, 114.4, 126.6, 127.8, 128.5, 130.1, 136.5, 153.6, 162.9, 170.8, 186.9

(8) 3-Benzyloxy-N-butyl-N-[4-[(tert-butyldiphenylsilyl)oxy]buty 1]-4-[2-(thiophen-2-yl)vinyl]aniline (compound 11-(Z/E)c)

[Chem. 62]

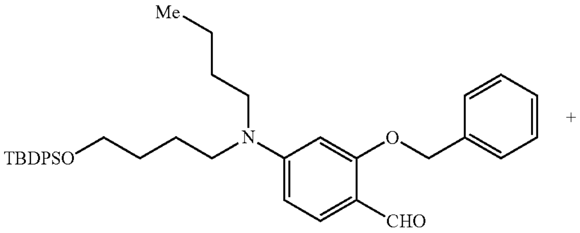

9c

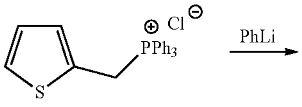

10c

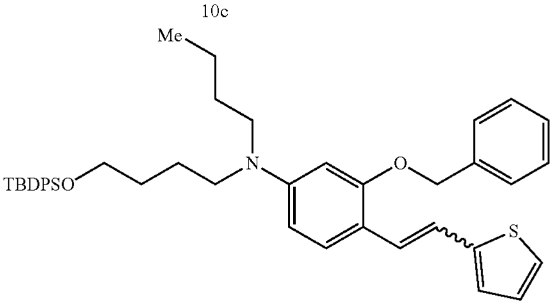

11-(Z/E)c 1.7 g (3.83 mmol) of phenyllithium (19% solution in dibutyl ether) was added to 20 mL of tetrahydrofuran under an argon atmosphere. To this, 1.38 g (3.49 mmol) of 2-thenyl triphenyl phosphonium chloride (10c) was added under ice-cooling over 5 minutes. After 10-minute stirring, a solution of 2.07 g (3.49 mmol) of 2-benzyloxy-4-[butyl[4-[(tert-butyldiphenylsilyl)oxy]butyl]amino]benzaldehyde (9c) in 50 mL of tetrahydrofuran was added dropwise. After 2-hour stirring under ice-cooling, the reaction mixture was poured into 150 mL of water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/4) to give 2.03 g of the desired compound 11-(Z/E)c as a light-brown oil (yield: 86.4%).

(9) 5-[(Z/E)-2-(Benzyloxy)-4-[butyl[4-[(tert-butyldiphenylsilyl)oxy]butyl]amino]styryl]thiophene-2-carbaldehyde (compound 12-(Z/E)c)

[Chem. 63]

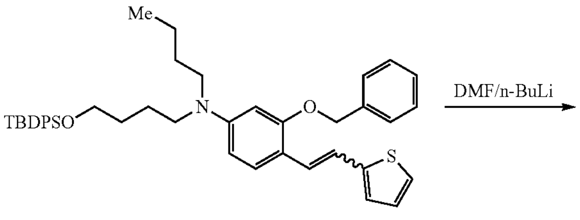

11-(Z/E)c

-continued

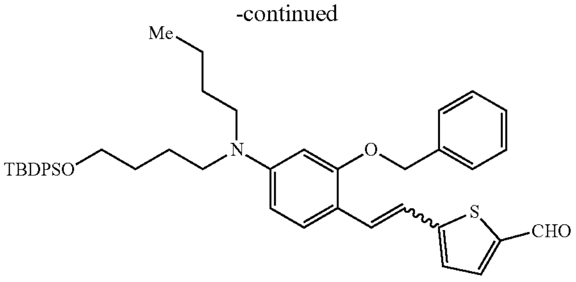

12-(Z/E)c 2.02 g (3.0 mmol) of 3-benzyloxy-N-butyl-N-[4-[(tert-butyldiphenylsilyl)oxy]buty 1]-4-[2-(thiophen-2-yl)vinyl]aniline (11-(Z/E)c) was dissolved in 20 mL of tetrahydrofuran under an argon atmosphere. To this, 2.8 mL (4.48 mmol) of n-butyllithium (1.6 mol solution in hexane) was added dropwise with cooling in a dry ice/acetone bath over 15 minutes. After 35-minute stirring, 0.3 mL (3.9 mmol) of N,N-dimethylformamide was added dropwise, and the mixture was stirred for 1.5 hours. The bath was removed, the reaction mixture was heated, and 10 mL of water was added dropwise. The mixture was stirred for 30 minutes. The reaction mixture was poured into 100 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (ethyl acetate/hexane=1/4) to give 1.43 g of the desired compound 12-(Z/E)c as a red-orange oil (yield: 68.1%).

(10 ) (E)-5-[2-(Benzyloxy)-4-[butyl[4-[(tert-butyldiphenylsilyl)oxy]butyl]amino]styryl]thiophene-2-carbaldehyde (compound 12-(E)c)

[Chem. 64]

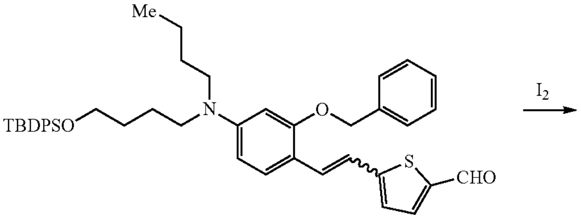

12-(Z/E)c

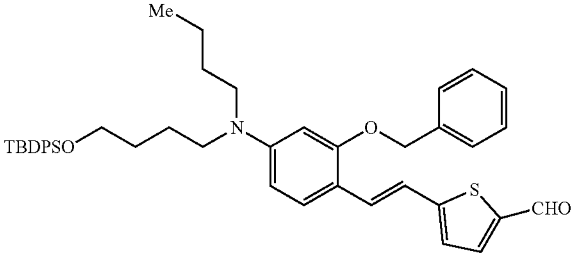

12-(E)c 1.43 g (2.04 mmol) of 5-[(Z/E)-2-(benzyloxy)-4-[butyl[4-[(tert-butyldiphenylsilyl)oxy]butyl]amino]styryl]thiophene-2-carbaldehyde (12-(Z/E)c) was dissolved in 150 mL of ether. To this, 50 mg of iodine flakes were added. After 30-minute stirring at room temperature, the reaction mixture was washed with 100 mL of a 5% aqueous sodium hydrogen sulfite solution. The reaction mixture was further washed with a saturated aqueous sodium chloride solution, dehydrated over anhydrous magnesium sulfate, and concentrated. The residue was purified by silica gel column chromatography (hexane/ethyl acetate=3/1) to give 1.21 g of the desired compound 12-(E)c as a red oil (yield: 84.6%).

The NMR measurement results of compound 12-(E)c are shown below.

$^1$H-NMR (600 MHz, $CDCl_3$) δ ppm: 0.93 (3H, t, J=7.7 Hz), 1.04 (9H, s), 1.26-1.31 (2H, m), 1.47-1.55 (4H, m), 1.60-1.64 (2H, m), 3.21 (2H, t, J=7.7 Hz), 3.24 (2H, t, J=7.7 Hz), 3.67 (2H, J=6.0 Hz), 5.13 (2H, s), 6.10 (1H, d, J=2.2 Hz), 6.25 (1H, dd, J=2.2 Hz, 8.8 Hz), 6.98 (1H, d, J=3.8 Hz), 7.10 (1H, d, J=15.9 Hz), 7.29-7.43 (12H, m), 7.46 (1H, d, J=15.9 Hz), 7.60 (1H, d, J=3.8 Hz), 7.65-7.66 (4H, m), 9.79 (1H, s) 13C-NMR (150 MHz, $CDCl_3$) δ ppm: 14.0, 19.2, 20.3, 23.9, 26.9, 29.5, 30.0, 50.9, 51.0, 63.6, 70.4, 96.5, 105.0, 112.8, 116.3, 124.4, 127.0, 127.7, 127.9, 128.7, 128.9, 129.3, 129.6, 133.9, 135.6, 137.2, 137.7, 139.7, 149.8, 155.7 and 158.3, 182.3

(11 ) (E)-5-[2-(Benzyloxy)-4-[butyl(4-hydroxybutyl)amino]styryl]thiophene-2-carbaldehyde (compound 13-(E)c)

[Chem. 65]

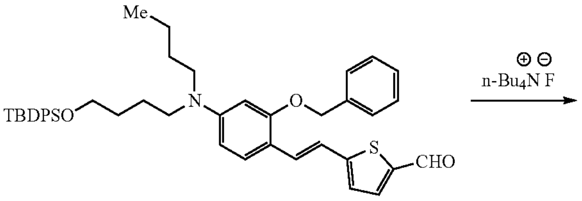

12-(E)c

-continued

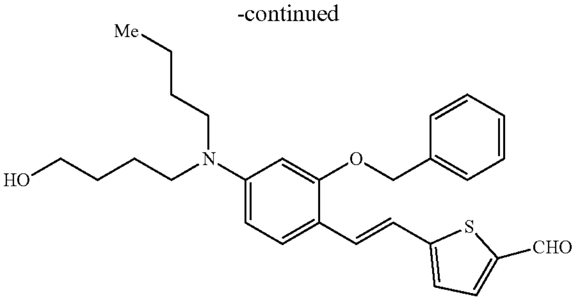

13-(E)c 1.2 g (1.71 mmol) of (E)-5-[2-(benzyloxy)-4-[butyl[4-[(tert-butyldiphenylsilyl)oxy]butyl]amino]styryl]thiophene-2-carbaldehyde (12-(E)c) was dissolved in 10 mL of tetrahydrofuran. To this, 7.6 mL of tetrabutylammonium fluoride (1 mol solution in tetrahydrofuran) was added dropwise with stirring at room temperature. After 1.5-hour stirring, the reaction mixture was poured into 80 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (chloroform/methanol=25/1, subsequently ethyl acetate/hexane=1/1) to give 554 mg of the desired compound 13-(E)c as red crystals (yield: 70.1%).

The NMR measurement results of compound 13-(E)c are shown below.

$^1$H-NMR (600 MHz, $CDCl_3$) δ ppm: 0.93 (3H, t, J=7.7 Hz), 1.28-1.34 (2H, m), 1.48-1.63 (6H, m), 3.24 (2H, t, J=7.7 Hz), 3.28 (2H, t, J=7.7 Hz), 3.65 (2H, J=6.0 Hz), 5.17 (2H, s), 6.13 (1H, d, J=2.2 Hz), 6.27 (1H, dd, J=2.2 Hz, 8.8 Hz), 6.98 (1H, d, J=3.8 Hz), 7.12 (1H, d, J=15.9 Hz), 7.32-7.48 (7H, m), 7.60 (1H, d, J=3.8 Hz), 9.79 (1H, s)

$^{13}$C-NMR (150 MHz, $CDCl_3$) δ ppm: 14.0, 20.3, 23.8, 29.5, 30.1, 50.9, 51.0, 62.6, 70.4, 96.6, 105.1, 113.0, 116.4, 124.5, 127.0, 127.9, 128.7, 128.9, 129.2, 137.2, 137.7, 139.7, 149.8, 155.7, 158.3, 182.3

(12) 2-[4-[(E)-2-[5-[(E)-2-(Benzyloxy)-4-[butyl(4-hydroxybutyl)amino]styryl]thiophen-2-yl]vinyl]-3-cyano-5-phenyl-5-(trifluoromethyl)furan-2(5H)-ylidene]malononitrile (EO-5)

[Chem. 66]

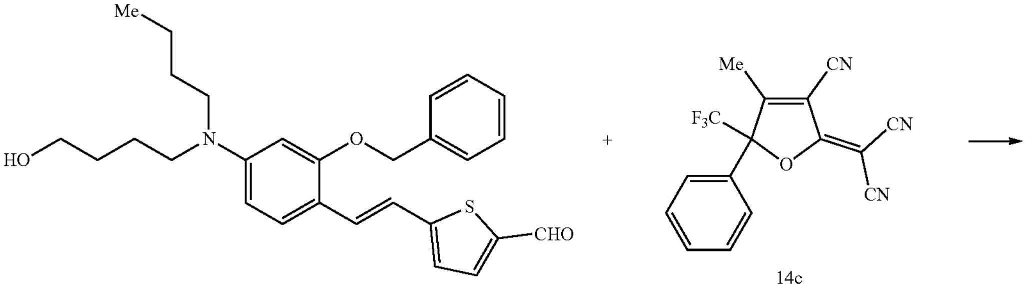

14c 13-(E)c

-continued

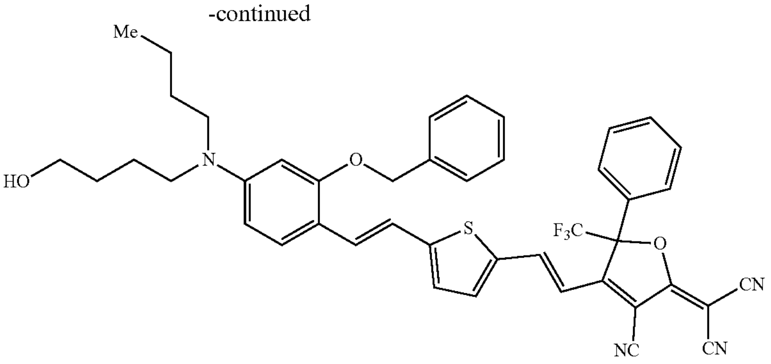

(EO-5)

155 mg (0.33 mmol) of (E)-5-[2-(benzyloxy)-4-[butyl(4-hydroxybutyl)amino]styryl]thiophene-2-carbaldehyde (13-(E)c) and 116 mg (0.37 mmol) of 2-(3-cyano-4-methyl-5-phenyl-5-trifluoromethyl-2(5H)-furanylidene) propanedinitrile (14c) were dissolved in 8 mL of ethanol. The solution was heated to 65° C. and stirred at the same temperature for 1 hour. The resulting tar-like substance was separated by decantation and purified by silica gel column chromatography (chloroform/methanol=10/1). The purified product was crystallized from methanol, and the crystals were collected by filtration. As a result, 153 mg of the title compound (EO-5) was obtained as dark-brown crystals with a melting point of 181 to 183° C. (yield: 60.2%).

The NMR measurement results of EO-5 are shown below.

$^1$H-NMR (600 MHz, $CDCl_3$) δ ppm: 0.93 (3H, t, J=7.1 Hz), 1.29-1.34 (2H, m), 1.48-1.64 (6H, m), 3.26 (2H, t, J=7.7 Hz), 3.31 (2H, t, J=7.1 Hz), 3.66 (2H, t, J=6.0 Hz), 5.21 (2H, s), 6.11 (1H, s), 6.28 (1H, d, J=8.8 Hz), 6.55 (1H, d, J=14.9 Hz), 6.94 (1H, d, J=3.8 Hz), 7.14 (1H, d, J=15.9 Hz), 7.20 (1H, d, J=3.8 Hz), 7.33-7.56 (12H, m), 7.78 (1H, d, J=14.9 Hz)

$^{13}$C-NMR (150 MHz, $CDCl_3$) δ ppm: 13.9, 20.3, 23.8, 29.5, 30.0, 51.0, 57.5, 62.5, 70.4, 96.2, 105.5, 110.9, 111.1, 111.2, 111.3, 113.0, 116.1, 122.3, 126.8, 126.9, 127.4, 128.1, 128.7, 129.7, 129.8, 129.9, 131.5, 132.7, 137.0, 137.8, 140.1, 141.6, 150.9, 159.2, 159.5, 161.7, 175.5

Synthesis Example 14: Production method of EO molecule (EO-6)

[Chem. 67]

(EO-6)

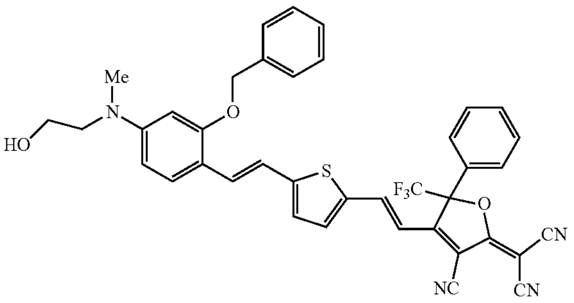

(1) 2-[(tert-Butyldiphenylsilyl)oxy]ethylmethylamine (compound 2d)

[Chem. 68]

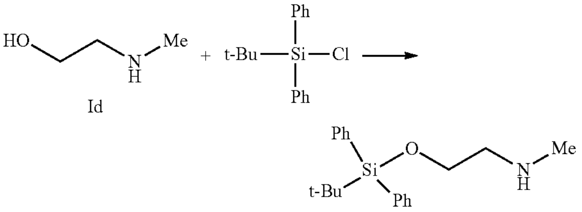

Id

2d 13.8 g (0.184 mol) of 2-methylaminoethanol (1d) and 50.0 g (0.362 mol) of anhydrous potassium carbonate were added to 300 mL of acetonitrile. To this, 50.5 g (0.184 mol) of tert-butylchlorodiphenylsilane was added dropwise with stirring at room temperature, and the mixture was stirred at room temperature for 18 hours. The reaction mixture was filtered, and the filtrate was concentrated. The residual liquid was purified by vacuum distillation to give 49.3 g of the desired compound 2d as a colorless oil with a boiling point of 153 to 158° C./1 mmHg (yield: 85.5%)

(2) 3-Benzyloxy-N-[2-(tert-butyldiphenylsilyl)oxy]ethyl-N-methylaniline (compound 4d)

[Chem. 69]

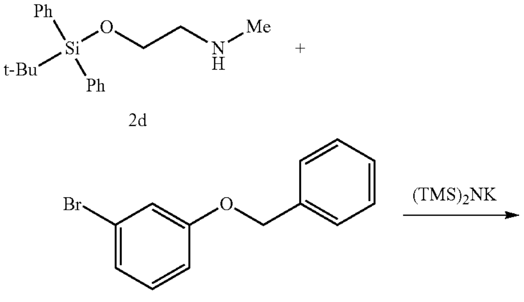

2d

3d

-continued

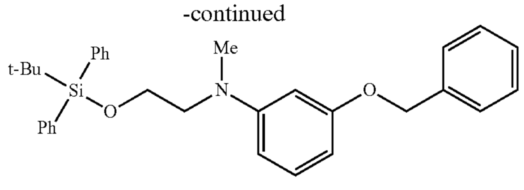

4d 51.3 g (0.164 mol) of 2-[(tert-butyldiphenylsilyl)oxy] ethylmethylamine (2d) and 40.9 g (0.155 mol) of 1-benzyloxy-3-bromobenzene (3d) were dissolved in 500 mL of toluene. To this, 37.1 g (0.186 mol) of potassium bis (trimethylsilyl) amide was added with stirring at room temperature. The mixture was stirred in an oil bath at 110° C. for 5 hours and then cooled. This was added to 300 mL of water, and the mixture was stirred. The resulting layers were separated, and the aqueous layer was subjected to extraction with 200 mL of toluene. The organic layers were combined, washed with a saturated aqueous sodium chloride solution, dried over anhydrous sodium sulfate, and concentrated to give 87.05 g of the desired compound 4d as an oil (crude yield: 113%).

(3) 2-[[3-(Benzyloxy)phenyl] (methyl)amino]ethanol (compound 5d)

[Chem. 70]

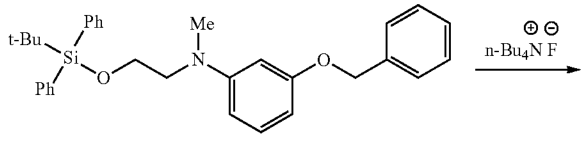

4d

5d 87.05 g of the crude 3-benzyloxy-N-[2-(tert-butyldiphenylsilyl)oxy]ethyl-N-methylaniline (4d) was dissolved in 230 mL of tetrahydrofuran. To this, 265 mL (0.265 mol) of tetrabutylammonium fluoride (1 mol solution in tetrahydrofuran) was added dropwise with stirring at room temperature. After 2.5-hour stirring, the reaction mixture was poured into 800 mL of water, and ethyl acetate extraction was performed. The extract was washed with a saturated aqueous sodium chloride solution, dehydrated over anhydrous sodium sulfate, and concentrated. The residue was purified by silica gel column chromatography (chloroform/ethyl acetate=2/1) to give 20.0 g of the desired compound 5d as a pink oil (yield: 44.3%).

(4) 2-[N-3-(Benzyloxyphenyl)-N-methylamino]ethyl acetate (compound 6d)

[Chem. 71]

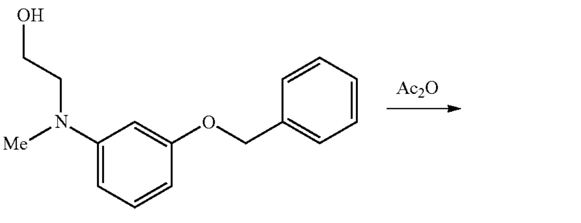

5d

6d 30 mL of acetic anhydride was added to 20.0 g (77.7 mmol) of 2-[[3-(benzyloxy)phenyl] (methyl)amino]ethanol (5d), and the mixture was stirred in an oil bath at 80° C. for 2 hours. After cooling, 250 mL of ether and 300 mL of water were added, and the mixture was stirred for 1 hour. The organic layer was separated, and the aqueous layer was further subjected to extraction with 200 mL of ether. The organic layers were combined and washed with a saturated aqueous sodium hydrogen carbonate solution and subsequently with a saturated aqueous sodium chloride solution. The washed organic layer was dehydrated over anhydrous magnesium sulfate and concentrated. The residual liquid was purified by silica gel column chromatography (ethyl acetate/hexane=1/2) to give 21.68 g of the desired compound 6d as a colorless oil (yield: 93.2%).

The NMR measurement results of compound 6d are shown below.

$^{1}$H-NMR (600 MHz, $CDCl_3$) δ ppm: 2.02 (3H, s), 2.96 (3H, s), 3.57 (2H, t, J=6.0 Hz), 4.22 (2H, t, J=6.0 Hz), 5.05 (2H, s), 6.36-6.38 (3H, m), 7.14 (1H, t, J=8.2 Hz), 7.32 (1H, t, J=7.7 Hz), 7.38 (2H, t, J=7.7 Hz), 7.44-7.45 (2H, m)

$^{13}$C-NMR (150 MHz, $CDCl_3$) δ ppm: 20.9, 38.8, 51.1, 61.5, 69.9, 99.8, 102.3, 105.6, 127.6, 127.9, 128.6, 129.9, 137.3, 150.4, 160.1, 171.0

(5) 2-[[3-(Benzyloxy)-4-formylphenyl] (methyl) amino]ethyl acetate (compound 7d)

[Chem. 72]

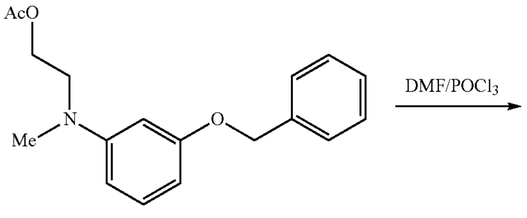

6d

-continued

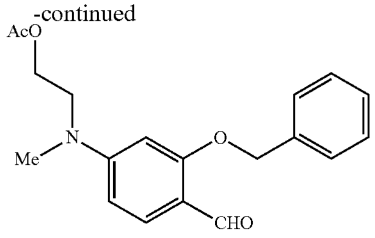

7d

-continued

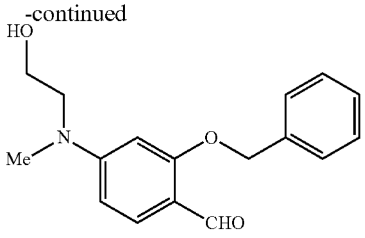

8d 4.24 g (27.66 mmol) of phosphorus oxychloride was added dropwise to 35 mL of N,N-dimethylformamide under ice-cooling. After 30 minutes, the ice bath was removed, and the reaction mixture was heated to 11° C. and stirred at the same temperature for 5 minutes. The reaction mixture was ice-cooled again, and a solution of 8.12 g (27.12 mmol) of 2-[N-3-(benzyloxyphenyl)-N-methylamino]ethyl acetate (6d) in 10 mL of N,N-dimethylformamide was added dropwise. The ice bath was removed, and the reaction mixture was stirred for 30 minutes, then gradually heated to 70° C. and stirred at the same temperature for 1 hour. To the reaction mixture under cooling in an ice bath, 50 mL of a 20% aqueous sodium acetate solution was added dropwise. After 15-minute stirring, ethyl acetate extraction was performed. The extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residue was subjected to crystallization from a mixed solvent of ethyl acetate/hexane. The crystals were collected by filtration, washed, and dried to give 6.62 g of the desired compound 7d. The filtrate and the wash solution were combined and purified by silica gel column chromatography (ethyl acetate/hexane=1.3/1) to further give 0.94 g of the desired compound 7d. 7.56 g in total (yield: 85.1%)

The NMR measurement results of compound 7d are shown below.

$^1$H-NMR (600 MHz, $CDCl_3$) δ ppm: 2.01 (3H, s, Ac), 3.05 (3H, s, NMe), 3.63 (2H, t, J=6.0 Hz, $NCH_2$), 4.22 (2H, t, J=6.0 Hz, $OCH_2$), 5.19 (2H, s, $PhCH_2O$), 6.20 (1H, d, J=2.2 Hz, Ar—H), 6.35 (1H, dd, J=2.2 Hz, 8.8 Hz, Ar—H), 7.34 (1H, t, J=7.1 Hz, Ar—H), 7.40 (2H, t, J=7.1 Hz, Ar—H), 7.45 (2H, t, J=7.1 Hz, Ar—H), 7.75 (1H, d, J=8.8 Hz, Ar—H)

$^{13}$C-NMR (150 MHz, $CDCl_3$) δ ppm: 20.8, 38.9, 50.7, 61.0, 70.2, 94.9, 104.8, 115.4, 127.2, 128.1, 128.7, 130.3, 136.5, 154.9, 163.1, 170.8, 187.4

(6) 2-Benzyloxy-4-[(2-hydroxyethyl)(methyl)amino]benzaldehyde (compound 8d)

[Chem. 73]

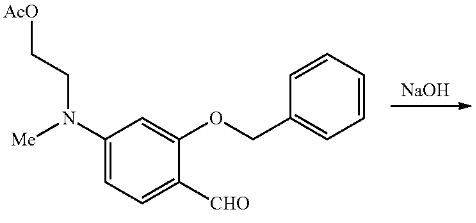

7d 7.56 g (23 mmol) of 2-[[3-(benzyloxy)-4-formylphenyl](methyl)amino]ethyl acetate (7d) was dissolved in 40 mL of ethanol. To this, 35 mL of a 7.4% aqueous sodium hydroxide solution was added dropwise, and the mixture was stirred at room temperature for 1 hour. The reaction mixture was poured into 120 mL of water, and chloroform extraction was performed. The extract was washed with a saturated aqueous sodium chloride solution, dehydrated over anhydrous sodium sulfate, and concentrated. 7.04 g of the residual yellow liquid was purified by silica gel column chromatography (chloroform/methanol=15/1) to give 6.5 g of the desired compound 8d as a yellow liquid (yield: 98.6%).

The NMR measurement results of compound 8d are shown below.

$^1$H-NMR (600 MHz, $CDCl_3$) δ ppm: 1.76 (1H, t, J=2.8 Hz), 3.07 (3H, s), 3.55 (2H, t, J=5.5 Hz), 3.80 (2H, q, J=5.5 Hz), 5.16 (2H, s), 6.17 (1H, d, J=2.2 Hz), 6.35 (1H, dd, J=2.2 Hz, 8.8 Hz), 7.35-7.45 (5H, m), 7.72 (1H, d, J=8.8 Hz)

$^{13}$C-NMR (150 MHz, $CDCl_3$) δ ppm: 39.3, 54.5, 60.2, 70.2, 95.0, 105.0, 115.2, 127.2, 128.1, 128.7, 130.3, 136.5, 155.4, 163.0, 187.4

(7) 2-Benzyloxy-4-[[2-[(tert-butyldiphenylsilyl)oxy]ethyl] (meth yl)amino]benzaldehyde (compound 9d)

[Chem. 74]

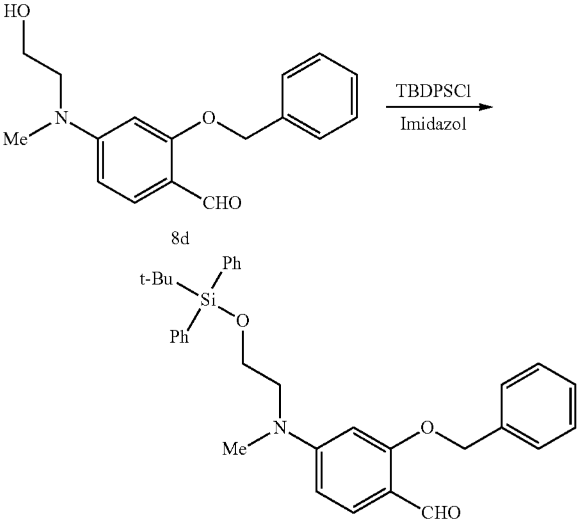

8d

9d 6.87 g (24.08 mmol) of 2-benzyloxy-4-[(2-hydroxyethyl)(methyl)amino]benzaldehyde (8d) and 4.2 g (61.69 mmol) of imidazole were dissolved in 60 mL of N,N-dimethylformamide. To this, 6.8 g (24.74 mmol) of tert-butylchlorodiphenylsilane was added dropwise with stirring at room temperature. After 2-hour stirring, the reaction mixture was added to 300 mL of water, and ethyl acetate extraction was performed. The extract was washed with a saturated aqueous sodium chloride solution, dehydrated over anhydrous sodium sulfate, and purified by silica gel column chromatography (ethyl acetate/hexane=1/2) to give 10.92 g of the desired compound 9d as a pale yellow oil (yield: 86.6%)

The NMR measurement results of compound 9d are shown below.

$^1$H-NMR (600 MHz, $CDCl_3$) δ ppm: 1.02 (9H, s), 3.01 (3H, s), 3.53 (2H, t, J=5.5 Hz), 3.76 (2H, t, J=5.5 Hz), 5.09 (2H, s), 6.03 (1H, d, J=2.2 Hz), 6.17 (1H, d, J=8.8 Hz), 7.28 (1H, t, J=7.7 Hz), 7.32-7.43 (6H, m), 7.58-7.59 (4H, m), 7.67 (1H, d, J=8.8 Hz)

$^{13}$C-NMR (150 MHz, $CDCl_3$) δ ppm: 19.0, 26.8, 39.6, 54.3, 61.0, 70.1, 94.6, 104.9, 114.9, 127.1, 127.8, 128.1, 128.6, 129.8, 130.2, 133.1, 135.5, 136.5, 155.0, 163.0, 187.4

(8) 3-Benzyloxy-N—[(Z/E)-2-[(tert-butyldiphenylsilyl)oxy] ethyl]-N-methyl-4-[2-(thiophen-2-yl)vinyl] aniline (compound 11-(Z/E)d)

[Chem. 75]

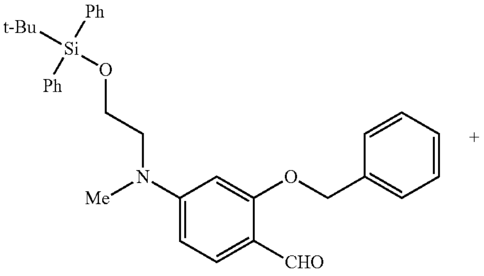

9d

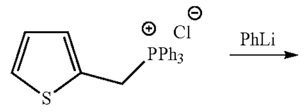

10d

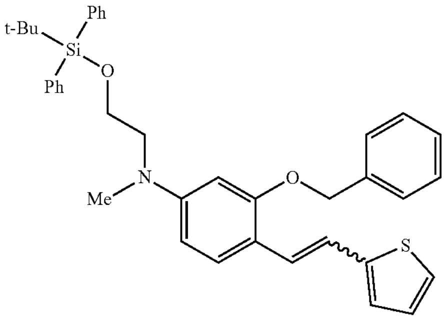

11-(Z/E)d 10.14 g (22.92 mmol) of phenyllithium (19% in $Bu_2O$) was added to 120 mL of tetrahydrofuran under an argon atmosphere. To this, 8.40 g (21.27 mmol) of 2-thenyl triphenyl phosphonium chloride (10d) was gradually added under ice-cooling. After 5-minute stirring, 30 mL of a solution of 10.9 g (20.81 mmol) of 2-benzyloxy-4-[[2-[(tert-butyldiphenylsilyl)oxy] ethyl](meth yl)amino]benzaldehyde (9d) in tetrahydrofuran was added dropwise. After 2-hour stirring under ice-cooling, the reaction mixture was poured into 300 mL of water, and ethyl acetate extraction was performed. The extract was washed with a saturated aqueous sodium chloride solution, dehydrated over anhydrous sodium sulfate, and concentrated. To the residue, 90 mL of an ethyl acetate/hexane (1/5) mixture was added, and the mixture was stirred and then ice-cooled. The precipitate was filtered off, and the filtrate was concentrated. The residue was purified by silica gel column chromatography (ethyl acetate/hexane=1/3) to give 11.0 g of the desired compound 11-(Z/E)d as a yellow oil (yield: 87.5%).

(9) 5-[(Z/E)-2-Benzyloxy-4-[[2-[(tert-butyldiphenylsilyl)oxy]ethyl](methyl)amino]styryl]thiophene-2-carbaldehyde (compound 12-(Z/E)d)

[Chem. 76]

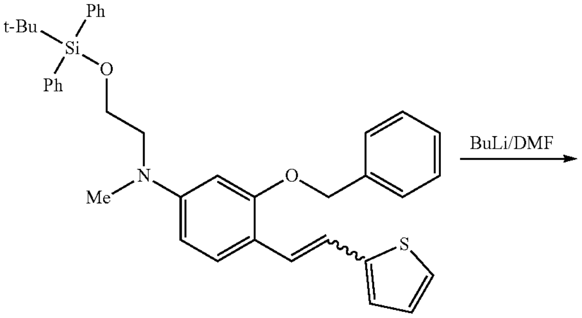

11-(Z/E)d

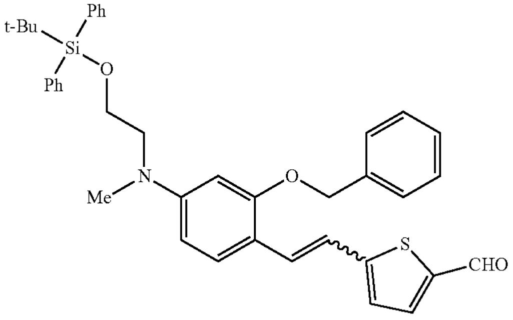

12-(Z/E)d 11.0 g (18.2 mmol) of 3-benzyloxy-N—[(Z/E)-2-[(tert-butyldiphenylsilyl)oxy]ethyl]-N-methyl-4-[2-(thiophen-2-yl)vinyl]aniline (11-(Z/E)d) was dissolved in 110 mL of tetrahydrofuran under an argon atmosphere. To this, 16.0 mL (25.6 mmol) of n-butyllithium (1.6 mol solution in hexane) was added dropwise with cooling in a dry ice/acetone bath. After 30-minute stirring, 1.7 g (23.3 mmol) of N,N-dimethylformamide was added dropwise. After 1-hour stirring, the bath was removed, the reaction mixture was heated, and 10 mL of water was added dropwise. After 15-minute stirring, the reaction mixture was poured into 250 mL of water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/2) to give 11.37 g of the desired compound 12-(Z/E)d as a red-orange oil (yield: 98.8%).

(10 ) (E)-5-[2-Benzyloxy-4-[[2-[(tert-butyldiphenylsilyl)oxy]ethyl](methyl)amino]styryl]thiophene-2-carbaldehyde (compound 12-(E)d)

[Chem. 77]

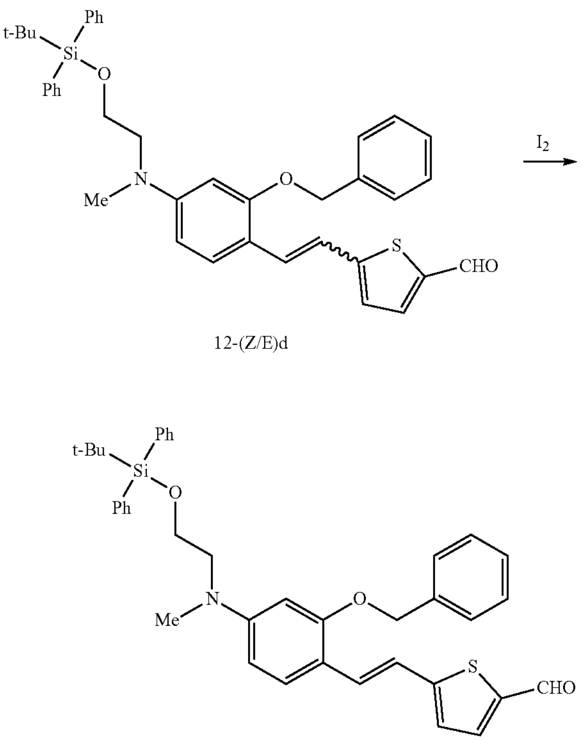

12-(Z/E)d 12-(E)d 11.37 g (18.0 mmol) of 5-[(Z/E)-2-benzyloxy-4-[[2-[(tert-butyldiphenylsilyl)oxy]ethyl](methyl)amino]styryl]thiophene-2-carbaldehyde (12-(Z/E)d) was dissolved in 600 mL of ether. To this, 370 mg of iodine flakes were added. After 30-minute stirring at room temperature, the reaction mixture was washed twice with 150 mL of a 5% aqueous sodium hydrogen sulfite solution. The reaction mixture was further washed with a saturated aqueous sodium chloride solution, dehydrated over anhydrous magnesium sulfate, and concentrated to give 10.52 g of the desired compound 12-(E)d as a red oil (crude yield: 92.5%).

The NMR measurement results of compound 12-(E)d are shown below.

$^1$H-NMR (600 MHz, $CDCl_3$) δ ppm: 1.03 (9H, s), 2.97 (3H, s), 3.50 (2H, t, J=6.1 Hz), 3.76 (2H, t, J=6.1 Hz), 5.08 (2H, s), 6.16 (1H, s), 6.20 (1H, d, J=8.8 Hz), 6.98 (1H, d, J=3.9 Hz), 7.12 (1H, d, J=15.9 Hz), 7.29-7.43 (14H, m), 7.60-7.61 (4H, m), 9.79 (1H, s)

$^{13}$C-NMR (150 MHz, $CDCl_3$) δ ppm: 19.1, 26.8, 39.4, 54.4, 61.2, 70.5, 96.6, 105.1, 113.5, 116.7, 124.5, 127.3, 127.8, 128.0, 128.6, 128.9, 129.2, 129.7, 133.3, 135.5, 150.8, 155.6, 158.1, 182.3

(11 ) (E)-5-[2-Benzyloxy-4-[(2-hydroxyethyl)(methyl)amino]styryl]thiophene-2-carbaldehyde (compound 13-(E)d)

[Chem. 78]

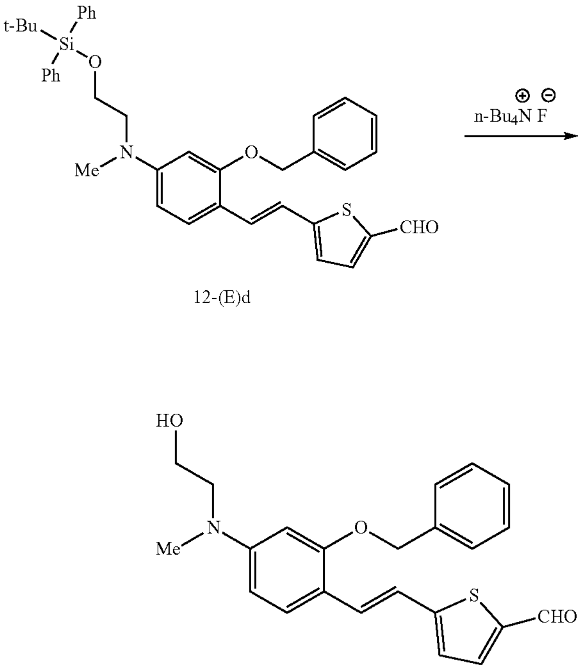

12-(E)d 13-(E)d 10.52 g (16.65 mmol) of the crude (E)-5-[2-benzyloxy-4-[[2-[(tert-butyldiphenylsilyl)oxy]ethyl](methyl)amino]styryl]thiophene-2-carbaldehyde (12-(E)d) was dissolved in 40 mL of tetrahydrofuran. To this, 40 mL of tetrabutylammonium fluoride (1 mol solution in tetrahydrofuran) was added dropwise with stirring at room temperature. After 2-hour stirring, the reaction mixture was poured into 250 mL of water, and ethyl acetate extraction was performed. The extract was washed with a saturated aqueous sodium chloride solution, dehydrated over anhydrous sodium sulfate, and concentrated. The residual liquid was purified by silica gel short column chromatography (ethyl acetate/hexane=25/1) to give 6.13 g of the desired compound 13-(E)d (yield: 93.6%).

The NMR measurement results of compound 13-(E)d are shown below.

$^1$H-NMR (600 MHz, $CDCl_3$) δ ppm: 3.01 (3H, s), 3.50 (2H, t, J=6.0 Hz), 3.78 (2H, t, J=6.0 Hz), 5.16 (2H, s), 6.30 (1H, d, J=2.2 Hz), 6.39 (1H, dd, J=2.2 Hz, 8.8 Hz), 6.99 (1H, d, J=3.9 Hz), 7.15 (1H, d, J=15.9 Hz), 7.34-7.48 (7H, m), 7.61 (1H, d, J=3.9 Hz), 9.80 (1H, s)

$^{13}$C-NMR (150 MHz, $CDCl_3$) δ ppm: 39.0, 54.9, 60.3, 70.5, 97.3, 105.6, 117.3, 124.8, 127.3, 128.0, 128.7, 128.86, 128.90, 136.9, 137.6, 140.0, 151.4, 155.3, 158.0, 182.4

(12) 2-[4-[(E)-2-[5-[(E)-2-Benzyloxy-4-[(2-hydroxyethyl) (methyl)amino]styryl]thiophen-2-yl]vinyl]-3-cyano-5-phenyl-5-(trifluoromethyl)furan-2(5H)-ylidene]malononitrile (EO-6)

[Chem. 79]

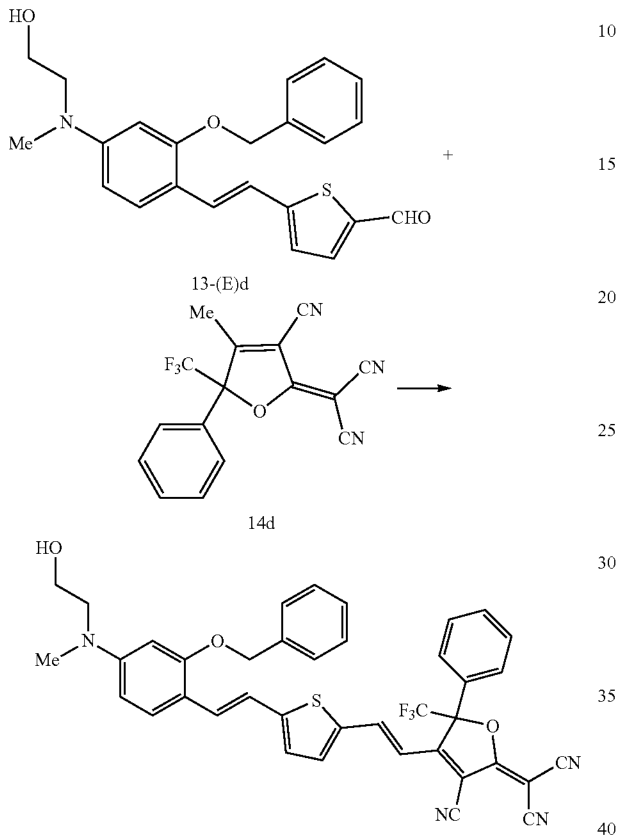

13-(E)d

14d (EO-6)

5.8 g (14.74 mmol) of (E)-5-[2-benzyloxy-4-[(2-hydroxyethyl) (methyl)amino]styryl]thiophene-2-carbaldehyde (13-(E)d) and 5.1 g (16.18 mmol) of 2-(3-cyano-4-methyl-5-phenyl-5-trifluoromethyl-2(5H)-furanylidene) propanedinitrile (14d) were dissolved in 100 mL of ethanol. The solution was heated to 40° C. and stirred at the same temperature for 2 hours. The reaction mixture was ice-cooled, and the precipitated crystals were collected by filtration and washed with ethanol. As a result, 8.925 g of the desired compound (EO-6) was obtained as dark brown crystals with a melting point of 217 to 218° C. (yield: 87.7%).

The NMR measurement results of EO-6 are shown below.

$^1$H-NMR (600 MHz, $CDCl_3$) δ ppm: 3.05 (3H, s), 3.52 (2H, t, J=5.5 Hz), 3.79 (2H, q, J=5.5 Hz), 5.19 (2H, s), 6.27 (1H, d, J=2.2 Hz), 6.39 (1H, dd, J=2.2 Hz, 8.8 Hz), 6.54 (1H, d, J=15.4 Hz), 6.92 (1H, d, J=4.4 Hz), 7.15 (1H, d, J=16.0 Hz), 7.37 (1H, d, J=8.8 Hz), 7.42 (1H, t, J=7.1 Hz), 7.40-7.57 (14H, m), 7.78 (1H, d, J=14.8 Hz)

$^{13}$C-NMR (150 MHz, $CDCl_3$) δ ppm: 39.1, 47.3, 54.7, 60.3, 70.6, 96.0, 96.8, 105.7, 110.7, 111.1, 111.4, 116.9, 120.7, 126.8, 127.3, 127.5, 128.2, 128.3, 128.7, 129.8, 131.5, 132.1, 136.8, 137.9, 139.9, 141.7, 152.2, 158.9, 161.9, 175.4

Example 1: Electro-Optic Polymer ($D_1$)

1.62 g of the copolymer ($A_1$) was dissolved in 70 mL of tetrahydrofuran (THF). To this, 1.10 g (3.05 mmol) of the EO molecule (EO-1) and 70 μL of DBTDL were added, and the mixture was stirred in an oil bath at 60° C. for 2 hours. Subsequently, 4 mL of methanol and 40 μL of DBTDL were added, and the mixture was stirred for 45 minutes. The reaction mixture was cooled and then poured into 860 mL of IPE, and the mixture was stirred. The precipitated powder was collected by filtration and washed with 100 mL of a THF/IPE (1/10) mixture and subsequently with IPE. The washed residue was dried in vacuo with heating at 70° C. to give 2.49 g of an electro-optic polymer ($D_1$) as a black powder. The Tg of this electro-optic polymer was 192° C. The electro-optic coefficient ($r_{33}$) of the electro-optic polymer ($D_1$) was 89 pm/V at the wavelength of 1308 nm and 68 pm/V at the wavelength of 1550 nm. That is, this polymer successfully showed electro-optic effect.

Example 2: Electro-Optic Polymer ($D_2$)

0.88 g of the copolymer ($A_2$) was dissolved in 34 mL of tetrahydrofuran (THF). To this, 0.48 g (0.67 mmol) of the EO molecule (EO-1) and 30 μL of DBTDL were added, and the mixture was stirred in an oil bath at 60° C. for 2 hours. Subsequently, 2 mL of methanol and 15 μL of DBTDL were added, and the mixture was stirred for 45 minutes. The reaction mixture was cooled and then poured into 420 mL of IPE, and the mixture was stirred. The precipitated powder was collected by filtration and washed with 50 mL of a THF/IPE (1/12) mixture and subsequently with IPE. The washed residue was dried in vacuo with heating at 70° C. to give 1.25 g of an electro-optic polymer ($D_2$) as a black powder. The Tg of this electro-optic polymer was 180° C. The electro-optic coefficient ($r_{33}$) of the electro-optic polymer ($D_2$) was on 65 pm/V at the wavelength of 1308 nm and 50 pm/V at the wavelength of 1550 nm. That is, this polymer successfully showed electro-optic effect.

Example 3: Electro-Optic Polymer ($E_1$)

1.03 g of the copolymer ($B_1$) was dissolved in 45 mL of tetrahydrofuran (THF). To this, 0.7 g (1.94 mmol) of the EO molecule (EO-1) and 45 μL of DBTDL were added, and the mixture was stirred in an oil bath at 60° C. for 2 hours. Subsequently, 2.5 mL of methanol and 25 μL of DBTDL were added, and the mixture was stirred for 45 minutes. The reaction mixture was cooled and then poured into 550 mL of IPE, and the mixture was stirred. The precipitated powder was collected by filtration and washed with 50 mL of a THF/IPE (1/12) mixture and subsequently with IPE. The washed residue was dried in vacuo with heating at 70° C. to give 1.55 g of an electro-optic polymer ($E_1$) as a black powder. The Tg of this electro-optic polymer was 199° C. The electro-optic coefficient ($r_{33}$) of the electro-optic polymer ($E_1$) was 80 pm/V at the wavelength of 1308 nm and 63 pm/V at the wavelength of 1550 nm. That is, this polymer successfully showed electro-optic effect.

Example 4: Electro-Optic Polymer ($E_2$)

1.32 g of the copolymer ($B_2$) was dissolved in 60 mL of tetrahydrofuran (THF). To this, 0.72 g (1.00 mmol) of the EO molecule (EO-1) and 40 μL of DBTDL were added, and the mixture was stirred in an oil bath at 60° C. for 2 hours. Subsequently, 3 mL of methanol and 25 μL of DBTDL were added, and the mixture was stirred for 35 minutes. The reaction mixture was cooled and then poured into 600 mL of IPE, and the mixture was stirred. The precipitated powder was collected by filtration and washed with IPE. The washed residue was dried in vacuo with heating at 70° C. to give 1.84 g of an electro-optic polymer ($E_2$) as a black powder. The Tg of this electro-optic polymer was 206° C. The electro-optic coefficient ($r_{33}$) of the electro-optic polymer ($E_2$) was 52 pm/V at the wavelength of 1308 nm and 40 pm/V at the wavelength of 1550 nm. That is, this polymer successfully showed electro-optic effect.

Example 5: Electro-Optic Polymer ($F_1$)

1.64 g of the copolymer ($C_1$) was dissolved in 85 mL of tetrahydrofuran (THF). To this, 1.74 g (2.41 mmol) of the EO molecule (EO-1) and 100 μL of DBTDL were added, and the mixture was stirred in an oil bath at 60° C. for 2 hours. Subsequently, 5 mL of methanol and 50 μL of DBTDL were added, and the mixture was stirred for 45 minutes. The reaction mixture was cooled and then poured into 900 mL of IPE, and the mixture was stirred. The precipitated powder was collected by filtration and washed with 130 mL of a THF/IPE (1/12) mixture and subsequently with IPE. The washed residue was dried in vacuo with heating at 70° C. to give 3.07 g of an electro-optic polymer ($F_1$) as a black powder. The Tg of this electro-optic polymer was 174° C.

Example 6: Electro-Optic Polymer ($F_2$)

0.9 g of the copolymer ($C_2$) was dissolved in 35 mL of tetrahydrofuran (THF). To this, 0.49 g (0.68 mmol) of the EO molecule (EO-1) and 30 μL of DBTDL were added, and the mixture was stirred in an oil bath at 60° C. for 2 hours. Subsequently, 2 mL of methanol and 15 μL of DBTDL were added, and the mixture was stirred for 45 minutes. The reaction mixture was cooled and then poured into 420 mL of IPE, and the mixture was stirred. The precipitated powder was collected by filtration and washed with IPE. The washed residue was dried in vacuo with heating at 70° C. to give 1.20 g of an electro-optic polymer ($F_2$) as a black powder. The Tg of this electro-optic polymer was 158° C. The electro-optic coefficient ($r_{33}$) of the electro-optic polymer ($F_2$) was 70 pm/V at the wavelength of 1308 nm and 52 pm/V at the wavelength of 1550 nm. That is, this polymer successfully showed electro-optic effect.

Example 7: Electro-Optic Polymer ($F_3$)

1.52 g of the copolymer ($C_3$) was dissolved in 70 mL of tetrahydrofuran (THF). To this, 1.09 g (1.51 mmol) of the EO molecule (EO-1), 0.467 g (1.486 mmol) of the azo-compound represented by the formula (DR-1) shown below, and 73 μL of DBTDL were added, and the mixture was stirred in an oil bath at 60° C. for 2 hours. Subsequently, 5 mL of methanol was added, and the mixture was stirred for 45 minutes. The reaction mixture was cooled and then poured into 840 mL of IPE, and the mixture was stirred. The precipitated powder was collected by filtration and washed with 130 mL of an IPE/THF (12/1) mixture and subsequently with IPE. The washed residue was dried in vacuo with heating at 70° C. to give 2.75 g of an electro-optic polymer ($F_3$) as a black powder. The Tg of this electro-optic polymer was 145° C.

[Chem. 80]

(DR-1)

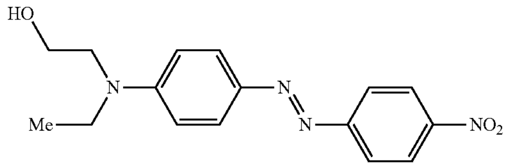

Example 8: Electro-Optic Polymer ($F_4$)

1.60 g of the copolymer ($C_1$) was dissolved in 85 mL of tetrahydrofuran (THF). To this, 1.155 g (1.60 mmol) of the EO molecule (EO-1), 0.495 g (1.50 mmol) of the azo-compound represented by the formula (DR-2) shown below, and 100 μL of DBTDL were added, and the mixture was stirred in an oil bath at 60° C. for 2 hours. Subsequently, 5 mL of methanol was added, and the mixture was stirred for 50 minutes. The reaction mixture was cooled and then poured into 1000 mL of IPE, and the mixture was stirred. The precipitated powder was collected by filtration and washed with 130 mL of an IPE/THF (12/1) mixture and subsequently with IPE. The washed residue was dried in vacuo with heating at 70° C. to give 2.933 g of an electro-optic polymer ($F_4$) as a black powder. The Tg of this electro-optic polymer was 171° C.

[Chem. 81]

(DR-2)

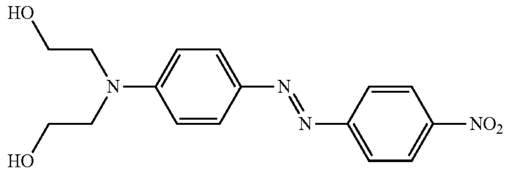

Example 9: Electro-Optic Polymer ($G_1$)

1.45 g of the copolymer ($A_1$) was dissolved in 65 mL of tetrahydrofuran (THF). To this, 1.0 g (2.37 mmol) of the EO molecule (EO-2) and 60 μL of DBTDL were added, and the mixture was stirred in an oil bath at 60° C. for 5 hours. Subsequently, 4 mL of methanol and 40 μL of DBTDL were added, and the mixture was stirred for 45 minutes. The reaction mixture was cooled and then poured into 800 mL of IPE, and the mixture was stirred. The precipitated powder was collected by filtration and washed with 120 mL of a THF/IPE (1/12) mixture and subsequently with IPE. The washed residue was dried in vacuo with heating at 70° C. to give 2.09 g of an electro-optic polymer ($G_1$) as a black powder. The Tg of this electro-optic polymer was 175° C.

Example 10: Electro-Optic Polymer ($H_1$)

1.20 g of the copolymer ($A_3$) was dissolved in 50 mL of tetrahydrofuran (THF). To this, 0.52 g (1.57 mmol) of the EO molecule (EO-4) and 40 μL of DBTDL were added, and the mixture was stirred in an oil bath at 60° C. for 2 hours. Subsequently, 2 mL of methanol and 20 μL of DBTDL were added, and the mixture was stirred for 1 hour. The reaction mixture was cooled and then poured into 650 mL of IPE, and the mixture was stirred. The precipitated powder was collected by filtration and washed with 320 mL of a THF/IPE (1/10) mixture and subsequently with IPE. The washed residue was dried in vacuo with heating at 70° C. to give 1.60 g of an electro-optic polymer ($H_1$) as a black powder. The Tg of this electro-optic polymer was 188° C.

Synthesis Examples 15 to 21

Copolymers (A-1) to (A-7) and their methyl carbamate derivatives were obtained in the same manner as described in Example 1 of Patent Literature 1 based on the feed ratios of DCPMA and MOI described in Table 2.

Synthesis Examples 22 and 23

Copolymers (B-1) and (B-2) and their methyl carbamate derivatives were obtained in the same manner as described in Examples 2 and 3 of Patent Literature 1 based on the feed ratios of AdMA and MOI described in Table 2.

Synthesis Examples 24 and 25

Copolymers (C-1) and (C-2) and their methyl carbamate derivatives were obtained in the same manner as described in Examples 4 and 5 of Patent Literature 1 based on the feed ratios of MA and MOI described in Table 2.

The Tgs, Mns and Mws of the methyl carbamate derivatives of the copolymers of Synthesis Examples 15 to 25 are shown in Table 2.

TABLE 2

| | Copolymer | Molar ratio of methacrylate/ MOI | Tg (° C.) | Mn | Mw |
|---|---|---|---|---|---|
| Synthesis Example 15 | (A-1) | 0.885/1 | 101 | 32,600 | 97,500 |
| Synthesis Example 16 | (A-2) | 1.49/1 | 116 | 31,200 | 82,600 |
| Synthesis Example 17 | (A-3) | 1.87/1 | 121 | 29,600 | 71,300 |
| Synthesis Example 18 | (A-4) | 2.17/1 | 125 | 36,600 | 89,100 |
| Synthesis Example 19 | (A-5) | 2.46/1 | 129 | 34,200 | 80,000 |
| Synthesis Example 20 | (A-6) | 2.83/1 | 130 | 45,700 | 96,200 |
| Synthesis Example 21 | (A-7) | 5.39/1 | 150 | 73,900 | 153,000 |
| Synthesis Example 22 | (B-1) | 0.884/1 | 116 | 27,500 | 86,500 |
| Synthesis Example 23 | (B-2) | 2.83/1 | 167 | 33,000 | 79,500 |
| Synthesis Example 24 | (C-1) | 0.884/1 | 106 | 30,300 | 63,900 |
| Synthesis Example 25 | (C-2) | 2.83/1 | 145 | 66,300 | 98,200 |

Comparative Example 1: Electro-Optic Polymer (D-1)

1.09 g of the copolymer (A-1) was dissolved in 55 mL of tetrahydrofuran. To this, 0.5 g (0.657 mmol) of the EO molecule (EO-5) and 40 μL of DBTDL were added, and the mixture was stirred in an oil bath at 60° C. for 2 hours. Subsequently, a solution of 0.4 g (2.08 mmol) of 2-hydroxyethyl cinnamate (HEC) in 1 mL of tetrahydrofuran, and 20 μL of DBTDL were added, and the mixture was stirred for 1.5 hours. 3 mL of methanol was further added, and the mixture was stirred for 0.5 hour. The reaction mixture was cooled and then poured into 440 mL of IPE, and the mixture was stirred. The precipitated powder was collected by filtration and washed with IPE. The washed residue was dried in vacuo with heating at 70° C. to give 1.76 g of a copolymer (D-1) as a black powder. The Tg of the obtained electro-optic polymer (D-1) was 103° C.

Comparative Example 2: Electro-optic polymer (D-2)

1.27 g of the copolymer (A-2) was dissolved in 55 mL of tetrahydrofuran. To this, 0.5 g (0.657 mmol) of the EO molecule (EO-5) and 40 μL of DBTDL were added, and the mixture was stirred in an oil bath at 60° C. for 2 hours. Subsequently, a solution of 0.2 g (1.041 mmol) of HEC in 1 mL of tetrahydrofuran, and μL of DBTDL were added, and the mixture was heated to 70° C. and stirred at the same temperature for 1.5 hours. 3 mL of methanol was further added, and the mixture was stirred for 0.5 hour. The reaction mixture was cooled and then poured into 660 mL of diisopropyl ether (IPE), and the mixture was stirred. The precipitated powder was collected by filtration and washed with IPE. The washed residue was dried in vacuo with heating at 70° C. to give 1.79 g of a copolymer (D-2) as a black powder. The Tg of the obtained electro-optic polymer (D-2) was 116° C.

Comparative Example 3: Electro-optic polymer (D-3)

1.28 g of the copolymer (A-3) was dissolved in 55 mL of tetrahydrofuran. To this, 0.5 g (0.657 mmol) of the EO molecule (EO-5) and 40 μL of DBTDL were added, and the mixture was stirred in an oil bath at 60° C. for 2 hours. Subsequently, a solution of 0.2 g (1.041 mmol) of HEC in 1 mL of tetrahydrofuran, and μL of DBTDL were added, and the mixture was stirred for 1 hour. The mixture was heated to 70° C. and stirred at the same temperature for 1 hours. 3 mL of methanol was further added, and the mixture was stirred for 0.5 hour. The reaction mixture was cooled and then poured into 660 mL of diisopropyl ether (IPE), and the mixture was stirred. The precipitated powder was collected by filtration and washed with IPE. The washed residue was dried in vacuo with heating at 70° C. to give 1.79 g of an electro-optic polymer (D-3) as a black powder. The Tg of the obtained electro-optic polymer (D-3) was 120° C.

Comparative Example 4: Electro-Optic Polymer (D-4)

1.29 g of the copolymer (A-4) and 0.5 g (0.657 mmol) of the EO molecule (EO-5) were dissolved in 55 mL of THF. To this, μL of DBTDL was added, and the mixture was stirred in an oil bath at 60° C. for 2 hours. Subsequently, a solution of 0.2 g (1.04 mmol) of HEC in 1 mL of THF, and 20 μL of DBTDL were added, and the mixture was stirred for 1.5 hours. 3 mL of methanol was further added, and the mixture was stirred for 45 minutes. The reaction mixture was cooled and then poured into 660 mL of diisopropyl ether (IPE), and the mixture was stirred. The precipitated powder was collected by filtration and washed with IPE. The washed residue was dried in vacuo with heating at 70° C. for 16 hours to give 1.72 g of an electro-optic polymer (D-4) as a black powder. The Tg of the obtained electro-optic polymer (D-4) was 126° C.

Comparative Example 5: Electro-Optic Polymer (D-5)

1.29 g of the copolymer (A-5) was dissolved in 55 mL of tetrahydrofuran. To this, 0.5 g (0.657 mmol) of the EO molecule (EO-5) and 40 μL of DBTDL were added, and the mixture was stirred in an oil bath at 60° C. for 2 hours. Subsequently, a solution of 0.2 g (1.04 mmol) of HEC in 1 mL of tetrahydrofuran, and 20 μL of DBTDL were added, and the mixture was stirred for 1.5 hours. 3 mL of methanol was further added, and the mixture was stirred for 0.5 hour. The reaction mixture was cooled and then poured into 660 mL of diisopropyl ether (IPE), and the mixture was stirred. The precipitated powder was collected by filtration and washed with IPE. The washed residue was dried in vacuo with heating at 70° C. to give 1.73 g of an electro-optic polymer (D-5) as a black powder. The Tg of the obtained electro-optic polymer (D-5) was 131° C.

Comparative Example 6: Electro-Optic Polymer (D-6)

1.28 g (1.644 mmol) of the copolymer (A-6) was dissolved in 55 mL of tetrahydrofuran. To this, 0.6 g (0.789 mmol) of the EO molecule (EO-5) and 40 μL of DBTDL were added. After purging with argon, the mixture was stirred in an oil bath at 60° C. for 2 hours. Subsequently, a solution of 0.1 g (0.520 mmol) of HEC in 1 mL of tetrahydrofuran was added, and 20 μL of DBTDL was further added. After 1.5-hour stirring, 3 mL of methanol was added, and the mixture was stirred for 40 minutes. The reaction mixture was cooled and then poured into 550 mL of diisopropyl ether, and the mixture was stirred. The precipitated black powder was collected by filtration with a glass filter and washed with diisopropyl ether. The washed residue was dried in vacuo with heating at 70° C. for 16 hours to give 1.73 g of an electro-optic polymer (D-6). The Tg of the obtained electro-optic polymer (D-6) was 139° C.

Comparative Example 7: Electro-Optic Polymer (D-7)

1.4 g (1.04 mmol) of the copolymer (A-7) was dissolved in 60 mL of tetrahydrofuran. To this, 0.61 g (0.883 mmol) of the EO molecule (EO-6) and 30 μL of DBTDL were added. After purging with argon, the mixture was stirred in an oil bath at 60° C. for 3.5 hours. Subsequently, 1 mL of methanol and 10 μL of DBTDL were added, and the mixture was stirred for 40 minutes. The reaction mixture was cooled and then poured into 450 mL of IPE, and the mixture was stirred. The precipitated black powder was collected by filtration and washed with IPE. The washed residue was dried in vacuo with heating at 70° C. to give 1.69 g of an electro-optic polymer (D-7). The Tg of the obtained electro-optic polymer (D-7) was 161° C.

Comparative Example 8: Copolymer (E-1)

1.22 g of the copolymer (B-I) was dissolved in 55 mL of tetrahydrofuran. To this, 0.6 g (0.788 mmol) of the EO molecule (EO-5) and 30 μL of DBTDL were added, and the mixture was stirred in an oil bath at 60° C. for 2 hours. Subsequently, a solution of 0.1 g (0.520 mmol) of HEC in 1 mL of tetrahydrofuran, and μL of DBTDL were added, and the mixture was stirred for 1.5 hours. 3 mL of methanol was further added, and the mixture was stirred for 1 hour. The reaction mixture was cooled and then poured into 550 mL of diisopropyl ether (IPE), and the mixture was stirred. The precipitated powder was collected by filtration and washed with IPE. The washed residue was dried in vacuo with heating at 70° C. to give 1.54 g of an electro-optic polymer (E-1) as a black powder. The Tg of the obtained electro-optic polymer (E-1) was 129° C.

Comparative Example 9: Copolymer (E-2)

1.28 g of the copolymer (B-2) was dissolved in 55 mL of tetrahydrofuran. To this, 0.6 g (0.7875 mmol) of the EO molecule (EO-5) and 40 μL of DBTDL were added, and the mixture was stirred in an oil bath at 60° C. for 2 hours. Subsequently, a solution of 0.1 g (0.5203 mmol) of HEC in 1 mL of tetrahydrofuran, and 15 μL of DBTDL were added, and the mixture was stirred for 1.5 hours. 3 mL of methanol was further added, and the mixture was stirred for 1 hour. The reaction mixture was cooled and then poured into 700 mL of diisopropyl ether (IPE), and the mixture was stirred. The precipitated powder was collected by filtration and washed with IPE. The washed residue was dried in vacuo with heating at 70° C. to give 1.67 g of an electro-optic polymer (E-2) as a black powder. The Tg of the obtained electro-optic polymer (E-2) was 166° C.

Comparative Example 10: Copolymer (F-1)

1.23 g of the copolymer (C-I) was dissolved in 50 mL of tetrahydrofuran. To this, 0.6 g (0.7885 mmol) of the EO molecule (EO-5) and 40 μL of DBTDL were added, and the mixture was stirred in an oil bath at 60° C. for 2 hours. Subsequently, a solution of 0.1 g (0.5202 mmol) of HEC in 1 mL of tetrahydrofuran, and 20 μL of DBTDL were added, and the mixture was stirred for 2 hours. 3 mL of methanol was further added, and the mixture was stirred for 30 minutes. The reaction mixture was cooled and then poured into 600 mL of diisopropyl ether (IPE), and the mixture was stirred. The precipitated powder was collected by filtration and washed with IPE. The washed residue was dried in vacuo with heating at 70° C. to give 1.74 g of an electro-optic polymer (F-1) as a black powder. The Tg of the obtained electro-optic polymer (F-I) was 122° C.

Comparative Example 11: Copolymer (F-2)

1.28 g of the copolymer (C-2) was dissolved in 50 mL of tetrahydrofuran. To this, 0.6 g (0.7885 mmol) of the EO molecule (EO-5) and 40 μL of DBTDL were added, and the mixture was stirred in an oil bath at 60° C. for 2 hours. Subsequently, a solution of 0.1 g (0.5202 mmol) of HEC in 1 mL of THF, and μL of DBTDL were added, and the mixture was stirred for 1.5 hours. 3 mL of methanol was further added, and the mixture was stirred for 30 minutes. The reaction mixture was cooled and then poured into 600 mL of diisopropyl ether (IPE), and the mixture was stirred. The precipitated powder was collected by filtration and washed with IPE. The washed residue was dried in vacuo with heating at 70° C. to give 1.73 g of an electro-optic polymer (F-2) as a black powder. The Tg of the obtained electro-optic polymer (F-2) was 153° C.

The results of the electro-optic polymers obtained in Examples 1 to 10 are shown in Table 3, and the results of the electro-optic polymers obtained in Comparative Examples 1 to 11 are shown in Table 4.

TABLE 3

| | Base polymer | | | EO molecule | | Electro-optic polymer | |
|---|---|---|---|---|---|---|---|
| | Type | Methacrylate | Molar ratio of methacrylate/MOI | Type | Feed (wt %) | Type | Tg (° C.) |
| Example 1 | $A_1$ | DCPMA | 1.223/1 | EO-1 | 40 | $D_1$ | 192 |
| Example 2 | $A_2$ | | 1.697/1 | | 35 | $D_2$ | 180 |
| Example 3 | $B_1$ | AdMA | 1.223/1 | | 40 | $E_1$ | 199 |
| Example 4 | $B_2$ | | 1.697/1 | | 35 | $E_2$ | 206 |
| Example 5 | $C_1$ | MMA | 0.51/1 | | 50 | $F_1$ | 174 |
| Example 6 | $C_2$ | | 3.74/1 | EO-1 | 35 | $F_2$ | 158 |
| Example 7 | $C_3$ | | 1.145/1 | EO-1 | 35 | $F_3$ | 145 |
| | | | | DR-1 | 15 | | |
| Example 8 | $C_1$ | | 0.51/1 | EO-1 | 35 | $F_4$ | 171 |
| | | | | DR-2 | 15 | | |
| Example 9 | $A_1$ | DCPMA | 1.223/1 | EO-2 | 40 | $G_1$ | 175 |
| Example 10 | $A_3$ | DCPMA | 2.074/1 | EO-4 | 30 | $H_1$ | 188 |

TABLE 4

| | Base polymer | | | EO molecule | | Electro-optic polymer | |
|---|---|---|---|---|---|---|---|
| | Type | Methacrylate | Molar ratio of methacrylate/MOI | Type | Feed (wt %) | Type | Tg (° C.) |
| Comparative Example 1 | A-1 | DCPMA | 0.885/1 | EO-5 | 25 | D-1 | 103 |
| Comparative Example 2 | A-2 | | 1.49/1 | | 25 | D-2 | 116 |
| Comparative Example 3 | A-3 | | 1.870/1 | | 25 | D-3 | 120 |
| Comparative Example 4 | A-4 | | 2.170/1 | | 25 | D-4 | 126 |
| Comparative Example 5 | A-5 | | 2.460/1 | | 25 | D-5 | 131 |
| Comparative Example 6 | A-6 | | 2.830/1 | | 30 | D-6 | 139 |
| Comparative Example 7 | A-7 | | 5.390/1 | EO-6 | 30 | D-7 | 161 |
| Comparative Example 8 | B-1 | AdMA | 0.884/1 | EO-5 | 30 | E-1 | 129 |
| Comparative Example 9 | B-2 | | 2.83/1 | | 30 | E-2 | 166 |
| Comparative Example 10 | C-1 | IBMA | 0.884/1 | | 30 | F-1 | 122 |
| Comparative Example 11 | C-2 | | 2.830/1 | | 30 | F-2 | 153 |

The electro-optic polymers of Examples 1 to 10 had favorable film-forming properties.

In addition, as shown in the results of Examples 1 to 4 and 9, the electro-optic polymers of the present invention had a high Tg although they had a low alicyclic methacrylate monomer content in the base polymer and a high EO molecule concentration.

In contrast, the electro-optic polymers of Comparative Examples 1 to 6, 8 and 10 had a low Tg.

Synthesis Example 26: Production Method of EO Molecule (EO-7)

[Chem. 82]

EO-7

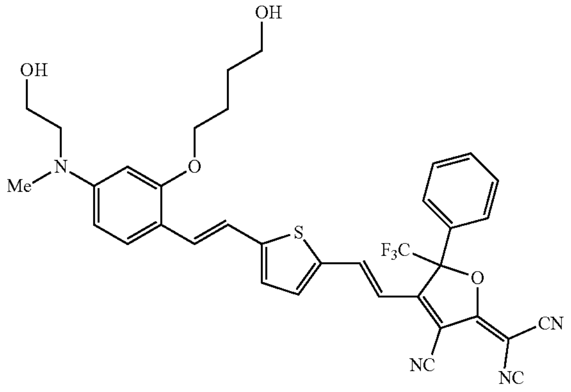

(1) [4-(3-Bromophenoxy)butoxy] (tert-butyl)diphenylsilane (compound 3e)

[Chem. 83]

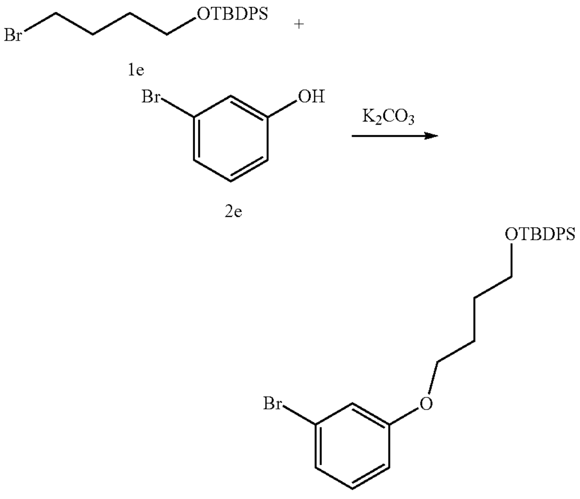

1e

2e

3e 13.75 g (79.5 mmol) of 3-bromophenol (2e) and 31.09 g (79.4 mmol) of (4-bromobutoxy) (tert-butyl)diphenylsilane (1e) were dissolved in 100 mL of 1-methylpyrrolidone. To this, 22.0 g (159.0 mmol) of potassium carbonate was added, and the mixture was stirred in an oil bath at 80° C. for 3 hours. After cooling, the reaction mixture was added to 300 mL of water, and ethyl acetate extraction was performed. The extract was washed with a saturated aqueous sodium chloride solution, dehydrated over anhydrous sodium sulfate, and concentrated. The residual liquid was purified by silica gel column chromatography (ethyl acetate/hexane=1/5) to give 34.06 g of the desired compound 3e as a colorless oil (yield: 88.7%).

The NMR measurement results of compound 3e are shown below.

$^1$H-NMR (600 MHz, $CDCl_3$) δ ppm: 1.05 (9H, s), 1.69-1.72 (2H, m), 1.85-1.88 (2H, m), 3.72 (2H, t, J=6.2 Hz), 3.91 (2H, t, J=6.2 Hz), 6.79 (1H, d, J=8.3 Hz), 7.01-7.13 (3H, m), 7.37-7.44 (6H, m), 7.66-7.67 (4H, m)

(2) 3-[4-[(tert-Butyldiphenylsilyl)oxy]butoxy]-N-[2-[(tert-butyldiphenylsilyl)oxy]ethyl]-N-methylaniline (compound 5e)

[Chem. 84]

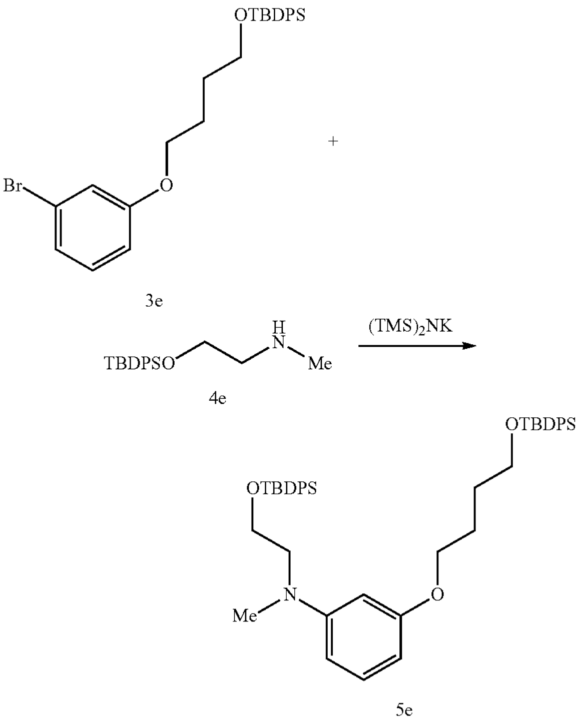

3e

4e

5e 9.9 g (20.48 mmol) of [4-(3-bromophenoxy)butoxy] (tert-butyl)diphenylsilane (3e) and 8.3 g (26.48 mmol) of 2-[(tert-butyldiphenylsilyl)oxy]-N-methyl ethanamine (4e) were dissolved in 80 mL of toluene. To this, 4.6 g (24.56 mmol) of potassium bis(trimethylsilyl) amide was added with stirring at room temperature. The mixture was stirred in an oil bath at 110° C. for 4 hours, cooled, and washed with a saturated aqueous sodium chloride solution. The washed reaction mixture was dehydrated over anhydrous sodium sulfate and concentrated. The residue was purified by silica gel column chromatography (chloroform/hexane=2/3) to give 11.6 g of the desired compound 5e as a colorless oil (yield: 79.1%).

The NMR measurement results of compound 5e are shown below.

$^1$H-NMR (600 MHz, $CDCl_3$) δ ppm: 1.03 (9H, s), 1.05 (9H, s), 1.69-1.73 (2H, m), 1.84-1.88 (2H, m), 3.91 (3H, s), 3.46 (2H, t, J=6.2 Hz), 3.72 (2H, t, J=6.2 Hz), 3.79 (2H, t, J=6.2 Hz), 3.90 (2H, t, J=6.2 Hz), 6.16-6.20 (3H, m), 7.03 (1H, t, J=8.2 Hz), 7.33-7.41 (12H, m), 7.62 (4H, d, J=7.6 Hz), 7.67 (4H, d, J=7.6 Hz)

$^{13}$C-NMR (150 MHz, $CDCl_3$) δ ppm: 19.07, 19.23, 25.95, 26.80, 26.87, 29.17, 39.17, 54.55, 61.22, 63.56, 67.47, 99.00, 101.33, 104.95, 127.61, 127.68, 129.54, 129.64, 133.48, 133.96, 135.57, 150.49, 160.23

(3) 4-[3-[(2-Hydroxyethyl) (methyl)amino]phenoxy] butan-1-ol (compound 6e)

[Chem. 85]

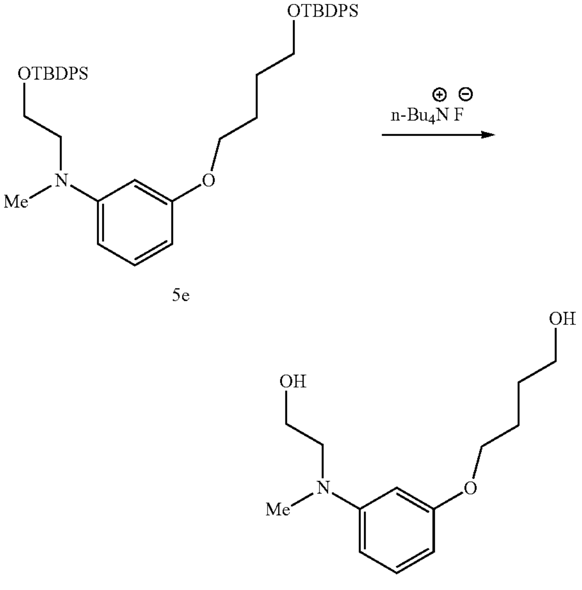

5e

6e 22.92 g (32.0 mmol) of 3-[4-[(tert-butyldiphenylsilyl) oxy]butoxy]-N-[2-[(tert-butyldiphenylsilyl)oxy]ethyl]-N-methylaniline (5e) was dissolved in 35 mL of tetrahydrofuran. To this, 64 mL of tetrabutylammonium fluoride (1 mol solution in tetrahydrofuran) was added dropwise with stirring at room temperature. After 1.5-hour stirring, the reaction mixture was poured into a saturated aqueous sodium chloride solution, and ethyl acetate extraction was performed. The extract was dehydrated over anhydrous sodium sulfate and concentrated. The residue was purified by silica gel column chromatography (chloroform/methanol=9/1) to give 5.69 g of the desired compound 6e as an oil (yield: 74.3%).

The NMR measurement results of compound 6e are shown below.

$^1$H-NMR (600 MHz, $CDCl_3$) δ ppm: 1.73-1.78 (2H, m), 1.85-1.90 (2H, m), 2.95 (3H, s), 3.46 (2H, t, J=5.5 Hz), 3.72 (2H, q, J=5.5 Hz), 3.80 (2H, q, J=5.5 Hz), 4.00 (2H, q, J=6.2 Hz), 6.31 (1H, dd, J=2.1 Hz, 8.2 Hz), 6.34 (1H, t, J=2.1 Hz), 6.41 (1H, dd, J=2.1 Hz, 8.2 Hz), 7.13 (1H, t, J=8.2 Hz)

$^{13}$C-NMR (150 MHz, $CDCl_3$) δ ppm: 25.88, 29.59, 38.85, 55.38, 60.15, 62.61, 67.58, 100.08, 102.55, 106.08, 129.90, 151.44, 160.01

(4) 2-[[3-(4-Acetoxybutoxy)phenyl] (methyl)amino] ethyl acetate (compound 7e)

[Chem. 86]

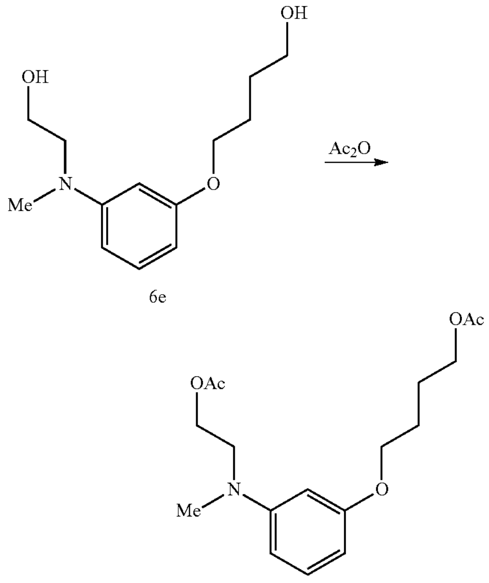

6e

7e 5.68 g (23.7 mmol) of 4-[3-[(2-hydroxyethyl) (methyl) amino]phenoxy]butan-1-ol (6e) was dissolved in 10 mL of acetic anhydride. The solution was stirred in an oil bath at 100° C. for 1 hour. After cooling, 30 mL of water and 50 mL of ether were added, and the mixture was stirred for 30 minutes. The ether layer was separated and washed with a saturated aqueous sodium hydrogen carbonate solution. The washed ether layer was dehydrated over anhydrous sodium sulfate and concentrated. The residue was purified by silica gel column chromatography (ethyl acetate/hexane=1/1) to give 6.4 g of the desired compound 7e as an oil (yield: 83.4%).

The NMR measurement results of compound 7e are shown below.

$^1$H-NMR (600 MHz, $CDCl_3$) δ ppm: 1.80-1.88 (4H, m), 2.02 (3H, s), 2.05 (3H, s), 2.97 (3H, s), 3.57 (2H, t, J=6.2 Hz), 3.98 (2H, t, J=6.2 Hz), 4.14 (2H, t, J=6.2 Hz), 4.24 (2H, t, J=6.2 Hz), 6.26-6.27 (2H, m), 6.35 (1H, dd, J=2.1 Hz, 8.3 Hz), 7.12 (1H, t, J=8.2 Hz)

$^{13}$C-NMR (150 MHz, $CDCl_3$) δ ppm: 20.92, 21.02, 25.43, 25.98, 38.78, 51.10, 61.55, 64.21, 67.05, 99.38, 101.96, 105.33, 129.91, 150.33, 160.16, 171.04, 171.23

(5) 2-[[3-(4-Acetoxybutoxy)-4-formylphenyl](methyl)amino]ethyl acetate (compound 8e)

[Chem. 87]

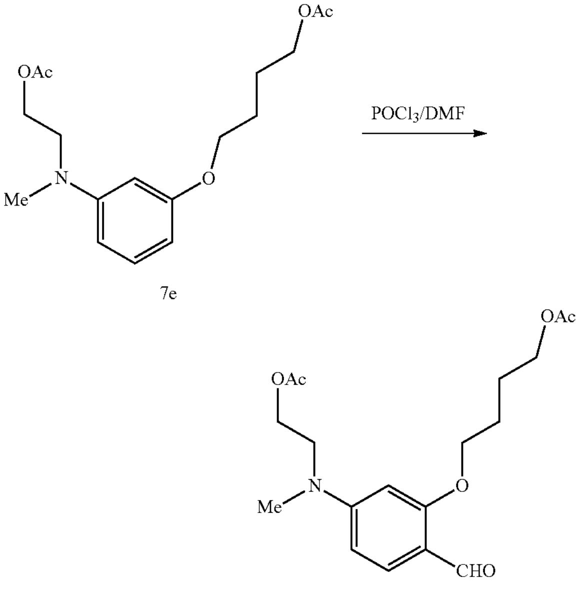

7e

8e 3.05 g (19.89 mmol) of phosphorus oxychloride was added dropwise to 20 mL of N,N-dimethylformamide with stirring under ice-cooling. After 20 minutes, the ice bath was removed, and the reaction mixture was heated to 14° C. and stirred at the same temperature for 5 minutes. The reaction mixture was then ice-cooled again. To this, a solution of 6.40 g (19.79 mmol) of 2-[[3-(4-acetoxybutoxy)phenyl] (methyl) amino]ethyl acetate (7e) in 8 mL of N,N-dimethylformamide was added dropwise. After 15 minutes, the reaction mixture was gradually heated to 70° C. and stirred at the same temperature for 2 hours. To the reaction mixture in an ice bath, 60 mL of a 20% aqueous sodium acetate solution was added dropwise, and the mixture was stirred for 50 minutes. Ethyl acetate extraction was performed, and the extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residue was purified by silica gel column chromatography (ethyl acetate/hexane=2/1) to give 4.85 g of the desired compound 8e (yield: 69.8%).

The NMR measurement results of compound 8e are shown below.

$^1$H-NMR (600 MHz, $CDCl_3$) δ ppm: 1.84-1.89 (2H, m), 1.91-1.98 (2H, m), 2.02 (3H, s), 2.06 (3H, s), 3.09 (3H, s), 3.67 (2H, t, J=6.2 Hz), 4.09 (2H, t, J=6.2 Hz), 4.15 (2H, t, J=6.2 Hz), 4.27 (2H, t, J=6.2 Hz), 6.14 (1H, s), 6.35 (1H, d, J=8.9 Hz), 7.73 (1H, d, J=8.9 Hz), 10.21 (1H, s)

$^{13}$C-NMR (150 MHz, $CDCl_3$) δ ppm: 20.85, 20.99, 25.37, 25.79, 38.91, 50.70, 60.95, 63.93, 67.42, 94.02, 104.60, 115.18, 130.17, 154.98, 163.39, 170.90, 171.1, 187.37

(6) 2-(4-Hydroxybutoxy)-4-[(2-hydroxyethyl)(methyl)amino]benzaldehyde (compound 9e)

[Chem. 88]

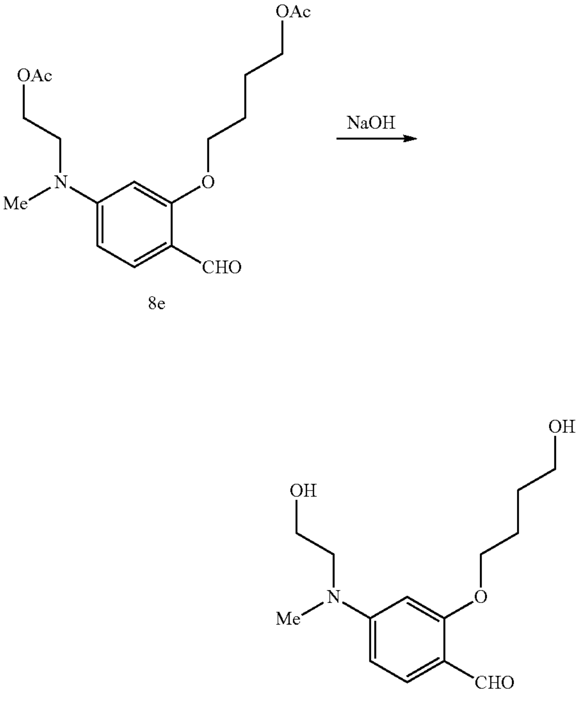

8e

9e 4.85 g (13.8 mmol) of 2-[[3-(4-acetoxybutoxy)-4-formylphenyl] (methyl)amino]ethyl acetate (8e) was dissolved in 30 mL of ethanol and 20 mL of tetrahydrofuran. To this, a solution of 1.38 g of sodium hydroxide in 19 mL of water was added dropwise. After 40-minute stirring at room temperature, the reaction mixture was poured into a saturated aqueous sodium chloride solution, and chloroform extraction was performed. The extract was dehydrated over anhydrous sodium sulfate and concentrated to give 3.70 g of the desired compound 9e (crude yield: 100.3%).

The NMR measurement results of compound 9e are shown below.

$^1$H-NMR (600 MHz, $CDCl_3$) δ ppm: 1.66 (2H, b), 1.75-1.79 (2H, m), 1.93-1.98 (2H, m), 3.11 (3H, s), 3.60 (2H, t, J=5.5H), 3.74 (2H, t, J=6.2 Hz), 3.87 (2H, t, J=5.5 Hz), 4.09 (2H, t, J=6.2H), 6.15 (1H, d, J=2.0 Hz), 6.35 (1H, dd, J=2.0 Hz, 9.0 Hz), 7.68 (1H, d, J=9.0 Hz), 10.12 (1H, s)

$^{13}$C-NMR (150 MHz, $CDCl_3$) δ ppm: 25.44, 29.38, 39.25, 54.52, 60.20, 62.26, 67.93, 94.20, 104.62, 115.00, 130.94, 155.51, 163.24, 187.56

(7) 2-[4-[(tert-Butyldiphenylsilyl)oxy]butoxy]-4-[[2-[(tert-butyldiphenylsilyl)oxy]ethyl] (methyl)amino] benzaldehyde (compound 10e)

[Chem. 89]

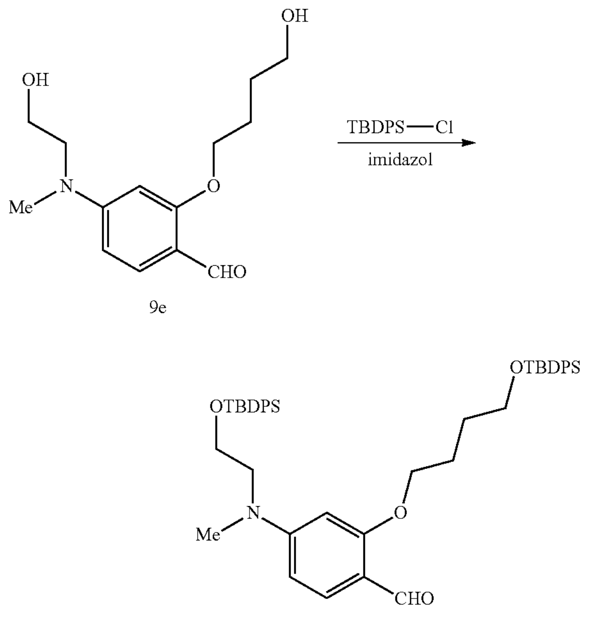

9e

10e 3.7 g (13.84 mmol) of 2-(4-hydroxybutoxy)-4-[(2-hydroxyethyl) (methyl)amino]benzaldehyde (9e) and 3.8 g (55.82 mmol) of imidazole were dissolved in 30 mL of N,N-dimethylformamide. To this, 7.75 g (28.20 mmol) of tert-butylchlorodiphenylsilane was added dropwise with stirring at room temperature. After 1.5-hour stirring, the reaction mixture was added to water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/2) to give 9.15 g of the desired compound 10e as a colorless oil (yield: 88.8%).

The NMR measurement results of compound 10e are shown below.

$^{1}$H-NMR (600 MHz, $CDCl_3$) δ ppm: 1.03 (9H, s), 1.05 (9H, s), 1.70-1.75 (2H, m), 1.88-1.93 (2H, m), 3.02 (3H, s), 3.55 (2H, t, J=6.2 Hz), 3.73 (2H, t, J=6.2 Hz), 3.81 (2H, t, J=6.2 Hz), 3.95 (2H, t, J=6.2 Hz), 5.95 (1H, d, J=2.0 Hz), 6.15 (1H, dd, J=2.1 Hz, 8.9 Hz), 7.33-7.43 (12H, m), 7.60-7.61 (4H, m), 7.64-7.67 (5H, m), 10.17 (1H, s)

$^{13}$C-NMR (150 MHz, $CDCl_3$) δ ppm: 19.04, 19.21, 25.82, 26.77, 26.87, 29.12, 39.53, 54.25, 61.04, 63.47, 67.77, 93.68, 104.52, 114.73, 127.63, 127.77, 129.59, 129.83, 133.05, 133.86, 134.78, 135.51, 135.54, 155.14, 163.57, 187.37

(8) 3-[4-[(tert-Butyldiphenylsilyl)oxy]butoxy]-N-[2-[(tert-butyidiphenylsilyl)oxy]ethyl]-N-methyl-4-[2-(thiophen-2-yl)vinyl]aniline (compound 12-(Z/E)e)

[Chem. 90]

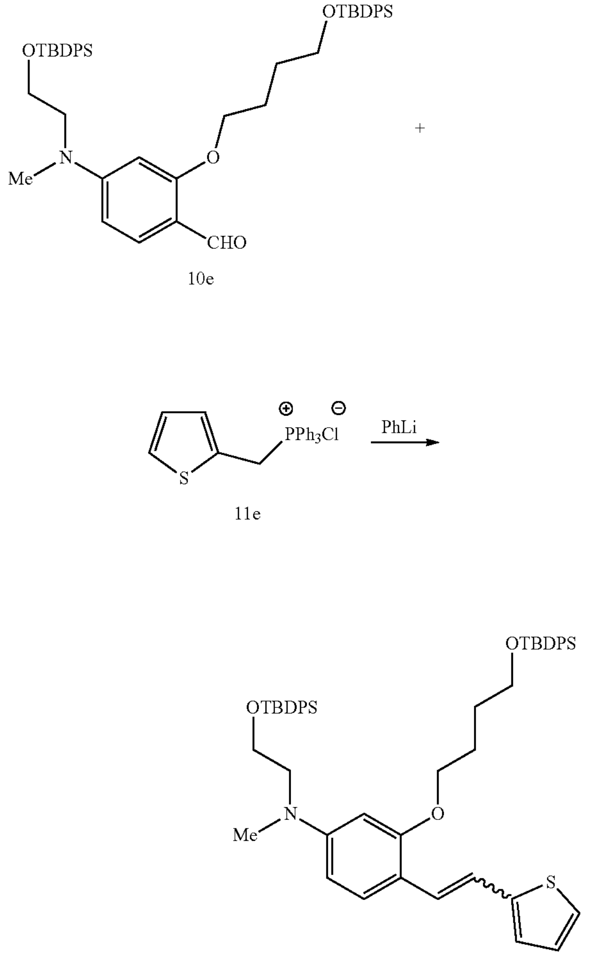

10e

11e 12-(Z/E)e 6.6 mL (13.86 mmol) of phenyllithium (2.1 mol solution in dibutyl ether) was added to 55 mL of tetrahydrofuran under an argon atmosphere. To this, 4.95 g (12.54 mmol) of 2-thenyl triphenyl phosphonium chloride (11e) was added under ice-cooling. After 30-minute stirring, 20 mL of a solution of 9.15 g (12.30 mmol) of 2-[4-[(tert-butyldiphenylsilyl)oxy]butoxy]-4-[[2-[(tert-butyldiphenylsilyl)oxy] ethyl] (methyl)amino]benzaldehyde (10e) in tetrahydrofuran was added dropwise. After 45-minute stirring under ice-cooling, the reaction mixture was poured into water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/3) to give 7.63 g of the desired compound 12-(Z/E)e as a yellow oil (yield: 75.2%).

(9) 5-[2-[4-[(tert-Butyldiphenylsilyl)oxy]butoxy]-4-[[2-[(tert-butyldiphenylsilyl)oxy]ethyl] (methyl) amino]styryl]thiophene-2-carbaldehyde (compound 13-(Z/E)e)

[Chem. 91]

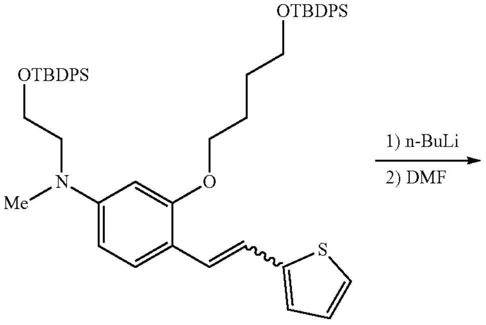

12-(Z/E)e

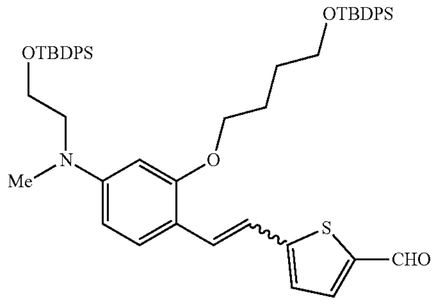

13-(Z/E)e 7.62 g (9.24 mmol) of 3-[4-[(tert-butyldiphenylsilyl)oxy] butoxy]-N-[2-[(tert-butyldiphenylsilyl)oxy]ethyl]-N-methyl-4-[2-(thiophen-2-yl)vinyl]aniline (12-(Z/E)e) was dissolved in 40 mL of tetrahydrofuran under an argon atmosphere. To this, 6.9 mL (11.04 mmol) of n-butyllithium (1.6 mol solution in hexane) was added dropwise with cooling in a dry ice/acetone bath. After 45-minute stirring, 0.88 g (12.04 mmol) of N,N-dimethylformamide was added dropwise. After 1.5-hour stirring, the reaction mixture was heated, and 5 mL of water was added dropwise. After 40-minute stirring, the reaction mixture was poured into a saturated aqueous sodium chloride solution, and ethyl acetate extraction was performed. The extract was dehydrated over anhydrous sodium sulfate and concentrated. The residue was purified by silica gel column chromatography (ethyl acetate/hexane=1/4) to give 6.77 g of the desired compound 13-(Z/E)e (yield: 85.9%).

(10 ) (E)-5-[2-[4-[(tert-Butyldiphenylsilyl)oxy]butoxy]-4-[[2-[(tert-butyldiphenylsilyl)oxy]ethyl] (methyl)amino]styryl]thiophene-2-carbaldehyde (compound 13-(E)e)

[Chem. 92]

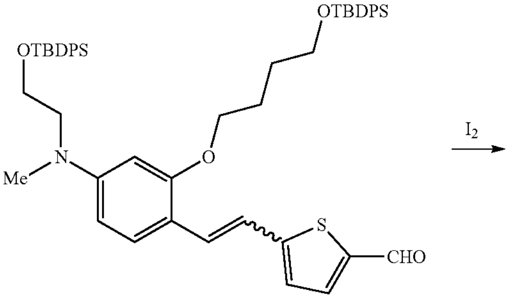

13-(Z/E)e

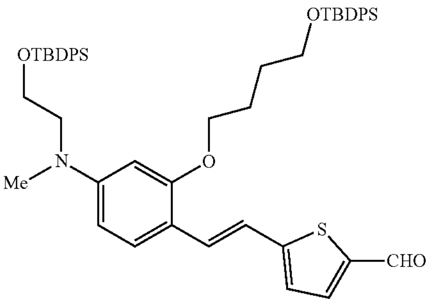

13-(E)e 7.45 g of 5-[2-[4-[(tert-butyldiphenylsilyl)oxy]butoxy]-4-[[2-[(tert-butyldiphenylsilyl)oxy]ethyl] (methyl)amino] styryl]thiophene-2-carbaldehyde (13-(Z/E)e) was dissolved in 300 mL of ether. To this, 250 mg of iodine flakes were added. After 30-minute stirring at room temperature, the reaction mixture was washed with a 5% aqueous sodium hydrogen sulfite solution and subsequently with a saturated aqueous sodium chloride solution. The washed reaction mixture was dehydrated over anhydrous magnesium sulfate and concentrated. The residue was purified by silica gel column chromatography (ethyl acetate/hexane=1/3) to give 6.29 g of the desired compound 13-(E)e as a red oil (yield: 84.4%).

The NMR measurement results of compound 13-(E)e are shown below.

$^1$H-NMR (600 MHz, $CDCl_3$) δ ppm: 1.04 (9H, s), 1.06 (9H, s), 1.75-1.80 (2H, m), 1.93-1.98 (2H, m), 2.98 (3H, s), 3.52 (2H, t, J=6.2 Hz), 3.76 (2H, t, J=6.2 Hz), 3.81 (2H, t, J=6.2 Hz), 3.95 (2H, t, J=6.2 Hz), 6.08 (1H, d, J=2.1 Hz), 6.18 (1H, dd, J=2.7 Hz, 9.0 Hz), 6.98 (1H, d, J=4.1 Hz), 7.10 (1H, d, J=15.8 Hz), 7.29 (1H, d, J=9.0 Hz), 7.33-7.42 (13H, m), 7.57 (1H, d, J=4.1 Hz), 7.62-7.63 (4H, m), 7.66-7.68 (4H, m), 9.78 (1H, s)

$^{13}$C-NMR (150 MHz, $CDCl_3$) δ ppm: 19.06, 19.23, 25.99, 26.79, 26.89, 29.27, 39.31, 54.41, 61.21, 63.52, 67.98, 95.61, 104.73, 113.16, 116.35, 124.45, 127.62, 127.72, 128.69, 129.32, 129.67, 129.74, 133.26, 133.89, 135.53, 137.67, 139.65, 150.96, 155.65, 158.52, 182.26

(11 ) (E)-5-[2-(4-Hydroxybutoxy)-4-[(2-hydroxyethyl) (methyl)amino]styryl]thiophene-2-carbaldehyde (compound 14-(E)e)

[Chem. 93]

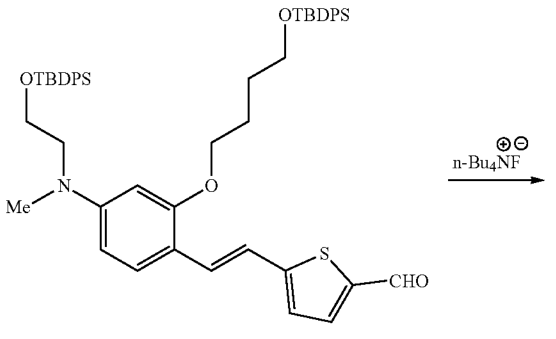

13-(E)e

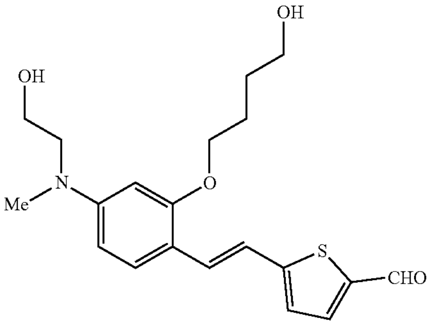

14-(E)e 6.29 g (7.38 mmol) of (E)-5-[2-[4-[(tert-butyldiphenylsilyl)oxy]butoxy]-4-[[2-[(tert-butyldiphenylsilyl)oxy]ethyl](methyl)amino] styryl]thiophene-2-carbaldehyde (13-(E)e) was dissolved in 50 mL of tetrahydrofuran. To this, 22 mL of tetrabutylammonium fluoride (1 mol solution in tetrahydrofuran) was added dropwise with stirring at room temperature. After 1-hour stirring, the reaction mixture was poured into a saturated aqueous sodium chloride solution, and ethyl acetate extraction was performed. The extract was dehydrated over anhydrous sodium sulfate and concentrated. The residue was washed with 100 mL of an ethyl acetate/hexane (1/10) mixture and subsequently with 100 mL of hexane. The insoluble residue was purified by silica gel column chromatography (chloroform/methanol=9/1) to give 2.61 g of the desired compound 14-(E)e as an oil (yield: 94.2%).

The NMR measurement results of compound 14-(E)e are shown below.

$^1$H-NMR (600 MHz, $CDCl_3$) δ ppm: 1.77-1.81 (2H, m), 1.93-1.97 (2H, m), 2.04 (1H, b), 2.27 (1H, b), 3.02 (3H, s), 3.52 (2H, t, J=6.2 Hz), 3.75 (2H, t, J=6.2 Hz), 3.82 (2H, t, J=6.2 Hz), 4.05 (2H, t, J=6.2 Hz), 6.24 (1H, d, J=2.0 Hz), 6.35 (1H, dd, J=2.0 Hz, 8.2 Hz), 7.01 (1H, d, J=4.1 Hz), 7.08 (1H, d, J=15.8 Hz), 7.36 (1H, d, J=8.2 Hz), 7.41 (1H, d, J=15.8 Hz), 7.59 (1H, d, J=4.1 Hz), 9.75 (1H, s)

(12) 2-[3-Cyano-4-[(E)-2-[5-[(E)-2-(4-hydroxybutoxy)-4-[(2-hydroxyethyl) (methyl)amino]styryl]thiophen-2-yl]vinyl]-5-phenyl-5-(trifluoromethyl)furan-2(5H)-ylidene]malononitrile (EO-7)

[Chem. 94]

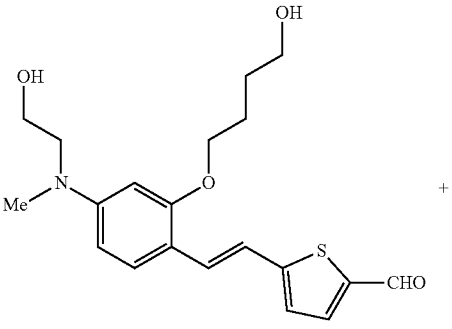

14-(E)e

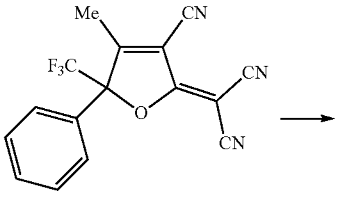

15c

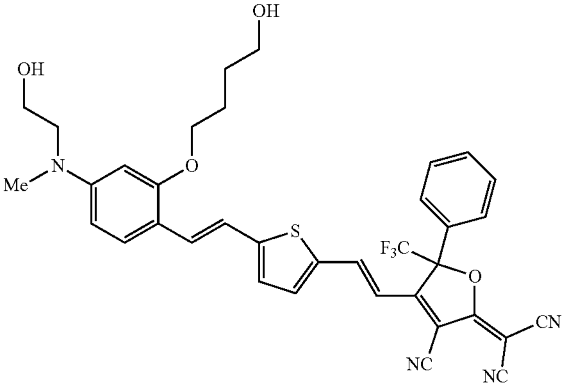

EO-7

1.58 g (4.21 mmol) of (E)-5-[2-(4-hydroxybutoxy)-4-[(2-hydroxyethyl) (methyl)amino]styryl]thiophene-2-carbaldehyde (14-(E)e) and 1.46 g (4.63 mmol) of 2-[3-cyano-4-methyl-5-phenyl-5-(trifluoromethyl)-2(5H)-furanylidene] propanedinitrile (15e) were added to 25 mL of ethanol. The mixture was stirred in an oil bath at 50° C. for 1 hour and subsequently at room temperature for 17 hours. The reaction mixture was ice-cooled and then filtered, and the residue was washed with ethanol. As a result, 2.30 g of the desired compound EO-7 was obtained as dark red-brown crystals with a melting point of 224 to 226° C. (yield: 81.3%)

The NMR measurement results of EO-7 are shown below.

$^1$H-NMR (600 MHz, DMSO-$d_6$) δ ppm: 1.62-1.65 (2H, m), 1.83-1.88 (2H, m), 3.05 (3H, s), 3.51 (4H, t, J=6.2 Hz), 3.58 (2H, t, J=6.2 Hz), 4.10 (2H, t, J=6.2 Hz), 4.56 (1H, b), 4.77 (1H, b), 6.25 (1H, d, J=2.2 Hz), 6.40 (1H, dd, J=2.0 Hz, 8.9 Hz), 6.50 (1H, d, J=15.1 Hz), 7.25 (1H, d, J=4.1 Hz), 7.38 (1H, d, J=15.8 Hz), 7.47 (1H, d, J=8.9 Hz), 7.48 (1H, d, J=15.8 Hz), 7.61-7.66 (3H, m), 7.69-7.71 (3H, m), 7.76 (1H, d, J=4.1 Hz)

$^{13}C$-NMR (150 MHz, DMSO-$d_6$) δ ppm: 25.25, 29.08, 54.01, 55.06, 58.23, 60.28, 67.76, 95.14, 105.40, 110.19, 111.18, 111.35, 112.01, 112.46, 116.04, 121.77, 126.78, 128.46, 129.27, 129.78, 130.60, 131.47, 133.24, 137.24, 140.65, 152.44, 159.32, 159.77, 159.99, 175.78

Synthesis Example 27: Production method of EO molecule (EO-8)

2-[3-Cyano-4-[(E)-2-[5-[(E)-2-(4-hydroxybutoxy)-4-[(2-hydroxyethyl) (methyl)amino]styryl]thiophen-2-yl]vinyl]-5,5-dimethylfuran-2 (5H)-ylidene]malononitrile (EO-8)

[Chem. 95]

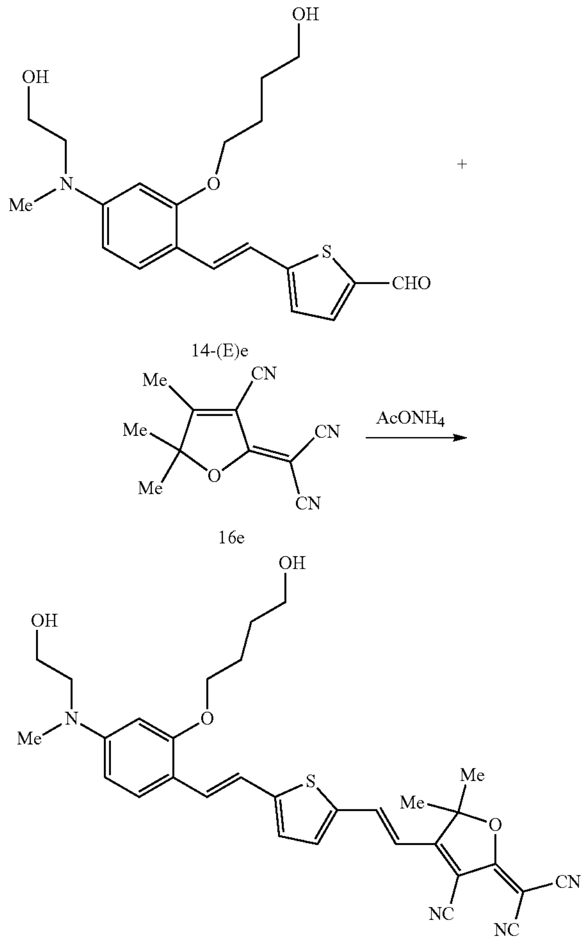

14-(E)e

16e

EO-8

1.02 g (4.21 mmol) of (E)-5-[2-(4-hydroxybutoxy)-4-[(2-hydroxyethyl) (methyl)amino]styryl]thiophene-2-carbaldehyde (14-(E)e) and 0.6 g (2.99 mmol) of 2-(3-cyano-4,5,5-trimethyl-2(5H)-furanylidene)propanedinitrile (16e) were added to 25 mL of ethanol. To this, 210 mg of ammonium acetate was added, and the mixture was stirred in an oil bath at 40° C. for 17 hours. The reaction mixture was ice-cooled and then filtered, and the residue was washed with ethanol. As a result, 1.18 g of the desired compound EO-8 was obtained as dark red-brown crystals with a melting point of 150 to 152° C. (yield: 78.2%).

The NMR measurement results of EO-8 are shown below.

$^{1}H$-NMR (600 MHz, DMSO-$d_6$) δ ppm: 1.63-1.67 (2H, m), 1.78 (6H, s), 1.83-1.87 (2H, m), 3.01 (3H), 3.46 (2H, t, J=6.2 Hz), 3.51 (2H, t, J=6.2H), 3.57 (2H, t, J=6.2 Hz), 4.08 (2H, t, J=6.2 Hz), 4.50 (1H, b), 4.74 (1H, b), 6.26 (1H, d, J=2.1 Hz), 6.36 (1H, dd, J=2.1 Hz, 8.9 Hz), 6.63 (1H, d, J=15.8 Hz), 7.20 (1H, d, J=4.1 Hz), 7.32 (1H, d, J=15.8 Hz), 7.35 (1H, d, J=15.8 Hz), 7.44 (1H, d, J=8.9 Hz), 7.75 (1H, d, J=4.1 Hz), 8.10 (1H, d, J=15.8 Hz) 13C-NMR (150 MHz, DMSO-$d_6$) δ ppm: 25.35, 25.44, 29.06, 52.26, 53.96, 58.15, 60.28, 67.62, 95.34, 95.43, 98.35, 104.76, 111.29, 112.10, 112.26, 113.05, 116.14, 127.13, 129.42, 129.87, 136.98, 139.05, 140.27, 151.37, 154.81, 158.41, 174.26, 176.79

Synthesis Example 28: Production Method of EO Molecule (EO-9)

[Chem. 96]

EO-9

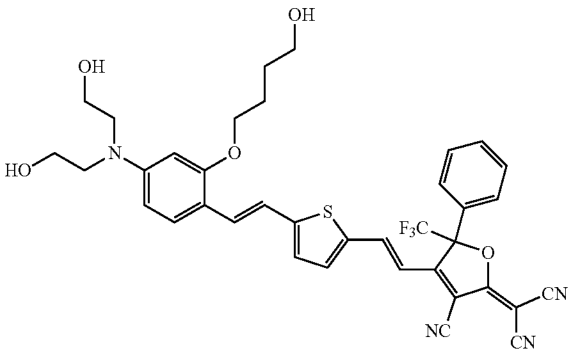

(1) N,N-Bis[2-[(tert-butyldimethylsilyl)oxy]ethyl]-3-[4-[(tert-butyldiphenylsilyl)oxy]butoxy]aniline (compound 3f)

[Chem. 97]

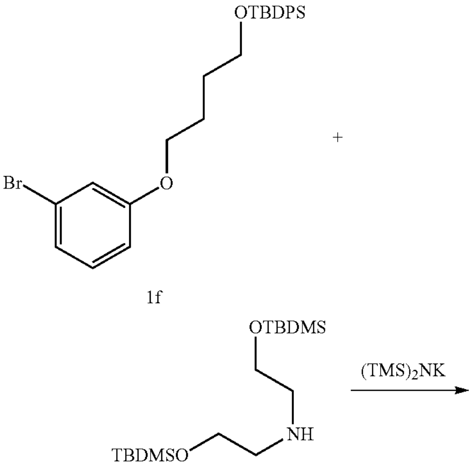

1f

2f

-continued

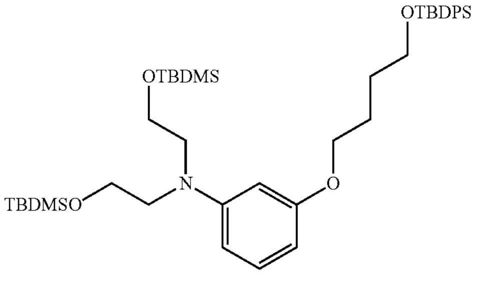

3f 11.3 g (23.37 mmol) of [4-(3-bromophenoxy)butoxy](tert-butyl)diphenylsilane (1f) and 10.13 g (30.36 mmol) of bis[2-[(tert-butyldimethylsilyl)oxy]ethyl]amine (2f) were dissolved in 100 mL of toluene. To this, 5.59 g (28.02 mol) of potassium bis(trimethylsilyl) amide was added with stirring at room temperature. The mixture was stirred in an oil bath at 110° C. for 6 hours, cooled, and washed with a saturated aqueous sodium chloride solution. The washed reaction mixture was dehydrated over anhydrous sodium sulfate and concentrated. The residue was purified by silica gel column chromatography (toluene) to give 9.1 g of the desired compound 3f as a light-brown oil (yield: 52.9%).

The NMR measurement results of compound 3f are shown below.

$^1$H-NMR (600 MHz, $CDCl_3$) δ ppm: 0.32 (12H, s), 0.88 (18H, s), 1.05 (9H, s), 1.69-1.74 (2H, m), 1.84-1.89 (2H, m), 3.47 (4H, t, J=6.2 Hz), 3.72 (2H, t, J=6.2 Hz), 3.74 (4H, t, J=6.2 Hz), 3.92 (2H, t, J=6.2 Hz), 6.18-6.21 (2H, m), 6.28 (1H, dd, J=2.1 Hz, 8.3 Hz), 7.07 (1H, t, J=8.3 Hz), 7.36-7.43 (6H, m), 7.66-7.68 (4H, m)

$^{13}$C-NMR (150 MHz, $CDCl_3$) δ ppm: 18.29, 19.23, 25.93, 26.87, 29.15, 53.56, 60.30, 63.54, 67.50, 98.66, 101.09, 104.55, 127.61, 129.55, 129.82, 133.97, 135.57, 149.21, 160.39

(2) 2,2'-[[3-(4-Hydroxybutoxy)phenyl]azanediyl]diethanol (compound 4f)

[Chem. 98]

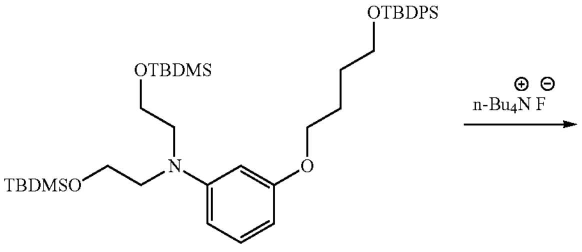

3f

-continued

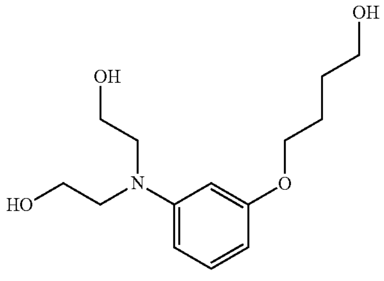

4f 22.35 g (30.36 mmol) of N,N-bis[2-[(tert-butyldimethylsilyl)oxy]ethyl]-3-[4-[(tert-butyldiphenylsilyl)oxy]butoxy]aniline (3f) was dissolved in 45 mL of tetrahydrofuran. To this, 137 mL of tetrabutylammonium fluoride (1 mol solution in tetrahydrofuran) was added dropwise with stirring at room temperature. After 1.5-hour stirring, the reaction mixture was poured into 250 mL of water, and ethyl acetate extraction was performed. The extract was washed with a saturated aqueous sodium chloride solution, dehydrated over anhydrous sodium sulfate, and concentrated. The residue was washed twice with 150 mL of hexane. As a result, 3.65 g of the desired compound 4f was obtained as white crystals (crude yield: 44.6%)

The NMR measurement results of compound 4f are shown below.

$^1$H-NMR (600 MHz, $CDCl_3$) δ ppm: 1.72-1.76 (2H, m), 1.84-1.95 (2H, m), 3.43 (2H, b), 3.56 (4H, t, J=4.8 Hz), 3.71 (2H, t, J=6.2 Hz), 3.85 (4H, t, J=4.8 Hz), 3.99 (2H, t, J=6.2 Hz), 6.25-6.32 (3H, m), 7.12 (1H, t, J=8.2 Hz)

$^{13}$C-NMR (150 MHz, $CDCl_3$) δ ppm: 25.87, 29.52, 55.35, 60.80, 62.56, 67.62, 99.94, 102.15, 105.78, 129.99, 149.28, 160.05

(3) [[3-(4-Acetoxybutoxy)phenyl]azanediyl]bis(ethane-2,1-diyl)diacetate (compound 5f)

[Chem. 99]

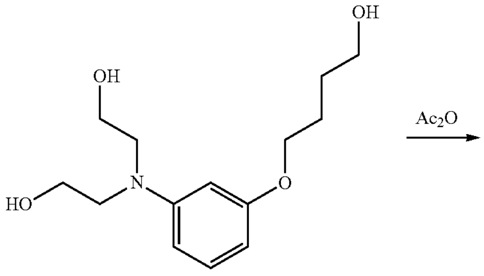

4f

-continued

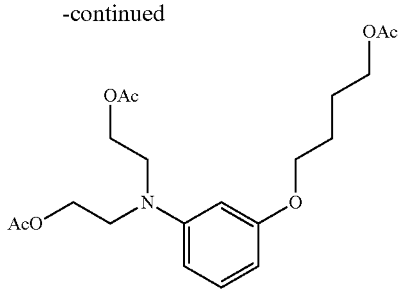

5f 10 mL of acetic anhydride was added to 3.65 g (13.55 mmol) of 2,2'-[[3-(4-hydroxybutoxy)phenyl]azanediyl]di-ethanol (4f), and the mixture was stirred in an oil bath at 100° C. for 2 hours. After cooling, 30 mL of ether and 40 mL of water were added, and the mixture was stirred for 40 minutes. The organic layer was separated, and the aqueous layer was further subjected to extraction with 30 mL of ether. The organic layers were combined and washed with a saturated aqueous sodium hydrogen carbonate solution and subsequently with a saturated aqueous sodium chloride solution. The washed organic layer was dehydrated over anhydrous magnesium sulfate and concentrated. The residual liquid was purified by silica gel column chromatography (ethyl acetate/hexane=1/1) to give 4.76 g of the desired compound 5f as a light-yellow oil (yield: 88.8%).

The NMR measurement results of compound 5f are shown below.

$^1$H-NMR (600 MHz, $CDCl_3$) δ ppm: 1.80-1.87 (4H, m), 2.056 (3H, s), 2.058 (6H, s), 3.60 (4H, t, J=6.2 Hz), 3.98 (2H, t, J=6.2 Hz), 4.13 (2H, t, J=6.2 Hz), 4.23 (4H, t, J=6.2 Hz), 6.28 (1H, dd, J=2.0 Hz, 8.2 Hz), 6.30 (1H, t, J=2.0 Hz), 6.35 (1H, dd, J=2.0 Hz, 8.2 Hz), 7.12 (1H, t, J=8.2 Hz)

(4) [[3-(4-Acetoxybutoxy)-4-formylphenyl] azanediyl]bis(ethane-2,1-diyl)diacetate (compound 6f)

[Chem. 100]

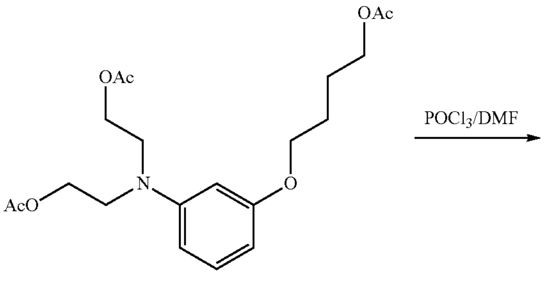

5f 6f

-continued

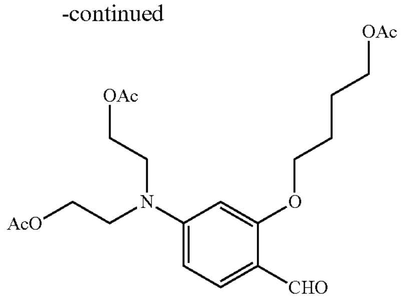

6f 1.88 g (12.26 mmol) of phosphorus oxychloride was added dropwise to 15 mL of N,N-dimethylformamide with stirring under ice-cooling. After 20-minute stirring, the ice bath was removed, and the reaction mixture was heated to 13° C. After 5 minutes, the reaction mixture was ice-cooled again. To this, a solution of 4.76 (12.04 mmol) of [[3-(4-acetoxybutoxy)phenyl]azanediyl]bis(ethane-2,1-diyl)diacetate (5f) in 10 mL of N,N-dimethylformamide was added dropwise. After 20 minutes, the reaction mixture was gradually heated to 60° C. and stirred at the same temperature for 2 hours. To the reaction mixture under cooling in an ice bath, 20 mL of a 20% aqueous sodium acetate solution was added dropwise, and the mixture was stirred for 40 minutes. Ethyl acetate extraction was performed, and the extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residue was recrystallized from an ethyl acetate/hexane (2/3) mixture to give 3.77 g of the desired compound 6f as colorless crystals. The filtrate was concentrated, and the residue was purified by silica gel column chromatography (ethyl acetate/hexane=2/1) to further give 0.27 g of the desired compound 6f (yield: 88.0%).

The NMR measurement results of compound 6f are shown below.

$^1$H-NMR (600 MHz, $CDCl_3$) δ ppm: 1.85-1.89 (2H, m), 1.92-1.96 (2H, m), 2.06 (9H, s), 3.68 (4H, t, J=5.5 Hz), 4.13 (2H, t, J=5.5 Hz), 4.15 (2H, t, J=6.2 Hz), 4.27 (4H, t, J=6.2 Hz), 6.32 (1H, d, J=2.0 Hz), 6.36 (1H, dd, J=2.0 Hz, 8.9 Hz), 7.73 (1H, d, J=8.9 Hz), 10.22 (1H, s)

$^{13}$C-NMR (150 MHz, $CDCl_3$) δ ppm: 20.86, 21.00, 25.39, 25.79, 49.60, 60.78, 63.97, 67.58, 94.48, 104.49, 115.63, 130.31, 153.78, 163.53, 170.89, 171.20, 187.42

(5) 4-[Bis(2-hydroxyethyl)amino]-2-(4-hydroxybutoxy)benzaldehyde (compound 7f)

[Chem. 101]

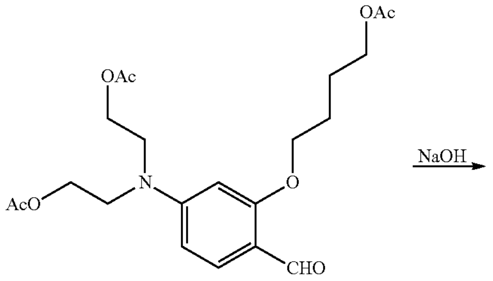

6f

-continued

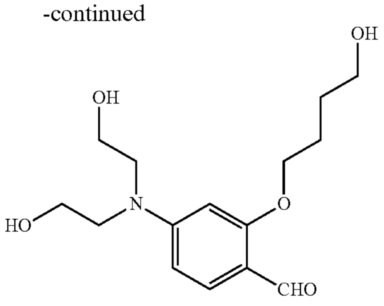

7f 4.48 g (10.58 mmol) of [[3-(4-acetoxybutoxy)-4-formylphenyl]azanediyl]bis(ethane-2,1-diyl)diacetate (6f) was dissolved in 20 mL of ethanol and 10 mL of tetrahydrofuran. To this, 26 mL of a 7% aqueous sodium hydroxide solution was added dropwise, and the mixture was stirred at room temperature for 30 minutes. The reaction mixture was poured into a saturated aqueous sodium chloride solution, and chloroform extraction was performed. The extract was dehydrated over anhydrous sodium sulfate and concentrated to give 2.11 g of the desired compound 7f. The aqueous layer was further subjected to extraction with 50 mL of ethyl acetate. The extract was dehydrated and concentrated similarly as above to further give 1.06 g of the desired compound 7f. 3.17 g in total (crude yield: 100.8%)

The NMR measurement results of compound 7f are shown below.

$^{1}$H-NMR (600 MHz, DMSO-$d_6$) δ ppm: 1.57-1.61 (2H, m), 1.75-1.81 (2H, m), 3.46 (2H, q, J=6.2 Hz), 3.53 (4H, t, J=5.5 Hz), 3.57 (4H, t, J=6.2 Hz), 4.08 (2H, t, J=6.2 Hz), 6.24 (1H, d, J=2.0 Hz), 6.38 (1H, dd, J=2.0 Hz, 8.9 Hz), 7.48 (1H, d, J=8.9 Hz), 10.02 (1H, s)

$^{13}$C-NMR (150 MHz, DMSO-$d_6$) δ ppm: 25.17, 28.96, 53.11, 57.99, 60.26, 67.55, 93.94, 104.42, 113.36, 129.02, 154.55, 162.97, 185.20

(6) 4-[Bis[2-[(tert-butyldiphenylsilyl)oxy]ethyl]amino]-2-[4-[(tert-butyldiphenylsilyl)oxy]butoxy]benzaldehyde (compound 8f)

[Chem. 102]

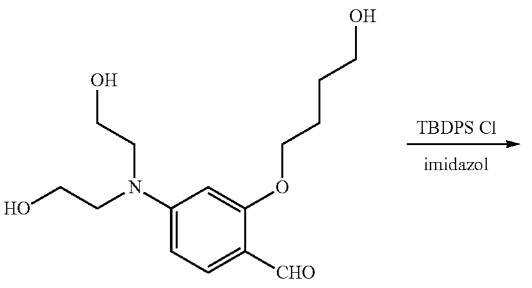

7f

-continued

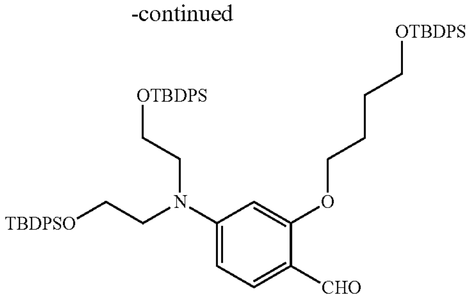

8f 3.17 g (10.66 mmol) of 4-[bis(2-hydroxyethyl)amino]-2-(4-hydroxybutoxy)benzaldehyde (7f) and 3.4 g (49.94 mmol) of imidazole were dissolved in 30 mL of N,N-dimethylformamide. To this, 9.23 g (33.58 mmol) of tert-butylchlorodiphenylsilane was added dropwise with stirring at room temperature. After 2-hour stirring, the reaction mixture was added to 150 mL of a saturated aqueous sodium chloride solution, and ethyl acetate extraction was performed. The extract was dehydrated over anhydrous sodium sulfate and concentrated. The residue was purified by silica gel column chromatography (ethyl acetate/hexane=1/3) to give 10.5 g of the desired compound 8f as a pale yellow oil (yield: 97.3%).

The NMR measurement results of compound 8f are shown below.

$^{1}$H-NMR (600 MHz, $CDCl_3$) δ ppm: 1.03 (18H, s), 1.04 (9H, s), 1.64-1.69 (2H, m), 1.79-1.84 (2H, m), 3.53 (4H, t J=6.2 Hz), 3.69 (2H, t, J=6.2 Hz), 3.75-3.78 (6H, m), 5.86 (1H, d, J=2.1 Hz), 5.92 (1H, dd, J=2.1 Hz, 8.9 Hz), 7.31-7.43 (18H, m), 7.53 (1H, d, J=8.9 Hz), 7.59 (8H, d, J=7.5 Hz), 7.65 (4H, d, J=7.6 Hz), 10.12 (1H, s)

$^{13}$C-NMR (150 MHz, $CDCl_3$) δ ppm: 19.06, 19.21, 26.55, 26.79, 26.47, 29.18, 53.01, 60.75, 63.48, 67.71, 93.61, 104.43, 127.63, 127.73, 127.78, 129.60, 129.85, 133.07, 133.87, 134.79, 135.50, 135.54, 154.31, 163.57, 187.22

(7) 3-[4-[(tert-Butyldiphenylsilyl)oxy]butoxy]-N,N-bis[2-[(tert-butyldiphenylsilyl)oxy]ethyl]-4-[2-(thiophen-2-yl)vinyl]aniline (compound 10-(Z/E)f)

[Chem. 103]

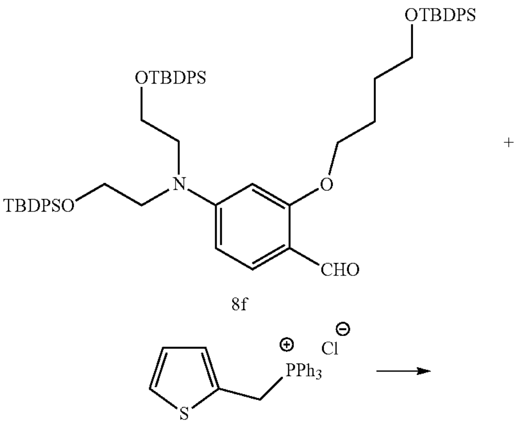

8f

9f

-continued

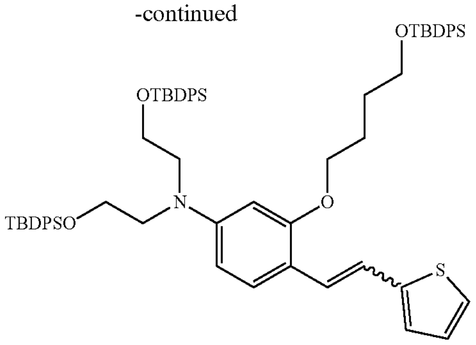

10-(Z/E)f 5.4 mL (11.34 mmol) of phenyllithium (2.1 mol solution in dibutyl ether) was added to 55 mL of tetrahydrofuran under an argon atmosphere. To this, 4.22 g (10.69 mmol) of 2-thenyl triphenyl phosphonium chloride (9f) was added under ice-cooling over 10 minutes. After 5-minute stirring, 15 mL of a solution of 10.5 g (10.37 mmol) of 4-[bis[2-[(tert-butyldiphenylsilyl)oxy]ethyl]amino]-2-[4-[(tert-butyldiphenylsilyl)oxy]butoxy]benzaldehyde (8f) in tetrahydrofuran was added dropwise. After 2.5-hour stirring under ice-cooling, the reaction mixture was poured into water, and ethyl acetate extraction was performed. The extract was washed with a saturated aqueous sodium chloride solution, dehydrated over anhydrous sodium sulfate, and concentrated. The residue was purified by silica gel column chromatography (ethyl acetate/hexane=1/5) to give 7.34 g of the desired compound 10-(Z/E)f as a yellow oil (yield: 64.8%).

(8) 5-[4-[Bis[2-[(tert-butyldiphenylsilyl)oxy]ethyl]amino]-2-[4-[(tert-butyldiphenylsilyl)oxy]butoxy]styryl]thiophene-2-carbaldehyde (compound 11-(Z/E)f)

[Chem. 104]

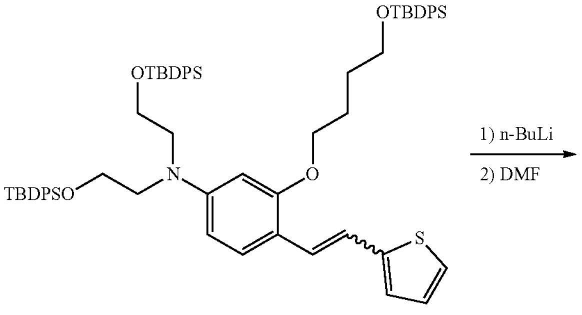

10-(Z/E)f

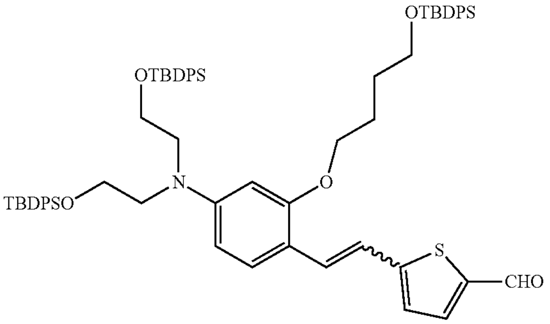

11-(Z/E)f 7.34 g (6.72 mmol) of 3-[4-[(tert-butyldiphenylsilyl)oxy]butoxy]-N,N-bis[2-[(tert-butyldiphenylsilyl)oxy]ethyl]-4-[2-(thiophen-2-yl)vinyl]aniline (10-(Z/E)f) was dissolved in 80 mL of tetrahydrofuran under an argon atmosphere. To this, 5.04 mL (8.06 mmol) of n-butyllithium (1.6 mol solution in hexane) was added dropwise with cooling in dry ice/acetone. After 20-minute stirring, 0.69 mL (9.01 mmol) of N,N-dimethylformamide was added dropwise. After 2-hour stirring, the reaction mixture was heated, and 5 mL of water was added dropwise. After 40-minute stirring, the reaction mixture was poured into 250 mL of a saturated aqueous sodium chloride solution, and ethyl acetate extraction was performed. The extract was dehydrated over anhydrous sodium sulfate and concentrated. The residue was purified by silica gel column chromatography (ethyl acetate/hexane=1/3) to give 6.82 g of the desired compound 11-(Z/E)f (yield: 90.5%).

(9 ) (E)-5-[4-[Bis[2-[(tert-butyldiphenylsilyl)oxy]ethyl]amino]-2-[4-[(tert-butyldiphenylsilyl)oxy]butoxy]styryl]thiophene-2-carbaldehyde (compound 11-(E)f)

[Chem. 105]

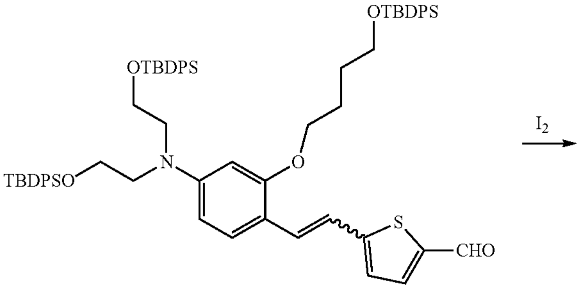

11-(Z/E)f

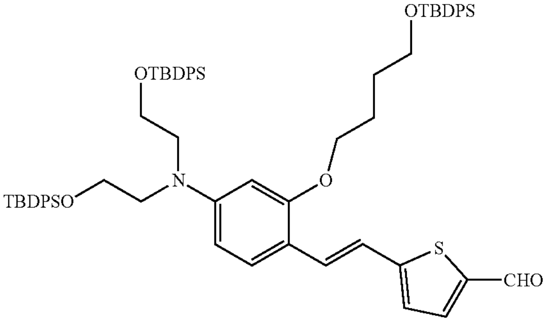

11-(E)f 6.81 g of 5-[4-[bis[2-[(tert-butyldiphenylsilyl)oxy]ethyl]amino]-2-[4-[(tert-butyldiphenylsilyl)oxy]butoxy]styryl]thiophene-2-carbaldehyde (11-(Z/E)f) was dissolved in 250 mL of ether. To this, 200 mg of iodine flakes were added. After 30-minute stirring at room temperature, the reaction mixture was washed with 60 mL of a 5% aqueous sodium hydrogen sulfite solution. The reaction mixture was further washed with a saturated aqueous sodium chloride solution, dehydrated over anhydrous magnesium sulfate, and concentrated. The residue was purified by silica gel column chromatography (ethyl acetate/hexane=1/3) to give 6.60 g of the desired compound 11-(E)f as a red oil (yield: 96.9%)

The NMR measurement results of compound 11-(E)f are shown below. 1H-NMR (600 MHz, $CDCl_3$) δ ppm: 1.04 (18H, s), 1.05 (9H, s), 1.70-1.75 (2H, m), 1.85-1.90 (2H, m), 3.52 (4H, t, J=6.2 Hz), 3.73 (2H, t, J=6.2 Hz), 3.77 (6H, t, J=6.2 Hz), 5.95 (1H, dd, J=2.0 Hz, 8.9 Hz), 5.98 (1H, d, J=2.0 Hz), 6.97 (1H, d, J=4.1 Hz), 7.07 (1H, d, J=15.8 Hz), 7.16 (1H, d, J=8.9 Hz), 7.32-7.42 (19H, m), 7.57 (1H, d, J=4.1 Hz), 7.61-7.62 (8H, m), 7.65-7.67 (4H, m), 9.78 (1H, s) 13C-NMR (150 MHz, $CDCl_3$) δ ppm: 19.09, 19.24, 25.93, 26.80, 26.89, 29.37, 53.07, 60.96, 63.53, 67.94, 95.38, 104.51, 113.06, 116.26, 124.42, 127.63, 127.73, 128.85, 129.29, 129.58, 129.76, 133.28, 133.91, 135.53, 137.67, 139.63, 149.78, 155.68, 158.55, 171.17, 182.25

(10 ) (E)-5-[4-[Bis(2-hydroxyethyl)amino]-2-(4-hydroxybutoxy) styryl]thiophene-2-carbaldehyde (compound 12-(E)f)

[Chem. 106]

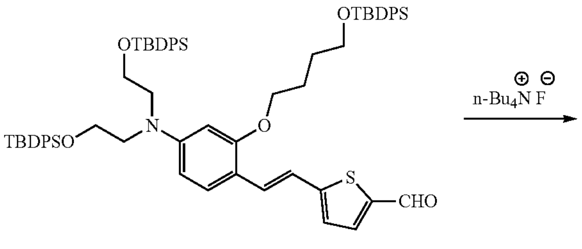

11-(E)f

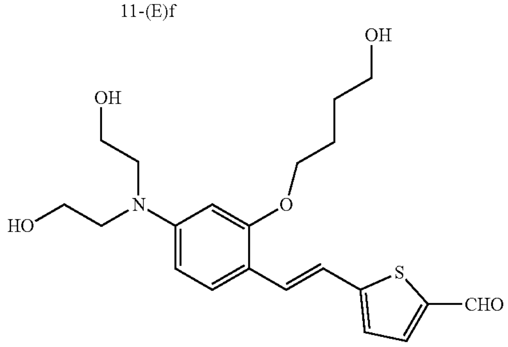

12-(E)f 6.59 g (5.88 mmol) of (E)-5-[4-[bis[2-[(tert-butyldiphenylsilyl)oxy]ethyl]amino]-2-[4-[(tert-butyldiphenylsilyl) oxy]butoxy]styryl]thiophene-2-carbaldehyde (11-(E)f) was dissolved in 30 mL of tetrahydrofuran. To this, 25 mL of tetrabutylammonium fluoride (1 mol solution in tetrahydrofuran) was added dropwise with stirring at room temperature. After 1.5-hour stirring, the reaction mixture was poured into 200 mL of a saturated aqueous sodium chloride solution, and chloroform extraction was performed. The extract was dehydrated over anhydrous sodium sulfate and concentrated. The residue was purified by silica gel column chromatography (chloroform/methanol=50/1 to 10/1) Further purification by silica gel column chromatography (chloroform/ethyl acetate/methanol=5/5/3) was performed to give 1.89 g of the desired compound 12-(E) f as a red oil (yield: 79.4%)

The NMR measurement results of compound 12-(E)f are shown below.

$^1$H-NMR (600 MHz, DMSO-$d_6$) δ ppm: 1.61-1.68 (2H, m), 1.81-1.86 (2H, m), 3.47 (4H, t, J=6.2 Hz), 3.50 (2H, t, J=6.2H), 3.56 (4H, t, J=6.2 Hz), 4.04 (2H, t, J=6.2 Hz), 6.26 (1H, d, J=2.1 Hz), 6.33 (1H, dd, J=2.1 Hz, 9.0 Hz), 7.19 (1H, d, J=3.4 Hz), 7.25 (1H, d, J=15.8 Hz), 7.33 (1H, d, J=15.8 Hz), 7.42 (1H, d, J=9.0 Hz), 7.90 (1H, d, J=3.4 Hz), 9.80 (1H, s)

$^{13}$C-NMR (150 MHz, DMSO-$d_6$) δ ppm: 25.35, 29.12, 53.12, 58.10, 60.28, 67.57, 95.34, 104.38, 111.61, 115.55, 125.21, 128.50, 128.65, 134.94, 139.32, 150.10, 154.32, 158.04, 183.00

(11) 2-[4-[(E)-2-[5-[(E)-4-[Bis(2-hydroxyethyl) amino]-2-(4-hydroxybutoxy)styryl]thiophen-2-yl] vinyl]-3-cyano-5-phenyl-5-(trifluoromethyl)furan-2 (5H)-ylidene]malononitrile (EO-9)

[Chem. 107]

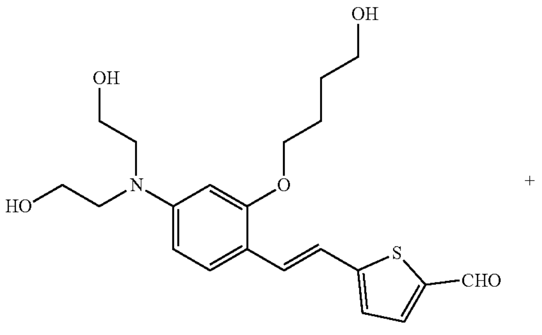

12-(E)f

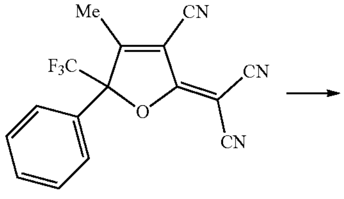

13f

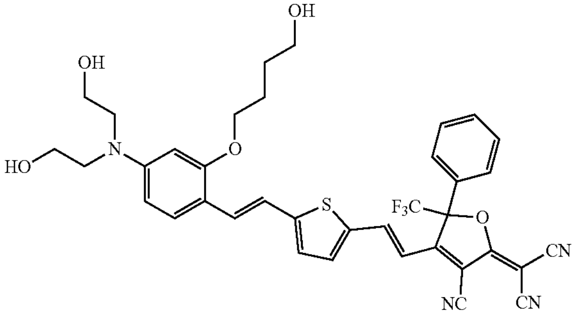

(EO-9)

1.62 g (4.00 mmol) of (E)-5-[4-[bis(2-hydroxyethyl) amino]-2-(4-hydroxybutoxy)styryl]thiophene-2-carbaldehyde (12-(E)f) and 1.38 g (4.38 mmol) of 2-[3-cyano-4-methyl-5-phenyl-5-(trifluoromethyl)furan-2 (5H)-ylidene] malononitrile (13f) were suspended in 30 mL of ethanol. The suspension was stirred at room temperature for 18 hours. The precipitated crystals were collected by filtration and washed with ethanol. As a result, 2.51 g of the desired compound EO-9 was obtained as dark red-brown crystals with a melting point of 219 to 220° C. (yield: 89.4%).

The NMR measurement results of EO-9 are shown below.

$^1$H-NMR (600 MHz, DMSO-$d_6$) δ ppm: 1.60-1.65 (2H, m), 1.83-1.87 (2H, m), 3.49-3.53 (6H, m), 3.58 (4H, t, J=6.2

Hz), 4.08 (2H, t, J=6.2H), 4.83 (3H, b), 6.28 (1H, d, J=2.1 Hz), 6.41 (1H, dd, J=2.1 Hz, 9.6 Hz), 6.50 (1H, d, J=15.1 Hz), 7.25 (1H, d, J=4.8 Hz), 7.37 (1H, d, J=15.8 Hz), 7.45 (1H, d, J=8.3 Hz), 7.47 (1H, d, J=15.1 Hz), 7.60-7.66 (3H, m), 7.69-7.72 (3H, m), 7.76 (1H, d, J=4.1 Hz)

$^{13}$C-NMR (150 MHz, DMSO-$d_6$) δ ppm: 25.23, 29.09, 53.22, 55.03, 58.21, 60.28, 67.76, 94.61, 95.18, 105.39, 110.18, 111.19, 111.36, 112.02, 112.45, 116.00, 126.79, 128.47, 129.28, 129.79, 130.72, 131.47, 133.21, 137.24, 140.63, 151.71, 159.37, 159.81, 159.97, 175.79

Synthesis Examples 29 to 31: Production of EO molecules (EO-10 to EO-12)

EO molecules (EO-10 to EO-12) were synthesized in the same manner as described in Synthesis Example 9 (11). The structures and the NMR measurement results of EO-10 to EO-12 are shown below.

TABLE 5

| | |
|---|---|
| Synthesis Example 29<br>EO-10<br>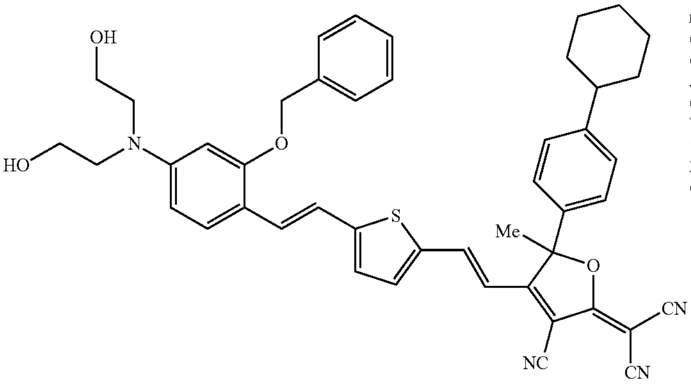 | $^{1}$H-NMR (600 MHz, $CDCl_3$) δ ppm: 1.24-1.28 (1H, m), 1.35-1.43 (4H, m), 1.75-1.77 (1H, m), 1.83-1.87 (4H, m), 2.08 (3H, s), 2.51-2.55 (1H, m), 2.89 (2H, s), 3.58 (4H, t, J = 4.8 Hz), 3.79 (4H, bs), 5.19 (2H, s), 6.19 (1H, d, J = 2.0 Hz), 6.32 (1H, dd, J = 2.0 Hz, 8.9 Hz), 6.55 (1H, d, J = 15.2 Hz), 6.87 (1H, d, J = 4.1 Hz), 7.11 (1H, d, J = 4.8 Hz), 7.12 (1H, d, J = 15.1 Hz), 7.23-7.45 (12H, m)<br>$^{13}$C-NMR (150 MHz, $CDCl_3$) δ ppm: 24.64, 26.00, 26.71, 34.17, 44.25, 55.10, 55.82, 60.61, 70.57, 96.45, 97.61, 98.69, 105.92, 111.04, 111.67, 112.16, 112.29, 114.20, 117.11, 125.99, 126.76, 127.06, 127.96, 128.16, 128.78, 129.15, 130.09, 132.99, 136.95, 137.38, 137.64, 140.37, 150.14, 150.74, 155.56, 158.31, 172.50, 175.95 |
| Synthesis Example 30<br>EO-11<br>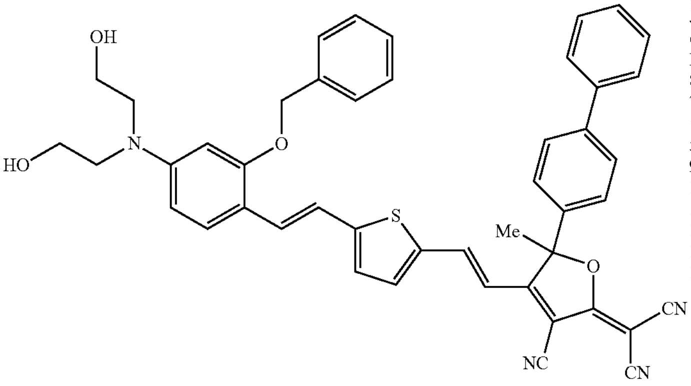 | $^{1}$H-NMR (600 MHz, $CDCl_3$) δ ppm: 2.12 (3H, s), 3.07 (2H, s), 3.56 (4H, t, J = 4.8 Hz), 3.79 (4H, t, J = 4.8 H), 5.18 (2H, s), 6.19 (1H, d, J = 2.1 Hz), 6.32 (1H, dd, J = 2.1 Hz, 9.0 H), 6.54 (1H, d, J = 15.2 Hz), 6.86 (1H, d, J = 4.1 Hz), 7.11 (1H, d, J = 3.4 Hz), 7.12 (1H, d, J = 8.2 Hz), 7.32-7.48 (13H, m), 7.58 (2H, d, J = 7.6 Hz), 7.66 (2H, d, J = 8.9 Hz)<br>$^{13}$C-NMR (150 MHz, $CDCl_3$) δ ppm: 24.59, 55.12, 55.89, 60.56, 70.56, 96.25, 97.52, 98.37, 105.95, 111.04, 111.63, 111.92, 112.25, 114.08, 117.02, 126.48, 126.88, 127.09, 127.15, 128.11, 128.16, 128.77, 129.00, 129.19, 130.27, 134.53, 136.90, 137.33, 137.92, 139.50, 140.40, 150.25, 155.89, 158.35, 172.13, 175.92 |
| Synthesis Example 31<br>EO-12<br>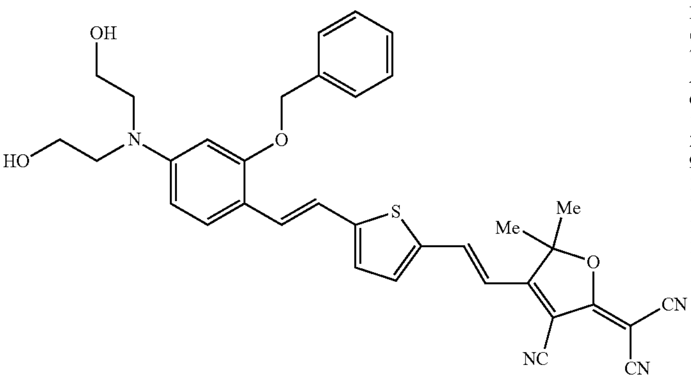 | $^{1}$H-NMR (600 MHz, DMSO-$d_6$) δ ppm: 1.78 (6H, s), 3.47 (4H, t, J = 6.2 Hz), 3.52 (4H, t, J = 6.2 Hz), 5.23 (2H, s), 6.34 (1H, d, J = 2.1 Hz), 6.37 (1H, dd, J = 2.1 Hz, 9.0 Hz), 6.63 (1H, d, J = 15.1 Hz), 7.14 (1H, d, J = 4.2 Hz), 7.30 (1H, d, J = 15.8 Hz), 7.33-7.52 (7H, m, Ar—H), 7.73 (1H, d, J = 4.1 Hz), 8.09 (1H, d, J = 15.8 H)<br>$^{13}$C-NMR (150 MHz, DMSO-$d_6$) δ ppm: 25.45, 52.33, 53.22, 58.11, 69.46, 95.72, 96.12, 98.35, 105.04, 111.23, 111.39, 112.19, 112.27, 113.04, 116.02, 127.34, 127.40, 127.80, 128.46, 128.92, 129.31, 137.02, 137.13, 139.18, 140.24, 150.33, 154.57, 157.81, 174.24, 176.77 |

Synthesis Examples 32 and 33: Production of EO molecules (EO-13 and EO-14)

EO molecules (EO-13 and EO-14) were synthesized in the same manner as described in Synthesis Example 11 (7). The structures and the NMR measurement results of EO-13 and EO-14 are shown below.

TABLE 6

| | |
|---|---|
| Synthesis Example 32<br>EO-13<br>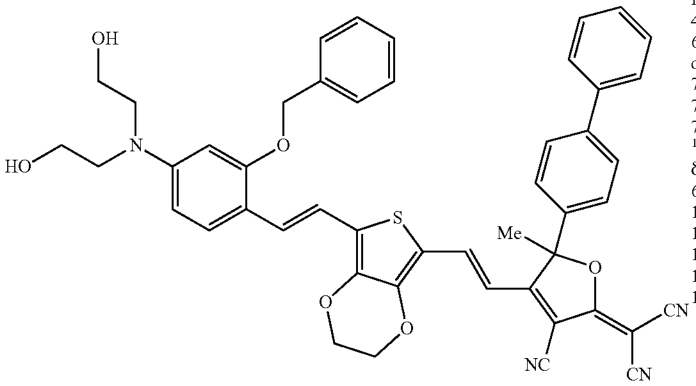 | $^1$H-NMR (600 MHz, DMSO-$d_6$, 50° C.)<br>δ ppm: 2.17 (3H, s), 3.48 (4H, t, J = 5.5 Hz), 3.55 (4H, t, J = 5.5 H), 4.30 (2H, bs), 4.42 (2H, bs), 4.69 (2H, b), 5.18 (2H, s), 6.37-6.39 (2H, m), 6.44 (1H, b), 7.12 (1H, d, J = 15.8 Hz), 7.31 (1H, t, J = 7.6 Hz), 7.39-7.41 (5H, m), 7.47-7.50 (5H, m), 7.61 (2H, d, J = 8.3 Hz), 7.70 (2H, d, J = 7.6 Hz), 7.77 (2H, d, J = 7.2 Hz)<br>$^{13}$C-NMR (150 MHz, DMSO-$d_6$, 50° C.)<br>δ ppm: 23.65, 51.40, 53.32, 58.36, 64.46, 66.11, 69.80, 96.43, 98.30, 105.57, 112.26, 112.54, 112.73, 113.18, 113.29, 126.77, 126.88, 127.29, 127.36, 127.73, 127.95, 128.40, 128.93, 129.63, 133.40, 135.55, 136.99, 141.68, 151.05, 154.95, 158.45, 171.74, 176.80 |
| Synthesis Example 33<br>EO-14<br>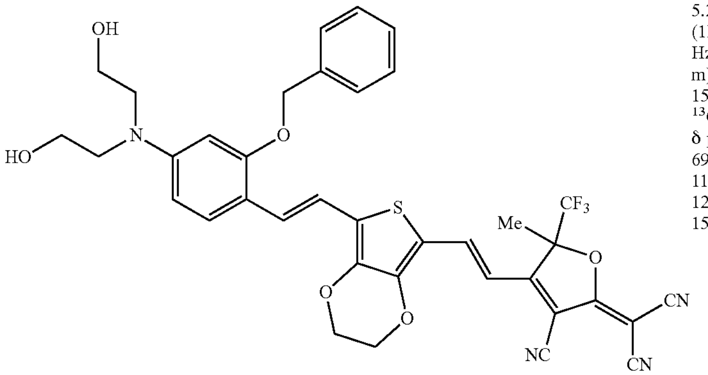 | $^1$H-NMR (600 MHz, DMSO-$d_6$, 50° C.)<br>δ ppm: 1.95 (3H, s), 3.54-3.58 (8H, m), 4.38-4.39 (2H, m), 4.54-4.55 (2H, m), 5.23 (2H, s), 6.34-6.41 (2H, m), 6.46 (1H, d, J = 9.0 Hz), 7.27 (1H, d, J = 15.1 Hz), 7.35-7.37 (1H, m), 7.42-7.45 (2H, m), 7.50-7.51 (3H, m), 7.64 (1H, d, J = 15.8 Hz), 8.13 (1H, b)<br>$^{13}$C-NMR (150 MHz, DMSO-$d_6$, 50° C.)<br>δ ppm: 18.39, 53.43, 58.42, 64.60, 66.52, 69.89, 79.09, 96.29, 106.31, 112.14, 112.47, 112.82, 113.16, 127.36, 127.81, 128.46, 130.86, 136.80, 138.99, 139.53, 152.36, 159.30, 159.40, 176.27 |

Synthesis Example 34: Production of EO molecule (EO-15)

[Chem. 108]

EO-15

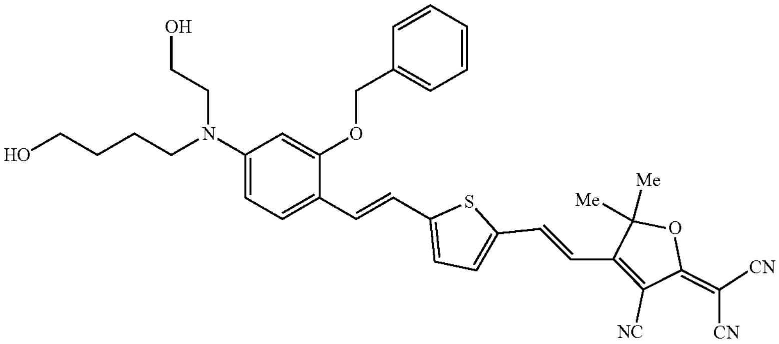

(1) 3-[Bis[4-[(tert-butyldiphenylsilyl)oxy]butyl]amino]phenol (compound 3g)

[Chem. 109]

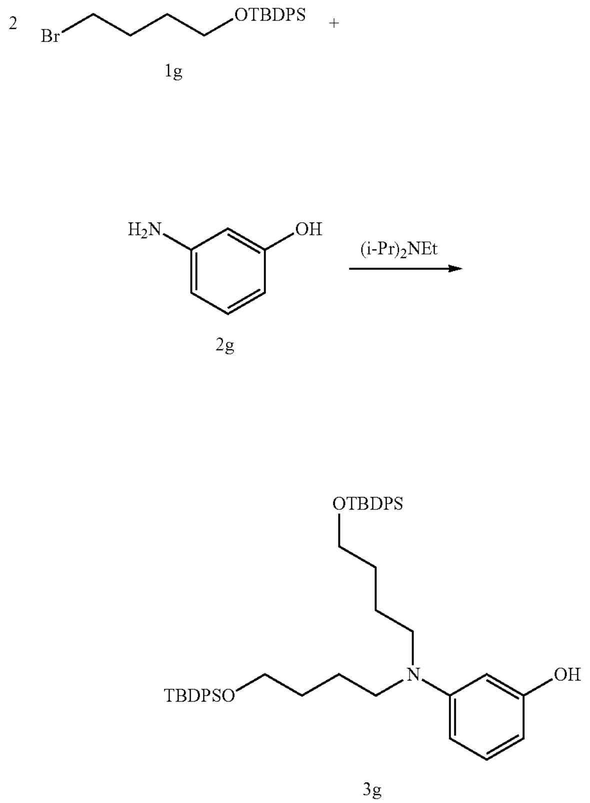

1g 2g 3g 28.88 g (73.8 mmol) of (4-bromobutoxy) (tert-butyl) diphenylsilane (1 g), 3.5 g (32.07 mmol) of m-aminophenol (2 g), and 9.9 g (76.6 mmol) of ethyl diisopropylamine were dissolved in 70 mL of acetonitrile. The solution was stirred under reflux for 24 hours. The reaction mixture was cooled and then filtered, and the filtrate was concentrated. The residue was dissolved in chloroform, and the solution was washed with water. The washed solution was dehydrated over anhydrous sodium sulfate and concentrated. The residue was purified by silica gel column chromatography (chloroform/methanol=30/1) to give 15.56 g of the desired compound 3g (yield: 66.5%).

The NMR measurement results of compound 3g are shown below.

$^1$H-NMR (600 MHz, $CDCl_3$) δ ppm: 1.04 (18H, s), 1.53-1.58 (4H, m), 1.62-1.67 (4H, m), 3.22 (4H, t, J=7.6 Hz), 3.67 (4H, t, J=6.2 Hz), 4.48 (1H, s), 6.08-6.10 (2H, m), 6.22 (1H, dd, J=2.2 Hz, 8.9 Hz), 7.01 (1H, t, J=8.2 Hz), 7.35-7.42 (12H, m), 7.65-7.67 (8H, m)

$^{13}$C-NMR (150 MHz, $CDCl_3$) δ ppm: 19.20, 23.61, 26.87, 30.06, 50.83, 63.63, 98.58, 102.20, 104.74, 127.63, 129.58, 130.06, 133.93, 135.55, 149.66, 156.66

(2) 3-(Benzyloxy)-N,N-bis[4-[(tert-butyldiphenylsilyl)oxy]butyl]aniline (compound 5g)

[Chem. 110]

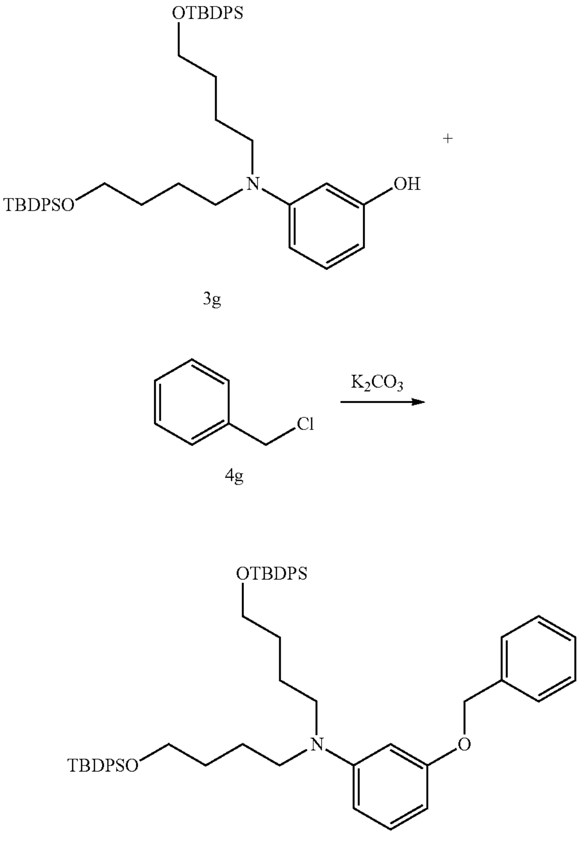

3g 4g 5g 46.74 g (64.02 mmol) of 3-[bis[4-[(tert-butyldiphenylsilyl)oxy]butyl]amino]phenol (3 g) and 10.53 g (83.18 mmol) of benzyl chloride (4 g) were dissolved in 300 mL of acetonitrile. To this, 17.7 g (128.07 mmol) of anhydrous potassium carbonate was added, and the mixture was stirred in an oil bath at 75° C. overnight. The reaction mixture was cooled and then filtered, and the filtrate was concentrated. The residue was purified by silica gel column chromatography (ethyl acetate/hexane=1/5) to give 50.86 g of the desired compound 5g as a pink oil (yield: 96.9%).

The NMR measurement results of compound 5g are shown below.

$^1$H-NMR (600 MHz, $CDCl_3$) δ ppm: 1.03 (18H, s), 1.52-1.64 (8H, m), 3.21 (4H, t, J=7.6 Hz), 3.66 (4H, t, J=6.2 Hz), 5.02 (2H, s), 6.23 (1H, t, J=2.4 Hz), 6.27 (2H, d, J=8.3 Hz), 7.08 (1H, t, J=8.3 Hz), 7.28 (1H, t, J=7.2 Hz), 7.34-7.42 (16H, m), 7.64-7.66 (8H, m) 13C-NMR (150 MHz, $CDCl_3$) δ ppm: 19.19, 23.66, 26.86, 30.11, 50.89, 63.68, 69.86, 99.20, 100.90, 105.30, 127.54, 127.62, 127.79, 128.52, 129.56, 129.82, 133.94, 135.55, 137.49, 149.44, 160.15

(3) 4,4'-[[3-(Benzyloxy)phenyl]azanediyl]bis(butan-1-ol) (compound 6g)

[Chem. 111]

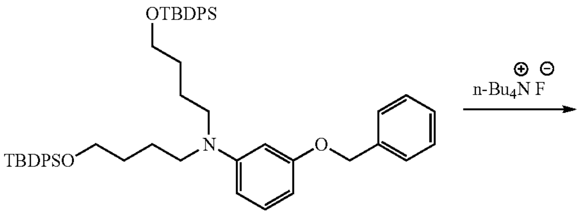

5g

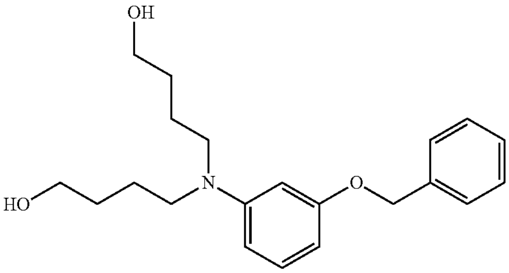

6g 23.1 g (28.16 mmol) of 3-(benzyloxy)-N,N-bis[4-[(tert-butyldiphenylsilyl)oxy]butyl]aniline (5 g) was dissolved in 50 mL of tetrahydrofuran. To this, 84.5 mL of tetrabutylammonium fluoride (1 mol solution in tetrahydrofuran) was added dropwise with stirring at room temperature. After 2-hour stirring, the reaction mixture was added to 300 mL of a 10% aqueous sodium chloride solution, and ethyl acetate extraction was performed. The extract was dehydrated over anhydrous sodium sulfate and concentrated. The residue was purified by silica gel column chromatography (chloroform/methanol=10/1) to give 9.33 g of the desired compound 6g as a pale yellow oil (yield: 96.5%).

The NMR measurement results of compound 6g are shown below.

$^{1}$H-NMR (600 MHz, $CDCl_3$) δ ppm: 1.55-1.66 (8H, m), 3.26 (4H, t, J=7.6 Hz), 3.65 (4H, b), 5.05 (2H, s), 6.29-6.33 (3H, m), 7.11 (1H, t, J=8.3 Hz), 7.30-7.44 (5H, m)

$^{13}$C-NMR (150 MHz, $CDCl_3$) δ ppm: 23.71, 30.28, 51.19, 62.72, 69.90, 100.09, 101.74, 106.04, 127.52, 127.84, 128.56, 129.90, 137.40, 149.42, 160.11

(4) [[3-(Benzyloxy)phenyl]azanediyl]bis(butane-4,1-diyl)diacetate (compound 7g)

[Chem. 112]

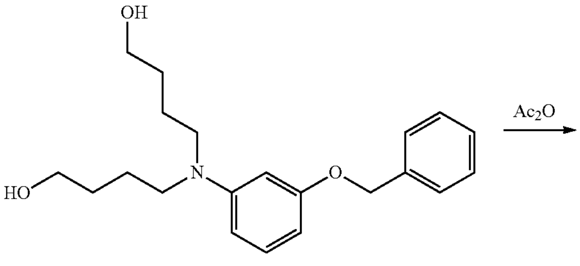

6g

-continued

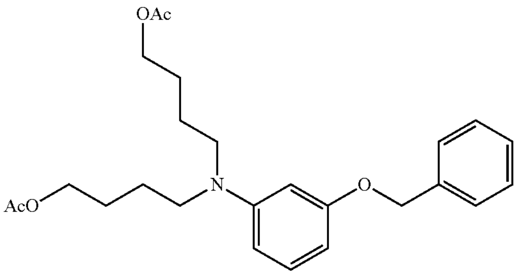

7g 9.3 g (27.08 mmol) of 4,4'-[[3-(benzyloxy)phenyl]azanediyl]bis(butan-1-ol) (6 g) was dissolved in 15 mL of acetic anhydride. The solution was stirred in an oil bath at 80° C. for 2 hours. The reaction mixture was cooled and then poured into 150 mL of water and 50 mL of ether, and the mixture was stirred for 30 minutes. The resulting layers were separated, and the aqueous layer was subjected to extraction with 100 mL of ether. The organic layers were combined and washed with a saturated aqueous sodium bicarbonate solution and subsequently with a saturated aqueous sodium chloride solution. The washed organic layer was dehydrated over anhydrous magnesium sulfate and concentrated. The residue was purified by silica gel column chromatography (ethyl acetate/hexane=2/5) to give 8.40 g of the desired compound 7g as a pale yellow oil (yield: 72.5%).

The NMR measurement results of compound 7g are shown below.

$^{1}$H-NMR (600 MHz, $CDCl_3$) δ ppm: 1.59-1.66 (8H, m), 2.04 (6H, s), 3.27 (4H, t, J=6.1 Hz), 4.07 (4H, t, J=6.2 Hz), 5.04 (2H, s), 6.25-6.31 (3H, m), 7.12 (1H, t, J=7.9 Hz), 7.29-7.44 (5H, m)

$^{13}$C-NMR (150 MHz, $CDCl_3$) δ ppm: 20.99, 23.76, 26.17, 50.68, 64.20, 69.92, 99.53, 101.21, 104.54, 105.37, 127.53, 127.84, 127.88, 128.57, 129.95, 137.34, 149.16, 160.19, 171.17

(5) [[3-(Benzyloxy)-4-formylphenyl]azanediyl]bis(butane-4,1-diyl)diacetate (compound 8g)

[Chem. 113]

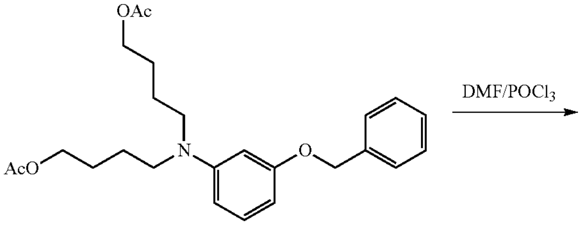

7g

-continued

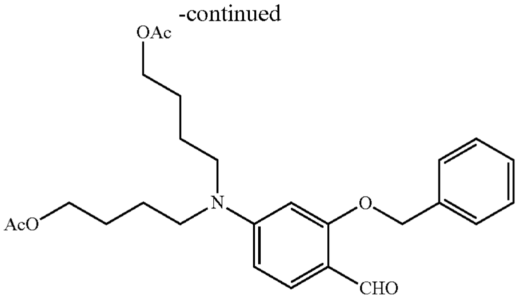

8g

-continued

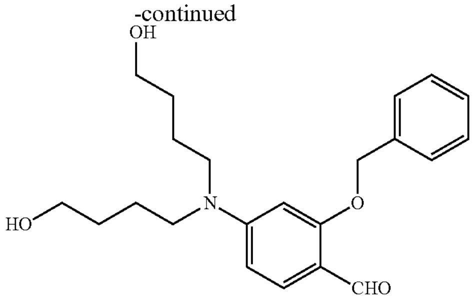

9g 3.1 g (20.22 mmol) of phosphorus oxychloride was added dropwise to 20 mL of N,N-dimethylformamide with stirring under ice-cooling. After 15 minutes, the ice bath was removed, and the reaction mixture was heated to 13° C. and stirred at the same temperature for 5 minutes. The reaction mixture was then ice-cooled again. To this, a solution of 8.40 g (19.65 mmol) of [[3-(benzyloxy)phenyl]azanediyl]bis(butane-4,1-diyl)diacetate (7 g) in 15 mL of N,N-dimethylformamide was added dropwise. After 30 minutes, the reaction mixture was gradually heated to 70° C. and stirred at the same temperature for 3 hours. To the reaction mixture under cooling in an ice bath, 45 mL of a 20% aqueous sodium acetate solution was added dropwise, and the mixture was stirred for 30 minutes. Chloroform extraction was performed, and the extract was washed successively with a saturated aqueous sodium chloride solution, a saturated aqueous sodium hydrogen carbonate solution and a saturated aqueous sodium chloride solution. The washed extract was dehydrated over anhydrous sodium sulfate and concentrated. The residue was purified by silica gel column chromatography (ethyl acetate/hexane=1/1) to give 6.83 g of the desired compound 8g (yield: 76.3%)

The NMR measurement results of compound 8g are shown below.

$^{1}$H-NMR (600 MHz, $CDCl_3$) δ ppm: 1.59-1.63 (8H, m), 2.05 (6H, s), 3.31 (4H, t, J=7.6 Hz), 4.07 (4H, t, J=6.2 Hz), 5.19 (2H, s), 6.00 (1H, d, J=2.8 Hz), 6.26 (1H, dd, J=2.1 Hz, 8.9 Hz), 7.33 (1H, t, J=7.3 Hz), 7.38-7.44 (4H, m), 7.73 (1H, d, J=9.0 Hz), 10.26 (1H, s)

$^{13}$C-NMR (150 MHz, $CDCl_3$) δ ppm: 21.00, 23.78, 26.09, 50.71, 63.87, 70.16, 94.69, 104.68, 114.84, 126.78, 128.07, 128.76, 130.43, 136.68, 153.69, 163.14, 171.08, 187.19

(6) 2-(Benzyloxy)-4-[bis(4-hydroxybutyl)amino] benzaldehyde (compound 9g)

[Chem. 114]

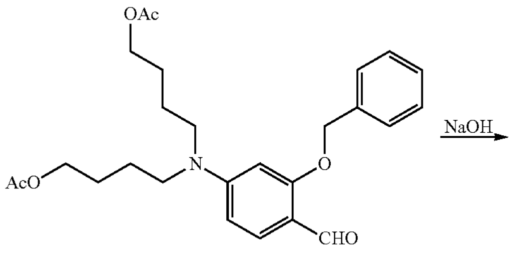

8g 12.99 g (28.52 mmol) of [[3-(benzyloxy)-4-formylphenyl]azanediyl]bis(butane-4,1-diyl)diacetate (8 g) was dissolved in 60 mL of ethanol. To this, 40 mL of a 7% aqueous sodium hydroxide solution was added dropwise, and the mixture was stirred at room temperature for 30 minutes. The reaction mixture was poured into 200 mL of water, and chloroform extraction was performed. The extract was washed with a saturated aqueous sodium chloride solution, dehydrated over anhydrous sodium sulfate, and concentrated to give 10.49 g of the desired compound 9g as a light-yellow solid (crude yield: 99.0%).

The NMR measurement results of compound 9g are shown below.

$^{1}$H-NMR (600 MHz, $CDCl_3$) δ ppm: 1.48 (2H, t, J=4.8 Hz), 1.53-1.59 (4H, m), 1.61-1.66 (4H, m), 3.33 (4H, t, J=7.6 Hz), 3.66 (4H, q, J=5.8 Hz), 5.19 (2H, s), 6.05 (1H, d, J=2.0 Hz), 6.27 (1H, dd, J=2.1 Hz, 8.9 Hz), 7.33 (1H, t, J=7.2 Hz), 7.38-7.44 (4H, m), 7.72 (1H, d, J=9.0 Hz), 10.24 (1H, s)

$^{13}$C-NMR (150 MHz, $CDCl_3$) δ ppm: 23.71, 29.83, 50.93, 62.40, 70.05, 94.55, 104.72, 114.55, 126.85, 127.97, 128.69, 130.35, 136.80, 153.96, 163.19, 187.20

(7) 2-(Benzyloxy)-4-[bis[4-[(tert-butyldiphenylsilyl) oxy]butyl]amino]benzaldehyde (compound 10g)

[Chem. 115]

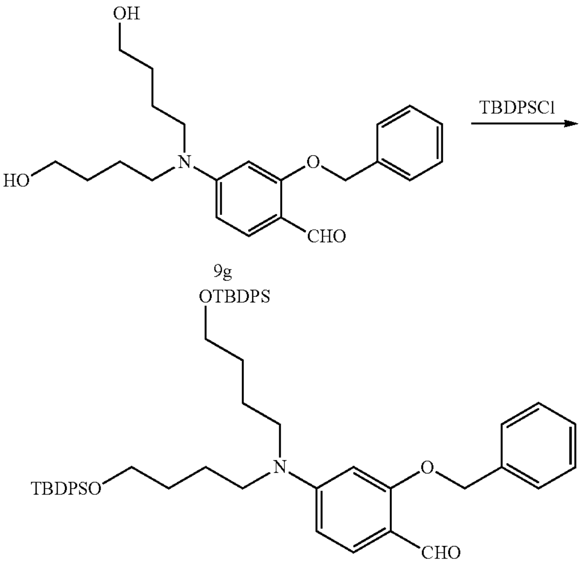

9g

10g 5.9 g (15.88 mmol) of 2-(benzyloxy)-4-[bis(4-hydroxybutyl)amino]benzaldehyde (9 g) and 4.43 g (65.07 mmol) of imidazole were dissolved in 40 mL of N,N-dimethylformamide. To this, 8.95 g (32.56 mmol) of tert-butylchlorodiphenylsilane was added dropwise with stirring at room temperature. After 2-hour stirring, the reaction mixture was added to a saturated aqueous sodium chloride solution, and ethyl acetate extraction was performed. The extract was dehydrated over anhydrous sodium sulfate and purified by silica gel column chromatography (ethyl acetate/hexane=2/5) to give 11.67 g of the desired compound 10g as a pale yellow oil (yield: 86.6%).

The NMR measurement results of compound 10g are shown below.

$^{1}$H-NMR (600 MHz, $CDCl_3$) δ ppm: 1.04 (18H, s), 1.49-1.54 (4H, m), 1.58-1.63 (4H, m), 3.26 (4H, t, J=7.6 Hz), 3.65 (4H, t, J=6.2 Hz), 5.11 (2H, s), 5.97 (1H, d, J=2.1 Hz), 6.24 (1H, dd, J=2.1 Hz, 8.9 Hz), 7.26-7.27 (1H, m), 7.32-7.43 (16H, m), 7.64-7.65 (8H, m), 7.70 (1H, d, J=8.9 Hz), 10.24 (1H, s)

$^{13}$C-NMR (150 MHz, $CDCl_3$) δ ppm: 19.19, 23.76, 26.85, 29.91, 51.03, 63.45, 70.03, 94.37, 104.75, 114.46, 126.89, 127.66, 127.99, 128.66, 129.67, 130.30, 133.73, 135.52, 136.66, 153.95, 163.14, 187.11

(8) 3-(Benzyloxy)-N,N-bis[4-[(tert-butyldiphenylsilyl)oxy]butyl]-4-[2-(thiophen-2-yl)vinyl]aniline (compound 12-(Z/E)g)

[Chem. 116]

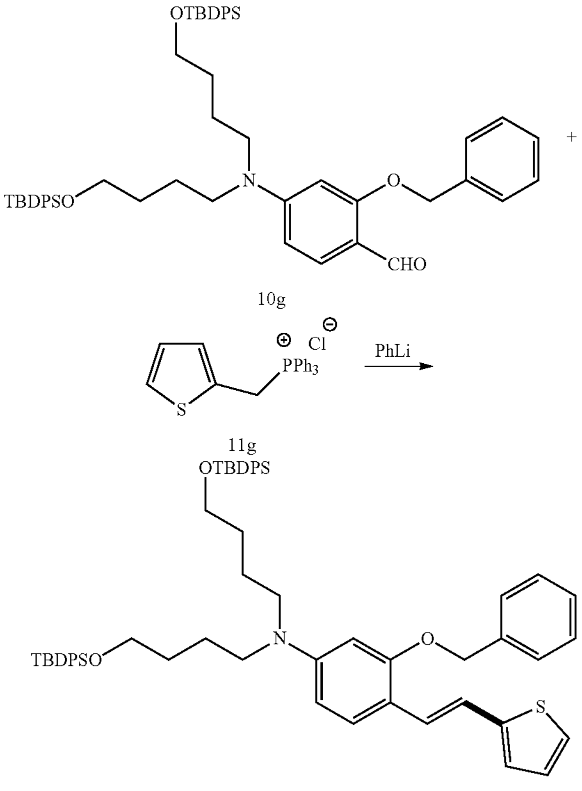

10g

11g 12-(Z/E)g 7.1 mL (14.9 mmol) of phenyllithium (2.1 mol solution in dibutyl ether) was added to 70 mL of tetrahydrofuran under an argon atmosphere. To this, 5.7 g (14.43 mmol) of 2-thenyl triphenyl phosphonium chloride (11 g) was added under ice-cooling. After 15-minute stirring, 30 mL of a solution of 11.67 g (13.76 mmol) of 2-(benzyloxy)-4-[bis[4-[(tert-butyldiphenylsilyl)oxy]butyl]amino]benzaldehyde (10 g) in tetrahydrofuran was added dropwise. After 2-hour stirring, the reaction mixture was poured into water, and ethyl acetate extraction was performed. The extract was washed with a saturated aqueous sodium chloride solution, dehydrated over anhydrous sodium sulfate, and concentrated. To the residue, 100 mL of an ethyl acetate/hexane (1/5) mixture was added, and the mixture was stirred and then ice-cooled. The precipitate was filtered off, and the filtrate was concentrated. The residue was purified by silica gel column chromatography (ethyl acetate/hexane=1/5) to give 9.50 g of the desired compound 12-(Z/E)g as an orange oil (yield: 74.3%).

(9) 5-[2-(Benzyloxy)-4-[bis[4-[(tert-butyldiphenylsilyl)oxy]butyl]amino]styryl]thiophene-2-carbaldehyde (compound 13-(Z/E)g)

[Chem. 117]

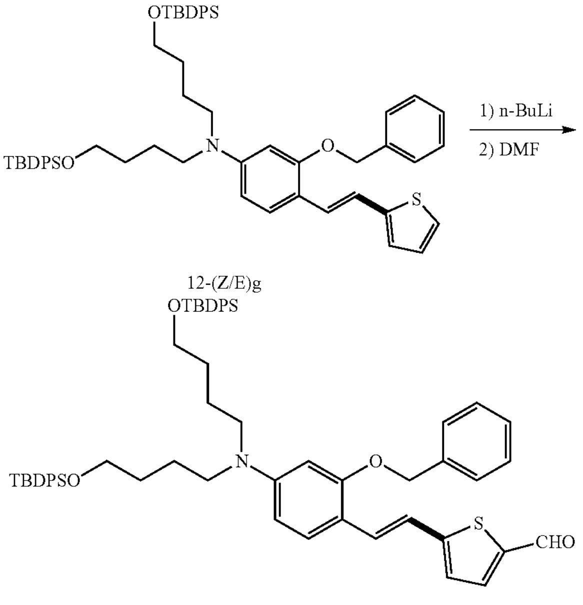

12-(Z/E)g 13-(Z/E)g 9.50 g (10.23 mmol) of 3-(benzyloxy)-N,N-bis[4-[(tert-butyldiphenylsilyl)oxy]butyl]-4-[2-(thiophen-2-yl)vinyl] aniline (12-(Z/E)g) was dissolved in 75 mL of tetrahydrofuran under an argon atmosphere. To this, 8.3 mL (13.28 mmol) of n-butyllithium (1.6 mol solution in hexane) was added dropwise with cooling at a temperature of −73 to −75° C. After 20-minute stirring, 0.93 g (12.7 mmol) of N,N-dimethylformamide was added dropwise. After 1.5-hour stirring, the reaction mixture was heated, and 5 mL of water was added dropwise. After 25-minute stirring, the reaction mixture was poured into a 10% aqueous sodium chloride solution, and ethyl acetate extraction was performed. The extract was dehydrated over anhydrous sodium sulfate and concentrated. The residue was purified by silica gel column chromatography (ethyl acetate/hexane=1/3) to give 8.41 g of the desired compound 13-(Z/E)g as a red oil (yield: 85.9%).

(10) (E)-5-[2-(Benzyloxy)-4-[bis[4-[(tert-butyldiphenylsilyl)oxy ]butyl]amino]styryl]thiophene-2-carbaldehyde (compound 13-(E) g)

[Chem. 118]

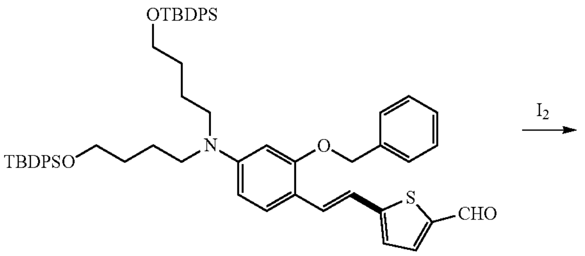

13-(Z/E)g

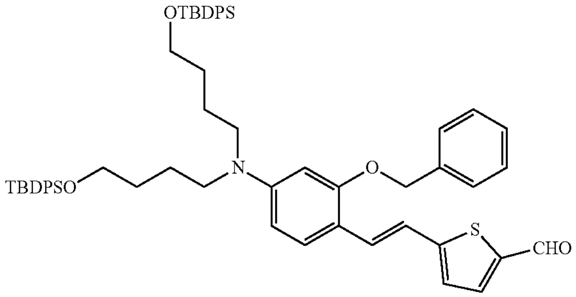

13-(E)g 8.41 g (8.79 mmol) of 5-[2-(benzyloxy)-4-[bis[4-[(tert-butyldiphenylsilyl)oxy]butyl]amino]styryl]thiophene-2-carbaldehyde (13-(Z/E)g) was dissolved in 400 mL of ether. To this, 300 mg of iodine flakes were added. After 30-minute stirring at room temperature, the reaction mixture was washed with a 5% aqueous sodium hydrogen sulfite solution and subsequently with a saturated aqueous sodium chloride solution. The washed reaction mixture was dehydrated over anhydrous magnesium sulfate and concentrated. The residue was purified by silica gel column chromatography (ethyl acetate/hexane=1/3) to give 7.09 g of the desired compound 13-(E)g as a red oil (yield: 84.3%).

The NMR measurement results of compound 13-(E)g are shown below.

$^1$H-NMR (600 MHz, $CDCl_3$) δ ppm: 1.04 (18H, s), 1.50-1.61 (8H, m), 3.22 (4H, t, J=7.6 Hz), 3.65 (4H, t, J=6.2 Hz), 5.10 (2H, s), 6.08 (1H, d, J=2.0 Hz), 6.25 (1H, dd, J=2.1 Hz, 8.9 Hz), 6.98 (1H, d, J=4.1 Hz), 7.10 (1H, d, J=15.8H), 7.27 (1H, t, J=7.6H), 7.32 (1H, d, J=9.0 Hz), 7.34-7.43 (16H, m), 7.45 (1H, d, J=16.5 Hz), 7.60 (1H, d, J=3.5 Hz), 7.64-7.66 (8H, m), 9.79 (1H, s)

$^{13}$C-NMR (150 MHz, $CDCl_3$) δ ppm: 19.20, 23.78, 26.86, 30.03, 50.95, 63.57, 70.35, 96.35, 105.00, 112.79, 116.31, 124.43, 127.02, 127.65, 127.90, 128.64, 128.93, 129.25, 129.62, 133.83, 135.53, 137.10, 137.77, 139.63, 149.71, 155.73, 158.22, 182.30

(11) (E)-5-[2-(Benzyloxy)-4-[bis(4-hydroxybutyl) amino]styryl]thiophene-2-carbaldehyde (compound 14-(E)g)

[Chem. 119]

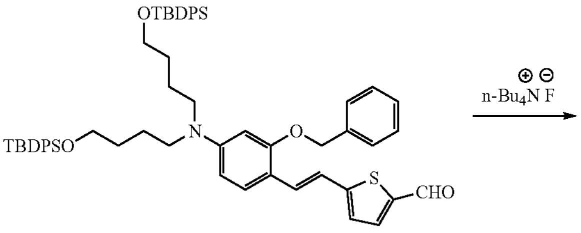

13-(E)g

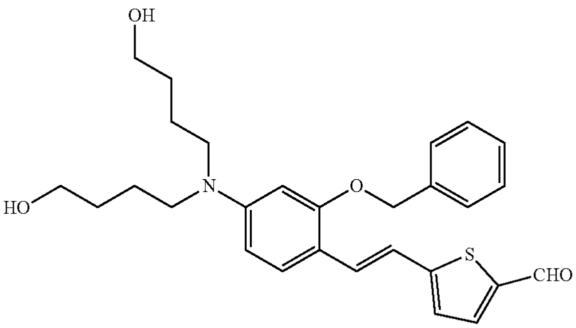

14-(E)g 7.08 g (7.40 mmol) of (E)-5-[2-(benzyloxy)-4-[bis[4-[(tert-butyldiphenylsilyl)oxy]butyl]amino]styryl]thiophene-2-carbaldehyde (13-(E)g) was dissolved in 30 mL of tetrahydrofuran. To this, 25 mL of tetrabutylammonium fluoride (1 mol solution in tetrahydrofuran) was added dropwise with stirring at room temperature. After 2-hour stirring, the reaction mixture was poured into a saturated aqueous sodium chloride solution, and ethyl acetate extraction was performed. The extract was dehydrated over anhydrous sodium sulfate and concentrated. The residue was purified by silica gel column chromatography (chloroform/methanol=10/1) to give 3.13 g of the desired compound 14-(E)g as a red oil (yield: 88.2%).

The NMR measurement results of compound 14-(E) g are shown below.

$^1$H-NMR (600 MHz, $CDCl_3$) δ ppm: 1.37 (2H, b), 1.52-1.64 (8H, m), 3.29 (4H, t, J=7.6 Hz), 3.65 (4H, q, J=6.2 Hz), 5.18 (2H, s), 6.15 (1H, d, J=2.0 Hz), 6.28 (1H, dd, J=2.1 Hz, 8.9 Hz), 6.89 (1H, d, J=4.1 Hz), 7.12 (1H, d, J=15.8 Hz), 7.32-7.47 (7H, m), 7.61 (1H, d, J=4.1 Hz), 9.79 (1H, s)

$^{13}$C-NMR (150 MHz, $CDCl_3$) δ ppm: 13.98, 20.30, 23.77, 29.44, 30.09, 50.87, 50.96, 62.64, 64.41, 65.42, 70.31, 96.53, 105.03, 112.81, 113.36, 113.86, 126.94, 127.72, 127.77, 127.87, 128.61, 129.65, 131.62, 134.78, 137.27, 149.58, 158.11, 178.92

(12) 2-[4-[(E)-2-[5-[(E)-2-(Benzyloxy)-4-[bis(4-hydroxybutyl)amino]styryl]thiophen-2-yl]vinyl]-3-cyano-5,5-dimethylfuran-2 (5H)-ylidene]malononitrile (EO-15)

[Chem. 120]

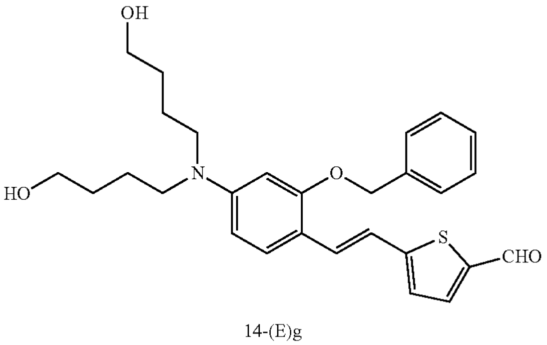

14-(E)g

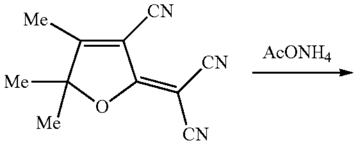

15g

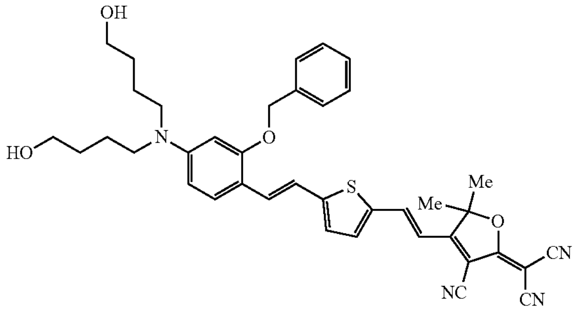

EO-15

1.1 g (2.29 mmol) of (E)-5-[2-(benzyloxy)-4-[bis(4-hydroxybutyl)amino]styryl]thiophene-2-carbaldehyde (14-(E) g) and 0.55 g (2.28 mmol) of 2-(3-cyano-4,5,5-trimethyl-2 (5H)-furanylidene)propanedinitrile (15 g) were dissolved in 30 mL of ethanol. To this, 180 mg (2.34 mmol) of ammonium acetate was added, and the mixture was stirred at room temperature for 3 days. The precipitated crystals were collected by filtration and washed with ethanol. As a result, 1.4 g of the desired compound EO-15 was obtained as dark brown crystals with a melting point of 218 to 219° C. (yield: 92.4%).

The NMR measurement results of EO-15 are shown below.

$^1$H-NMR (600 MHz, $CDCl_3$) δ ppm: 1.29 (2H, s), 1.52-1.66 (8H, m), 1.74 (6H, s), 3.31 (4H, t, J=7.5 Hz), 3.65 (4H, t, J=6.2 Hz), 5.22 (2H, s), 6.14 (1H, d, J=2.1 Hz), 6.90 (1H, dd, J=2.1 Hz, 9.0 Hz), 6.53 (1H, d, J=15.1 Hz), 6.96 (1H, d, J=4.2 Hz), 7.15 (1H, d, J=15.8 Hz), 7.34-7.46 (7H, m), 7.48 (1H, J=15.8 Hz), 7.76 (1H, d, J=15.8 Hz)

$^{13}$C-NMR (150 MHz, $CDCl_3$) δ ppm: 24.05, 26.60, 30.17, 51.10, 56.06, 62.59, 70.77, 95.74, 96.75, 97.19, 105.79, 111.14, 111.34, 111.48, 112.28, 113.63, 116.61, 126.52, 127.10, 128.09, 128.78, 129.49, 130.83, 137.23, 137.34, 137.60, 139.40, 150.53, 156.12, 158.92, 172.78, 175.82

Synthesis Example 35: Production of EO Molecule (EO-16)

An EO molecule (EO-16) was synthesized in the same manner as described in Synthesis Example 34 (12). The structure and the NMR measurement results of EO-16 are shown below.

TABLE 7

| | |
|---|---|
| Synthesis Example 35<br>EO-16<br>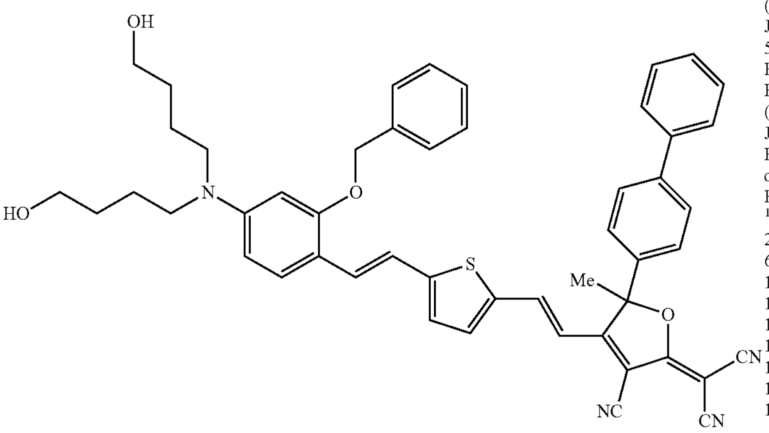 | $^1$H-NMR (600 MHz, $CDCl_3$) δ ppm: 1.32 (2H, t, J = 4.5 Hz), 1.52-1.64 (8H, m), 2.15 (3H, s), 3.30 (4H, t, J = 7.1 Hz), 3.65 (4H, q, J = 6.0 Hz), 5.21 (2H, s), 6.12 (1H, d, J = 2.7 Hz), 6.28 (1H, dd, J = 2.7 Hz, 8.9 Hz), 6.59 (1H, d, J = 15.1 Hz), 6.87 (1H, d, J = 4.2 Hz), 7.10 (1H, d, J = 15.8 Hz), 7.15 (1H, d, J = 4.2 Hz), 7.32-7.48 (13H, m), 7.60 (2H, d, J = 7.6 Hz), 7.68 (2H, d, J = 8.2 Hz)<br>$^{13}$C-NMR (150 MHz, $CDCl_3$) δ ppm: 23.79, 24.71, 29.94, 50.95, 55.81, 62.50, 70.35, 95.96, 96.45, 98.26, 105.32, 111.13, 111.70, 112.30, 113.07, 116.30, 126.52, 126.62, 126.87, 127.18, 127.98, 128.12, 128.71, 128.98, 129.40, 130.88, 134.60, 137.08, 137.12, 138.15, 139.57, 140.45, 143.34, 150.22, 156.60, 158.69, 172.15, 175.98 |

Synthesis Example 36: Production of EO molecule (EO-17)

[Chem. 121]

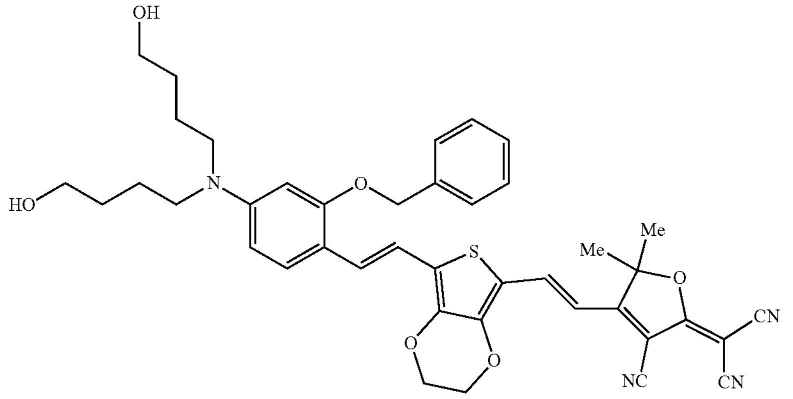

EO-17

(1) 3-(Benzyloxy)-N,N-bis[4-[(tert-butyldiphenylsilyl)oxy]butyl]-4-[2-(2,3-dihydrothieno[3,4-b][1,4]dioxin-5-yl) vinyl]aniline (compound 3-(Z/E)h)

[Chem. 122]

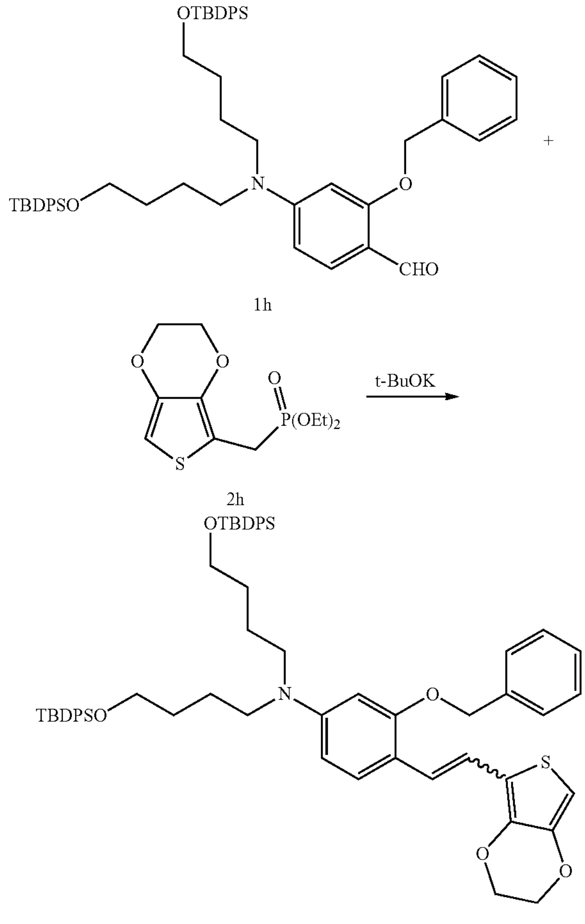

1h

2h 3-(Z/E)h 23.1 g (27.23 mmol) of 2-(benzyloxy)-4-[bis[4-[(tert-butyldiphenylsilyl)oxy]butyl]amino]benzaldehyde (1h) and 8.12 g (27.8 mmol) of diethyl[(2,3-dihydrothieno[3,4-b][1,4]dioxin-5-yl)methyl]phosphonate (2h) were dissolved in 120 mL of tetrahydrofuran. To this, a solution of 3.67 g (32.7 mmol) of potassium t-butoxide in 130 mL of tetrahydrofuran was added dropwise with cooling in a dry ice/acetone bath. After 1 hour, the reaction mixture was slowly heated and then added to a saturated aqueous sodium chloride solution, and ethyl acetate extraction was performed. The extract was dehydrated over anhydrous sodium sulfate and concentrated. The residue was purified by silica gel column chromatography (ethyl acetate/toluene=1/50) to give 26.11 g of the desired compound 3-(Z/E)h as a red oil (yield: 97.6%).

(2) 7-[2-(Benzyloxy)-4-[bis[4-[(tert-butyldiphenylsilyl)oxy]butyl]amino]styryl]-2,3-dihydrothieno[3,4-b][1,4]dioxin-5-carb aldehyde (compound 4-(Z/E)h)

[Chem. 123]

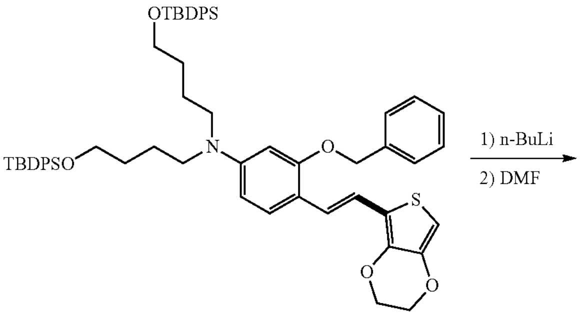

3-(Z/E)h

-continued

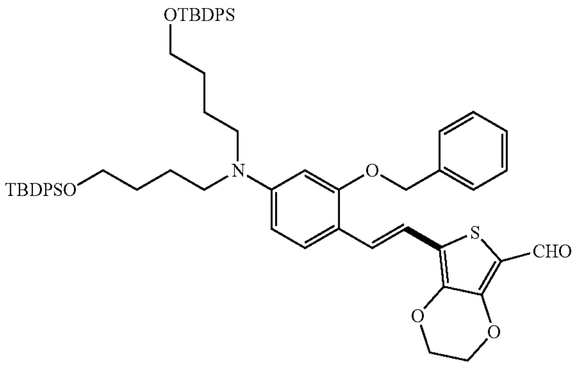

4-(Z/E)h 26.11 g (26.47 mmol) of 3-(benzyloxy)-N,N-bis[4-[(tert-butyldiphenylsilyl)oxy]butyl]-4-[2-(2,3-dihydrothieno[3,4-b][1,4]dioxin-5-yl)vinyl]aniline (3-(Z/E)h) was dissolved in 180 mL of tetrahydrofuran under an argon atmosphere. To this, 21.6 mL (34.56 mmol) of n-butyllithium (1.6 mol solution in hexane) was added dropwise with cooling in a dry ice/acetone bath. After 50-minute stirring, 2.6 mL (32.7 mmol) of N,N-dimethylformamide was added dropwise, and the mixture was stirred for 1.5 hours. The bath was removed, the reaction mixture was heated, and 10 mL of water was added dropwise. After 30-minute stirring, the reaction mixture was poured into a saturated aqueous sodium chloride solution, and ethyl acetate extraction was performed. The extract was dehydrated over anhydrous sodium sulfate and concentrated to give 26.31 g of the desired compound 4-(Z/E)h as a red oil (crude yield: 98.0%).

(3) (E)-7-[2-(Benzyloxy)-4-[bis[4-[(tert-butyldiphenylsilyl)oxy]butyl]amino]styryl]-2,3-dihydrothieno[3,4-b][1,4]dioxin-5-carbaldehyde (compound 4-(E)h)

[Chem. 124]

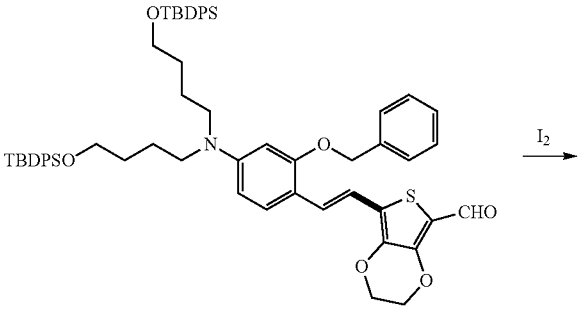

4-(Z/E)h

-continued

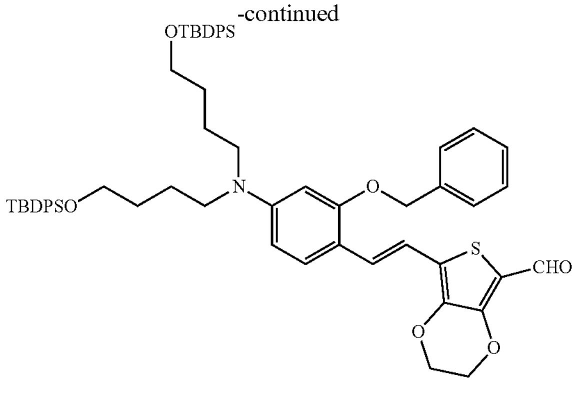

4-(E)h 26.31 g of the crude 7-[2-(benzyloxy)-4-[bis[4-[(tert-butyldiphenylsilyl)oxy]butyl]amino]styryl]-2,3-dihydrothieno[3,4-b][1,4]dioxin-5-carb aldehyde (4-(Z/E)h) was dissolved in 400 mL of ether. To this, 790 mg of iodine flakes were added. After 30-minute stirring at room temperature, the reaction mixture was washed with a 5% aqueous sodium hydrogen sulfite solution and subsequently with a saturated aqueous sodium chloride solution. The washed reaction mixture was dehydrated over anhydrous magnesium sulfate, and the ether was evaporated off. The residue was purified by silica gel column chromatography (ethyl acetate/hexane=1/2 to 2/3) to give 20.28 g of the desired compound 4-(E)h as a red oil (yield: 84.5%).

The NMR measurement results of compound 4-(E)h are shown below.

$^1$H-NMR (600 MHz, $CDCl_3$) δ ppm: 1.04 (18H, s), 1.50-1.59 (8H, m), 3.26 (4H, t, J=6.7 Hz), 3.65 (4H, t, J=6.2 Hz), 4.29-4.30 (2H, m), 4.35-4.36 (2H, m), 5.08 (2H, s), 6.07 (1H, d, J=2.0 Hz), 6.23 (1H, dd, J=2.0 Hz, 8.9 Hz), 7.04 (1H, d, J=16.5 Hz), 7.26 (1H, t, J=7.2 Hz), 7.32-7.42 (17H, m), 7.46 (1H, d, J=15.8 Hz), 7.65 (8H, d, J=8.2 Hz)

$^{13}$C-NMR (150 MHz, $CDCl_3$) δ ppm: 19.21, 23.81, 26.87, 30.05, 50.94, 63.60, 64.41, 65.42, 70.32, 96.43, 105.06, 112.74, 113.29, 113.85, 126.99, 127.65, 127.76, 127.98, 128.55, 128.64, 129.62, 131.69, 133.85, 135.53, 137.07, 137.20, 149.58, 158.12, 178.90

(4) (E)-7-[2-(Benzyloxy)-4-[bis(4-hydroxybutyl)amino] styryl]-2,3-dihydrothieno[3,4-b][1,4]dioxin-5-carbaldehyde (compound 5-(E)h)

[Chem. 125]

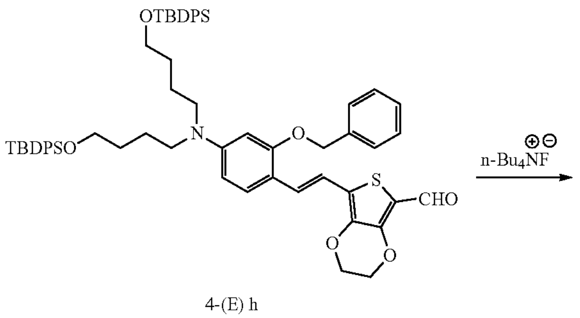

4-(E) h

-continued

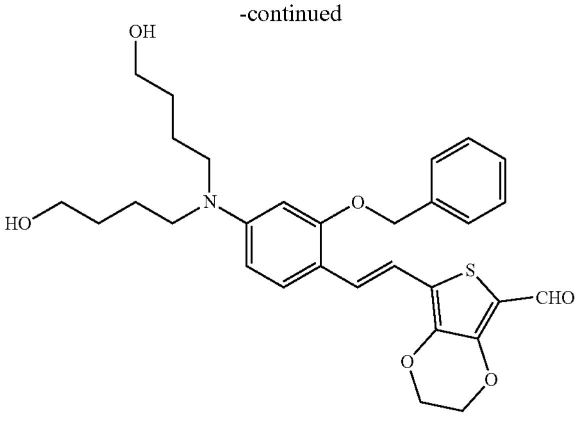

5-(E) h 20.2 g (19.9 mmol) of (E)-7-[2-(benzyloxy)-4-[bis[4-[(tert-butyldiphenylsilyl)oxy]butyl]amino]styryl]-2,3-dihydrothieno[3,4-b][1,4]dioxin-5-carbaldehyde (4-(E)h) was dissolved in 80 mL of tetrahydrofuran. To this, 59.7 mL of tetrabutylammonium fluoride (1 mol solution in tetrahydrofuran) was added dropwise with stirring at room temperature. After 0.5-hour stirring, the reaction mixture was added to a saturated aqueous sodium chloride solution, and ethyl acetate extraction was performed. The extract was dehydrated over anhydrous sodium sulfate and concentrated. The residue was purified by silica gel column chromatography (chloroform/methanol=10/1) to give 10.59 g of the desired compound 5-(E)h as an orange oil (yield: 91.0%).

The NMR measurement results of compound 5-(E)h are shown below.

$^1$H-NMR (600 MHz, $CDCl_3$) δ ppm: 1.39 (2H, s), 1.52-1.57 (4H, m), 1.59-1.64 (4H, m), 3.29 (4H, t, J=7.5 Hz), 3.65 (4H, t, J=5.2 Hz), 4.29-4.30 (2H, m), 4.35-4.37 (2H, m), 5.16 (2H, s), 6.15 (1H, d, J=2.1 Hz), 6.27 (1H, dd, J=2.1 Hz, 8.9 Hz), 7.06 (1H, d, J=16.5 Hz), 7.32 (1H, t, J=7.2 Hz), 7.37-7.41 (3H, m), 7.45-7.47 (3H, m), 9.82 (1H, s)

$^{13}$C-NMR (150 MHz, $CDCl_3$) δ ppm: 23.78, 30.06, 50.97, 62.58, 64.43, 65.42, 70.34, 96.84, 105.24, 113.02, 113.67, 113.94, 126.94, 127.76, 127.81, 128.61, 128.65, 131.53, 137.17, 137.32, 149.52, 158.11, 178.95

(5) 2-[4-[(E)-2-[7-[(E)-2-(Benzyloxy)-4-[bis(4-hydroxybutyl)amino]styryl]-2,3-dihydrothieno[3,4-b][1,4]dioxin-5-yl]vinyl]-3-cyano-5,5-dimethylfuran-2(5H)-ylidene]malononitrile (EO-17)

[Chem. 126]

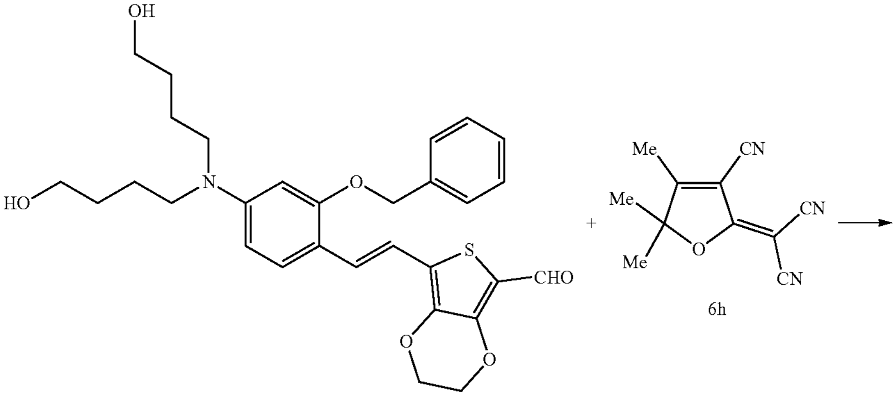

5-(E)h

6h

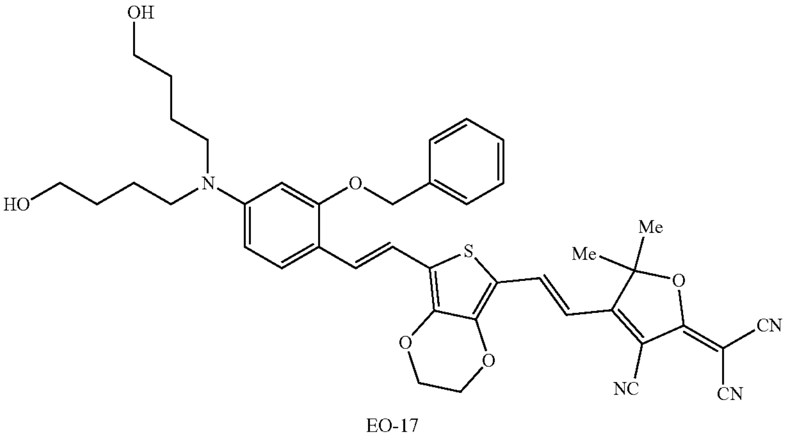

EO-17

2.42 g (4.5 mmol) of (E)-7-[2-(benzyloxy)-4-[bis(4-hydroxybutyl)amino] styryl]-2,3-dihydrothieno[3,4-b][1,4]dioxin-5-carbaldehyde (5-(E)h) and 0.98 g (4.9 mmol) of 2-(3-cyano-4,5,5-trimethyl-2(5H)-furanylidene)propanedinitrile (6h) were dissolved in 50 mL of ethanol and 10 mL of tetrahydrofuran. The solution was stirred at room temperature at 3 days and nights and further stirred at 50° C. for 5 hours. The precipitated crystals were collected by hot filtration and washed with hot ethanol. As a result, 1.75 g of the desired compound EO-17 was obtained as dark red-brown crystals with a melting point of 229 to 230° C. (yield: 54.1%)

The NMR measurement results of EO-17 are shown below.

$^1$H-NMR (600 MHz, $CDCl_3$) δ ppm: 1.30 (2H, s), 1.53-1.67 (8H, m), 1.72 (6H, s), 3.31 (4H, t, J=7.6 Hz), 3.65 (4H, bs), 4.29-4.31 (2H, m), 4.40-4.41 (2H, m), 5.21 (2H, s), 6.14 (1H, d, J=2.1 Hz), 6.29 (1H, d, J=2.7 Hz, 8.9 Hz), 6.41 (1H, b), 7.13 (1H, d, J=15.8 Hz), 7.33-7.47 (6H, m), 7.48 (1H, d, J=15.8 Hz), 7.72 (1H, b)

$^{13}$C-NMR (150 MHz, $CDCl_3$) δ ppm: 23.52, 25.55, 29.61, 50.01, 50.27, 60.36, 64.43, 66.05, 69.29, 95.77, 97.56, 105.10, 111.98, 112.06, 112.34, 112.74, 113.17, 113.58, 127.08, 127.67, 128.44, 129.68, 129.75, 130.45, 133.03, 137.04, 138.42, 150.25, 58.23, 177.03

Synthesis Examples 37 and 38: Production of EO Molecules (EO-18 and EO-19)

EO molecules (EO-18 and EO-19) were synthesized in the same manner as described in Synthesis Example 36 (5). The structures and the NMR measurement results of EO-18 and EO-19 are shown below.

TABLE 8

| | |
|---|---|
| Synthesis Example 37<br>EO-18<br>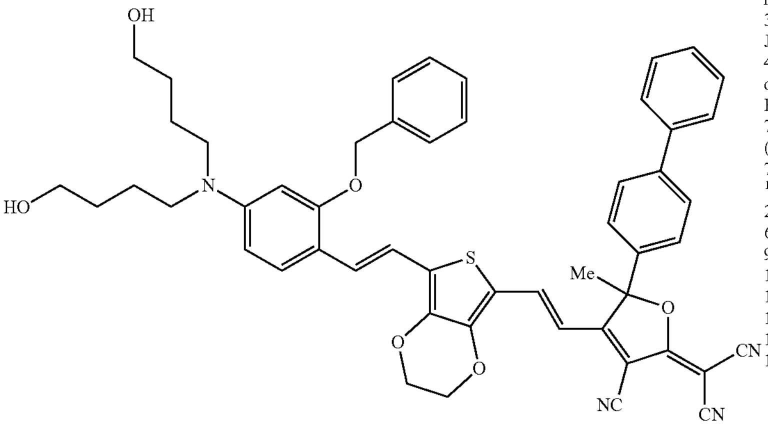 | $^1$H-NMR (600 MHz, $CDCl_3$, 50.0° C.) δ ppm: 1.24 (2H, s), 1.52-1.59 (4H, m), 1.62-1.65 (4H, m), 2.11 (3H, s), 3.30 (4H, t, J = 7.6 Hz), 3.64 (4H, d, J = 6.2 Hz), 4.19-4.22 (2H, m), 4.29-4.31 (2H, m), 5.17 (2H, s), 6.15 (1H, d, J = 2.1 Hz), 6.28 (1H, dd, J = 2.1 Hz, 8.9 Hz), 6.50 (1H, d, J = 14.5 Hz), 7.07 (1H, d, J = 16.5 Hz), 7.19-7.46 (13H, m), 7.58 (2H, d, J = 6.9 Hz), 7.65 (2H, d, J = 8.2 Hz)<br>$^{13}$C-NMR (150 MHz, $CDCl_3$) δ ppm: 23.83, 24.94, 29.95, 50.97, 53.85, 62.50, 64.39, 65.90, 70.31, 96.37, 97.66, 105.42, 111.80, 112.37, 113.00, 113.44, 125.47, 126.48, 126.89, 127.17, 127.98, 128.65, 128.97, 129.41, 134.55, 135.42, 137.14, 139.77, 142.94, 150.34, 158.81, 160.13, 171.84, 176.49 |
| Synthesis Example 38<br>EO-19<br>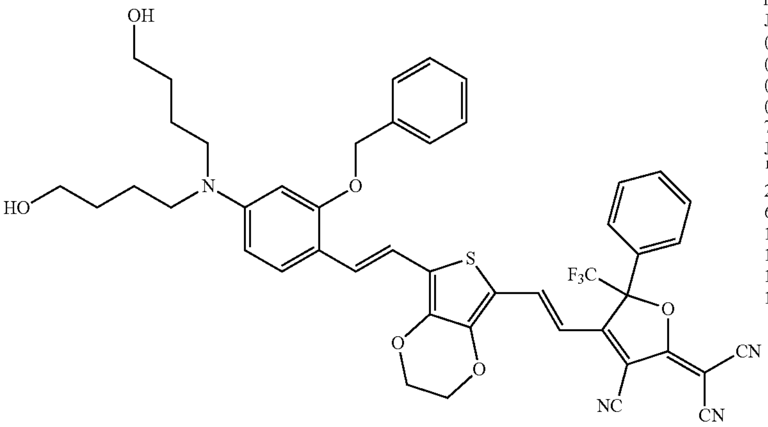 | $^1$H-NMR (600 MHz, $CDCl_3$, 50.0° C.) δ ppm: 1.25 (2H, s), 1.53-1.58 (4H, m), 1.62-1.67 (4H, m), 3.33 (4H, t, J = 7.6 Hz), 3.65 (4H, s), 4.24-4.26 (2H, m), 4.32-4.35 (2H, m), 5.18 (2H, s), 6.16 (1H, d, J = 2.1 Hz), 6.30 (1H, dd, J = 2.1 Hz, 9.0 Hz), 6.46 (1H, b), 7.12 (1H, d, J = 15.8 Hz), 7.31-7.51 (11H, m), 7.53 (1H, d, J = 15.8 Hz), 7.90 (1H, b)<br>$^{13}$C-NMR (150 MHz, $CDCl_3$) δ ppm: 23.87, 29.87, 51.01, 62.44, 64.42, 65.97, 70.34, 96.14, 105.68, 112.24, 112.48, 113.47, 126.77, 126.91, 127.96, 128.68, 129.49, 130.61, 131.06, 136.94, 138.80, 143.70, 150.80, 159.39 |

Synthesis Example 39: Production of EO Molecule (EO-20)

[Chem. 127]

EO-20

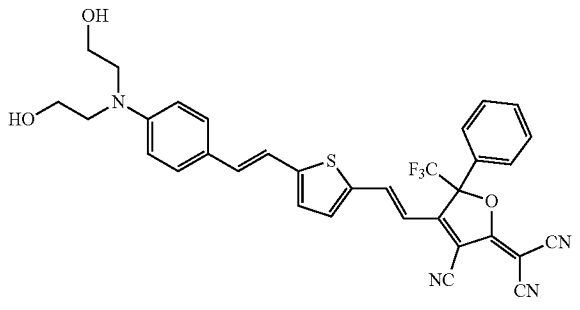

(1) 4-[Bis[2-[(tert-butyldiphenylsilyl)oxy]ethyl] amino]benzaldehyde (compound 2i)

[Chem. 128]

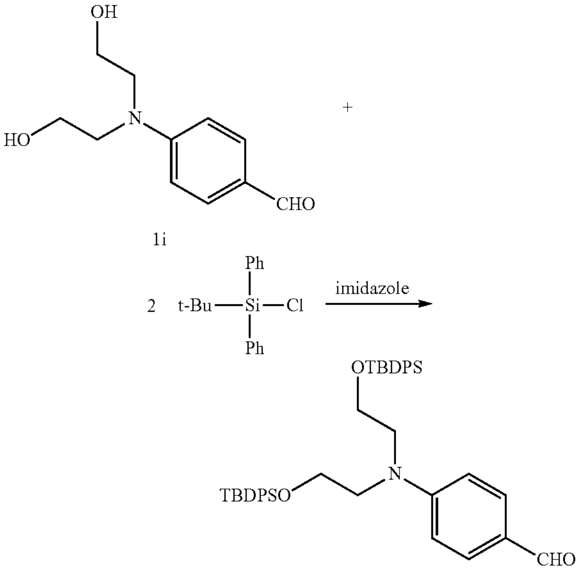

1i

2i 5.11 g (24.42 mmol) of 4-[bis(2-hydroxyethyl)amino] benzaldehyde (1i) and 5.1 g (74.92 mmol) of imidazole were dissolved in 40 mL of N,N-dimethylformamide. To this, 13.76 g (60.06 mmol) of tert-butylchlorodiphenylsilane was added dropwise with stirring at room temperature. After 2-hour stirring, the reaction mixture was added to 150 mL of water, and ethyl acetate extraction was performed. The extract was washed with a saturated aqueous sodium chloride solution, dehydrated over anhydrous sodium sulfate, and concentrated. The residue was recrystallized from an ethyl acetate/hexane mixture to give 15.51 g of the desired compound 2i as crystals with a melting point of 122 to 123° C. (yield: 92.6%).

The NMR measurement results of compound 2i are shown below.

$^{1}$H-NMR (600 MHz, $CDCl_3$) δ ppm: 1.03 (18H, s), 3.51 (4H, t, J=6.2 Hz), 3.76 (4H, t, J=6.2 Hz), 6.31 (2H, d, J=9.0 Hz), 7.32-7.35 (8H, m), 7.41-7.44 (4H, m), 7.50 (2H, d, J=8.9 Hz), 7.60-7.61 (8H, m), 9.66 (1H, s)

$^{13}$C-NMR (150 MHz, $CDCl_3$) δ ppm: 19.04, 26.79, 52.82, 60.50, 110.81, 125.04, 127.78, 129.85, 132.06, 133.09, 135.55, 152.68, 190.12

(2) N,N-[Bis[2-[(tert-butyldiphenylsilyl)oxy]ethyl]-4-[2-(thiophen-2-yl)vinyl]aniline (compound 4-(Z/E)i)

[Chem. 129]

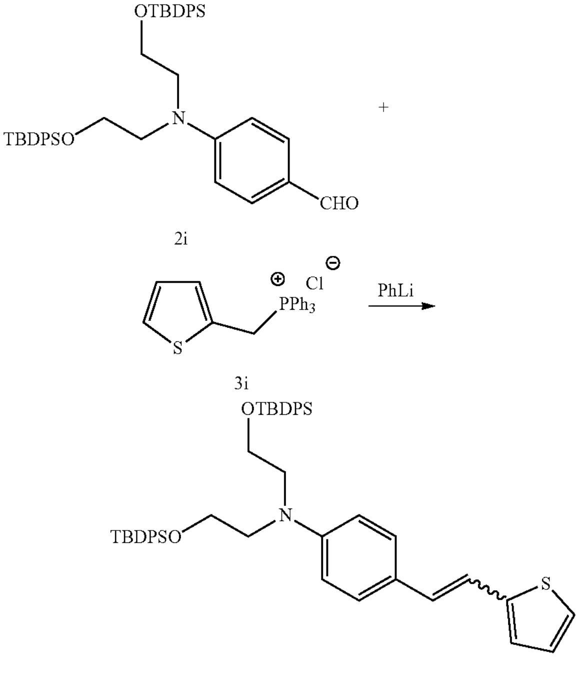

2i

3i 4-(Z/E)i 12.4 mL (26.04 mmol) of phenyllithium (2.1 mol solution in dibutyl ether) was added to 75 mL of THF under an argon atmosphere. To this, 9.37 g (23.7 mmol) of 2-thenyl triphenyl phosphonium chloride (3i) was added under ice-cooling. After 10-minute stirring, 40 mL of a solution of 15.5 g (22.6 mmol) of 4-[bis[2-[(tert-butyldiphenylsilyl)oxy]ethyl] amino]benzaldehyde (2i) in tetrahydrofuran was added dropwise. After 1-hour stirring under ice-cooling, the reaction mixture was poured into 350 mL of water, and ethyl acetate extraction was performed. The extract was washed with a saturated aqueous sodium chloride solution, dehydrated over anhydrous sodium sulfate, and concentrated. To the residue, 240 mL of an ethyl acetate/hexane (1/5) mixture was added, and the mixture was stirred and then ice-cooled. The precipitate was filtered off, and the filtrate was concentrated. The residue was purified by silica gel column chromatography (ethyl acetate/hexane=1/4) to give 13.76 of the desired compound 4-(Z/E)i as a yellow oil (yield: 79.5%).

(3) 5-[4-[Bis[2-[(tert-butyldiphenylsilyl)oxy]ethyl]amino]styryl]thiophene-2-carbaldehyde (compound 5-(Z/E)i)

[Chem. 130]

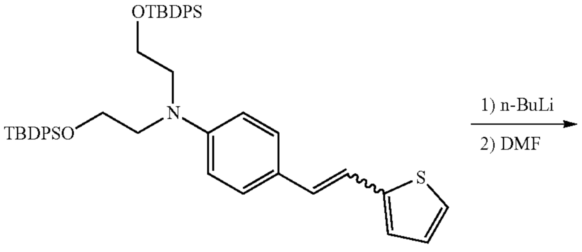

4-(Z/E)i

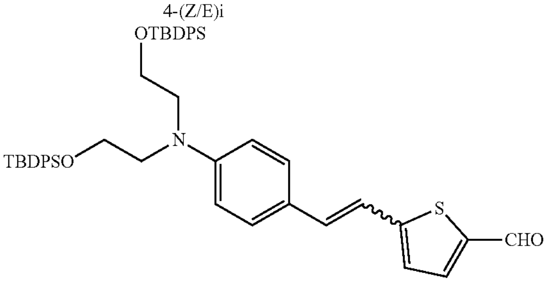

5-(Z/E)i 13.7 g (17.9 mmol) of N,N-[bis[2-[(tert-butyldiphenylsilyl)oxy]ethyl]-4-[2-(thiophen-2-yl)vinyl]aniline (4-(Z/E)i) was dissolved in 100 mL of tetrahydrofuran under an argon atmosphere. To this, 14.5 mL (23.2 mmol) of n-butyllithium (1.6 mol solution in hexane) was added dropwise with cooling at a temperature of −72 to −74° C. After 30-minute stirring, 1.6 g (21.9 mmol) of N,N-dimethylformamide was added dropwise. After 1.5-hour stirring, the reaction mixture was heated, and 10 mL of water was added dropwise. The mixture was stirred for 40 minutes. The reaction mixture was poured into 350 mL of water, and ethyl acetate extraction was performed. The extract was washed with a saturated aqueous sodium chloride solution, dehydrated over anhydrous sodium sulfate, and concentrated to give 13.99 g of the desired compound 5-(Z/E)i as a dark red oil (crude yield: 98.5%).

(4) (E)-5-[4-[Bis[2-[(tert-butyldiphenylsilyl)oxy]ethyl]amino]styryl]thiophene-2-carbaldehyde (compound 5-(E)i)

[Chem. 131]

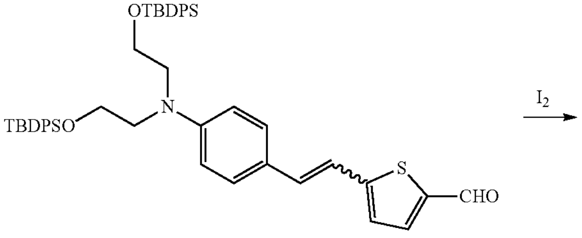

5-(Z/E)i

-continued

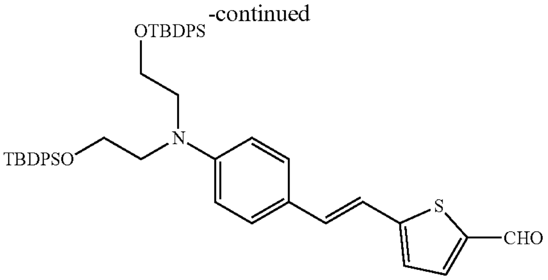

5-(E)i 13.99 g (17.6 mmol) of the crude 5-[4-[bis[2-[(tert-butyldiphenylsilyl)oxy]ethyl]amino]styryl]thiophene-2-carbaldehyde (5-(Z/E)i) was dissolved in 250 mL of ether. To this, 400 mg of iodine flakes were added. After 30-minute stirring at room temperature, the reaction mixture was washed twice with 200 mL of a 5% aqueous sodium hydrogen sulfite solution. The reaction mixture was further washed with a saturated aqueous sodium chloride solution, dehydrated over anhydrous magnesium sulfate, and concentrated. The residue was purified by silica gel column chromatography (ethyl acetate/hexane=1/3) to give 12.03 g of the desired compound 5-(E)i as a red oil (yield: 86.0%).

The NMR measurement results of compound 5-(E)i are shown below.

$^1$H-NMR (600 MHz, $CDCl_3$) δ ppm: 1.04 (18H, s), 3.48 (4H, t, J=6.2 Hz), 3.75 (4H, t, J=6.2 Hz), 6.29 (2H, d, J=8.3 Hz), 6.92 (1H, d, J=15.8 Hz), 7.03 (1H, d, J=15.8 Hz), 7.04 (1H, d, J=3.5 Hz), 7.15 (2H, d, J=8.3 Hz), 7.33-7.36 (8H, m), 7.41-7.44 (4H, m), 7.62-7.63 (9H, m), 9.81 (1H, s)

(5) (E)-5-[4-[Bis(2-hydroxyethyl)amino]styryl]thiophene-2-carbaldehyde (compound 6-(E)i)

[Chem. 132]

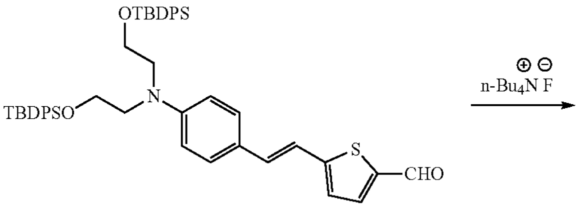

5-(E)i

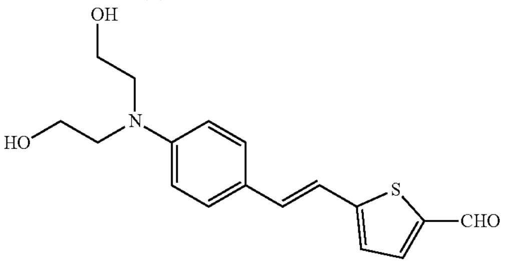

6-(E)i 12.0 g (15.1 mmol) of (E)-5-[4-[Bis[2-[(tert-butyldiphenylsilyl)oxy]ethyl]amino]styryl]thiophene-2-carbaldehyde (5-(E)i) was dissolved in 50 mL of tetrahydrofuran. To this, 45 mL of tetrabutylammonium (1 mol solution in tetrahydrofuran) was added dropwise with stirring at room temperature. After 1-hour stirring, the reaction mixture was poured into water, and ethyl acetate extraction was performed. The extract was washed with a saturated aqueous sodium chloride solution, dehydrated over anhydrous sodium sulfate, and concentrated. The residual solid was purified by recrystallization from an ethanol/hexane mixture to give 4.07 g of the desired compound 6-(E)i as red crystals with a melting point of 142 to 143° C. (yield: 84.9%).

The NMR measurement results of compound 6-(E)i are shown below.

$^1$H-NMR (600 MHz, $CDCl_3$) δ ppm: 3.15 (2H, s), 3.65 (4H, t, J=4.8 Hz), 3.90 (4H, t, J=4.8 Hz), 6.69 (2H, d, J=8.9 Hz), 7.00 (1H, d, J=15.8 Hz), 7.08 (1H, d, J=15.8 Hz), 7.06 (1H, d, J=4.5 Hz), 7.38 (2H, d, J=9.0 Hz), 7.63 (1H, d, J=4.1 Hz), 9.81 (1H, s)

$^{13}$C-NMR (150 MHz, $CDCl_3$) δ ppm: 55.09, 60.79, 112.55, 116.70, 124.60, 125.26, 128.44, 133.12, 137.60, 140.37, 148.36, 153.95, 182.45

(6) 2-[4-[(E)-2-[5-[(E)-4-[Bis(2-hydroxyethyl) amino]styryl]thio phen-2-yl]vinyl]-3-cyano-5-phenyl-5-(trifluoromethyl)furan-2(5H)-ylidene]malononitrile (EO-20)

[Chem. 133]

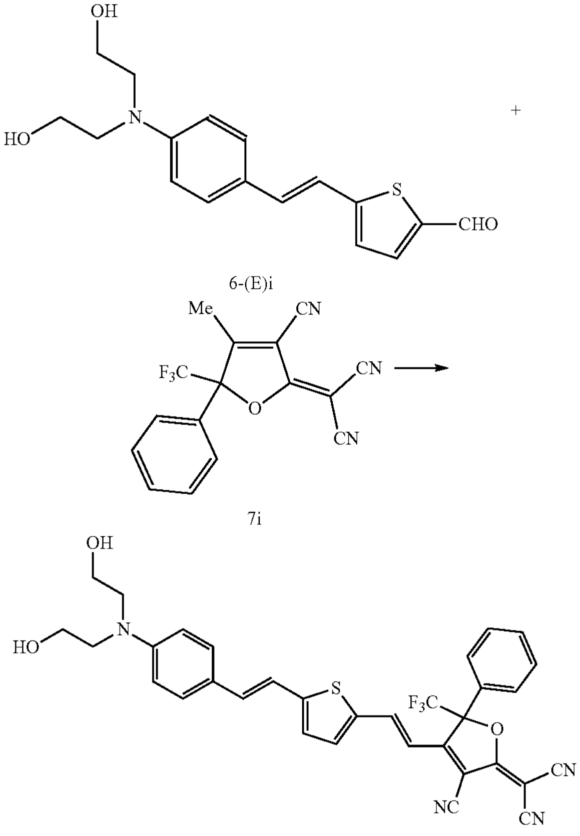

6-(E)i

7i

EO-20

2.0 g (6.30 mmol) of (E)-5-[4-[bis(2-hydroxyethyl) amino] styryl]thiophene-2-carbaldehyde (6-(E)i) and 2.18 g (6.9 mmol) of 2-(3-cyano-4-methyl-5-phenyl-5-trifluoromethyl-2(5H)-furanylidene)propanedinitrile (7i) were added to 40 mL of ethanol and 10 mL of tetrahydrofuran. The mixture was stirred at room temperature for 23 hours. The precipitated crystals were collected by filtration and washed with ethanol. The crystals were purified by silica gel column chromatography (chloroform/methanol=10/1) and then washed with ethanol. As a result, 3.52 g of the desired compound EO-20 was obtained as a dark brown powder with a melting point of 225 to 226° C. (yield: 91.0%).

The NMR measurement results of EO-20 are shown below.

$^1$H-NMR (600 MHz, $CDCl_3$) δ ppm: 2.96 (2H, s), 3.68 (4H, t, J=4.8 Hz), 3.92 (4H, t, J=4.8 Hz), 6.60 (1H, d, J=15.1 Hz), 6.71 (2H, d, J=8.9 Hz), 7.00 (1H, d, J=15.8 Hz), 7.03 (1H, d, J=4.1 Hz), 7.09 (1H, d, J=15.8 Hz), 7.29 (1H, d, J=4.1 Hz), 7.39 (2H, d, J=8.9 Hz), 7.50-7.59 (5H, m), 7.79 (1H, d, J=15.1 Hz)

$^{13}$C-NMR (150 MHz, $CDCl_3$) δ ppm: 55.02, 58.67, 60.69, 97.21, 110.48, 110.81, 110.92, 111.91, 112.69, 116.32, 124.18, 126.81, 127.76, 129.15, 129.48, 129.82, 131.62, 135.65, 138.17, 139.42, 141.71, 149.19, 156.42, 162.09, 175.18

Synthesis Example 40: Production of EO Molecule (EO-21)

[Chem. 134]

EO-21

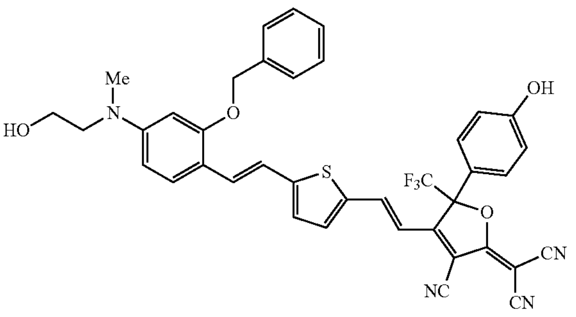

(1) 1-[4-[(tert-Butyldiphenylsilyl)oxy]phenyl]-2,2,2-trifluoroethanone (compound 2j)

[Chem. 135]

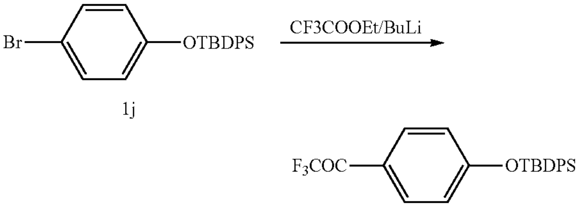

1j

2j 100 mL of tert-butyllithium (1.9 mol solution in pentane) was added to 500 mL of tetrahydrofuran under an argon atmosphere. To this, a solution of 43.0 g (0.105 mol) of 4-(bromophenoxy) (tert-butyl)diphenylsilane (1j) in 50 mL of tetrahydrofuran was added dropwise with cooling in a dry ice/acetone bath. The cooling bath was removed, and the reaction mixture was heated to 5° C. The reaction mixture was cooled again to −70° C. or less, and 20.0 g (0.141 mol) of ethyl trifluoroacetate was added dropwise. After 1-hour stirring, the reaction mixture was heated to 10° C., and 200 mL of a saturated ammonium chloride solution was added. The precipitate was filtered off, and the tetrahydrofuran in the filtrate was evaporated off. The residue was dissolved in 500 mL of ether, and the solution was washed with a saturated aqueous sodium chloride solution. The washed solution was dehydrated over anhydrous magnesium sulfate and concentrated. The residual liquid was purified by silica gel column chromatography (chloroform/hexane=6/4) to give 22.1 g of the desired compound 2j as a colorless oil (yield: 49.1%).

(2) 4,4,4-Trifluoro-3-hydroxy-3-[4-[(tert-butyldiphenylsilyl)ox y]phenyl]butan-2-one (compound 3j)

[Chem. 136]

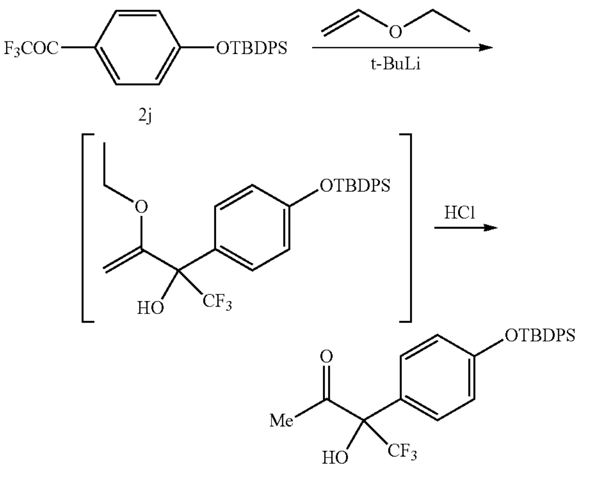

2j

3j 7.6 g (0.105 mol) of ethyl vinyl ether was dissolved in 300 mL of tetrahydrofuran under an argon atmosphere. To this, 50 mL (0.095 mol) of tert-butyllithium (1.9 mol solution in pentane) was added dropwise with cooling in a dry ice/acetone bath at −70° C. The resulting yellow slurry was stirred for 1 hour, the cooling bath was removed, and the reaction mixture was heated to −10° C. This was cooled again to −73° C., and 20 mL of a solution of 22.0 g (0.0513 mol) of 1-[4-[(tert-butyldiphenylsilyl)oxy]phenyl]-2,2,2-trifluoroethanone (2j) in tetrahydrofuran was added dropwise. After 1-hour stirring, the reaction mixture was slowly heated to room temperature and stirred at the same temperature for 2 hours. 100 mL of ethyl acetate was added, and the mixture was washed with a saturated aqueous sodium chloride solution and concentrated. The residue was dissolved in 100 mL of methanol. To this, 100 mL of 5% hydrochloric acid was added under ice-cooling, and the mixture was stirred for 2 hours. The reaction mixture was subjected to chloroform extraction. The extract was washed with a saturated aqueous sodium chloride solution, dehydrated over anhydrous magnesium sulfate, and concentrated. The residue was subjected to crystallization from hexane to give 14.5 g of the desired compound 3j (yield: 59.8%).

(3) 2-[5-[4-[(tert-Butyldiphenylsilyl)oxy]phenyl]-3-cyano-4-methyl-5-(trifluoromethyl)furan-2(5H)-ylidene]malononitrile (compound 4j)

[Chem. 137]

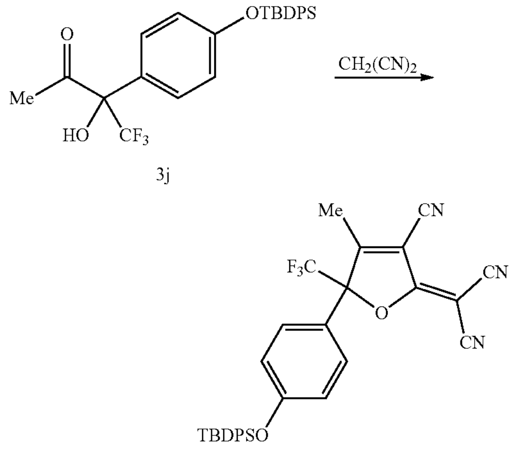

3j

4j 0.47 g (0.99 mmol) of 4,4,4-trifluoro-3-hydroxy-3-[4-[(tert-butyldiphenylsilyl)ox y]phenyl]butan-2-one (3j) and 0.15 g (2.27 mmol) of malononitrile were dissolved in 5 mL of ethanol. To this, 0.1 mL (0.294 [mol) of sodium ethoxide (20% solution in ethanol) was added, and the mixture was heated under reflux for 1 hour. The reaction mixture was concentrated, and the residue was purified by silica gel column chromatography to give 0.33 g of the desired compound 4j (yield: 58.5%).

(4) 2-[4-[(E)-2-[5-[(E)-2-(Benzyloxy)-4-[[2-[(tert-butyldiphenylsilyl)oxy]ethyl] (methyl)amino] styryl] thiophen-2-yl]vinyl]-5-[4-[(tert-butyldiphenylsilyl) oxy]phenyl]-3-cyano-5-(trifluoromethyl)furan-2 (5H)-ylidene]malononitrile (compound 5j)

[Chem. 138]

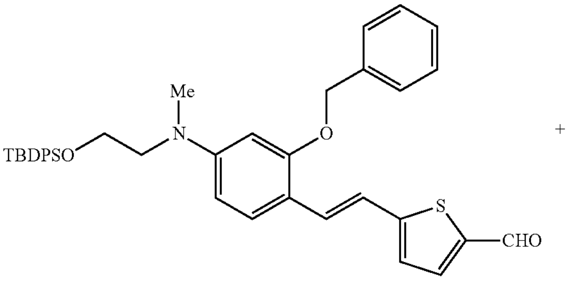

12-(E)d

-continued

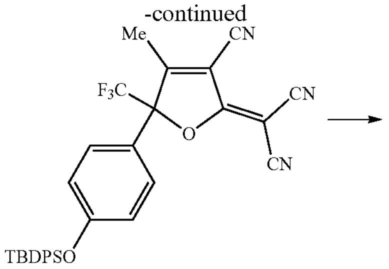

4j

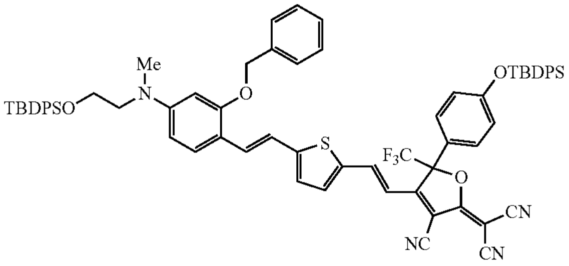

5j

Synthesis Example (14)

2.5 g (3.96 mmol) of the compound described in the above (10), i.e., (E)-5-[2-(benzyloxy)-4-[[2-[(tert-butyldiphenylsilyl)oxy]ethyl](methyl)amino]styryl]thiophene-2-carbaldehyde (12-(E)d) and 2.51 g (4.41 mmol) of 2-[5-[4-[(tert-butyldiphenylsilyl)oxy]phenyl]-3-cyano-4-methyl-5-(trifluoromethyl)furan-2(5H)-ylidene]malononitrile (4j) were added to 30 mL of ethanol. The mixture was stirred with heating at 70° C. for 0.5 hour. The ethanol was evaporated off, and the residue was purified by silica gel column chromatography to give 3.5 g of the desired compound 5j as a black powder (yield: 74.6%).

The NMR measurement results of compound 5j are shown below.

$^{1}$H-NMR (600 MHz, $CDCl_3$) δ ppm: 1.03 (9H, s), 1.08 (9H, s), 2.99 (3H, s), 3.51 (2H, t, J=5.5 Hz), 3.79 (2H, t, J=5.5H), 5.11 (2H, s), 6.13 (1H, d, J=2.0 Hz), 6.18 (1H, dd, J=2.0 Hz, 9.0H), 6.51 (1H, d, J=15.1 Hz), 6.84 (2H, d, J=9.0 Hz), 6.93 (1H, d, J=4.1 Hz), 7.16 (1H, d, J=15.8 Hz), 7.20-7.21 (3H, m), 7.28-7.44 (19H, m), 7.50 (1H, d, J=15.8 Hz), 7.60 (4H, d, J=6.2 Hz), 7.67-7.69 (4H, m)

$^{13}$C-NMR (150 MHz, $CDCl_3$) δ ppm: 19.06, 19.4, 26.40, 26.79, 39.53, 54.40, 57.61, 61.13, 70.48, 96.27, 105.52, 110.86, 111.00, 111.33, 111.46, 113.39, 116.51, 120.87, 121.13, 121.62, 127.22, 127.75, 128.00, 128.17, 128.45, 128.68, 129.80, 130.27, 131.91, 132.32, 133.15, 135.40, 135.53, 136.73, 137.74, 141.69, 151.74, 158.17, 158.79, 158.93, 162.20, 175.38

(5) 2-[4-[(E)-2-[5-[(E)-2-(Benzyloxy)-4-[(2-hydroxyethyl) (methy 1)amino]styryl]thiophen-2-yl]vinyl]-3-cyano-4-(hydroxyphenyl)-5-(trifluoromethyl)furan-2(5H)-ylidene]malononitrile (EO-21)

[Chem. 139]

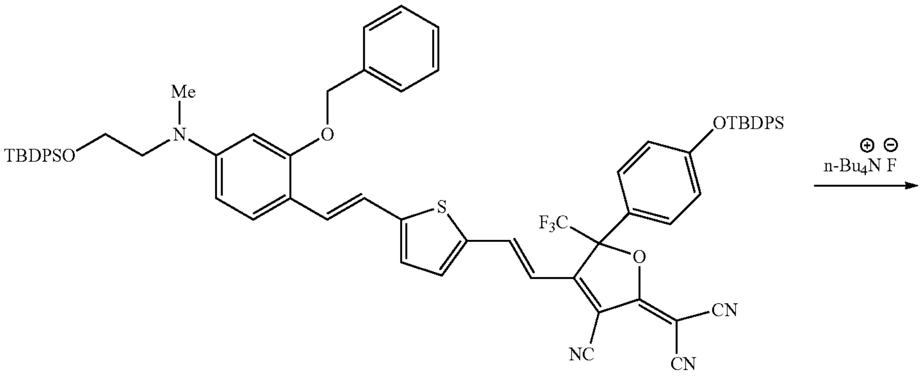

5j

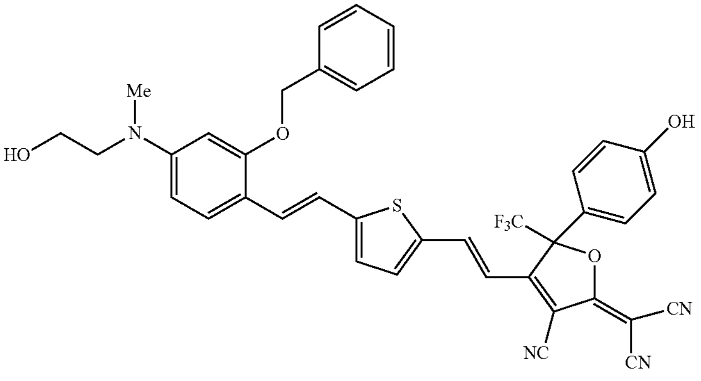

EO-21

1.0 g (0.845 mmol) of 2-[4-[(E)-2-[5-[(E)-2-(benzyloxy)-4-[[2-[(tert-butyldiphenylsilyl)oxy]ethyl] (methyl)amino]styryl]thiophen-2-yl]vinyl]-5-[4-[(tert-butyldiphenylsilyl)oxy]phenyl]-3-cyano-5-(trifluoromethyl)furan-2(5H)-ylidene]malononitrile (5j) was dissolved in 20 mL of tetrahydrofuran. To this, 3 mL of tetrabutylammonium fluoride (1 mol solution in tetrahydrofuran) was added dropwise with stirring at room temperature. After 0.5-hour stirring, the reaction mixture was poured into water, and ethyl acetate extraction was performed. The extract was washed with a saturated aqueous sodium chloride solution, dehydrated over anhydrous sodium sulfate, and concentrated. The residue was purified by silica gel column chromatography (chloroform/methanol=10/1) to give 0.3 g of the desired compound EO-21 as black crystals with a melting point of 175 to 176° C. (yield: 50.3%)

The NMR measurement results of EO-21 are shown below.

$^1$H-NMR (600 MHz, CDCl$_3$) δ ppm: 3.04 (3H, s), 3.53 (2H, t, J=5.5 Hz), 3.79 (2H, t, J=5.5H), 5.20 (2H, s), 5.51 (1H, s), 6.28 (1H, d, J=2.1 Hz), 6.39 (1H, dd, J=2.1 Hz, 8.2H), 6.58 (1H, d, J=15.1 Hz), 6.93-6.95 (3H, m), 7.16 (1H, d, J=15.8 Hz), 7.35-7.47 (8H, m), 7.48 (1H, d, J=4.1 Hz), 7.50 (1H, d, J=16.5 Hz), 7.72 (1H, m)

Synthesis Examples 41 to 51

Copolymers (A-8) to (A-18) and their methyl carbamate derivatives were obtained in the same manner as described in Example 1 of Patent Literature 1 based on the feed ratios of DCPMA and MOI described in the table given below (Table 9)

Synthesis Examples 52 to 56

Copolymers (C-4) to (C-8) and their methyl carbamate derivatives were obtained in the same manner as described in Examples 4 to 5 of Patent Literature 1 based on the feed ratios of MMA and MOI described in the table given below (Table 9)

The Tgs, Mns and Mws of the methyl carbamate derivatives of the copolymers of Synthesis Examples 41 to 56 are shown in the table given below (Table 9).

TABLE 9

| | Copolymer | Molar ratio of methacrylate/ MOI | Tg (° C.) | Mn | Mw |
|---|---|---|---|---|---|
| Synthesis Example 41 | (A-8) | 2.11/1 | 121 | 35,600 | 77,700 |
| Synthesis Example 42 | (A-9) | 1.62/1 | 117 | 30,700 | 68.500 |
| Synthesis Example 43 | (A-10) | 1.25/1 | 108 | 26,800 | 60,500 |
| Synthesis Example 44 | (A-11) | 1.772/1 | 121 | 29,800 | 69,400 |
| Synthesis Example 45 | (A-12) | 1.825/1 | 121 | 29,600 | 60,900 |
| Synthesis Example 46 | (A-13) | 1.96/1 | 109 | 31,200 | 64,800 |
| Synthesis Example 47 | (A-14) | 1.697/1 | 118 | 31,500 | 78,400 |
| Synthesis Example 48 | (A-15) | 0.51/1 | — | 45,800 | 148,000 |
| Synthesis Example 49 | (A-16) | 1.968/1 | 120 | 33,000 | 74,100 |
| Synthesis Example 50 | (A-17) | 2.082/1 | 113 | 33,300 | 69,600 |

TABLE 9-continued

| | Copolymer | Molar ratio of methacrylate/ MOI | Tg (° C.) | Mn | Mw |
|---|---|---|---|---|---|
| Synthesis Example 51 | (A-18) | 1.339/1 | 111 | 25,700 | 58,700 |
| Synthesis Example 52 | (C-4) | 5.37/1 | 102 | 29,200 | 59,500 |
| Synthesis Example 53 | (C-5) | 4.548/1 | 100 | 34,400 | 60,900 |
| Synthesis Example 54 | (C-6) | 5.835 | 103 | 41,400 | 70,800 |
| Synthesis Example 55 | (C-7) | 5.09/1 | 100 | 27,200 | 52,000 |
| Synthesis Example 56 | (C-8) | 6.377/1 | 102 | 30,600 | 59,200 |

Example 11: Electro-Optic Polymer (I$_1$)

1.82 g of the copolymer (A-8) was dissolved in 70 mL of tetrahydrofuran (THF). To this, 0.79 g (2.349 mmol) of the EO molecule (EO-7) and 55 μL of DBTDL were added, and the mixture was stirred in an oil bath at 60° C. for 2.5 hours. Subsequently, 3.5 mL of methanol was added, and the mixture was stirred for 45 minutes. The reaction mixture was cooled and then poured into 860 mL of diisopropyl ether (IPE), and the mixture was stirred. The precipitated powder was collected by filtration and washed with 100 mL of a THF/IPE (1/10) mixture and subsequently with IPE. The washed residue was dried in vacuo with heating at 70° C. to give 2.42 g of an electro-optic polymer (I$_1$) as a black powder. The Tg of this electro-optic polymer was 180° C. The electro-optic coefficient (r$_{33}$) of the electro-optic polymer (D$_1$) was 89 pm/V at the wavelength of 1308 nm and 68 pm/V at the wavelength of 1550 nm. That is, this polymer successfully showed electro-optic effect.

Example 12: Electro-Optic Polymer (I$_2$)

The same procedure as in Example 11 was performed using 1.70 g of the copolymer (A-9) and 0.74 g (2.659 mmol) of the EO molecule (EO-8) as starting materials to give 2.22 g of an electro-optic polymer (I$_2$) as a black powder. The Tg of this electro-optic polymer was 185° C. The electro-optic coefficient (r$_{33}$) of the electro-optic polymer (I$_1$) was 72 pm/V at the wavelength of 1308 nm and 46 pm/V at the wavelength of 1550 nm. That is, this polymer successfully showed electro-optic effect.

Example 13: Electro-Optic Polymer (I$_3$)

The same procedure as in Example 11 was performed using 1.70 g of the copolymer (A-10) and 0.74 g (3.159 mmol) of the EO molecule (EO-9) as starting materials to give 2.18 g of an electro-optic polymer (I$_3$) as a black powder. The Tg of this electro-optic polymer was 193° C. The electro-optic coefficient (r$_{33}$) of the electro-optic polymer (I$_2$) was 50 pm/V at the wavelength of 1308 nm and 39 pm/V at the wavelength of 1550 nm. That is, this polymer successfully showed electro-optic effect.

Examples 14 to 18: Electro-Optic Polymers (D$_8$ to D$_{12}$)

The same procedure as in Examples 1 and 2 was performed using the copolymers (A-11 to A-15) and the EO molecules (EO-11, EO-12, EO-16, EO-1 and DR-2) as starting materials to give electro-optic polymers ($D_8$ to $D_{12}$) as a black powder. The Tgs of these electro-optic polymers are shown in the table given below (Table 10).

Examples 19 and 20: Electro-Optic Polymers ($H_2$ and $H_3$)

The same procedure as in Example 10 was performed using the copolymers (A-16 and A-17) and the EO molecules (EO-13 and EO-19) as starting materials to give electro-optic polymers ($H_2$ and $H_3$) as a black powder. The Tgs of these electro-optic polymers are shown in the table given below (Table 10).

Example 21: Electro-Optic Polymer ($J_1$)

2.05 g of the copolymer (A-18) was dissolved in 90 mL of tetrahydrofuran. To this, 1.12 g (3.644 mmol) of the EO molecule (EO-20) and 100 μL of DBTDL were added, and the mixture was stirred in an oil bath at 60° C. for 2 hours. Subsequently, 3 mL of methanol was added, and the mixture was stirred for 45 minutes. The reaction mixture was cooled and then poured into 1080 mL of diisopropyl ether, and the mixture was stirred. The precipitated powder was collected by filtration and washed with 200 mL of a THF/IPE (1/12) mixture and subsequently with IPE. The washed residue was dried in vacuo with heating at 70° C. to give 2.82 g of an electro-optic polymer ($J_1$) as a black powder. The Tg of this electro-optic polymer was 195° C.

Examples 22 to 25: Electro-Optic Polymers ($F_5$ to $F_8$)

The same procedure as in Example 6 was performed using the copolymers (C-4 to C-6) and the EO molecules (EO-10, EO-11, EO-15 and EO-16) as starting materials to give electro-optic polymers ($F_5$ to $F_8$) as a black powder. The Tgs of these electro-optic polymers are shown in the table given below (Table 10).

Example 26: Electro-Optic Polymer ($K_1$)

1.71 g of the copolymer (C-7) was dissolved in 65 mL of tetrahydrofuran. To this, 0.74 g (2.059 mmol) of the EO molecule (EO-17) and 75 μL of DBTDL were added, and the mixture was stirred in an oil bath at 60° C. for 3 hours. Subsequently, 3 mL of methanol and 40 μL of DBTDL were added, and the mixture was stirred for 45 minutes. The reaction mixture was cooled and then poured into 780 mL of diisopropyl ether, and the mixture was stirred. The precipitated powder was collected by filtration and washed with 130 mL of a THF/IPE (1/12) mixture and subsequently with IPE. The washed residue was dried in vacuo with heating at 70° C. to give 2.26 g of an electro-optic polymer ($K_1$) as a black powder. The Tg of this electro-optic polymer was 146° C.

Example 27: Electro-Optic Polymer ($K_2$)

The same procedure as in Example 26 was performed using the copolymer (C-8) and the EO molecule (EO-18) as starting materials to give an electro-optic polymer ($K_2$) as a black powder. The Tg of this electro-optic polymer is shown in the given below table (Table 10).

The results of electro-optic polymers obtained in Examples 11 to 27 are summarized and shown in the table given below (Table 10).

TABLE 10

| | Base polymer | | | EO molecule | | Electro-optic polymer | |
|---|---|---|---|---|---|---|---|
| | Type | Methacrylate | Molar ratio of methacrylate/MOI | Type | Feed (wt %) | Type | Tg (° C.) |
| Example 11 | $A_8$ | DCPMA | 2.11/1 | EO-7 | 30 | $I_1$ | 180 |
| Example 12 | $A_9$ | DCPMA | 1.62/1 | EO-8 | 30 | $I_2$ | 185 |
| Example 13 | $A_{10}$ | DCPMA | 1.25/1 | EO-9 | 30 | $I_3$ | 193 |
| Example 14 | $A_{11}$ | DCPMA | 1.772/1 | EO-11 | 35 | $D_8$ | 189 |
| Example 15 | $A_{12}$ | DCPMA | 1.825/1 | EO-12 | 30 | $D_9$ | 177 |
| Example 16 | $A_{13}$ | DCPMA | 1.96/1 | EO-16 | 35 | $D_{10}$ | 177 |
| Example 17 | $A_{14}$ | DCPMA | 1.697/1 | EO-1 | 25 | $D_{11}$ | 178 |
| | | | | DR-2 | 5.7 | | |
| Example 18 | $A_{15}$ | DCPMA | 0.51/1 | EO-1 | 35 | $D_{12}$ | 171 |
| | | | | DR-2 | 15 | | |
| Example 19 | $A_{16}$ | DCPMA | 1.968/1 | EO-13 | 35 | $H_2$ | 196 |
| Example 20 | $A_{17}$ | DCPMA | 2.082/1 | EO-19 | 35 | $H_3$ | 172 |
| Example 21 | $A_{18}$ | DCPMA | 1.339/1 | EO-20 | 35 | $J_1$ | 195 |
| Example 22 | $C_4$ | MMA | 5.37/1 | EO-10 | 30 | $F_5$ | 155 |
| Example 23 | $C_4$ | MMA | 5.37/1 | EO-11 | 30 | $F_6$ | 156 |
| Example 24 | $C_5$ | MMA | 4.548/1 | EO-15 | 30 | $F_7$ | 142 |
| Example 25 | $C_6$ | MMA | 5.835/1 | EO-16 | 30 | $F_8$ | 148 |
| Example 26 | $C_7$ | MMA | 5.09/1 | EO-17 | 30 | $K_1$ | 146 |
| Example 27 | $C_8$ | MMA | 6.377/1 | EO-18 | 30 | $K_2$ | 148 |

The electro-optic polymers of Examples 11 to 27 had favorable film-forming properties.

In addition, as shown in the results of Examples 11 to 21, the electro-optic polymers of the present invention had a high Tg although they had a low alicyclic methacrylate monomer content in the base polymer and a high EO molecule concentration.

Furthermore, a similar tendency was observed in the electro-optic polymer produced from the EO molecule (EO-21) obtained in Synthesis Example 40.

INDUSTRIAL APPLICABILITY

The present invention provides an electro-optic polymer with a high Tg, an electro-optic polymer with favorable film-forming properties, etc. Such an electro-optic polymer can be used to produce an electro-optic device that is highly stable for a long period of time.

The invention claimed is:

1. A polymer comprising (a) a base polymer having a reactive group (A), (b) an electro-optic molecule having a plurality of reactive groups (B), and a bond (C) formed by reaction of the reactive group (A) with the plurality of reactive groups (B), wherein the bond (C) is at least one type of bond selected from the group consisting of a (thio)ester bond, a (thio)urethane bond, a (thio)urea bond and a (thio) amide bond, wherein the (a) base polymer is a methacrylate-based base polymer, wherein the (b) electro-optic molecule comprises a compound represented by the following formula (1):

(1)

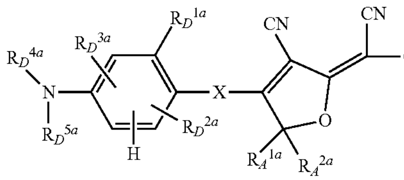

wherein:

$R_D^{1a}$, $R_D^{2a}$ and $R_D^{3a}$ independently represent a hydrogen atom, an alkyl group, an alkoxy group, an aryloxy group, an aralkyloxy group, a silyloxy group, an alkenyloxy group, an alkynyloxy group, a hydroxy group, $—R^1—OH$ (wherein $R^1$ is a hydrocarbon group), $—OR^2—OH$ (wherein $R^2$ is a hydrocarbon group), $—OC(=O)R^3$ (wherein $R^3$ is a hydrocarbon group), an amino group, $—R^4—NH_2$ (wherein $R^4$ is a hydrocarbon group), a thiol group, $—R^5—SH$ (wherein $R^5$ is a hydrocarbon group), —NCO or $—R^6—NCO$ (wherein $R^6$ is a hydrocarbon group);

$R_D^{4a}$ and $R_D^{5a}$ independently represent a hydrogen atom, an alkyl group, a haloalkyl group, an acyloxyalkyl group, a silyloxyalkyl group, $—R^1—OH$ (wherein $R^1$ is a hydrocarbon group), $—R^4—NH_2$ (wherein $R^4$ is a hydrocarbon group), an aryl group, $—R^5—SH$ (wherein $R^5$ is a hydrocarbon group) or $—R^6—NCO$ (wherein $R^6$ is a hydrocarbon group);

X represents a linking group; and $R_A^{1a}$ and $R_A^{2a}$ independently represent a hydrogen atom, an alkyl group, an alkenyl group, a cycloalkyl group, a cycloalkenyl group, an alkoxy group, a haloalkyl group, an aryl group, a hydroxy group, $—R^1—OH$ (wherein $R^1$ is a hydrocarbon group), $—OR^2—OH$ (wherein $R^2$ is a hydrocarbon group), an amino group, $—R^4—NH_2$ (wherein $R^4$ is a hydrocarbon group), a thiol group, $—R^5—SH$ (wherein $R^5$ is a hydrocarbon group), —NCO or $—R^6—NCO$ (wherein $R^6$ is a hydrocarbon group), with the proviso that the compound has two or more reactive groups (B) selected from the group consisting of hydroxy, $—R^1—OH$, $—OR^2—OH$, amino, $—R^4—NH_2$, thiol, $—R^5—SH$, —NCO and $—R^6—NCO$ contained in the formula (1), and wherein the polymer satisfies any one of the following (I) and (II):

(I) $R_D^{1a}$ is the reactive group (B) and at least one of $R_D^{4a}$, $R_D^{5a}$, $R_A^{1a}$ and $R_A^{2a}$ is the reactive group (B); and (II) $R_D^{4a}$ and $R_D^{5a}$ are the reactive groups (B).

2. The polymer according to claim 1, wherein the reactive group (A) or the reactive groups (B) are at least one type of group selected from the group consisting of an iso(thio) cyanato group, a hydroxy group, a thiol group, an amino group, a carboxyl group and an acid anhydride group.

3. The polymer according to claim 1, wherein the reactive group (A) or the reactive groups (B) comprise an iso(thio) cyanato group.

4. The polymer according to claim 1, wherein the (a) base polymer is a methacrylate-based base polymer having an iso(thio)cyanato group.

5. The polymer according to claim 4, wherein the methacrylate-based base polymer comprises a structural unit derived from (a1) an iso(thio)cyanato group-containing (meth)acrylate.

6. The polymer according to claim 4, wherein the methacrylate-based base polymer comprises a structural unit derived from (a2) an iso(thio)cyanato group-free methacrylate containing an alicyclic methacrylate.

7. The polymer according to claim 5, wherein the methacrylate-based base polymer further comprises a structural unit derived from (a2) an iso(thio)cyanato group-free methacrylate containing an alicyclic methacrylate.

8. The polymer according to claim 7, wherein the methacrylate-based base polymer comprises the structural unit derived from (a2) an iso(thio)cyanato group-free methacrylate and the structural unit derived from (a1) an iso(thio) cyanato group-containing (meth)acrylate at a molar ratio of 0.1:1 to 19:1.

9. The polymer according to claim 7, wherein the methacrylate-based base polymer comprises a structural unit derived from an alicyclic methacrylate and the structural unit derived from (a1) an iso(thio)cyanato group-containing (meth)acrylate at a molar ratio of 0.01:1 to 19:1.

10. The polymer according to claim 8, wherein the methacrylate-based base polymer comprises a structural unit derived from an alicyclic methacrylate and the structural unit derived from (a1) an iso(thio)cyanato group-containing (meth)acrylate at a molar ratio of 0.01:1 to 19:1.

11. The polymer according to claim 1, wherein the (b) electro-optic molecule is a compound having a structure represented by D (a donor structure)-B (a bridge structure)-A (an acceptor structure).

12. The polymer according to claim 1, wherein the reactive group (A) is an iso(thio)cyanato group, and the reactive groups (B) are at least one type of group selected from the group consisting of a hydroxy group, a thiol group, an amino group, a carboxyl group and an acid anhydride group.

13. The polymer according to claim 1, which satisfies any one of the following (A) and (B):

(A) $R_D^{1a}$ is a hydroxyalkoxy group, and at least one of $R_D^{4a}$, $R_D^{5a}$, $R_A^{1a}$ and $R_A^{2a}$ is a hydroxyalkyl group, a hydroxyaryl group or a hydroxyaralkyl group; and (B) $R_D^{4a}$ and $R_D^{5a}$ are each a hydroxyalkyl group, a hydroxyaryl group or a hydroxyaralkyl group.

14. The polymer according to claim 1, wherein the (a) base polymer and the (b) electro-optic molecule are contained at a weight ratio of 30:70 to 90:10.

15. An optical element comprising the polymer according to claim 1.

* * * * *